United States Patent
Stadlwieser et al.

(10) Patent No.: US 8,816,085 B2
(45) Date of Patent: Aug. 26, 2014

(54) METHYLPYRROLOPYRIDINECARBOXAMIDES

(75) Inventors: Josef Stadlwieser, Constance (DE); Beate Schmidt, Allensbach (DE); Heiko Bernsmann, Frankfurt (DE); Alexander Sudau, Leichlingen (DE); Torsten Dunkern, Jüchen Gierath (DE); Ragna Hussong, Deißlingen (DE); Ewald Benediktus, Biberach (DE); Andreas Pahl, Ahrensburg (DE)

(73) Assignee: Takeda GmbH, Konstanz (DE)

( * ) Notice: Subject to any disclaimer, the term of this patent is extended or adjusted under 35 U.S.C. 154(b) by 156 days.

(21) Appl. No.: 13/390,942

(22) PCT Filed: Aug. 24, 2010

(86) PCT No.: PCT/EP2010/062338
§ 371 (c)(1),
(2), (4) Date: Feb. 24, 2012

(87) PCT Pub. No.: WO2011/023696
PCT Pub. Date: Mar. 3, 2011

(65) Prior Publication Data
US 2012/0142633 A1 Jun. 7, 2012

(30) Foreign Application Priority Data
Aug. 26, 2009 (EP) .................................. 09168682

(51) Int. Cl.
*A61K 31/437* (2006.01)
*C07D 471/04* (2006.01)

(52) U.S. Cl.
USPC ........................................... 546/113; 514/300

(58) Field of Classification Search
USPC ........................................... 546/113; 514/300
See application file for complete search history.

(56) References Cited

U.S. PATENT DOCUMENTS 7,405,210 B2 * 7/2008 Bradley et al. ............. 514/231.5

FOREIGN PATENT DOCUMENTS

| EP | 0 556 738 A1 | 8/1993 |
|---|---|---|
| WO | 01/47922 A2 | 7/2001 |
| WO | 01/47922 A3 | 7/2001 |
| WO | 2006/042102 A2 | 4/2006 |
| WO | 2006/042102 A3 | 4/2006 |

OTHER PUBLICATIONS

Boswell-Smith, Victoria "Phosphodiesterase inhibitors" British Journal of Pharmacology (2006) 147, S252—S257.*

P.C. Belanger, et al., "Facile Preparations of 4-Fluororesorcinol", Canadian Journal of Chemistry, 1988, vol. 66, pp. 1479-1482.
G.H. Birnberg, et al., "The Synthesis of 5-Arylpyrrolo[3,2-b]pyridines and 7-Aryl-pyrrolo[3,2-b] pyridines: Addition of 3-Aminopyrroles to Aryl Enaminones", J. Heterocycl. Chem., 1995, vol. 32, pp. 1293-1298.
S.D. Erickson, et al., "Potent, selective MCH-1 receptor antagonists", Bioorganic & Medicinal Chemistry Letters, 2008, vol. 18, pp. 1402-1406.
J. Freedman, et al., "The Preparation of 3,4-Dihydro-1-benzoxepin-5(2H)-ones", J. Heterocycl. Chem., 1989, vol. 26, pp. 1547-1554.
J.R. Hwu, et al, "The Trimethylsilyl Cationic Species as a Bulky Proton. Application to Chemoselective Dioxolanation", J. Org. Chem., 1985, vol. 50, pp. 3946-3948.
J.M. Muchowski, et al., "Protecting Groups for the Pyrrole and Indole Nitrogen Atom. The [2-(Trimethylsilyl)ethoxy] methyl Moiety. Lithiation of 1-[[2-(Trimethylsilyl)ethoxy]methyl]pyrrole", J. Org. Chem., 1984, vol. 49, pp. 203-205.
M. Murata, et al., "Palladium-Catalyzed Borylation of Aryl Halides or Triflates with Dialkoxyborane: A Novel and Facile Synthetic Route to Arylboronates", J. Org. Chem., 2000, vol. 65, pp. 164-168.
M. Murata, et al., "Novel Palladium(0)-Catalyzed Coupling Reaction of Dialkoxyborane with Aryl Halides: Convenient Synthetic Route to Arylboronates", J. Organic Chemistry, 1997, vol. 62, pp. 6458-6459.
Y. Yamamoto, et al., "Synthesis of arylboronates via Cp*RuCl-catalyzed cycloaddition of alkynylboronates", Tetrahedron, 2006, vol. 62, pp. 4294-4305.
S. Zhao, et al., "Synthetic Studies Towards A trans-3, 4-Diamine Derivative Of Piperidine Mimicking Buspironea", Heterocycles, 1994, vol. 39, No. 1, pp. 163-170.

* cited by examiner

*Primary Examiner* — David K O Dell
(74) *Attorney, Agent, or Firm* — Nath, Goldberg & Meyer; Sheldon M. McGee

(57) ABSTRACT

The compounds of Formula (I),

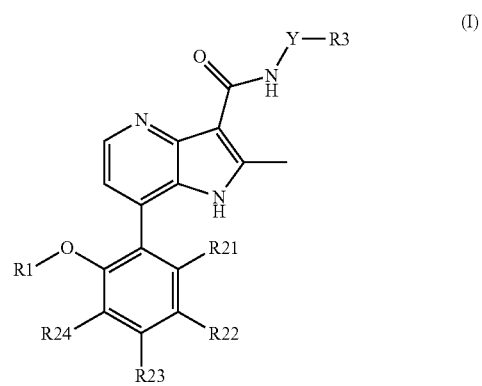

wherein R1, R21, R22, R23, R24, Y and R3 have the meanings as given in the description, the salts thereof, the stereoisomers of the compounds and the salts thereof are effective inhibitors of the type 5 phosphodiesterase.

7 Claims, No Drawings

METHYLPYRROLOPYRIDINECARBOXAMIDES

This application is filed under 35 U.S.C. 371 as the national stage of PCT/EP2010/062338, filed Aug. 24, 2010, which claims priority to EP 09168682.4, filed Aug. 26, 2009.

FIELD OF APPLICATION OF THE PRESENT SUBJECT MATTER

The present subject matter relates to methylpyrrolopyridinecarboxamide compounds, processes for their preparation, pharmaceutical compositions comprising said compounds and the use thereof in the treatment or prophylaxis of diseases.

BACKGROUND OF THE INVENTION

Substituted azaindoles, their preparation, pharmaceutical compositions containing these compounds, and their pharmaceutical use in the treatment of disease states capable of being modulated by the inhibition of the protein kinases are described in WO01/47922. Pyrrolo-pyridine, pyrrolo-pyrimidine and related heterocyclic compounds that act as modulators of mammalian complement C5a receptors are described in WO2006/042101. EP0556738 disclose arylcarbonylaminoalkyl-dihydro-oxo-pyridines and the use thereof in the treatment or prophylaxis of diseases such as hypertension, cardiac insufficiency, of disturbances of peripheral blood flow or obstructions of the airways.

DESCRIPTION OF THE PRESENT SUBJECT MATTER

It has now been found that the methylpyrrolopyridinecarboxamide compounds, which are described in detail below, have surprising and advantageous properties.

The present subject matter relates to compounds of formula (I)

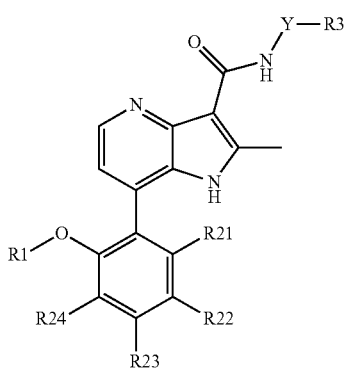

wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy, —C(O)-1-4C-alkyl or 1-4C-fluoroalkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R5 is 1-4C-alkoxy, hydroxy or halogen,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

1-4C-Alkyl is a straight-chain or branched alkyl group having 1 to 4 carbon atoms. Examples are methyl, ethyl, n-propyl, iso-propyl, n-butyl, iso-butyl, sec-butyl and tert-butyl.

2-4C-Alkyl is a straight-chain or branched alkyl group having 2 to 4 carbon atoms. Examples are ethyl, n-propyl, iso-propyl, n-butyl, iso-butyl, sec-butyl and tert-butyl.

1-4C-Fluoroalkyl is a straight-chain or branched alkyl moiety having 1 to 4 carbon atoms, wherein one or more of the hydrogen atoms of the alkyl moiety are replaced by fluorine. Examples include, but are not limited to, a trifluoromethyl, difluoromethyl, fluoromethyl, perfluoroethyl, 1,1,1-trifluoro-2-fluoroethyl, 1,1,1-trifluoroethyl, 1,1-difluoro-2,2-difluoroethyl, 1,1-difluoro-2-fluoroethyl, 1,1-difluoroethyl, 1-fluoro-2,2-difluoroethyl, 1-fluoro-2-fluoroethyl, 1-fluoroethyl, 2,2-difluoroethyl, 2-fluoroethyl, n-perfluoropropyl, and n-perfluorobutyl group.

Halogen includes fluorine, chlorine, bromine and iodine. In case of R22 and/or R23 and/or R5 being halogen, fluorine is preferred.

3-6C-Cycloalkyl is a cycloalkyl group having 3 to 6 carbon atoms, examples of which include the cyclopropyl, cyclobutyl, cyclopentyl and cyclohexyl group. In case of R3 being 3-6C-cycloalkyl, cyclohexyl is preferred.

3-4C-Cycloalkyl is a cycloalkyl group having 3 to 4 carbon atoms, examples of which include the cyclopropyl and cyclobutyl group.

1-4C-Alkoxy represents a group which, in addition to the oxygen atom, contains a straight-chain or branched alkyl moiety having 1 to 4 carbon atoms. Examples are methoxy, ethoxy, n-propoxy, iso-propoxy, n-butoxy, iso-butoxy, sec-butoxy and tert-butoxy.

1-2C-Alkoxy represents a group which, in addition to the oxygen atom, contains a straight-chain alkyl moiety having 1 to 2 carbon atoms. Examples are methoxy and ethoxy, 1-4C-Fluoroalkoxy represents a group which, in addition to the oxygen atom, contains a straight-chain or branched alkyl moiety having 1 to 4 carbon atoms, wherein one or more of the hydrogen atoms of the alkyl moiety are replaced by fluorine. Examples include, but are not limited to, a trifluoromethoxy, difluoromethoxy, fluoromethoxy, perfluoroethoxy, 1,1,1-trifluoro-2-fluoroethoxy, 1,1,1-trifluoroethoxy, 1,1-difluoro-2,2-difluoroethoxy, 1,1-difluoro-2-fluoroethoxy, 1,1-difluoroethoxy, 1-fluoro-2,2-difluoroethoxy, 1-fluoro-2-fluoroethoxy, 1-fluoroethoxy, 2,2-difluoroethoxy, 2-fluoroethoxy, n-perfluoropropoxy, and n-perfluorobutoxy group.

The group —C(O)-1-4C-alkyl represents a group which, in addition to the carbonyl group —C(O)—, contains a straight-chain or branched alkyl moiety having 1 to 4 carbon atoms. Examples are methylcarbonyl, ethylcarbonyl, n-propylcarbonyl, iso-propylcarbonyl, n-butylcarbonyl, iso-butylcarbonyl, sec-butylcarbonyl and tert-butylcarbonyl.

The group —C(O)-1-2C-alkyl represents a group which, in addition to the carbonyl group —C(O)—, contains a straight-chain or branched alkyl moiety having 1 to 2 carbon atoms. Examples are methylcarbonyl and ethylcarbonyl.

The group —C(O)-3-6C-cycloalkyl represents a group which, in addition to the carbonyl group —C(O)—, contains a cycloalkyl group having 3 to 6 carbon atoms. Examples are cyclopropylcarbonyl, cyclobutylcarbonyl, cyclopentylcarbonyl and cyclohexylcarbonyl.

The group —C(O)—O-1-4C-alkyl represents a group which, in addition to the oxycarbonyl group —C(O)—O—, contains a straight-chain or branched alkyl moiety having 1 to 4 carbon atoms. Examples are methyloxycarbonyl, ethyloxycarbonyl, n-propyloxycarbonyl, iso-propyloxycarbonyl, n-butyloxycarbonyl, iso-butyloxycarbonyl, sec-butyloxycarbonyl and tert-butyloxycarbonyl.

The 4- to 7-membered saturated heterocyclic ring containing one nitrogen atom and optionally one oxygen atom includes, but is not limited to, azetidinyl, oxazetidinyl, pyrrolidinyl, oxazolidinyl, piperidinyl, morpholinyl, azepanyl and oxazepanyl, in particular azetidinyl, 1,3-oxazetidinyl, pyrrolidinyl, 1,3-oxazolidinyl, piperidinyl, morpholinyl, azepanyl and 1,3-oxazepanyl, preferably azetidin-3-yl, pyrrolidin-3-yl, morpholin-2-yl, piperidin-3-yl and piperidin-4-yl.

The 4- to 6-membered saturated heterocyclic ring containing one nitrogen atom and optionally one oxygen atom includes, but is not limited to, azetidinyl, oxazetidinyl, pyrrolidinyl, oxazolidinyl, piperidinyl and morpholinyl, in particular azetidinyl, 1,3-oxazetidinyl, pyrrolidinyl, 1,3-oxazolidinyl, piperidinyl, morpholinyl, preferably azetidin-3-yl, pyrrolidin-3-yl, morpholin-2-yl, piperidin-3-yl and piperidin-4-yl.

The 5- to 6-membered saturated heterocyclic ring containing one nitrogen atom and optionally one oxygen atom includes, but is not limited to, pyrrolidinyl, oxazolidinyl, piperidinyl and morpholinyl, in particular pyrrolidinyl, 1,3-oxazolidinyl, piperidinyl, morpholinyl, preferably pyrrolidin-3-yl, morpholin-2-yl, piperidin-3-yl and piperidin-4-yl.

In one embodiment, the present subject matter relates to compounds of formula (I), wherein
R1 is —CH$_2$-3-4C-cycloalkyl or 2-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, 1-4C-fluoroalkoxy, —C(O)-1-4C-alkyl or 1-4C-fluoroalkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R5 is 1-4C-alkoxy, hydroxy or fluoro,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl or 2-4C-alkyl,
R21 is hydrogen,
R22 is hydrogen, halogen, 1-4C-alkyl, 1-4C-alkoxy, 1-4C-fluoroalkoxy, —C(O)-1-4C-alkyl or 1-4C-fluoroalkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R5 is 1-4C-alkoxy, hydroxy or fluoro,
R6 is —NH—C(O)—R7, —C(O)—NR8R9 or NH$_2$, R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl or 2-4C-alkyl,
R21 is hydrogen,
R22 is hydrogen, halogen, 1-4C-alkyl, 1-4C-alkoxy, 1-4C-fluoroalkoxy, —C(O)-1-4C-alkyl or 1-4C-fluoroalkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0,
R3 is a 4- to 6-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R6 is —NH—C(O)—R7 or NH$_2$,
R5 is 1-4C-alkoxy, hydroxy or fluoro,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R21 is hydrogen,
R22 is hydrogen, halogen, 1-4C-alkyl, 1-4C-alkoxy, 1-4C-fluoroalkoxy, —C(O)-1-4C-alkyl or 1-4C-fluoroalkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0,
R3 is a 4- to 6-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is 1-4C-alkoxy or hydroxy,
R6 is —NH—C(O)—R7 or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R21 is hydrogen,
R22 is hydrogen, halogen, 1-4C-alkyl, 1-4C-alkoxy, 1-4C-fluoroalkoxy, —C(O)-1-4C-alkyl or 1-4C-fluoroalkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0,
R3 is a 5- to 6-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
R5 is hydroxy,
R6 is —NH—C(O)—R7 or NH$_2$,
R7 is 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R21 is hydrogen,
R22 is hydrogen, halogen, 1-4C-alkyl or 1-4C-alkoxy,
or R21 and R22 combine to form a group —O—CH$_2$—O—,
R23 is hydrogen, halogen, 1-4C-alkyl, 1-4C-alkoxy or hydroxy,
R24 is hydrogen,
Y is —(CH$_2$)$_n$—,
n is 0,
R3 is a 5- to 6-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
R5 is hydroxy,
R6 is —NH—C(O)—R7,
R7 is 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R21 is hydrogen,
R22 is hydrogen, halogen, 1-4C-alkyl or 1-2C-alkoxy,
or R21 and R22 combine to form a group —O—CH$_2$—O—,
R23 is hydrogen, halogen, 1-2C-alkoxy, R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom and said heterocyclic ring being optionally substituted by R5, or a cyclohexyl group substituted by R6,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
R5 is hydroxy,
R6 is —NH—C(O)—R7,
R7 is 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R21 is hydrogen,
R22 is hydrogen, halogen, 1-4C-alkyl or 1-2C-alkoxy, or R21 and R22 combine to form a group —O—CH$_2$—O—,
R23 is hydrogen, halogen, 1-2C-alkoxy,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl group substituted by R6,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
R6 is —NH—C(O)—R7,
R7 is 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R21 is hydrogen,
R22 is hydrogen, fluoro, methyl or methoxy,
or R21 and R22 combine to form a group —O—CH$_2$—O—,
R23 is hydrogen, fluoro or methoxy,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl group substituted by R6,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
R6 is —NH—C(O)—R7,
R7 is 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl or 1-4C-alkyl,
R21 is hydrogen,
R22 is hydrogen, halogen, 1-4C-alkyl, 1-4C-alkoxy, hydroxy, 1-4C-fluoroalkoxy, —C(O)-1-4C-alkyl or 1-4C-fluoroalkyl,
or R21 and R22 combine to form a group —O—CH$_2$—O—,
R23 is hydrogen, halogen, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is 1-4C-alkoxy, hydroxy or fluoro,
R6 is —NH—C(O)—R7 or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is hydrogen, halogen, 1-4C-alkyl, 1-4C-alkoxy, —C(O)-1-4C-alkyl or 1-4C-fluoroalkyl,
or R21 and R22 combine to form a group —O—CH$_2$—O—,
R23 is hydrogen, halogen, 1-4C-alkoxy, or 1-4C-fluoroalkoxy,
R24 is hydrogen,
Y is —(CH$_2$)$_n$—,
n is 0,
R3 is a 4- to 6-membered saturated heterocyclic ring containing one nitrogen atom, said heterocyclic ring being optionally substituted by R4 and/or R5, or a 3-6C-cycloalkyl group substituted by R6,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is 1-4C-alkoxy hydroxy or fluoro,
R6 is —NH—C(O)—R7 or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy, a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is hydrogen, halogen, 1-4C-alkyl, 1-4C-alkoxy, —C(O)-1-4C-alkyl or 1-4C-fluoroalkyl,
or R21 and R22 combine to form a group —O—CH$_2$—O—,
R23 is hydrogen, halogen or 1-4C-alkoxy, R24 is hydrogen,
Y is —(CH$_2$)$_n$—,
n is 0,
R3 is a 4- to 6-membered saturated heterocyclic ring containing one nitrogen atom, said heterocyclic ring being substituted by R4 at said nitrogen atom, or a cyclohexyl group substituted by R6,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R6 is —NH—C(O)—R7 or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is hydrogen, fluoro, methyl, ethyl, isopropyl, methoxy or ethoxy, or R21 and R22 combine to form a group —O—CH$_2$—O—,
R23 is hydrogen, fluoro or methoxy,
R24 is hydrogen,
Y is —(CH$_2$)$_n$—,
n is 0,
R3 is a 4- to 6-membered saturated heterocyclic ring containing one nitrogen atom, said heterocyclic ring being substituted by R4 at said nitrogen atom, or a cyclohexyl group substituted by R6,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R6 is —NH—C(O)—R7,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is hydrogen, fluoro, methyl or methoxy,
R23 is hydrogen, fluoro or methoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43, R41 is 1-4C-alkoxy or hydroxy,
R43 is 1-4C-alkoxy or hydroxy,
R5 is 1-4C-alkoxy, hydroxy or fluoro,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is hydrogen, fluoro, methyl or methoxy,
R23 is hydrogen, fluoro or methoxy,
R24 is hydrogen,
Y is —(CH$_2$)$_n$—,
n is 0,
R3 is a 4- to 6-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is 1-4C-alkoxy or hydroxy,
R6 is —NH—C(O)—R7,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R21 is hydrogen,
R22 is hydrogen, fluoro, methyl or methoxy,
R23 is hydrogen, fluoro or methoxy,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom and said heterocyclic ring being optionally substituted by R5, or a cyclohexyl group substituted by R6,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
R5 is hydroxy,
R6 is —NH—C(O)—R,
R7 is hydrogen, 1-4C-alkyl, which is optionally substituted by R71, or 1-4C-alkoxy, R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is hydrogen,
R23 is fluoro or methoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R5 is 1-4C-alkoxy, hydroxy or fluoro,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R21 is hydrogen,
R22 is hydrogen,
R23 is fluoro or methoxy,
R24 is hydrogen,
Y is —(CH$_2$)$_n$—,
n is 0,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is 1-4C-alkoxy, hydroxy or fluoro,
R6 is —NH—C(O)—R7 or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R21 is hydrogen,
R22 is hydrogen,
R23 is fluoro or methoxy,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom and said heterocyclic ring being optionally substituted by R5, or a cyclohexyl group substituted by R6,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
R5 is hydroxy,
R6 is —NH—C(O)—R7 or NH$_2$,
R7 is hydrogen, 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is hydrogen,
R23 is fluoro or methoxy,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl group substituted by R6,
R4 is —C(O)-1-4C-alkyl, wherein the 1-4C-alkyl group is optionally substituted by R41,
R41 is 1-4C-alkoxy or hydroxy,
R6 is —NH—C(O)—R7,
R7 is 1-4C-alkyl, which is optionally substituted by R71,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is fluoro or methoxy,
R23 is hydrogen,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy, R42 is 1-4C-alkoxy or hydroxy,
R43 is 1-4C-alkoxy or hydroxy,
R5 is 1-4C-alkoxy, hydroxy or fluoro,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is fluoro or methoxy,
R23 is hydrogen,
R24 is hydrogen,
Y is —(CH$_2$)$_n$—,
n is 0,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is 1-4C-alkoxy, hydroxy or fluoro,
R6 is —NH—C(O)—R7 or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is fluoro or methoxy,
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom and said heterocyclic ring being optionally substituted by R5, or a cyclohexyl group substituted by R6,
R4 is —C(O)-1-4C-alkyl, wherein the 1-4C-alkyl group is optionally substituted by R41,
R41 is 1-4C-alkoxy or hydroxy,
R5 is hydroxy,
R6 is —NH—C(O)—R7,
R7 is 1-4C-alkyl, which is optionally substituted by R71,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is fluoro or methoxy,
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl group substituted by R6,
R4 is —C(O)-1-4C-alkyl, wherein the 1-4C-alkyl group is optionally substituted by R41,
R41 is 1-4C-alkoxy or hydroxy,
R6 is —NH—C(O)—R7,
R7 is 1-4C-alkyl, which is optionally substituted by R71,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is methoxy,
R23 is fluoro,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R5 is 1-4C-alkoxy, hydroxy or fluoro,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is methoxy,
R23 is fluoro, R24 is hydrogen,
Y is —(CH$_2$)$_n$—,
n is 0,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is 1-4C-alkoxy, hydroxy or fluoro,
R6 is —NH—C(O)—R7 or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is methoxy,
R23 is fluoro,
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom and said heterocyclic ring being optionally substituted by R5, or a cyclohexyl group substituted by R6,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is hydroxy,
R6 is —NH—C(O)—R7,
R7 is hydrogen, 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is methoxy,
R23 is fluoro,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl group substituted by R6,
R4 is —C(O)-1-4C-alkyl, wherein the 1-4C-alkyl group is optionally substituted by R41,
R41 is 1-4C-alkoxy or hydroxy,
R6 is —NH—C(O)—R7,
R7 is 1-4C-alkyl, which is optionally substituted by R71,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is fluoro,
R23 is methoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R5 is 1-4C-alkoxy, hydroxy or fluoro,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is fluoro,
R23 is methoxy,
R24 is hydrogen,
Y is —(CH$_2$)$_n$—,
n is 0,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is 1-4C-alkoxy, hydroxy or fluoro,
R6 is —NH—C(O)—R7 or NH$_2$,
R7 is hydrogen, 1-4C-alkyl, which is optionally substituted by R71, or 1-4C-alkoxy, which is optionally substituted by R73,
R71 is 1-4C-alkoxy or hydroxy, R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is fluoro,
R23 is methoxy,
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom and said heterocyclic ring being optionally substituted by R5, or a cyclohexyl group substituted by R6,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
R5 is hydroxy,
R6 is —NH—C(O)—R7,
R7 is hydrogen, 1-4C-alkyl, which is optionally substituted by R71,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is fluoro,
R23 is methoxy,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl group substituted by R6,
R4 is —C(O)-1-4C-alkyl, wherein the 1-4C-alkyl group is optionally substituted by R41,
R41 is 1-4C-alkoxy or hydroxy,
R6 is —NH—C(O)—R7,
R7 is 1-4C-alkyl, which is optionally substituted by R71,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is 1-4C-alkyl,
R23 is hydrogen,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R5 is 1-4C-alkoxy, hydroxy or fluoro,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is 1-4C-alkyl,
R23 is hydrogen,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R5 is 1-4C-alkoxy, hydroxy or fluoro,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is 1-4C-alkyl,
R23 is hydrogen,
R24 is hydrogen, Y is —(CH$_2$)$_n$—,
n is 0,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is 1-4C-alkoxy, hydroxy or fluoro,
R6 is —NH—C(O)—R7 or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is 1-4C-alkyl,
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl group substituted by R6,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
R6 is —NH—C(O)—R7 or NH$_2$,
R7 is hydrogen, 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is methyl,
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl group substituted by R6,
R4 is —C(O)-1-4C-alkyl, wherein the 1-4C-alkyl group is optionally substituted by R41,
R41 is 1-4C-alkoxy or hydroxy,
R6 is —NH—C(O)—R7,
R7 is hydrogen, 1-4C-alkyl, which is optionally substituted by R71,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 and R22 combine to form a group —O—CH$_2$—O—,
R23 is hydrogen,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R5 is 1-4C-alkoxy, hydroxy or fluoro,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 and R22 combine to form a group —O—CH$_2$—O—,
R23 is hydrogen,
R24 is hydrogen,
Y is —(CH$_2$)$_n$—,
n is 0,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R5 is 1-4C-alkoxy, hydroxy or fluoro,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen, R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 and R22 combine to form a group —O—CH$_2$—O—,
R23 is hydrogen,
R24 is hydrogen,
Y is —(CH$_2$)$_n$—,
n is 0,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is 1-4C-alkoxy, hydroxy or fluoro,
R6 is —NH—C(O)—R7 or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 and R22 combine to form a group —O—CH$_2$—O—,
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom and said heterocyclic ring being optionally substituted by R5, or a cyclohexyl group substituted by R6,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is hydroxy,
R6 is —NH—C(O)—R7 or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 and R22 combine to form a group —O—CH$_2$—O—,
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl group substituted by R6,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
R6 is —NH—C(O)—R7,
R7 is hydrogen, 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy, —C(O)-1-4C-alkyl or 1-4C-fluoroalkyl, or R21 and R22 combine to form a group —O—CH$_2$—O—,
R23 is hydrogen, halogen, 1-4C-alkyl, 1-4C-alkoxy, hydroxy or 1-4C-fluoroalkoxy, or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or R5,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R5 is 1-4C-alkoxy, hydroxy or fluoro,
a salt thereof, or a stereoisomer of the compound or a salt thereof.

In an alternative embodiment, the present subject matter relates to compounds of formula (I), wherein
R1 is —CH$_2$-3-6C-cycloalkyl or 1-4C-alkyl,
R21 is hydrogen,
R22 is hydrogen, halogen, 1-4C-alkyl, 1-4C-alkoxy, 1-4C-fluoroalkoxy, —C(O)-1-4C-alkyl or 1-4C-fluoroalkyl, or R21 and R22 combine to form a group —O—CH$_2$—O—,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 5- to 6-membered saturated heterocyclic ring containing one nitrogen atom and optionally one oxygen atom, said heterocyclic ring being optionally substituted by R4 and/or R5,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43, R41 is 1-4C-alkoxy or hydroxy,
R43 is 1-4C-alkoxy or hydroxy,
R5 is 1-4C-alkoxy, hydroxy or fluoro,
a salt thereof, or a stereoisomer of the compound or a salt thereof.

In an alternative embodiment, the present subject matter relates to compounds of formula (I), wherein
R1 is —$CH_2$-3-6C-cycloalkyl,
R21 is hydrogen,
R22 is hydrogen, halogen, 1-4C-alkyl or 1-4C-alkoxy,
or R21 and R22 combine to form a group —O—$CH_2$—O—,
R23 is hydrogen, halogen, 1-4C-alkyl or 1-4C-alkoxy,
R24 is hydrogen,
Y is —$(CH_2)_n$—,
n is 0,
R3 is a 5- to 6-membered saturated heterocyclic ring containing one nitrogen atom, said heterocyclic ring being substituted by R4 at said nitrogen atom and said heterocyclic ring being optionally substituted by R5,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is hydroxy,
a salt thereof, or a stereoisomer of the compound or a salt thereof.

In an alternative embodiment, the present subject matter relates to compounds of formula (I), wherein
R1 is —$CH_2$-3-6C-cycloalkyl,
R21 is hydrogen,
R22 is hydrogen, halogen, 1-4C-alkyl or 1-4C-alkoxy, or R21 and R22 combine to form a group —O—$CH_2$—O—,
R23 is hydrogen, halogen, 1-4C-alkyl or 1-4C-alkoxy,
R24 is hydrogen,
Y is —$(CH_2)_n$—,
n is 0,
R3 is a 6-membered saturated heterocyclic ring containing one nitrogen atom, said heterocyclic ring being substituted by R4 at said nitrogen atom,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
a salt thereof, or a stereoisomer of the compound or a salt thereof.

In an alternative embodiment, the present subject matter relates to compounds of formula (I), wherein
R1 is —$CH_2$-3-6C-cycloalkyl,
R21 is hydrogen,
R22 is hydrogen, halogen, 1-4C-alkyl or 1-4C-alkoxy, or R21 and R22 combine to form a group —O—$CH_2$—O—,
R23 is hydrogen, halogen, 1-4C-alkyl or 1-4C-alkoxy,
R24 is hydrogen,
Y is —$(CH_2)_n$—,
n is 0,
R3 is a 5-membered saturated heterocyclic ring containing one nitrogen atom, said heterocyclic ring being substituted by R4 at said nitrogen atom,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
a salt thereof, or a stereoisomer of the compound or a salt thereof.

In an alternative embodiment, the present subject matter relates to compounds of formula (I), wherein
R1 is —$CH_2$-3-6C-cycloalkyl,
R21 is hydrogen,
R22 is hydrogen, halogen, 1-4C-alkyl or 1-4C-alkoxy, or R21 and R22 combine to form a group —O—$CH_2$—O—,
R23 is hydrogen, halogen or 1-4C-alkoxy,
R24 is hydrogen,
Y is —$(CH_2)_n$—,
n is 0,
R3 is a 5- to 6-membered saturated heterocyclic ring containing one nitrogen atom, said heterocyclic ring being substituted by R4 at said nitrogen atom,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
a salt thereof, or a stereoisomer of the compound or a salt thereof.

In an alternative embodiment, the present subject matter relates to compounds of formula (I), wherein
R1 is —$CH_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy, —C(O)-1-4C-alkyl or 1-4C-fluoroalkyl,
or R21 and R22 combine to form a group —O—$CH_2$—O—,
R23 is hydrogen, halogen, 1-4C-alkyl, 1-4C-alkoxy, hydroxy or 1-4C-fluoroalkoxy,
or R22 and R23 combine to form a group —O—$CH_2$—O—,
R24 is hydrogen,
Y is —$(CH_2)_n$—,
n is 0 or 1,
R3 is a 3-6C-cycloalkyl group substituted by R6,
R6 is —NH—C(O)—R7, —C(O)—NR8R9 or $NH_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —$CH_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, 1-4C-fluoroalkoxy, —C(O)-1-4C-alkyl or 1-4C-fluoroalkyl,
or R21 and R22 combine to form a group —O—$CH_2$—O—,
R23 is hydrogen, halogen, 1-4C-alkyl, 1-4C-alkoxy, hydroxy or 1-4C-fluoroalkoxy,
R24 is hydrogen,
Y is —$(CH_2)_n$—,
n is 0 or 1, R3 is a cyclohexyl group substituted by R6,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is hydrogen, halogen, 1-4C-alkyl, 1-4C-alkoxy, 1-4C-fluoroalkoxy, —C(O)-1-4C-alkyl or 1-4C-fluoroalkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0,
R3 is a 3-6C-cycloalkyl group substituted by R6,
R6 is —NH—C(O)—R7 or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is hydrogen, halogen, 1-4C-alkyl or 1-4C-alkoxy, or R21 and R22 combine to form a group —O—OH$_2$—O—,
R23 is hydrogen, halogen, 1-4C-alkyl or 1-4C-alkoxy,
R24 is hydrogen,
Y is —(CH$_2$)$_n$—,
n is 0,
R3 is a cyclohexyl group substituted by R6,
R6 is —NH—C(O)—R7,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is hydrogen, halogen, 1-4C-alkyl or 1-4C-alkoxy, or R21 and R22 combine to form a group —O—CH$_2$—O—,
R23 is hydrogen, halogen or 1-4C-alkoxy,
R24 is hydrogen,
Y is —(CH$_2$)$_n$—,
n is 0,
R3 is a 3-6C-cycloalkyl group substituted by R6, R6 is —NH—C(O)—R7 or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is hydrogen, halogen, 1-4C-alkyl or 1-4C-alkoxy, or R21 and R22 combine to form a group —O—CH$_2$—O—,
R23 is hydrogen, halogen or 1-4C-alkoxy,
R24 is hydrogen,
Y is —(CH$_2$)$_n$—,
n is 0,
R3 is a cyclohexyl group substituted by R6,
R6 is —NH—C(O)—R7,
R7 is 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy, —C(O)-1-4C-alkyl or 1-4C-fluoroalkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy, or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is 1-4C-alkoxy, hydroxy or fluoro,
R6 is —NH—C(O)—R7 or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is hydrogen, halogen, 1-4C-alkyl, 1-4C-alkoxy, 1-4C-fluoroalkoxy, —C(O)-1-4C-alkyl or 1-4C-fluoroalkyl,
or R21 and R22 combine to form a group —O—CH$_2$—O—, R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)-1-4C-alkyl, wherein the 1-4C-alkyl group is optionally substituted by R41,
R41 is 1-4C-alkoxy or hydroxy,
R5 is hydroxy,
R6 is —NH—C(O)—R7 or NH$_2$,
R7 is hydrogen, 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is hydrogen, halogen, 1-4C-alkyl or 1-4C-alkoxy, or R21 and R22 combine to form a group —O—CH$_2$—O—,
R23 is hydrogen, halogen, 1-4C-alkyl or 1-4C-alkoxy,
R24 is hydrogen,
Y is —(CH$_2$)$_n$—,
n is 0 or 1,
R3 is a 5- to 6-membered saturated heterocyclic ring containing one nitrogen atom, said heterocyclic ring being optionally substituted by R4 and said heterocyclic ring being optionally substituted by R5, or a cyclohexyl group substituted by R6,
R4 is —C(O)-1-4C-alkyl, wherein the 1-4C-alkyl group is optionally substituted by R41,
R41 is 1-4C-alkoxy or hydroxy,
R5 is hydroxy,
R6 is —NH—C(O)—R7 or NH$_2$,
R7 is hydrogen, 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is hydrogen, halogen, 1-4C-alkyl or 1-4C-alkoxy,
or R21 and R22 combine to form a group —O—CH$_2$—O—,
R23 is hydrogen, halogen or 1-4C-alkoxy,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl group substituted by R6,
R4 is —C(O)-1-4C-alkyl, wherein the 1-4C-alkyl group is optionally substituted by R41,
R41 is 1-4C-alkoxy or hydroxy,
R6 is —NH—C(O)—R7,
R7 is 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is hydrogen, halogen, 1-4C-alkyl, 1-4C-alkoxy, hydroxy, 1-4C-fluoroalkoxy, —C(O)-1-4C-alkyl or 1-4C-fluoroalkyl, or R21 and R22 combine to form a group —O—CH$_2$—O—,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—O-1-4C-alkyl, wherein the 1-4C-alkyl group is optionally substituted by R43,
R43 is 1-4C-alkoxy or hydroxy,
R5 is hydroxy,
R6 is —NH—C(O)—R7 or NH$_2$,
R7 is hydrogen, 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is hydrogen, halogen, 1-4C-alkyl or 1-4C-alkoxy, or R21 and R22 combine to form a group —O—CH$_2$—O—,
R23 is hydrogen, halogen, 1-4C-alkyl or 1-4C-alkoxy,
R24 is hydrogen,
Y is —(CH$_2$)$_n$—,
n is 0 or 1,
R3 is a 5- to 6-membered saturated heterocyclic ring containing one nitrogen atom, said heterocyclic ring being optionally substituted by R4 and said heterocyclic ring being optionally substituted by R5, or a cyclohexyl group substituted by R6,
R4 is —C(O)—O-1-4C-alkyl, wherein the 1-4C-alkyl group is optionally substituted by R43,
R43 is 1-4C-alkoxy or hydroxy,
R5 is hydroxy,
R6 is —NH—C(O)—R7 or NH$_2$,
R7 is hydrogen, 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R21 is hydrogen,
R22 is hydrogen, halogen, 1-4C-alkyl or 1-4C-alkoxy, or R21 and R22 combine to form a group —O—CH$_2$—O—,
R23 is hydrogen, halogen or 1-4C-alkoxy,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl group substituted by R6, R4 is —C(O)—O-1-4C-alkyl, wherein the 1-4C-alkyl group is optionally substituted by R43,
R43 is 1-4C-alkoxy or hydroxy,
R6 is —NH—C(O)—R7,
R7 is 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I) or salts thereof, wherein R1 is —CH$_2$-3-6C-cycloalkyl or 1-4C-alkyl, R21, R22, R23, R24, Y, n, R3, R4, R41, R42, R43, R5, R6, R7, R71, R72, R73, R8, R9, R91 and R92 are as described above or below.

In an alternative embodiment, the present subject matter relates to compounds of formula (I) or salts thereof, wherein R1 is —CH$_2$-3-6C-cycloalkyl, R21, R22, R23, R24, Y, n, R3, R4, R41, R42, R43, R5, R6, R7, R71, R72, R73, R8, R9, R91 and R92 are as described above or below.

In an alternative embodiment, the present subject matter relates to compounds of formula (I) or salts thereof, wherein R1 is —CH$_2$-3-4C-cycloalkyl, R21, R22, R23, R24, Y, n, R3, R4, R41, R42, R43, R5, R6, R7, R71, R72, R73, R8, R9, R91 and R92 are as described above or below.

In an alternative embodiment, the present subject matter relates to compounds of formula (I) or salts thereof, wherein R22 is hydrogen, halogen, 1-4C-alkyl, 1-4C-alkoxy, or R21 and R22 combine to form a group —O—CH$_2$—O—, R1, R11, R21, R23, R24, Y, n, R3, R4, R41, R42, R43, R5, R6, R7, R71, R72, R73, R8, R9, R91 and R92 are as described above or below.

In an alternative embodiment, the present subject matter relates to compounds of formula (I) or salts thereof, wherein R22 is hydrogen, fluoro, methy, ethyl, isopropyl, methoxy, or R21 and R22 combine to form a group —O—CH$_2$—O—, R1, R11, R21, R23, R24, Y, n, R3, R4, R41, R42, R43, R5, R6, R7, R71, R72, R73, R8, R9, R91 and R92 are as described above or below.

In an alternative embodiment, the present subject matter relates to compounds of formula (I) or salts thereof, wherein R23 is hydrogen, halogen, or 1-4C-alkoxy, R1, R11, R21, R22, R24, Y, n, R3, R4, R41, R42, R43, R5, R6, R7, R71, R72, R73, R8, R9, R91 and R92 are as described above or below.

In an alternative embodiment, the present subject matter relates to compounds of formula (I) or salts thereof, wherein R23 is hydrogen, fluoro, or methoxy, R1, R11, R21, R22, R24, Y, n, R3, R4, R41, R42, R43, R5, R6, R7, R71, R72, R73, R8, R9, R91 and R92 are as described above or below.

In an alternative embodiment, the present subject matter relates to compounds of formula (I) or salts thereof, wherein n is 0, R1, R11, R21, R22, R23, R24, Y, R3, R4, R41, R42, R43, R5, R6, R7, R71, R72, R73, R8, R9, R91 and R92 are as described above or below.

In an alternative embodiment, the present subject matter relates to compounds of formula (I) or salts thereof, wherein R3 is a 5- to 6-membered saturated heterocyclic ring containing one nitrogen atom, said heterocyclic ring being substituted by R4 at said nitrogen atom, or a cyclohexyl group substituted by R6, R1, R11, R21, R22, R23, R24, Y, R4, R41, R42, R43, R5, R6, R7, R71, R72, R73, R8, R9, R91 and R92 are as described above or below.

In an alternative embodiment, the present subject matter relates to compounds of formula (I) or salts thereof, wherein R3 is piperidine substituted by R4 at the nitrogen atom, or a cyclohexyl group substituted by R6, R1, R11, R21, R22, R23, R24, Y, R4, R41, R42, R43, R5, R6, R7, R71, R72, R73, R8, R9, R91 and R92 are as described above or below.

In an alternative embodiment, the present subject matter relates to compounds of formula (I) or salts thereof, wherein R4 is —C(O)-1-4C-alkyl, wherein the 1-4C-alkyl group is optionally substituted by R41, R1, R11, R21, R22, R23, R24, Y, R3, R41, R42, R43, R5, R6, R7, R71, R72, R73, R8, R9, R91 and R92 are as described above or below.

In an alternative embodiment, the present subject matter relates to compounds of formula (I) or salts thereof, wherein R5 is hydroxy or fluoro, R1, R11, R21, R22, R23, R24, Y, R3, R4, R41, R42, R43, R6, R7, R71, R72, R73, R8, R9, R91 and R92 are as described above or below.

In an alternative embodiment, the present subject matter relates to compounds of formula (I) or salts thereof, wherein R5 is hydroxy, R1, R11, R21, R22, R23, R24, Y, R3, R4, R41, R42, R43, R6, R7, R71, R72, R73, R8, R9, R91 and R92 are as described above or below.

In an alternative embodiment, the present subject matter relates to compounds of formula (I) or salts thereof, wherein R5 is fluoro, R1, R11, R21, R22, R23, R24, Y, R3, R4, R41, R42, R43, R6, R7, R71, R72, R73, R8, R9, R91 and R92 are as described above or below.

In an alternative embodiment, the present subject matter relates to compounds of formula (I) or salts thereof, wherein R6 is —NH—C(O)—R7 or NH$_2$, R1, R11, R21, R22, R23, R24, Y, R3, R4, R41, R42, R43, R5, R7, R71, R72 and R73 are as described above or below.

In an alternative embodiment, the present subject matter relates to compounds of formula (I) or salts thereof, wherein R6 is —NH—C(O)—R7, R1, R11, R21, R22, R23, R24, Y, R3, R4, R41, R42, R43, R5, R7, R71, R72 and R73 are as described above or below.

In an alternative embodiment, the present subject matter relates to compounds of formula (I) or salts thereof, wherein R7 is 1-4C-alkyl, which is optionally substituted by R71, or 1-4C-alkoxy, R1, R11, R21, R22, R23, R24, Y, R3, R4, R41, R42, R43, R5, R6, R71, R8, R9, R91 and R92 are as described above or below.

In an alternative embodiment, the present subject matter relates to compounds of formula (I) or salts thereof, wherein R1 is —CH$_2$-3-4C-cycloalkyl, n is 0, R3 is a 5- to 6-membered saturated heterocyclic ring containing one nitrogen atom, said heterocyclic ring being substituted by R4 at said nitrogen atom, or a cyclohexyl group substituted by R6, R4 is —C(O)-1-4C-alkyl, wherein the 1-4C-alkyl group is optionally substituted by R41, R6 is —NH—C(O)—R7, R7 is 1-4C-alkyl, which is optionally substituted by R71, or 1-4C-alkoxy, R21, R22, R23, R24, Y, R41 and R71 are as described above.

In an alternative embodiment, the present subject matter relates to compounds of formula (I), selected from tert-Butyl 4-[({7-[5-(cyclopropylmethoxy)-1,3-benzodioxol-4-yl]-2-methyl-1H-pyrrolo[3,2-b]pyridin-3-yl}carbonyl)amino]piperidine-1-carboxylate; tert-Butyl {trans-4-[({7-[5-(cyclopropylmethoxy)-1,3-benzodioxol-4-yl]-2-methyl-1H-pyrrolo[3,2-b]pyridin-3-yl}carbonyl)amino]cyclohexyl}carbamate; tert-Butyl {cis-4-[({7-[5-(cyclopropylmethoxy)-1,3-benzodioxol-4-yl]-2-methyl-1H-pyrrolo[3,2-b]pyridin-3-yl}carbonyl)amino]cyclohexyl}carbamate; tert-Butyl 4-{[(7-[2-(cyclopropylmethoxy)-4-fluorophenyl]-2-methyl-1-

{[2-(trimethylsilyl)ethoxy]methyl}-1H-pyrrolo[3,2-b]pyridin-3-yl)carbonyl]amino}piperidine-1-carboxylate; tert-Butyl {trans-4-[({7-[2-(cyclopropylmethoxy)-4-fluorophenyl]-2-methyl-1H-pyrrolo[3,2-b]pyridin-3-yl}carbonyl)amino]cyclohexyl}carbamate; tert-Butyl {cis-4-[({7-[2-(cyclopropylmethoxy)-4-fluorophenyl]-2-methyl-1H-pyrrolo[3,2-b]pyridin-3-yl}carbonyl)amino]cyclohexyl}carbamate; tert-Butyl 4-[({7-[2-(cyclopropylmethoxy)-5-fluorophenyl]-2-methyl-1H-pyrrolo[3,2-b]pyridin-3-yl}carbonyl)amino]piperidine-1-carboxylate; tert-Butyl {trans-4-[({7-[2-(cyclopropylmethoxy)-5-fluorophenyl]-2-methyl-1H-pyrrolo[3,2-b]pyridin-3-yl}carbonyl)amino]cyclohexyl}carbamate; tert-Butyl {cis-4-[({7-[2-(cyclopropylmethoxy)-5-fluorophenyl]-2-methyl-1H-pyrrolo[3,2-b]pyridin-3-yl}carbonyl)amino]cyclohexyl}carbamate; tert-Butyl (3R*,4R*)-4-[({7-[2-(cyclopropylmethoxy)-5-fluorophenyl]-2-methyl-1H-pyrrolo[3,2-b]pyridin-3-yl}carbonyl)amino]-3-hydroxypiperidine-1-carboxylate; tert-Butyl 4-[({7-[2-(cyclopropylmethoxy)-4-methoxyphenyl]-2-methyl-1H-pyrrolo[3,2-b]pyridin-3-yl}carbonyl)amino]piperidine-1-carboxylate; tert-Butyl {trans-4-[({7-[2-(cyclopropylmethoxy)-4-methoxyphenyl]-2-methyl-1H-pyrrolo[3,2-b]pyridin-3-yl}carbonyl)amino]cyclohexyl}carbamate; tert-Butyl {cis-4-[({7-[2-(cyclopropylmethoxy)-4-methoxyphenyl]-2-methyl-1H-pyrrolo[3,2-b]pyridin-3-yl}carbonyl)amino]cyclohexyl}carbamate; tert-Butyl 4-[({7-[2-(cyclopropylmethoxy)-5-methoxyphenyl]-2-methyl-1H-pyrrolo[3,2-b]pyridin-3-yl}carbonyl)amino]piperidine-1-carboxylate; tert-Butyl {trans-4-[({7-[2-(cyclopropylmethoxy)-5-methoxyphenyl]-2-methyl-1H-pyrrolo[3,2-b]pyridin-3-yl}carbonyl)amino]cyclohexyl}carbamate; tert-Butyl {cis-4-[({7-[2-(cyclopropylmethoxy)-5-methoxyphenyl]-2-methyl-1H-pyrrolo[3,2-b]pyridin-3-yl}carbonyl)amino]cyclohexyl}carbamate; tert-Butyl-(3R*,4R*)-3-[({7-[2-(cyclopropylmethoxy)-5-methoxyphenyl]-2-methyl-1H-pyrrolo[3,2-b]pyridin-3-yl}carbonyl)amino]-4-hydroxypyrrolidine-1-carboxylate; tert-Butyl 4-[({7-[2-(cyclopropylmethoxy)-5-methylphenyl]-2-methyl-1H-pyrrolo[3,2-b]pyridin-3-yl}carbonyl)amino]piperidine-1-carboxylate; tert-Butyl {trans-4-[({7-[2-(cyclopropylmethoxy)-5-methylphenyl]-2-methyl-1H-pyrrolo[3,2-b]pyridin-3-yl}carbonyl)amino]cyclohexyl}carbamate; tert-Butyl {cis-4-[({7-[2-(cyclopropylmethoxy)-5-methylphenyl]-2-methyl-1H-pyrrolo[3,2-b]pyridin-3-yl}carbonyl)amino]cyclohexyl}carbamate; tert-Butyl 4-[({7-[2-(cyclopropylmethoxy)-4-fluoro-5-methoxyphenyl]-2-methyl-1H-pyrrolo[3,2-b]pyridin-3-yl}carbonyl)amino]piperidine-1-carboxylate; tert-Butyl {trans-4-[({7-[2-(cyclopropylmethoxy)-4-fluoro-5-methoxyphenyl]-2-methyl-1H-pyrrolo[3,2-b]pyridin-3-yl}carbonyl)amino]cyclohexyl}carbamate; tert-Butyl {cis-4-[({7-[2-(cyclopropylmethoxy)-4-fluoro-5-methoxyphenyl]-2-methyl-1H-pyrrolo[3,2-b]pyridin-3-yl}carbonyl)amino]cyclohexyl}carbamate; tert-Butyl (3R*,4R*)-3-[({7-[2-(cyclopropylmethoxy)-4-fluoro-5-methoxyphenyl]-2-methyl-1H-pyrrolo[3,2-b]pyridin-3-yl}carbonyl)amino]-4-hydroxypyrrolidine-1-carboxylate; tert-Butyl (3R*,4R*)-4-[({7-[2-(cyclopropylmethoxy)-4-fluoro-5-methoxyphenyl]-2-methyl-1H-pyrrolo[3,2-b]pyridin-3-yl}carbonyl)amino]-3-hydroxypiperidine-1-carboxylate; tert-Butyl 4-[({7-[2-(cyclopropylmethoxy)-5-fluoro-4-methoxyphenyl]-2-methyl-1H-pyrrolo[3,2-b]pyridin-3-yl}carbonyl)amino]piperidine-1-carboxylate; tert-Butyl {trans-4-[({7-[2-(cyclopropylmethoxy)-5-fluoro-4-methoxyphenyl]-2-methyl-1H-pyrrolo[3,2-b]pyridin-3-yl}carbonyl)amino]cyclohexyl}carbamate; tert-Butyl {cis-4-[({7-[2-(cyclopropylmethoxy)-5-fluoro-4-methoxyphenyl]-2-methyl-1H-pyrrolo[3,2-b]pyridin-3-yl}carbonyl)amino]cyclohexyl}carbamate; N-(1-Acetylpiperidin-4-yl)-7-[5-(cyclopropylmethoxy)-1,3-benzodioxol-4-yl]-2-methyl-1H-pyrrolo[3,2-b]pyridine-3-carboxamide; 7-[5-(Cyclopropylmethoxy)-1,3-benzodioxol-4-yl]-2-methyl-N-(1-propionylpiperidin-4-yl)-1H-pyrrolo[3,2-b]pyridine-3-carboxamide; 7-[5-(Cyclopropylmethoxy)-1,3-benzodioxol-4-yl]-N-[1-(methoxyacetyl)piperidin-4-yl]-2-methyl-1H-pyrrolo[3,2-b]pyridine-3-carboxamide; Ethyl 4-[({7-[5-(cyclopropylmethoxy)-1,3-benzodioxol-4-yl]-2-methyl-1H-pyrrolo[3,2-b]pyridin-3-yl}carbonyl)amino]piperidine-1-carboxylate; N-(trans-4-Acetamidocyclohexyl)-7-[5-(cyclopropylmethoxy)-1,3-benzodioxol-4-yl]-2-methyl-1H-pyrrolo[3,2-b]pyridine-3-carboxamide; N-(cis-4-acetamidocyclohexyl)-7-[5-(cyclopropylmethoxy)-1,3-benzodioxol-4-yl]-2-methyl-1H-pyrrolo[3,2-b]pyridine-3-carboxamide; 7-[5-(Cyclopropylmethoxy)-1,3-benzodioxol-4-yl]-2-methyl-N-[cis-4-(propionylamino)cyclohexyl]-1H-pyrrolo[3,2-b]pyridine-3-carboxamide; 7-[5-(Cyclopropylmethoxy)-1,3-benzodioxol-4-yl]-N-{cis-4-[(methoxyacetyl)amino]cyclohexyl}-2-methyl-1H-pyrrolo[3,2-b]pyridine-3-carboxamide; Ethyl {cis-4-[({7-[5-(cyclopropylmethoxy)-1,3-benzodioxol-4-yl]-2-methyl-1H-pyrrolo[3,2-b]pyridin-3-yl}carbonyl)amino]cyclohexyl}carbamate; N-(1-Acetylpiperidin-4-yl)-7-[2-(cyclopropylmethoxy)-4-fluorophenyl]-2-methyl-1H-pyrrolo[3,2-b]pyridine-3-carboxamide; 7-[2-(Cyclopropylmethoxy)-4-fluorophenyl]-2-methyl-N-(1-propanoylpiperidin-4-yl)-1H-pyrrolo[3,2-b]pyridine-3-carboxamide; 7-[2-(Cyclopropylmethoxy)-4-fluorophenyl]-N-[1-(methoxyacetyl)piperidin-4-yl]-2-methyl-1H-pyrrolo[3,2-b]pyridine-3-carboxamide; N-[trans-4-(Acetylamino)cyclohexyl]-7-[2-(cyclopropylmethoxy)-4-fluorophenyl]-2-methyl-1H-pyrrolo[3,2-b]pyridine-3-carboxamide; 7-[2-(Cyclopropylmethoxy)-4-fluorophenyl]-2-methyl-N-[trans-4-(propanoylamino)cyclohexyl]-1H-pyrrolo[3,2-b]pyridine-3-carboxamide; 7-[2-(Cyclopropylmethoxy)-4-fluorophenyl]-N-{trans-4-[(methoxyacetyl)amino]cyclohexyl}-2-methyl-1H-pyrrolo[3,2-b]pyridine-3-carboxamide; N-[cis-4-(Acetylamino)cyclohexyl]-7-[2-(cyclopropylmethoxy)-4-fluorophenyl]-2-methyl-1H-pyrrolo[3,2-b]pyridine-3-carboxamide; 7-[2-(Cyclopropylmethoxy)-5-fluorophenyl]-2-methyl-N-[cis-4-(propanoylamino)cyclohexyl]-1H-pyrrolo[3,2-b]pyridine-3-carboxamide; 7-[2-(Cyclopropylmethoxy)-4-fluorophenyl]-N-{cis-4-[(methoxyacetyl)amino]cyclohexyl}-2-methyl-1H-pyrrolo[3,2-b]pyridine-3-carboxamide; N-(1-Acetylpiperidin-4-yl)-7-[2-(cyclopropylmethoxy)-5-fluorophenyl]-2-methyl-1H-pyrrolo[3,2-b]pyridine-3-carboxamide; 7-[2-(Cyclopropylmethoxy)-5-fluorophenyl]-2-methyl-N-(1-propanoylpiperidin-4-yl)-1H-pyrrolo[3,2-b]pyridine-3-carboxamide; 7-[2-(Cyclopropylmethoxy)-5-fluorophenyl]-N-[1-(methoxyacetyl)piperidin-4-yl]-2-methyl-1H-pyrrolo[3,2-b]pyridine-3-carboxamide;

N-[trans-4-(Acetylamino)cyclohexyl]-7-[2-(cyclopropylmethoxy)-5-fluorophenyl]-2-methyl-1H-pyrrolo[3,2-b]pyridine-3-carboxamide; 7-[2-(Cyclopropylmethoxy)-5-fluorophenyl]-2-methyl-N-[trans-4-(propanoylamino)cyclohexyl]-1H-pyrrolo[3,2-b]pyridine-3-carboxamide; 7-[2-(Cyclopropylmethoxy)-5-fluorophenyl]-N-{trans-4-[(methoxyacetyl)amino]cyclohexyl}-2-methyl-1H-pyrrolo[3,2-b]pyridine-3-carboxamide; N-[cis-4-(Acetylamino)cyclohexyl]-7-[2-(cyclopropylmethoxy)-5-fluorophenyl]-2-methyl-1H-pyrrolo[3,2-b]pyridine-3-carboxamide; 7-[2-(Cyclopropylmethoxy)-5-fluorophenyl]-2-methyl-N-[cis-4-(propanoylamino)cyclohexyl]-1H-pyrrolo[3,2-b]pyridine-3-carboxamide; 7-[2-(Cyclopropylmethoxy)-5-fluorophenyl]-N-{cis-4-[(methoxyacetyl)amino]cyclohexyl}-2-methyl-1H-pyrrolo[3,2-b]pyridine-3-carboxamide; N-[(3R*,4R*)-1-Acetyl-3-hydroxypiperidin-4-yl]-7-[2-(cyclopropylmethoxy)-5-fluorophenyl]-2-methyl-1H-pyrrolo[3,2-b]pyridine-3-carboxamide; 7-[2-(Cyclopropylmethoxy)-5-fluorophenyl]-N-[(3R*,4R*)-3-hydroxy-1-propanoylpiperidin-4-yl]-2-methyl-1H-pyrrolo[3,2-b]pyridine-3-carboxamide; 7-[2-(Cyclopropylmethoxy)-5-fluorophenyl]-N-[(3R*,4R*)-3-hydroxy-1-(methoxyacetyl)piperidin-4-yl]-2-methyl-1H-pyrrolo[3,2-b]pyridine-3-carboxamide; N-(1-Acetylpiperidin-4-yl)-7-[2-(cyclopropylmethoxy)-4-methoxyphenyl]-2-methyl-1H-pyrrolo[3,2-b]pyridine-3-carboxamide; 7-[2-(Cyclopropylmethoxy)-4-methoxyphenyl]-2-methyl-N-(1-propanoylpiperidin-4-yl)-1H-pyrrolo[3,2-b]pyridine-3-carboxamide; 7-[2-(Cyclopropylmethoxy)-4-methoxyphenyl]-N-[1-(methoxyacetyl)piperidin-4-yl]-2-methyl-1H-pyrrolo[3,2-b]pyridine-3-carboxamide; N-[trans-4-(Acetylamino)cyclohexyl]-7-[2-(cyclopropylmethoxy)-4-methoxyphenyl]-2-methyl-1H-pyrrolo[3,2-b]pyridine-3-carboxamide; 7-[2-(Cyclopropylmethoxy)-4-methoxyphenyl]-2-methyl-N-[trans-4-(propanoylamino)cyclohexyl]-1H-pyrrolo[3,2-b]pyridine-3-carboxamide; 7-[2-(Cyclopropylmethoxy)-4-methoxyphenyl]-N-{trans-4-[(methoxyacetyl)amino]cyclohexyl}-2-methyl-1H-pyrrolo[3,2-b]pyridine-3-carboxamide; N-[cis-4-(Acetylamino)cyclohexyl]-7-[2-(cyclopropylmethoxy)-4-methoxyphenyl]-2-methyl-1H-pyrrolo[3,2-b]pyridine-3-carboxamide; 7-[2-(Cyclopropylmethoxy)-4-methoxyphenyl]-2-methyl-N-[cis-4-(propanoylamino)cyclohexyl]-1H-pyrrolo[3,2-b]pyridine-3-carboxamide; 7-[2-(Cyclopropylmethoxy)-4-methoxyphenyl]-N-{cis-4-[(methoxyacetyl)amino]cyclohexyl}-2-methyl-1H-pyrrolo[3,2-b]pyridine-3-carboxamide; N-(1-Acetylpiperidin-4-yl)-7-[2-(cyclopropylmethoxy)-5-methoxyphenyl]-2-methyl-1H-pyrrolo[3,2-b]pyridine-3-carboxamide; 7-[2-(cyclopropylmethoxy)-5-methoxyphenyl]-2-methyl-N-(1-propanoylpiperidin-4-yl)-1H-pyrrolo[3,2-b]pyridine-3-carboxamide; 7-[2-(cyclopropylmethoxy)-5-methoxyphenyl]-N-[1-(methoxyacetyl)piperidin-4-yl]-2-methyl-1H-pyrrolo[3,2-b]pyridine-3-carboxamide; N-[trans-4-(Acetylamino)cyclohexyl]-7-[2-(cyclopropylmethoxy)-5-methoxyphenyl]-2-methyl-1H-pyrrolo[3,2-b]pyridine-3-carboxamide; 7-[2-(Cyclopropylmethoxy)-5-methoxyphenyl]-2-methyl-N-[trans-4-(propanoylamino)cyclohexyl]-1H-pyrrolo[3,2-b]pyridine-3-carboxamide; 7-[2-(Cyclopropylmethoxy)-5-methoxyphenyl]-N-{trans-4-[(methoxyacetyl)amino]cyclohexyl}-2-methyl-1H-pyrrolo[3,2-b]pyridine-3-carboxamide; N-[cis-4-(Acetylamino)cyclohexyl]-7-[2-(cyclopropylmethoxy)-5-methoxyphenyl]-2-methyl-1H-pyrrolo[3,2-b]pyridine-3-carboxamide; 7-[2-(Cyclopropylmethoxy)-5-methoxyphenyl]-2-methyl-N-[cis-4-(propanoylamino)cyclohexyl]-1H-pyrrolo[3,2-b]pyridine-3-carboxamide; 7-[2-(Cyclopropylmethoxy)-5-methoxyphenyl]-N-{cis-4-[(methoxyacetyl)amino]cyclohexyl}-2-methyl-1H-pyrrolo[3,2-b]pyridine-3-carboxamide; N-[(3R*,4R*)-1-Acetyl-4-hydroxypyrrolidin-3-yl]-7-[2-(cyclopropylmethoxy)-5-methoxyphenyl]-2-methyl-1H-pyrrolo[3,2-b]pyridine-3-carboxamide; 7-[2-(Cyclopropylmethoxy)-5-methoxyphenyl]-N-[(3R*,4R*)-4-hydroxy-1-propanoylpyrrolidin-3-yl]-2-methyl-1H-pyrrolo[3,2-b]pyridine-3-carboxamide; 7-[2-(Cyclopropylmethoxy)-5-methoxyphenyl]-N-[(3R*,4R*)-4-hydroxy-1-(methoxyacetyl)pyrrolidin-3-yl]-2-methyl-1H-pyrrolo[3,2-b]pyridine-3-carboxamide; N-(1-Acetylpiperidin-4-yl)-7-[2-(cyclopropylmethoxy)-5-methylphenyl]-2-methyl-1H-pyrrolo[3,2-b]pyridine-3-carboxamide; 7-[2-(Cyclopropylmethoxy)-5-methylphenyl]-2-methyl-N-(1-propanoylpiperidin-4-yl)-1H-pyrrolo[3,2-b]pyridine-3-carboxamide; 7-[2-(Cyclopropylmethoxy)-5-methylphenyl]-N-[1-(methoxyacetyl)piperidin-4-yl]-2-methyl-1H-pyrrolo[3,2-b]pyridine-3-carboxamide; N-[trans-4-(Acetylamino)cyclohexyl]-7-[2-(cyclopropylmethoxy)-5-methylphenyl]-2-methyl-1H-pyrrolo[3,2-b]pyridine-3-carboxamide; 7-[2-(Cyclopropylmethoxy)-5-methylphenyl]-2-methyl-N-[trans-4-(propanoylamino)cyclohexyl]-1H-pyrrolo[3,2-b]pyridine-3-carboxamide; 7-[2-(Cyclopropylmethoxy)-5-methylphenyl]-N-{trans-4-[(methoxyacetyl)amino]cyclohexyl}-2-methyl-1H-pyrrolo[3,2-b]pyridine-3-carboxamide; N-[cis-4-(Acetylamino)cyclohexyl]-7-[2-(cyclopropylmethoxy)-5-methylphenyl]-2-methyl-1H-pyrrolo[3,2-b]pyridine-3-carboxamide; 7-[2-(Cyclopropylmethoxy)-5-methylphenyl]-2-methyl-N-[cis-4-(propanoylamino)cyclohexyl]-1H-pyrrolo[3,2-b]pyridine-3-carboxamide; 7-[2-(Cyclopropylmethoxy)-5-methylphenyl]-N-{cis-4-[(methoxyacetyl)amino]cyclohexyl}-2-methyl-1H-pyrrolo[3,2-b]pyridine-3-carboxamide; N-(1-Acetylpiperidin-4-yl)-7-[2-(cyclopropylmethoxy)-4-fluoro-5-methoxyphenyl]-2-methyl-1H-pyrrolo[3,2-b]pyridine-3-carboxamide; 7-[2-(Cyclopropylmethoxy)-4-fluoro-5-methoxyphenyl]-2-methyl-N-(1-propanoylpiperidin-4-yl)-1H-pyrrolo[3,2-b]pyridine-3-carboxamide; 7-[2-(Cyclopropylmethoxy)-4-fluoro-5-methoxyphenyl]-N-[1-(methoxyacetyl)piperidin-4-yl]-2-methyl-1H-pyrrolo[3,2-b]pyridine-3-carboxamide; N-[trans-4-(Acetylamino)cyclohexyl]-7-[2-(cyclopropylmethoxy)-4-fluoro-5-methoxyphenyl]-2-methyl-1H-pyrrolo[3,2-b]pyridine-3-carboxamide; 7-[2-(Cyclopropylmethoxy)-4-fluoro-5-methoxyphenyl]-2-methyl-N-[trans-4-(propanoylamino)cyclohexyl]-1H-pyrrolo[3,2-b]pyridine-3-carboxamide; 7-[2-(Cyclopropylmethoxy)-4-fluoro-5-methoxyphenyl]-N-{trans-4-[(methoxyacetyl)amino]cyclohexyl}-2-methyl-1H-pyrrolo[3,2-b]pyridine-3-carboxamide; N-[cis-4-(Acetylamino)cyclohexyl]-7-[2-(cyclopropylmethoxy)-4-fluoro-5-methoxyphenyl]-2-methyl-1H-pyrrolo[3,2-b]pyridine-3-carboxamide; 7-[2-(Cyclopropylmethoxy)-4-fluoro-5-methoxyphenyl]-2-methyl-N-[cis-4-(propanoylamino)cyclohexyl]-1H-pyrrolo[3,2-b]pyridine-3-carboxamide; 7-[2-(Cyclopropylmethoxy)-4-fluoro-5-methoxyphenyl]-N-{cis-4-[(methoxyacetyl)amino]cyclohexyl}-2-methyl-1H- pyrrolo[3,2-b]pyridine-3-carboxamide; N-[(3R*,4R*)-1-Acetyl-4-hydroxypyrrolidin-3-yl]-7-[2-(cyclopropylmethoxy)-4-fluoro-5-methoxyphenyl]-2-methyl-1H-pyrrolo[3,2-b]pyridine-3-carboxamide; 7-[2-(Cyclopropylmethoxy)-4-fluoro-5-methoxyphenyl]-N-[(3R*,4R*)-4-hydroxy-1-propanoylpyrrolidin-3-yl]-2-methyl-1H-pyrrolo[3,2-b]pyridine-3-carboxamide; 7-[2-(Cyclopropylmethoxy)-4-fluoro-5-methoxyphenyl]-N-[(3R*,4R*)-4-hydroxy-1-(methoxyacetyl)pyrrolidin-3-yl]-2-methyl-1H-pyrrolo[3,2-b]pyridine-3-carboxamide; N-[(3R*,4R*)-1-Acetyl-3-hydroxypiperidin-4-yl]-7-[2-(cyclopropylmethoxy)-4-fluoro-5-methoxyphenyl]-2-methyl-1H-pyrrolo[3,2-b]pyridine-3-carboxamide; 7-[2-(Cyclopropylmethoxy)-4-fluoro-5-methoxyphenyl]-N-[(3R*,4R*)-3-hydroxy-1-propanoylpiperidin-4-yl]-2-methyl-1H-pyrrolo[3,2-b]pyridine-3-carboxamide; 7-[2-(Cyclopropylmethoxy)-4-fluoro-5-methoxyphenyl]-N-[(3R*,4R*)-3-hydroxy-1-(methoxyacetyl)piperidin-4-yl]-2-methyl-1H-pyrrolo[3,2-b]pyridine-3-carboxamide; N-(1-Acetylpiperidin-4-yl)-7-[2-(cyclopropylmethoxy)-5-fluoro-4-methoxyphenyl]-2-methyl-1H-pyrrolo[3,2-b]pyridine-3-carboxamide; 7-[2-(Cyclopropylmethoxy)-5-fluoro-4-methoxyphenyl]-2-methyl-N-(1-propionylpiperidin-4-yl)-1H-pyrrolo[3,2-b]pyridine-3-carboxamide; 7-[2-(Cyclopropylmethoxy)-5-fluoro-4-methoxyphenyl]-N-[1-(methoxyacetyl)piperidin-4-yl]-2-methyl-1H-pyrrolo[3,2-b]pyridine-3-carboxamide; N-(trans-4-Acetamidocyclohexyl)-7-[2-(cyclopropylmethoxy)-5-fluoro-4-methoxyphenyl]-2-methyl-1H-pyrrolo[3,2-b]pyridine-3-carboxamide; 7-[2-(Cyclopropylmethoxy)-5-fluoro-4-methoxyphenyl]-2-methyl-N-[trans-4-(propionylamino)cyclohexyl]-1H-pyrrolo[3,2-b]pyridine-3-carboxamide; 7-[2-(Cyclopropylmethoxy)-5-fluoro-4-methoxyphenyl]-N-{trans-4-[(methoxyacetyl)amino]cyclohexyl}-2-methyl-1H-pyrrolo[3,2-b]pyridine-3-carboxamide; N-(cis-4-Acetamidocyclohexyl)-7-[2-(cyclopropylmethoxy)-5-fluoro-4-methoxyphenyl]-2-methyl-1H-pyrrolo[3,2-b]pyridine-3-carboxamide; 7-[2-(Cyclopropylmethoxy)-5-fluoro-4-methoxyphenyl]-2-methyl-N-[cis-4-(propionylamino)cyclohexyl]-1H-pyrrolo[3,2-b]pyridine-3-carboxamide; 7-[2-(Cyclopropylmethoxy)-5-fluoro-4-methoxyphenyl]-N-{cis-4-[(methoxyacetyl)amino]cyclohexyl}-2-methyl-1H-pyrrolo[3,2-b]pyridine-3-carboxamide; 4-[5-(Cyclopropylmethoxy)-1,3-benzodioxol-4-yl]-N-(1-glycoloylpiperidin-4-yl)-6-methyl-5H-pyrrolo[3,2-d]pyrimidine-7-carboxamide; 7-[5-(Cyclopropylmethoxy)-1,3-benzodioxol-4-yl]-N-{1-[(2S)-2-hydroxypropanoyl]piperidin-4-yl}-2-methyl-1H-pyrrolo[3,2-b]pyridine-3-carboxamide; 7-[5-(Cyclopropylmethoxy)-1,3-benzodioxol-4-yl]-N-[1-(methoxyacetyl)piperidin-4-yl]-2-methyl-1H-pyrrolo[3,2-b]pyridine-3-carboxamide; 7-[5-(Cyclopropylmethoxy)-1,3-benzodioxol-4-yl]-N-[cis-4-(glycoloylamino)cyclohexyl]-2-methyl-1H-pyrrolo[3,2-b]pyridine-3-carboxamide; 7-[5-(Cyclopropylmethoxy)-1,3-benzodioxol-4-yl]-N-(cis-4-{[(2S)-2-hydroxypropanoyl]amino}cyclohexyl)-2-methyl-1H-pyrrolo[3,2-b]pyridine-3-carboxamide; 7-[2-(Cyclopropylmethoxy)-4-fluorophenyl]-N-[1-(methoxyacetyl)piperidin-4-yl]-2-methyl-1H-pyrrolo[3,2-b]pyridine-3-carboxamide; 7-[2-(Cyclopropylmethoxy)-4-fluorophenyl]-N-{1-[(2S)-2-hydroxypropanoyl]piperidin-4-yl}-2-methyl-1H-pyrrolo[3,2-b]pyridine-3-carboxamide; 7-[2-(Cyclopropylmethoxy)-4-fluorophenyl]-N-{trans-4-[(hydroxyacetyl)amino]cyclohexyl}-2-methyl-1H-pyrrolo[3,2-b]pyridine-3-carboxamide; 7-[2-(Cyclopropylmethoxy)-4-fluorophenyl]-N-(trans-4-{[(2S)-2-hydroxypropanoyl]amino}cyclohexyl)-2-methyl-1H-pyrrolo[3,2-b]pyridine-3-carboxamide; 7-[2-(Cyclopropylmethoxy)-4-fluorophenyl]-N-{cis-4-[(hydroxyacetyl)amino]cyclohexyl}-2-methyl-1H-pyrrolo[3,2-b]pyridine-3-carboxamide; 7-[2-(Cyclopropylmethoxy)-4-fluorophenyl]-N-(cis-4-{[(2S)-2-hydroxypropanoyl]amino}cyclohexyl)-2-methyl-1H-pyrrolo[3,2-b]pyridine-3-carboxamide; 7-[2-(Cyclopropylmethoxy)-5-fluorophenyl]-N-[1-(hydroxyacetyl)piperidin-4-yl]-2-methyl-1H-pyrrolo[3,2-b]pyridine-3-carboxamide; 7-[2-(Cyclopropylmethoxy)-5-fluorophenyl]-N-{1-[(2S)-2-hydroxypropanoyl]piperidin-4-yl}-2-methyl-1H-pyrrolo[3,2-b]pyridine-3-carboxamide; 7-[2-(Cyclopropylmethoxy)-5-fluorophenyl]-N-{trans-4-[(hydroxyacetyl)amino]cyclohexyl}-2-methyl-1H-pyrrolo[3,2-b]pyridine-3-carboxamide; 7-[2-(Cyclopropylmethoxy)-5-fluorophenyl]-N-(trans-4-{[(2S)-2-hydroxypropanoyl]amino}cyclohexyl)-2-methyl-1H-pyrrolo[3,2-b]pyridine-3-carboxamide; 7-[2-(Cyclopropylmethoxy)-5-fluorophenyl]-N-{cis-4-[(hydroxyacetyl)amino]cyclohexyl}-2-methyl-1H-pyrrolo[3,2-b]pyridine-3-carboxamide; 7-[2-(Cyclopropylmethoxy)-5-fluorophenyl]-N-(cis-4-{[abs.(2S)-2-hydroxypropanoyl]amino}cyclohexyl)-2-methyl-1H-pyrrolo[3,2-b]pyridine-3-carboxamide; 7-[2-(Cyclopropylmethoxy)-5-fluorophenyl]-N-[rel.(3R,4R)-3-hydroxy-1-(hydroxyacetyl)piperidin-4-yl]-2-methyl-1H-pyrrolo[3,2-b]pyridine-3-carboxamide; 7-[2-(Cyclopropylmethoxy)-5-fluorophenyl]-N-{(3R,4R)-3-hydroxy-1-[(2S)-2-hydroxypropanoyl]piperidin-4-yl}-2-methyl-1H-pyrrolo[3,2-b]pyridine-3-carboxamide; 7-[2-(cyclopropylmethoxy)-5-fluorophenyl]-N-{(3S,4S)-3-hydroxy-1-[(2S)-2-hydroxypropanoyl]piperidin-4-yl}-2-methyl-1H-pyrrolo[3,2-b]pyridine-3-carboxamide; 7-[2-(Cyclopropylmethoxy)-4-methoxyphenyl]-N-[1-(hydroxyacetyl)piperidin-4-yl]-2-methyl-1H-pyrrolo[3,2-b]pyridine-3-carboxamide; 7-[2-(Cyclopropylmethoxy)-4-methoxyphenyl]-N-{1-[(2S)-2-hydroxypropanoyl]piperidin-4-yl}-2-methyl-1H-pyrrolo[3,2-b]pyridine-3-carboxamide; 7-[2-(Cyclopropylmethoxy)-4-methoxyphenyl]-N-{trans-4-[(hydroxyacetyl)amino]cyclohexyl}-2-methyl-1H-pyrrolo[3,2-b]pyridine-3-carboxamide; 7-[2-(Cyclopropylmethoxy)-4-methoxyphenyl]-N-(trans-4-{[(2S)-2-hydroxypropanoyl]amino}cyclohexyl)-2-methyl-1H-pyrrolo[3,2-b]pyridine-3-carboxamide; 7-[2-(Cyclopropylmethoxy)-4-methoxyphenyl]-N-{cis-4-[(hydroxyacetyl)amino]cyclohexyl}-2-methyl-1H-pyrrolo[3,2-b]pyridine-3-carboxamide; 7-[2-(Cyclopropylmethoxy)-4-methoxyphenyl]-N-(cis-4-{[(2S)-2-hydroxypropanoyl]amino}cyclohexyl)-2-methyl-1H-pyrrolo[3,2-b]pyridine-3-carboxamide; 7-[2-(Cyclopropylmethoxy)-5-methoxyphenyl]-N-[1-(hydroxyacetyl)piperidin-4-yl]-2-methyl-1H-pyrrolo[3,2-b]pyridine-3-carboxamide; 7-[2-(Cyclopropylmethoxy)-5-methoxyphenyl]-N-{1-[(2S)-2-hydroxypropanoyl]piperidin-4-yl}-2-methyl-1H-pyrrolo[3,2-b]pyridine-3-carboxamide; 7-[2-(Cyclopropylmethoxy)-5-methoxyphenyl]-N-{trans-4-[(hydroxyacetyl)amino]cyclohexyl}-2-methyl-1H-pyrrolo[3,2-b]pyridine-3-carboxamide; 7-[2-(Cyclopropylmethoxy)-5-methoxyphenyl]-N-(trans-4-{[abs.(2S)-2- hydroxypropanoyl]amino}cyclohexyl)-2-methyl-1H-pyrrolo[3,2-b]pyridine-3-carboxamide; 7-[2-(Cyclopropylmethoxy)-5-methoxyphenyl]-N-{cis-4-[(hydroxyacetyl)amino]cyclohexyl}-2-methyl-1H-pyrrolo[3,2-b]pyridine-3-carboxamide; 7-[2-(Cyclopropylmethoxy)-5-methoxyphenyl]-N-(cis-4-{[(2S)-2-hydroxypropanoyl]amino}cyclohexyl)-2-methyl-1H-pyrrolo[3,2-b]pyridine-3-carboxamide; 7-[2-(Cyclopropylmethoxy)-5-methoxyphenyl]-N-[(3R*,4R*)-4-hydroxy-1-(hydroxyacetyl)pyrrolidin-3-yl]-2-methyl-1H-pyrrolo[3,2-b]pyridine-3-carboxamide; 7-[2-(Cyclopropylmethoxy)-5-methoxyphenyl]-N-{(3R*,4R*)-4-hydroxy-1-[(2S)-2-hydroxypropanoyl]pyrrolidin-3-yl}-2-methyl-1H-pyrrolo[3,2-b]pyridine-3-carboxamide; 7-[2-(cyclopropylmethoxy)-5-methoxyphenyl]-N-{(3S*,4S*)-4-hydroxy-1-[(2S)-2-hydroxypropanoyl]pyrrolidin-3-yl}-2-methyl-1H-pyrrolo[3,2-b]pyridine-3-carboxamide; 7-[2-(Cyclopropylmethoxy)-5-methylphenyl]-N-[1-(hydroxyacetyl)piperidin-4-yl]-2-methyl-1H-pyrrolo[3,2-b]pyridine-3-carboxamide; 7-[2-(cyclopropylmethoxy)-5-methylphenyl]-N-{1-[abs.(2S)-2-hydroxypropanoyl]piperidin-4-yl}-2-methyl-1H-pyrrolo[3,2-b]pyridine-3-carboxamide; 7-[2-(Cyclopropylmethoxy)-5-methylphenyl]-N-{trans-4-[(hydroxyacetyl)amino]cyclohexyl}-2-methyl-1H-pyrrolo[3,2-b]pyridine-3-carboxamide; 7-[2-(Cyclopropylmethoxy)-5-methylphenyl]-N-(trans-4-{[(2S)-2-hydroxypropanoyl]amino}cyclohexyl)-2-methyl-1H-pyrrolo[3,2-b]pyridine-3-carboxamide; 7-[2-(Cyclopropyl methoxy)-5-methylphenyl]-N-{cis-4-[(hydroxyacetyl)amino]cyclohexyl}-2-methyl-1H-pyrrolo[3,2-b]pyridine-3-carboxamide; 7-[2-(Cyclopropylmethoxy)-5-methylphenyl]-N-(cis-4-{[(2S)-2-hydroxypropanoyl]amino}cyclohexyl)-2-methyl-1H-pyrrolo[3,2-b]pyridine-3-carboxamide; 7-[2-(Cyclopropylmethoxy)-4-fluoro-5-methoxyphenyl]-N-[1-(hydroxyacetyl)piperidin-4-yl]-2-methyl-1H-pyrrolo[3,2-b]pyridine-3-carboxamide; 7-[2-(Cyclopropylmethoxy)-4-fluoro-5-methoxyphenyl]-N-{1-[(2S)-2-hydroxypropanoyl]piperidin-4-yl}-2-methyl-1H-pyrrolo[3,2-b]pyridine-3-carboxamide; 7-[2-(Cyclopropylmethoxy)-4-fluoro-5-methoxyphenyl]-N-{trans-4-[(hydroxyacetyl)amino]cyclohexyl}-2-methyl-1H-pyrrolo[3,2-b]pyridine-3-carboxamide; 7-[2-(Cyclopropylmethoxy)-4-fluoro-5-methoxyphenyl]-N-(trans-4-{[(2S)-2-hydroxypropanoyl]amino}cyclohexyl)-2-methyl-1H-pyrrolo[3,2-b]pyridine-3-carboxamide; 7-[2-(Cyclopropylmethoxy)-4-fluoro-5-methoxyphenyl]-N-{cis-4-[(hydroxyacetyl)amino]cyclohexyl}-2-methyl-1H-pyrrolo[3,2-b]pyridine-3-carboxamide; 7-[2-(Cyclopropylmethoxy)-4-fluoro-5-methoxyphenyl]-N-(cis-4-{[abs.(2S)-2-hydroxypropanoyl]amino}cyclohexyl)-2-methyl-1H-pyrrolo[3,2-b]pyridine-3-carboxamide; 7-[2-(Cyclopropylmethoxy)-4-fluoro-5-methoxyphenyl]-N-[(3R*,4R*)-4-hydroxy-1-(hydroxyacetyl)pyrrolidin-3-yl]-2-methyl-1H-pyrrolo[3,2-b]pyridine-3-carboxamide; 7-[2-(cyclopropylmethoxy)-4-fluoro-5-methoxyphenyl]-N-{(3R,4R)-4-hydroxy-1-[(2S)-2-hydroxypropanoyl]pyrrolidin-3-yl}-2-methyl-1H-pyrrolo[3,2-b]pyridine-3-carboxamide; 7-[2-(cyclopropylmethoxy)-4-fluoro-5-methoxyphenyl]-N-{(3S,4S)-4-hydroxy-1-[(2S)-2-hydroxypropanoyl]pyrrolidin-3-yl}-2-methyl-1H-pyrrolo[3,2-b]pyridine-3-carboxamide; 7-[2-(Cyclopropylmethoxy)-4-fluoro-5-methoxyphenyl]-N-[(3R*,4R*)-3-hydroxy-1-(hydroxyacetyl)piperidin-4-yl]-2-methyl-1H-pyrrolo[3,2-b]pyridine-3-carboxamide; 7-[2-(Cyclopropylmethoxy)-4-fluoro-5-methoxyphenyl]-N-{(3R,4R)-3-hydroxy-1-[(2S)-2-hydroxypropanoyl]piperidin-4-yl}-2-methyl-1H-pyrrolo[3,2-b]pyridine-3-carboxamide; 7-[2-(Cyclopropylmethoxy)-4-fluoro-5-methoxyphenyl]-N-{(3S,4S)-3-hydroxy-1-[(2S)-2-hydroxypropanoyl]piperidin-4-yl}-2-methyl-1H-pyrrolo[3,2-b]pyridine-3-carboxamide; 7-[2-(Cyclopropylmethoxy)-5-fluoro-4-methoxyphenyl]-N-(1-glycoloylpiperidin-4-yl)-2-methyl-1H-pyrrolo[3,2-b]pyridine-3-carboxamide; 7-[2-(Cyclopropylmethoxy)-5-fluoro-4-methoxyphenyl]-N-{1-[(2S)-2-hydroxypropanoyl]piperidin-4-yl}-2-methyl-1H-pyrrolo[3,2-b]pyridine-3-carboxamide; 7-[2-(Cyclopropylmethoxy)-5-fluoro-4-methoxyphenyl]-N-[trans-4-(glycoloylamino)cyclohexyl]-2-methyl-1H-pyrrolo[3,2-b]pyridine-3-carboxamide; 7-[2-(Cyclopropylmethoxy)-5-fluoro-4-methoxyphenyl]-N-(trans-4-{[(2S)-2-hydroxypropanoyl]amino}cyclohexyl)-2-methyl-1H-pyrrolo[3,2-b]pyridine-3-carboxamide; 7-[2-(Cyclopropylmethoxy)-5-fluoro-4-methoxyphenyl]-N-[cis-4-(glycoloylamino)cyclohexyl]-2-methyl-1H-pyrrolo[3,2-b]pyridine-3-carboxamide; 7-[2-(Cyclopropylmethoxy)-5-fluoro-4-methoxyphenyl]-N-(cis-4-{[(2S)-2-methoxypropanoyl]amino}cyclohexyl)-2-methyl-1H-pyrrolo[3,2-b]pyridine-3-carboxamide;

a salt thereof, or a stereoisomer of the compound or a salt thereof.

It is to be understood that the present subject matter covers all combinations of substituent groups referred to hereinabove. In particular, the present subject matter covers all combinations of preferred or alternative groups described hereinabove.

Salts of the compounds according to the present subject matter and the stereoisomers thereof include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, gluconates including D-gluconates and L-gluconates, glucuronates including D-glucuronates and L-glucuronates, benzoates, 2-(4-hydroxybenzoyl)benzoates, butyrates, salicylates, sulfosalicylates, maleates, laurates, malates including L-malates and D-malates, lactates including L-lactates and D-lactates, fumarates, succinates, oxalates, tartarates including L-tartarates, D-tartarates and meso-tartarates, stearates, benzenesulfonates (besilates), toluenesulfonates (tosilates), methanesulfonates (mesilates), laurylsulfonates, 3-hydroxy-2-naphthoates, lactobionates (salts of 4-O-beta-D-galactopyranosyl-D-gluconic acid), galactarates, embonates and ascorbates.

Examples of salts with bases include, but are not limited to, lithium, sodium, potassium, calcium, aluminum, magnesium, titanium, ammonium, meglumine and guanidinium salts.

The salts include water-insoluble and, particularly, water-soluble salts.

The compounds according to the present subject matter, the salts thereof, the stereoisomers of the compounds and the salts thereof may contain, e.g. when isolated in crystalline form, varying amounts of solvents. Included within the scope of the present subject matter are, therefore, all solvates of the compounds of formula (I), the salts thereof, the stereoisomers of the compounds and the salts thereof. Hydrates are a preferred example of said solvates.

Some of the compounds of formula 1, salts thereof, stereoisomers thereof or salts of the latter may exist in different crystalline forms (polymorphs), which are within the scope of the invention. The obtained solids of the compounds of formula 1, salts thereof, stereoisomers thereof or salts of the latter are re-crystalised in different crystalline forms (polymorphs) with solvents or mixtures of the solvents selected from water, methanol, ethanol, isopropanol, n-butanol, dichloromethane, tert-butylmethylether, acetonitril, dioxan, methylethylketon, aceton, glycole, ethylene glycol, methylisobutylketon.

The compounds according to the present subject matter and the salts thereof include stereoisomers.

Examples of stereoisomers include, but are not limited to, compounds of formula (I) wherein R3 is a 3-6C-cycloalkyl group substituted by R6. Stereoisomers of one exemplified compound of formula (I) wherein R3 is a 3-6C-cycloalkyl group substituted by R6 are shown below (cis/trans stereoisomers):

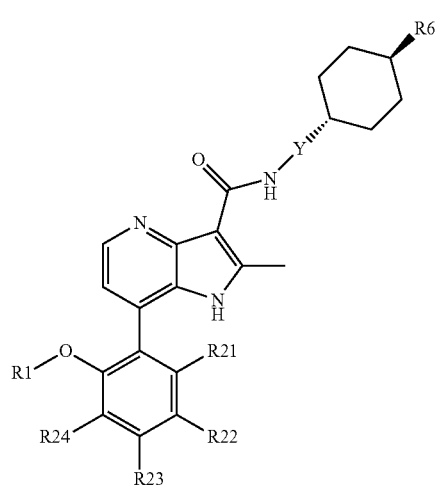

(S1)

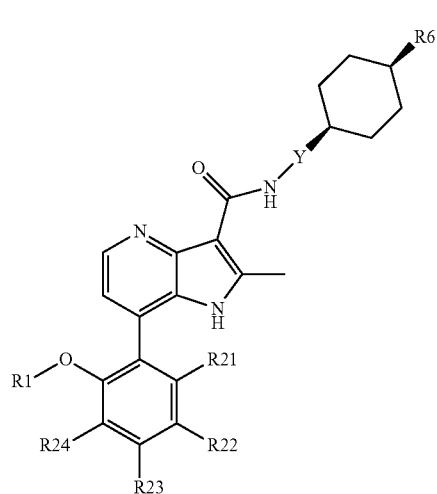

(S2)

Y = ―(CH$_2$)$_0$― or ―(CH$_2$)―

Further examples of stereoisomers include, but are not limited to, compounds of formula (I) wherein R3 is a 4- to 7-membered saturated heterocyclic ring containing one nitrogen atom and optionally one oxygen atom, said heterocyclic ring being optionally substituted by R4 and wherein said heterocyclic ring contains a stereogenic center. Stereoisomers of an exemplified compound of formula (I) wherein R3 is a 4- to 7-membered saturated heterocyclic ring containing one nitrogen atom, said heterocyclic ring being optionally substituted by R4 and said heterocyclic ring containing a stereogenic center are shown below:

(S3)

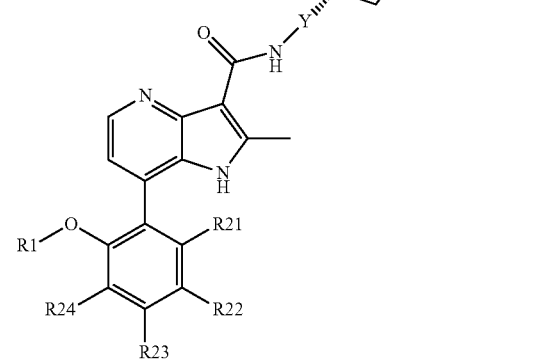

(S4)

Y = ―(CH$_2$)$_0$― or ―(CH$_2$)―

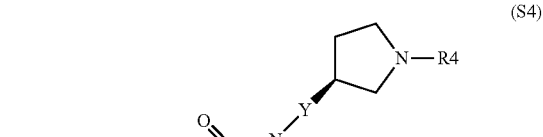

Further examples of stereoisomers include, but are not limited to, compounds of formula (I) wherein R3 is a 4- to 7-membered saturated heterocyclic ring containing one nitrogen atom and optionally one oxygen atom, said heterocyclic ring being optionally substituted by R4 and/or R5 and wherein said heterocyclic ring contains stereogenic centers. The present subject matter includes the pure (R,R)-isomers, (R,S)-isomers, (S,R)-isomers and (S,S)-isomers, and mixtures of two or more thereof in any ratio. An example of said isomers is shown below:

(S5)
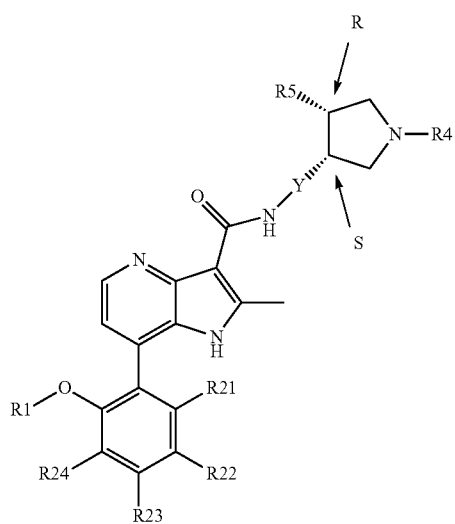
(S8)
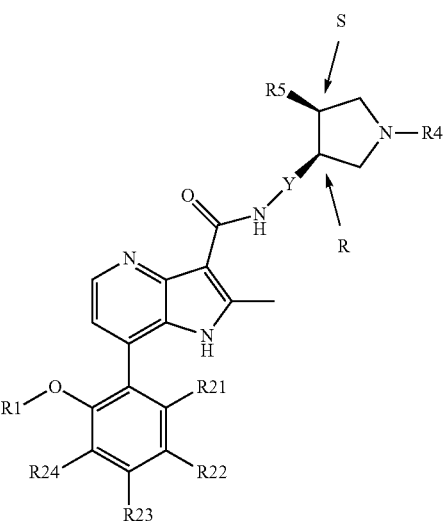
(S6)
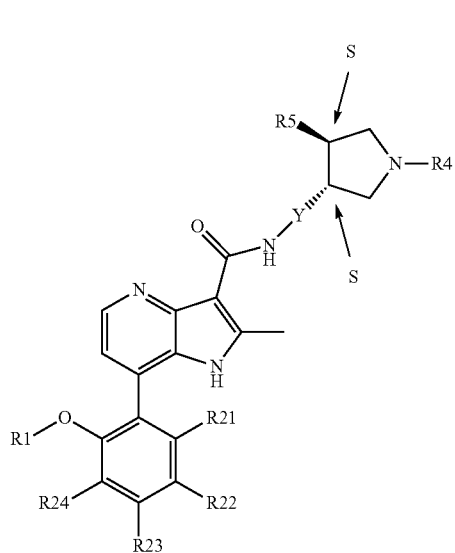
$Y = -(CH_2)_0-$
Furthermore the present subject matter includes the pure (R,R)-isomers, (R,S)-isomers, (S,R)-isomers and (S,S)-isomers, and mixtures of two or more thereof in any ratio. An example of said isomers is shown below:
(S7)
(S9)
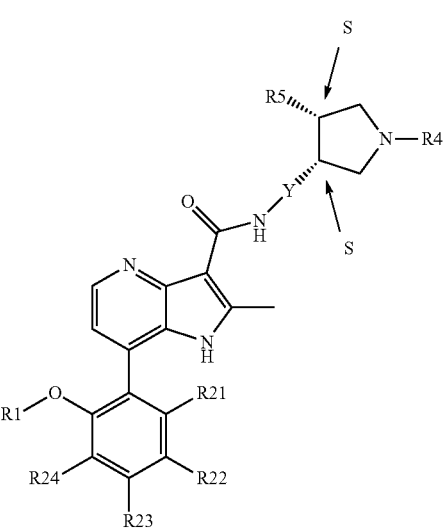

-continued

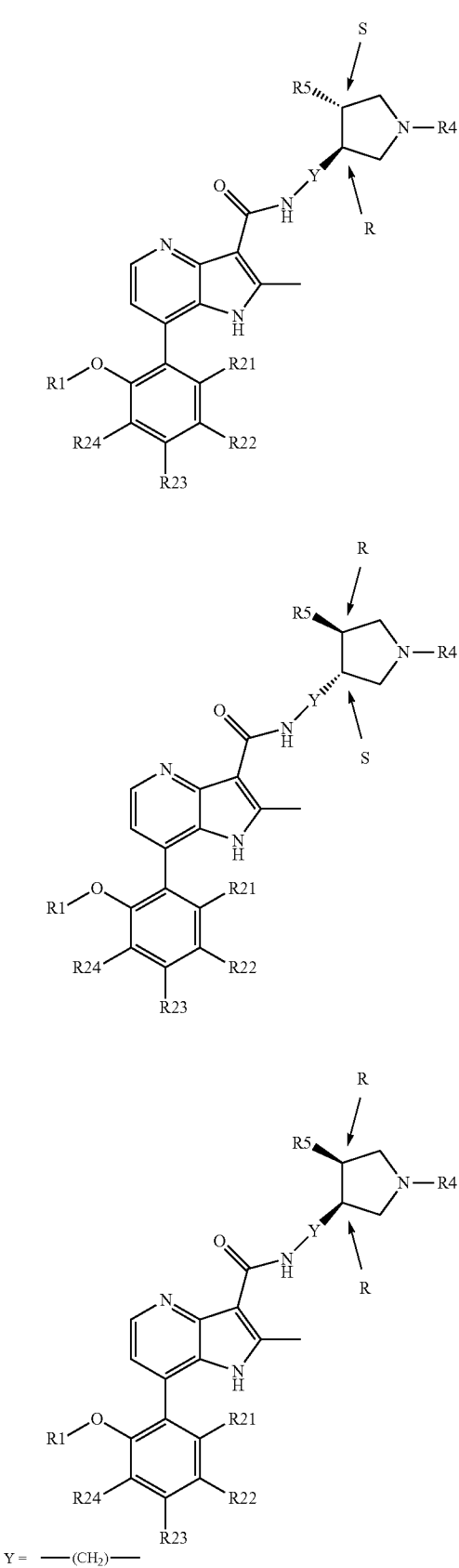

Stereoisomers of a further exemplified compound of formula (I) wherein R3 is a 4- to 7-membered saturated heterocyclic ring containing one nitrogen atom, said heterocyclic ring being optionally substituted by R4 and said heterocyclic ring containing a stereogenic center are shown below:

Y = —(CH$_2$)$_0$— or —(CH$_2$)—

Stereoisomers of a further exemplified compound of formula (I) wherein R3 is a 4- to 7-membered saturated heterocyclic ring containing one nitrogen atom, said heterocyclic ring being optionally substituted by R4 and/or R5 and said heterocyclic ring containing stereogenic centers. The present subject matter includes the pure (R,R)-isomers, (R,S)-isomers, (S,R)-isomers and (S,S)-isomers, and mixtures of two or more thereof in any ratio. An example of said isomers is shown below:

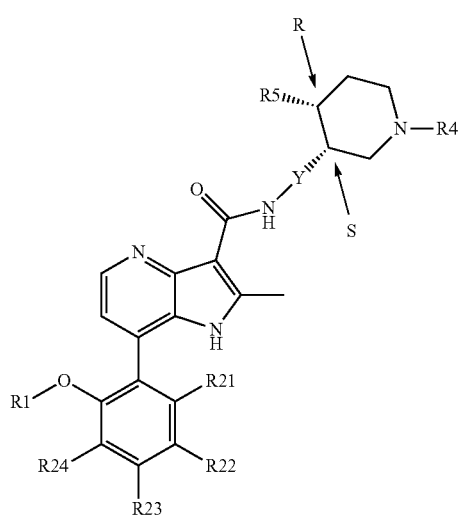
(S15)
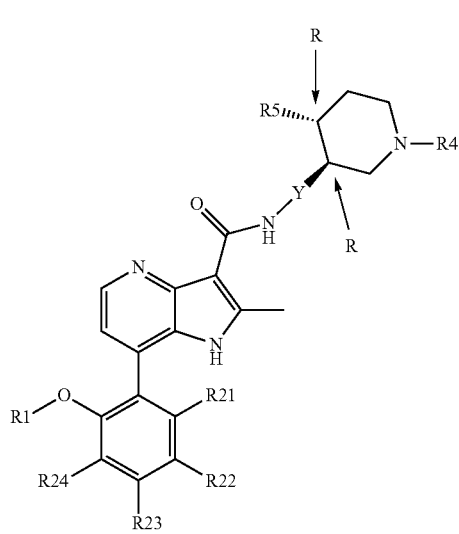
(S16)
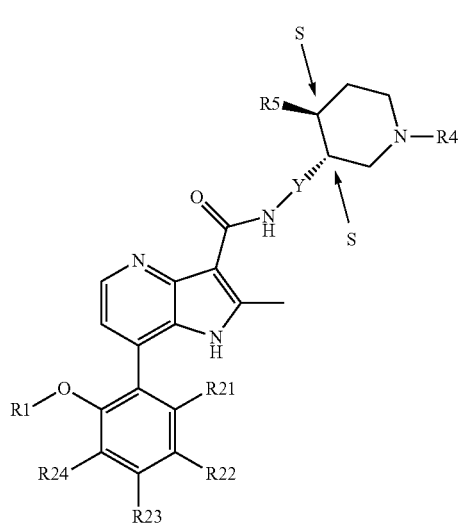
(S17)
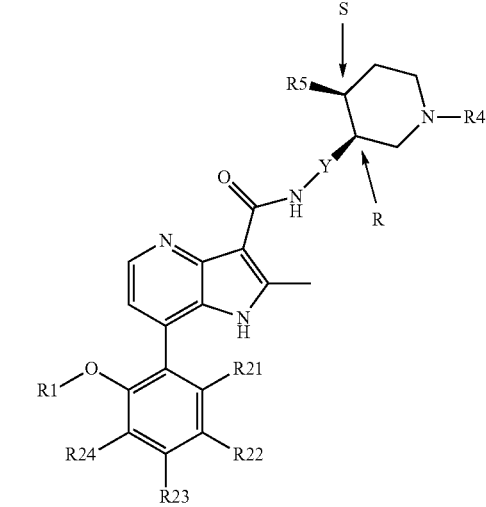
(S18)
$$Y = -(CH_2)_0- \quad \text{or} \quad -(CH_2)-$$
Furthermore, the present subject matter includes the pure (R,R)-isomers, (R,S)-isomers, (S,R)-isomers and (S,S)-isomers, and mixtures of two or more thereof in any ratio. An example of said isomers is shown below:
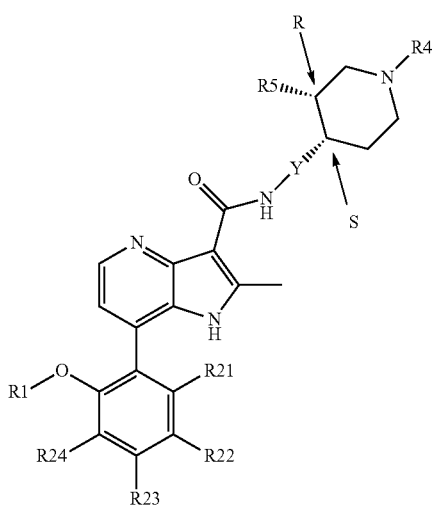
(S19)

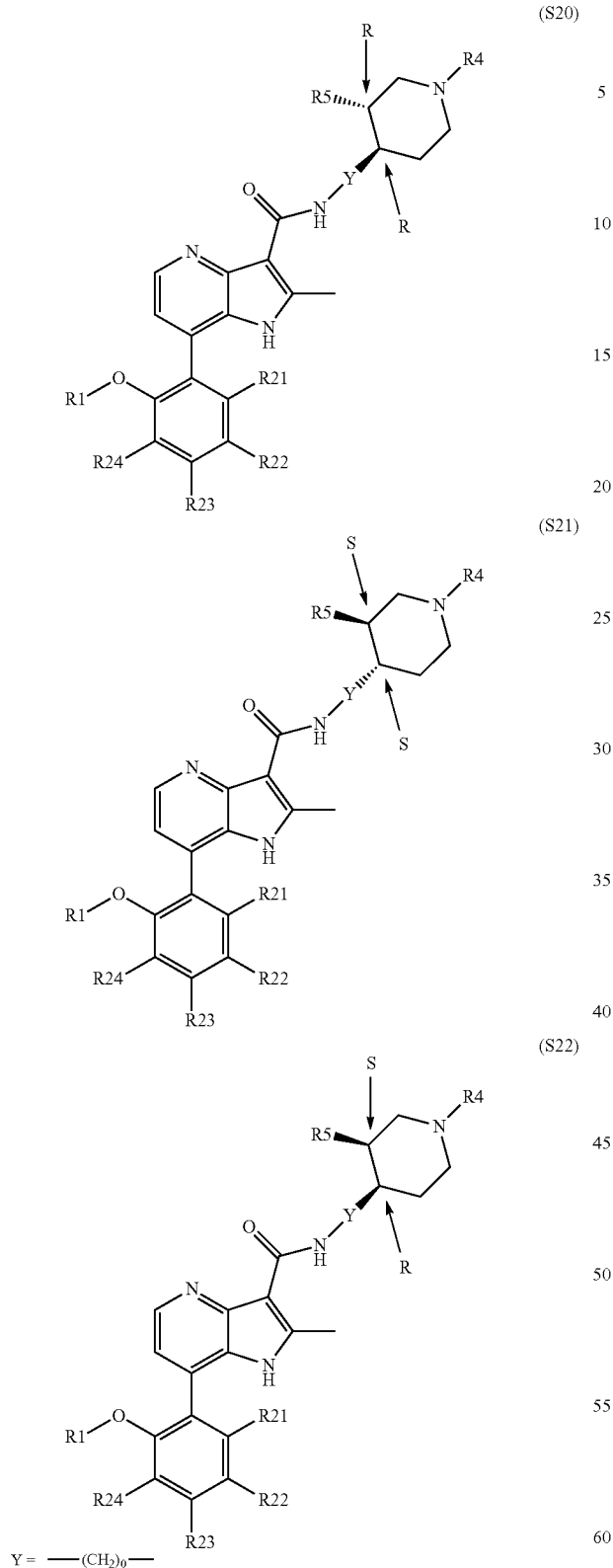
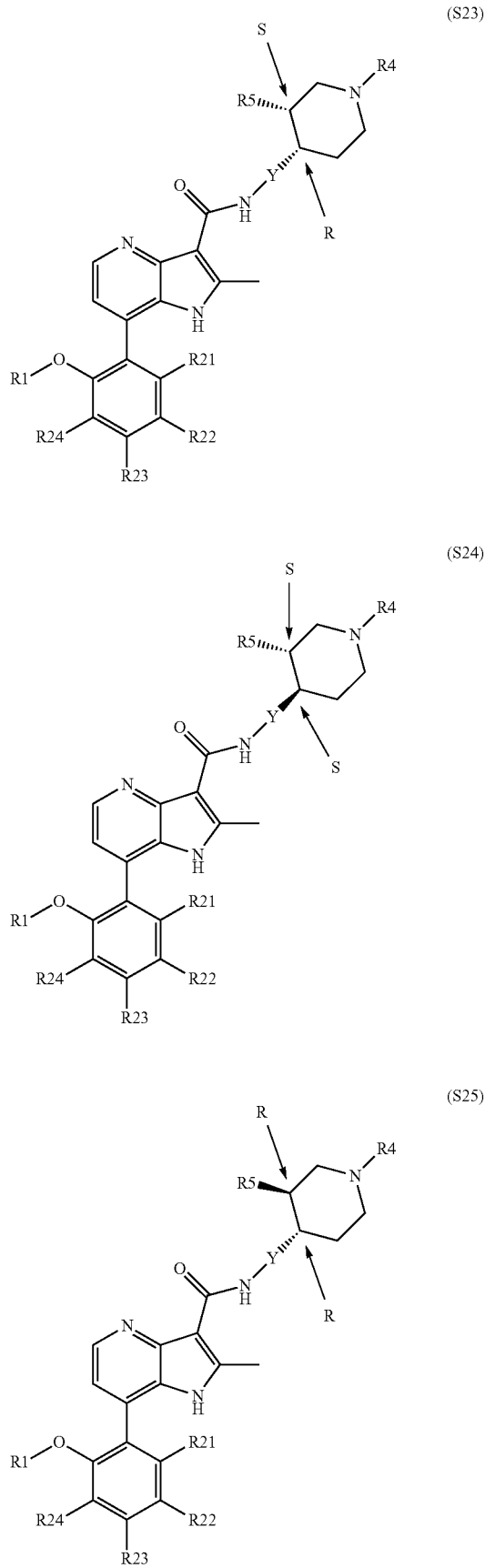
Furthermore, the present subject matter includes the pure (R,R)-isomers, (R,S)-isomers, (S,R)-isomers and (S,S)-isomers, and mixtures of two or more thereof in any ratio. An example of said isomers is shown below:

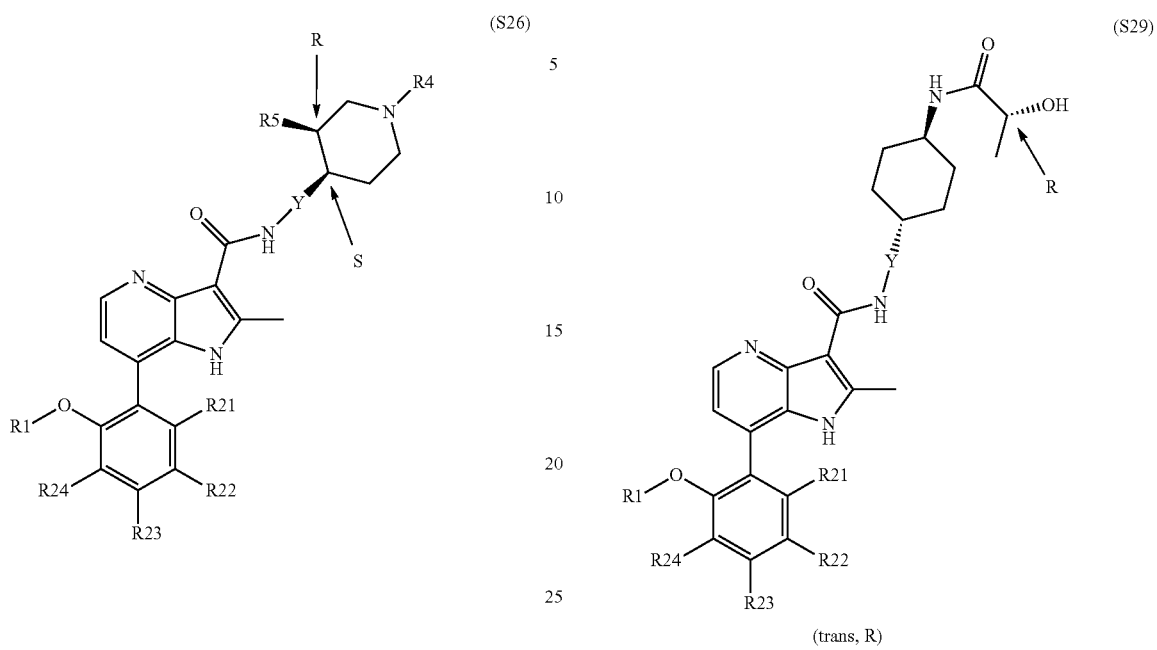

Further examples of stereoisomers include, but are not limited to, compounds of formula (I) wherein R4 is a group having a stereogenic center, such as a group —C(O)—CH(CH₃)—OH. Further examples of stereoisomers include, but are not limited to, compounds of formula (I) wherein R6 is a group having a stereogenic center, such as a group —NH—C(O)—CH(CH₃)—OCH₃.

Each of said stereogenic centers may have the absolute configuration R or the absolute configuration S (according to the rules of Cahn, Ingold and Prelog).

The present subject matter relates to the pure stereoisomers and to mixtures of the stereoisomers independent of the ratio, including the racemates. Accordingly, the present subject matter relates to the pure (cis)-isomers, the pure (trans)-isomers, and mixtures thereof, the pure (R)-isomers, the pure (S)-isomers, and mixtures thereof, the pure (RS)-isomers, the pure (SS)-isomers, the pure (SR)-isomers, the pure (RR)-isomers, and mixtures of two or more thereof in any ratio.

Furthermore, the present subject matter includes the pure (trans,R)-isomers, (trans,S)-isomers, (cis,R)-isomers and (cis,S)-isomers, and mixtures of two or more thereof in any ratio. An example of said isomers is shown below:

-continued
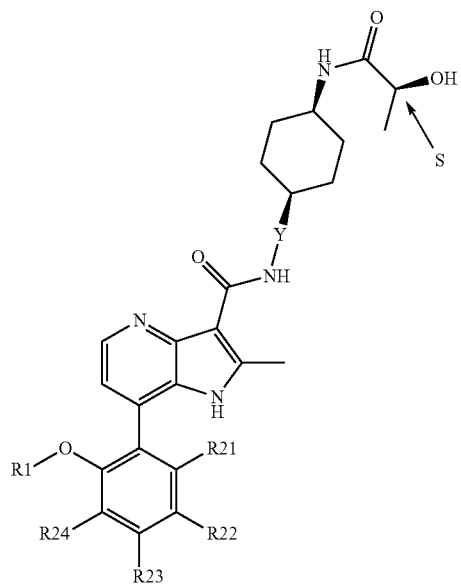
(S30)
(cis, S)
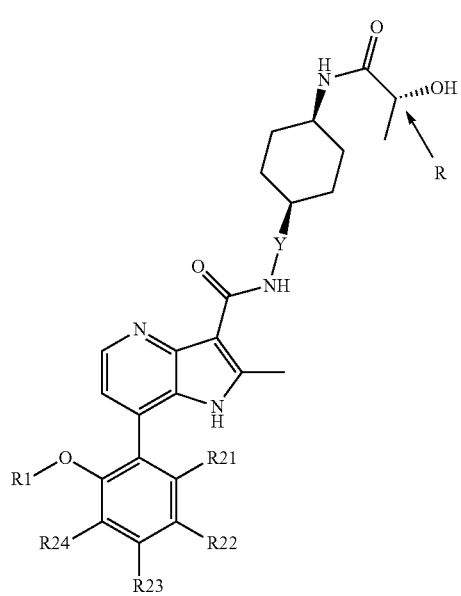
(S31)
(cis, R)
Y = —(CH₂)₀— or —(CH₂)—
Furthermore, the present subject matter includes the pure (R,R)-isomers, (R,S)-isomers, (S,R)-isomers and (S,S)-isomers, and mixtures of two or more thereof in any ratio. An example of said isomers is shown below:
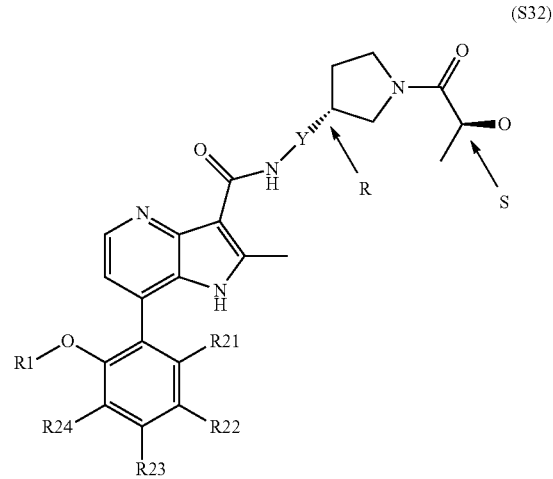
(S32)
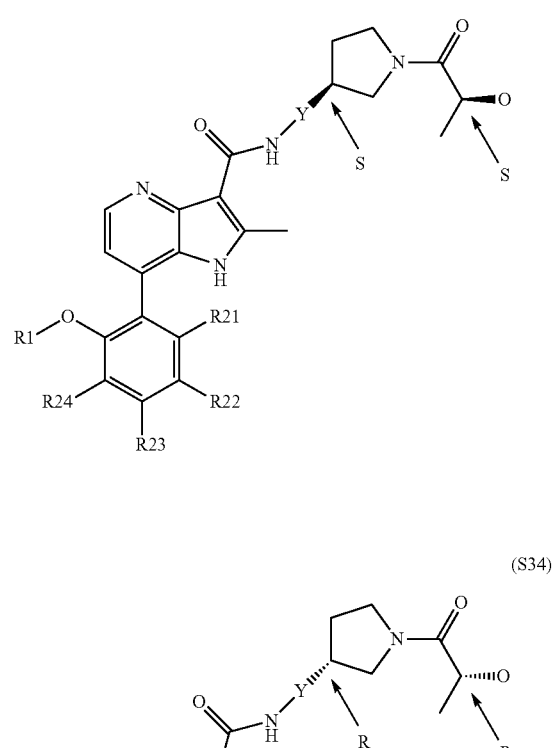
(S33)
(S34)

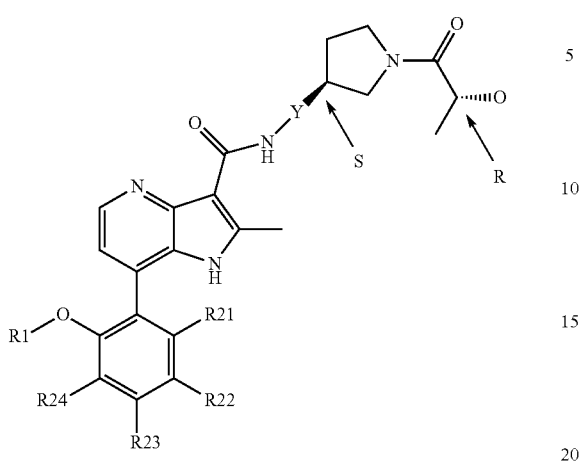

(S35)

Y = —(CH₂)₀—

Furthermore, the present subject matter includes the pure (R,R)-isomers, (R,S)-isomers, (S,R)-isomers and (S,S)-isomers, and mixtures of two or more thereof in any ratio. An example of said isomers is shown below:

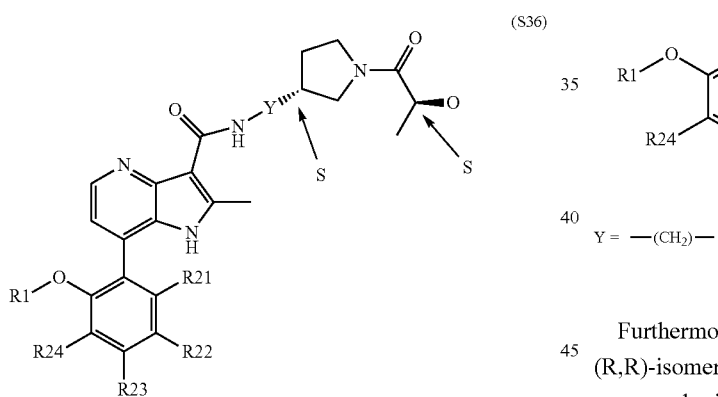

(S36)

(S37)

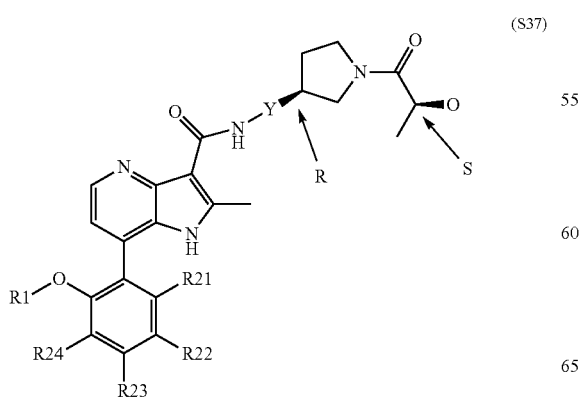

(S38)

(S39)

Y = —(CH₂)—

Furthermore, the present subject matter includes the pure (R,R)-isomers, (R,S)-isomers, (S,R)-isomers and (S,S)-isomers, and mixtures of two or more thereof in any ratio. An example of said isomers is shown below:

(S40)

(R,S)

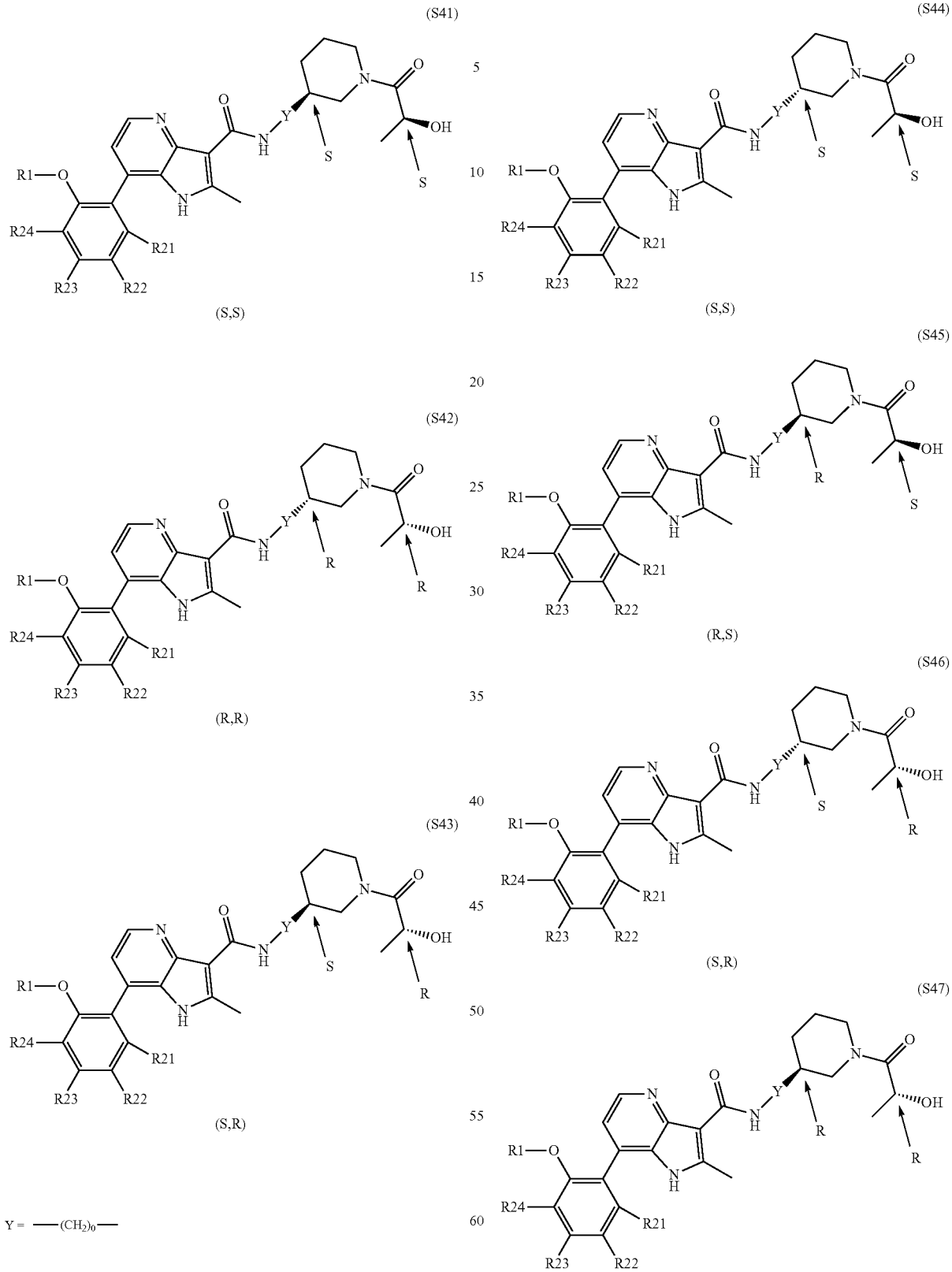
Furthermore, the present subject matter includes the pure (R,R)-isomers, (R,S)-isomers, (S,R)-isomers and (S,S)-isomers, and mixtures of two or more thereof in any ratio. An example of said isomers is shown below:

Furthermore, the present subject matter includes the pure (S,R,S)-isomers, (R,R,S)-isomers, (S,R,R)-isomers, (R,R,R)-isomers, (S,S,S)-isomers, (R,S,S)-isomers and (S,S,R)-isomers, (R,S,R)-isomers and mixtures of two or more thereof in any ratio. An example of said isomers is shown below:
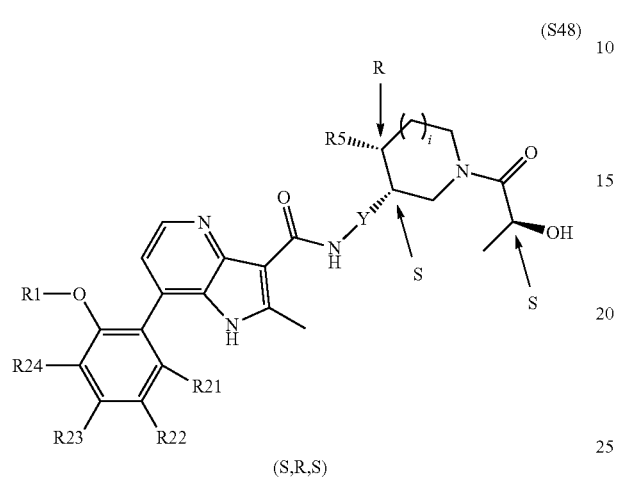
(S,R,S) (S48)
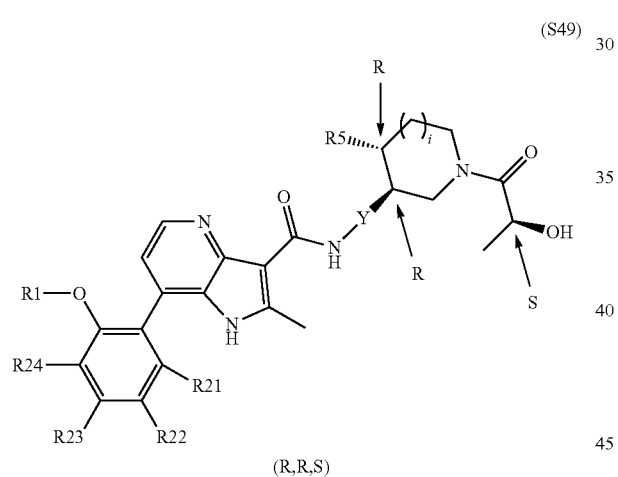
(R,R,S) (S49)
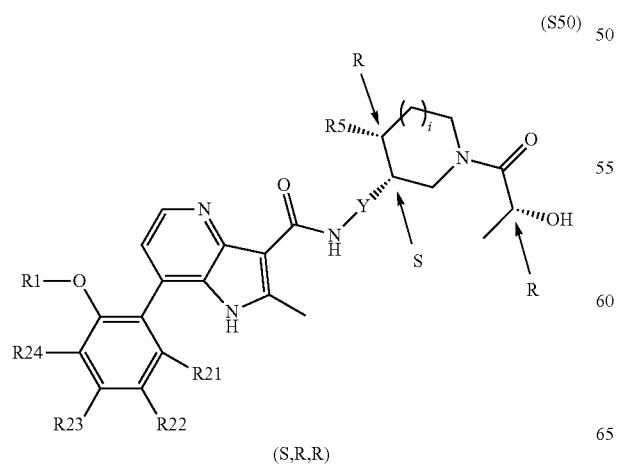
(S,R,R) (S50)
-continued
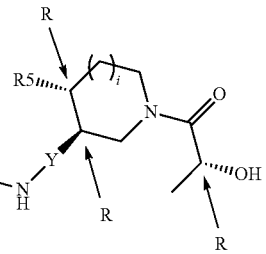
(R,R,R) (S51)
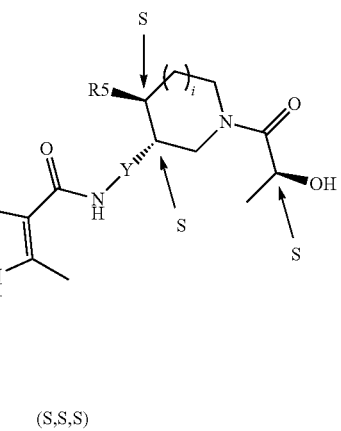
(S,S,S) (S52)
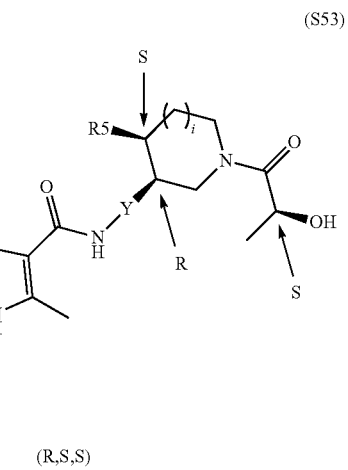
(R,S,S) (S53)

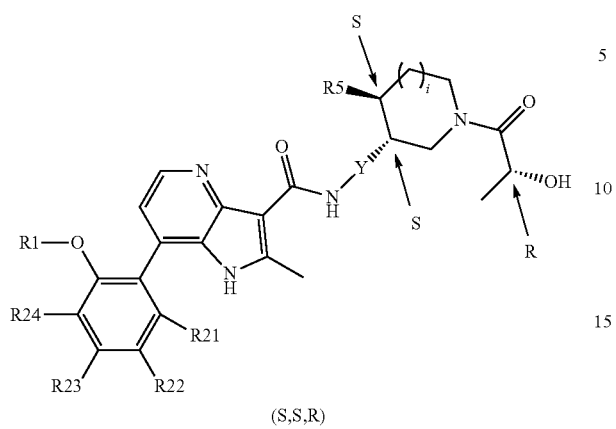
(S54)
(S,S,R)
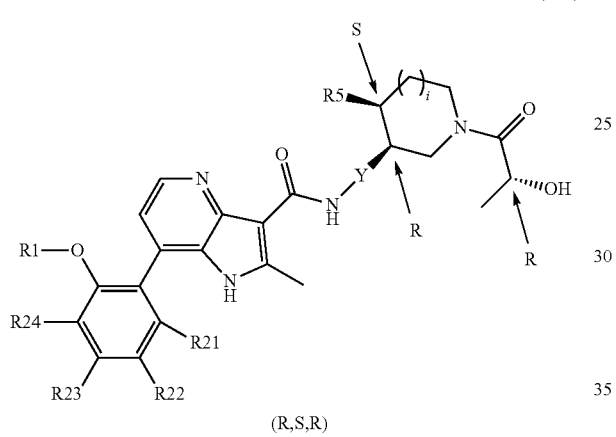
(S55)
(R,S,R)
Y = —(CH₂)₀— or —(CH₂)—
i = 1 or 2
Furthermore, the present subject matter includes the pure (S,R,S)-isomers, (R,R,S)-isomers, (S,R,R)-isomers, (R,R,R)-isomers, (S,S,S)-isomers, (R,S,S)-isomers and (S,S,R)-isomers, (R,S,R)-isomers and mixtures of two or more thereof in any ratio. An example of said isomers is shown below:
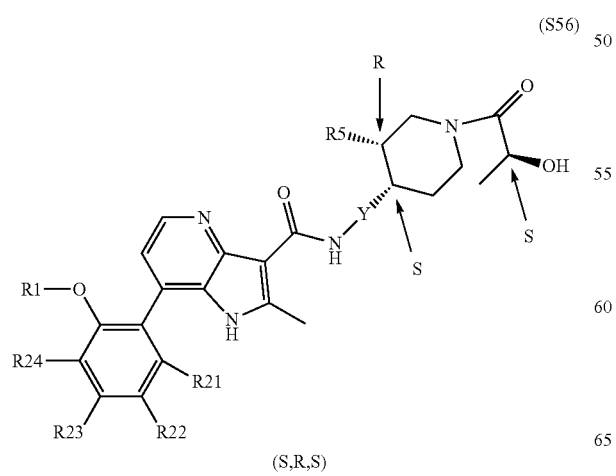
(S56)
(S,R,S)
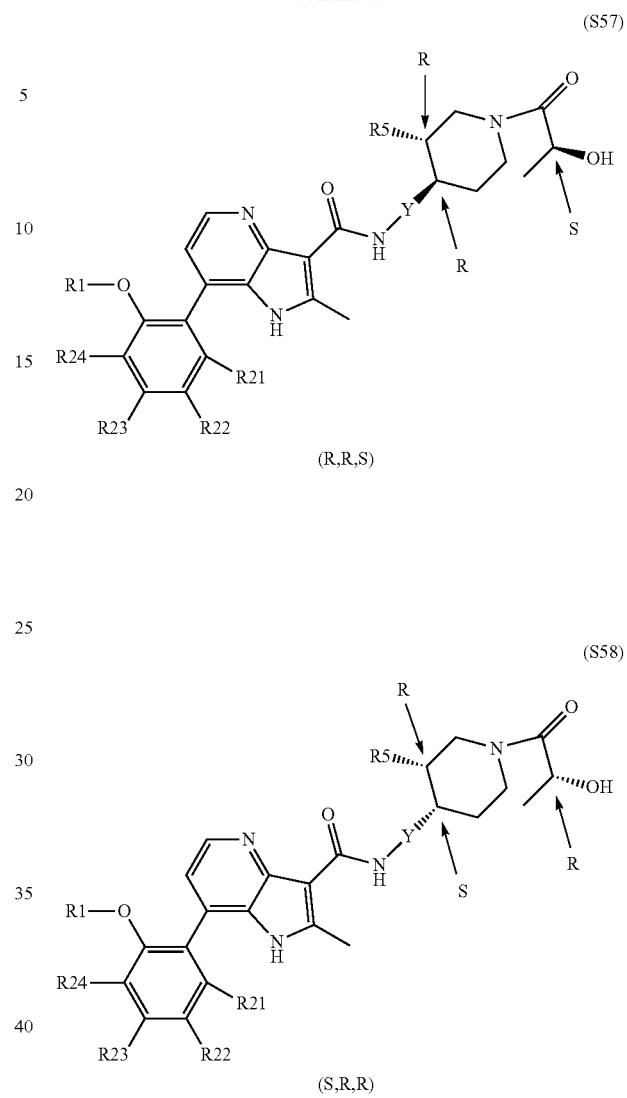
(S57) (R,R,S)
(S58) (S,R,R)
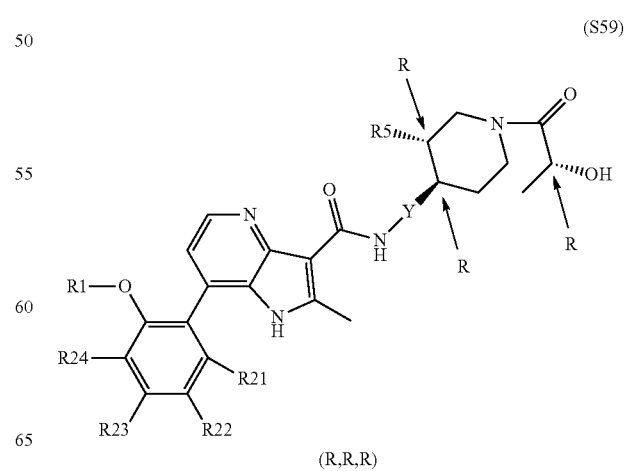
(S59)
(R,R,R)

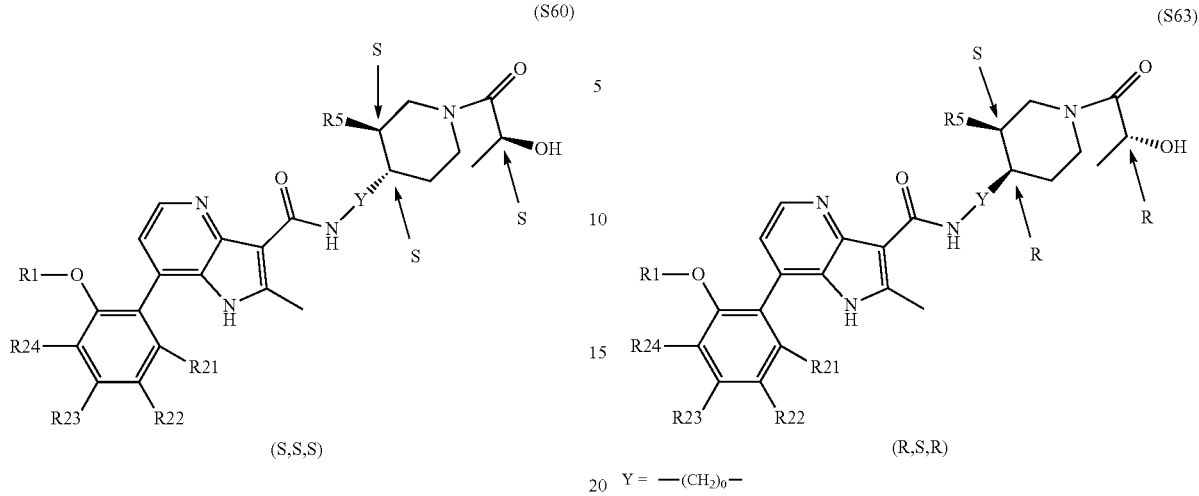
Furthermore, the present subject matter includes the pure (S,R,S)-isomers, (R,R,S)-isomers, (S,R,R)-isomers, (R,R,R)-isomers, (S,S,S)-isomers, (R,S,S)-isomers and (S,S,R)-isomers, (R,S,R)-isomers and mixtures of two or more thereof in any ratio. An example of said isomers is shown below:

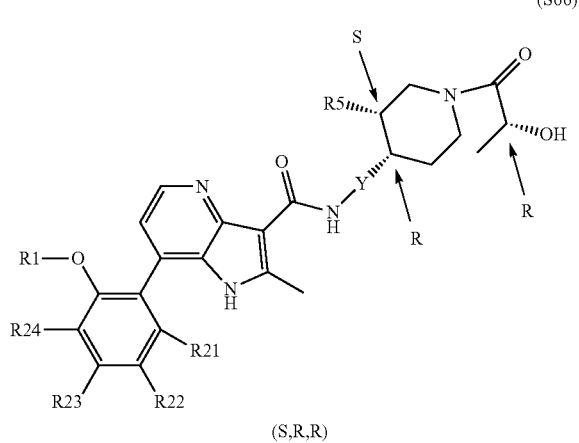
(S66)
(S,R,R)
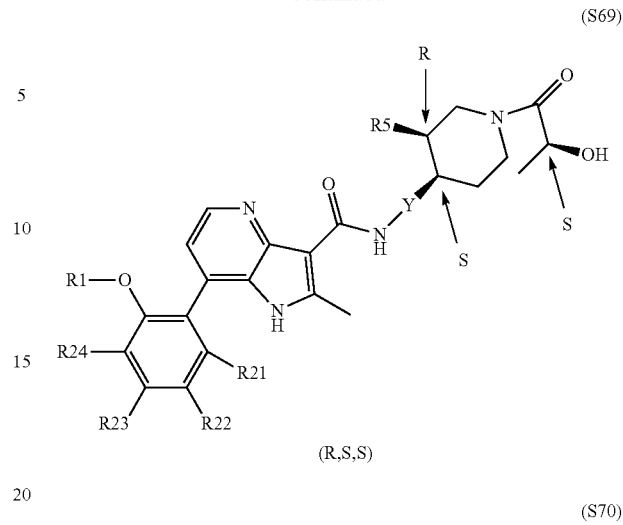
(S69)
(R,S,S)
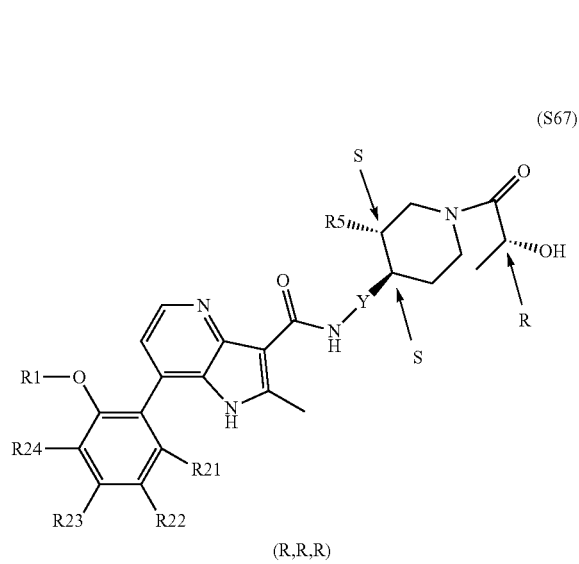
(S67)
(R,R,R)
(S68)
(S,S,S)
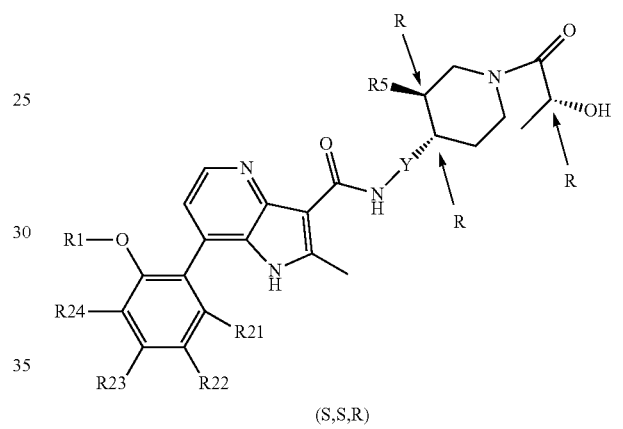
(S70)
(S,S,R)
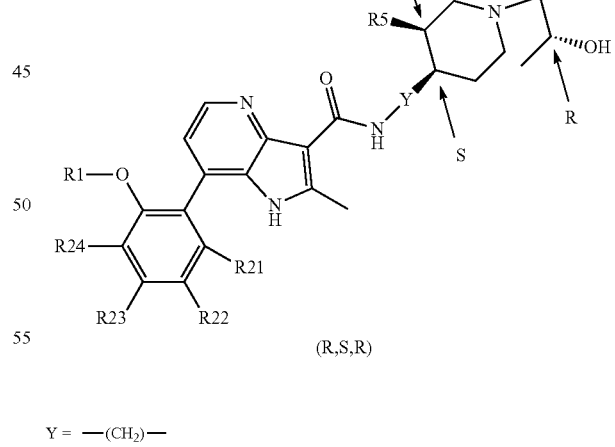
(S71)
(R,S,R)
Y = —(CH₂)—
Furthermore, the present subject matter includes the pure (S,R,S)-isomers, (R,R,S)-isomers, (S,R,R)-isomers, (R,R,R)-isomers, (S,S,S)-isomers, (R,S,S)-isomers and (S,S,R)-isomers, (R,S,R)-isomers and mixtures of two or more thereof in any ratio. An example of said isomers is shown below:

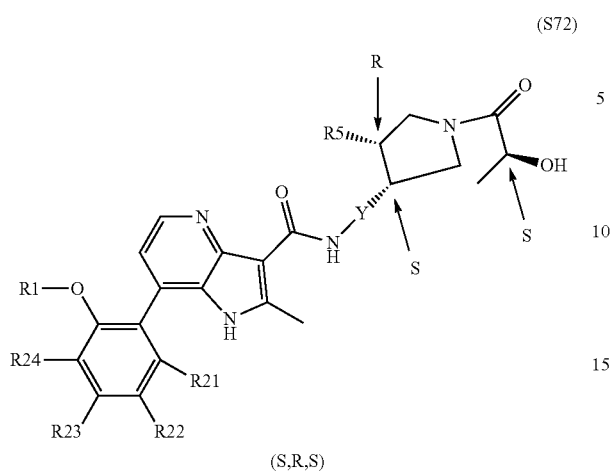
(S72) (S,R,S)
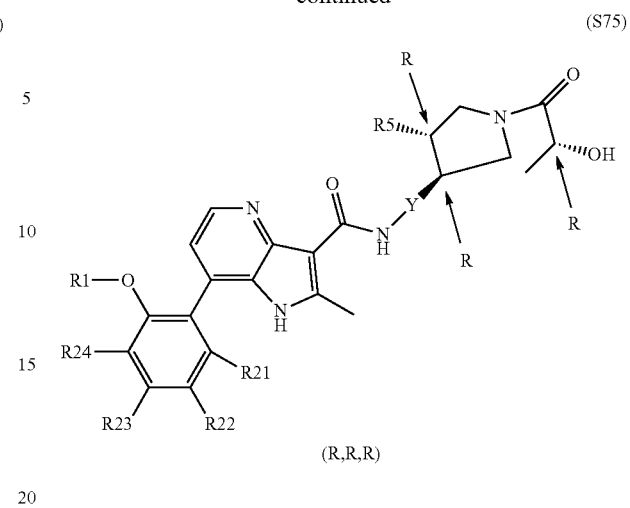
(S75) (R,R,R)
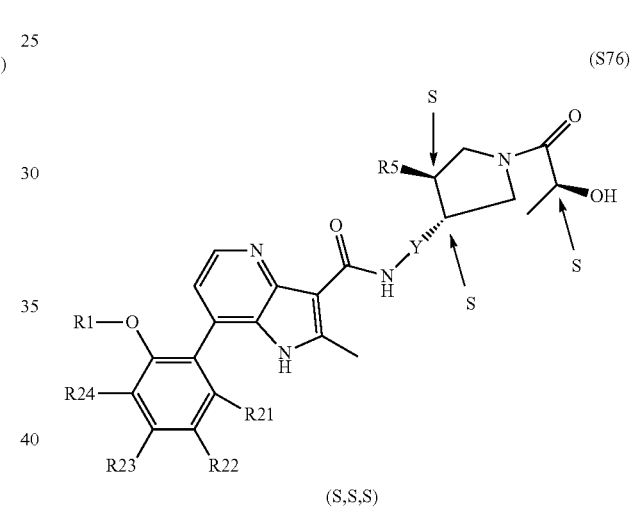
(S73) (R,R,S)
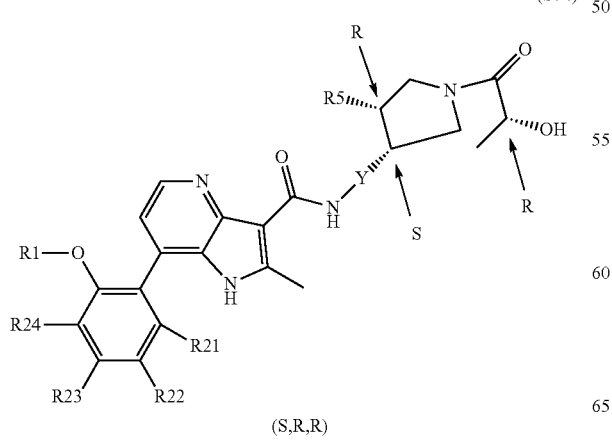
(S74) (S,R,R)
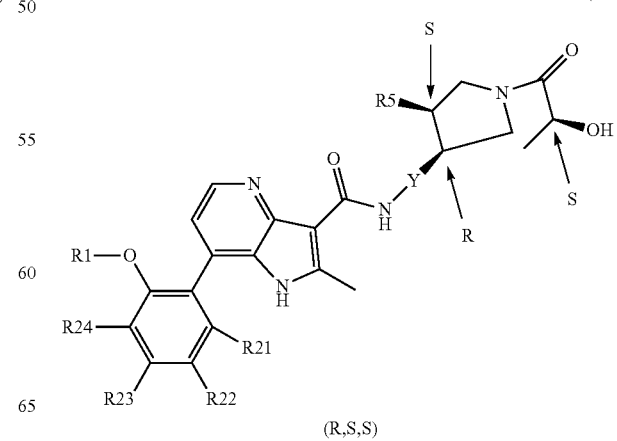
(S76) (S,S,S)
(S77) (R,S,S)

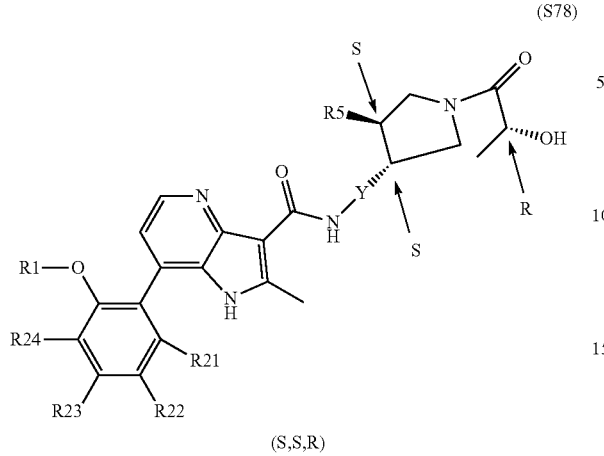
(S78)
(S,S,R)
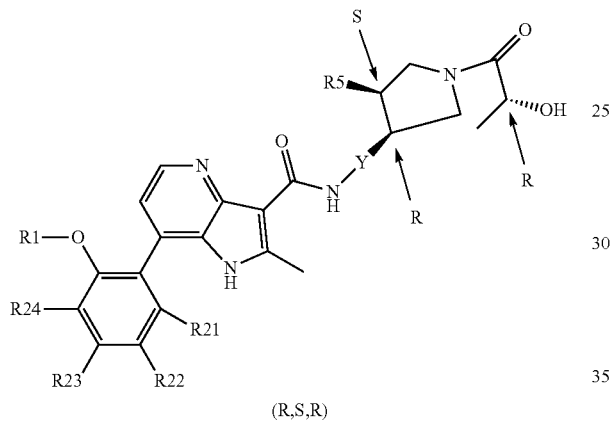
(S79)
(R,S,R)
Y = —(CH₂)₀—
Furthermore, the present subject matter includes the pure (S,R,S)-isomers, (R,R,S)-isomers, (S,R,R)-isomers, (R,R,R)-isomers, (S,S,S)-isomers, (R,S,S)-isomers and (S,S,R)-isomers, (R,S,R)-isomers and mixtures of two or more thereof in any ratio. An example of said isomers is shown below:
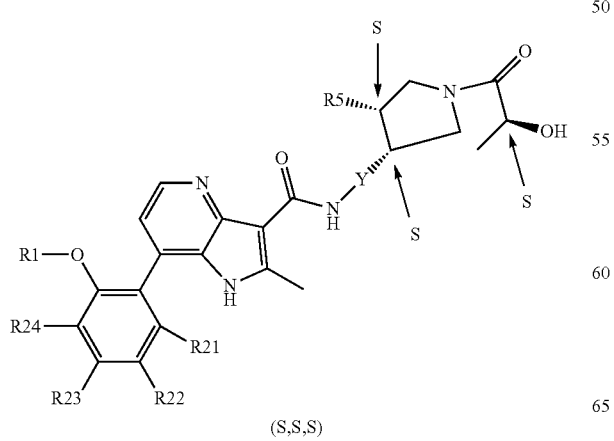
(S80)
(S,S,S)
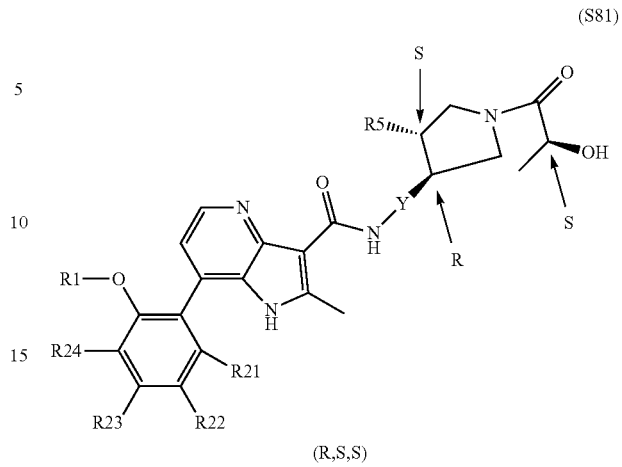
(S81)
(R,S,S)
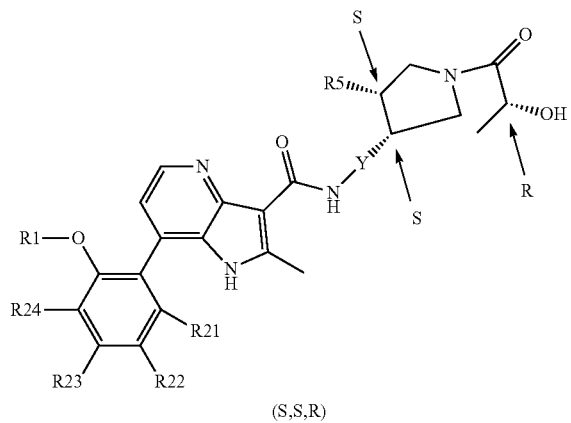
(S82)
(S,S,R)
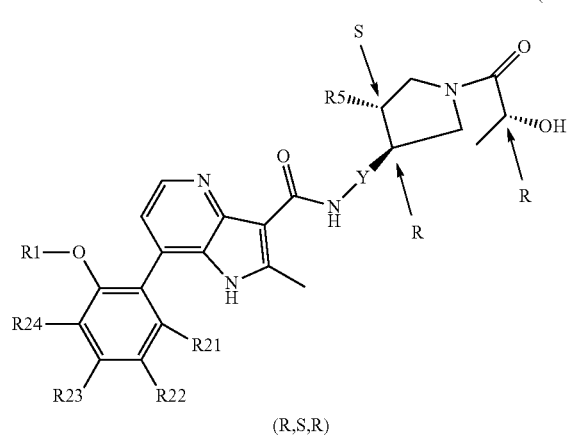
(S83)
(R,S,R)

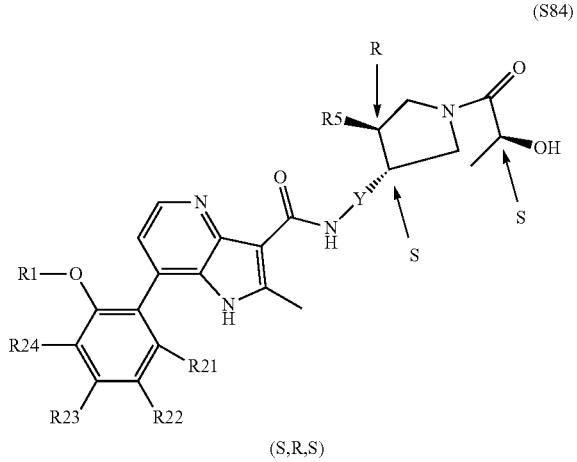

(S84)

(S,R,S)

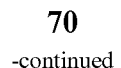

(S85)

(R,R,S)

(S86)

(S,R,R)

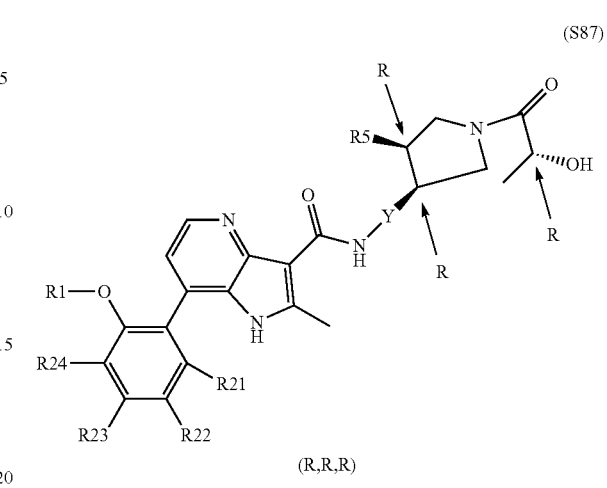

(S87)

(R,R,R)

Y = —(CH₂)—

Furthermore, derivatives of the compounds according to the present subject matter, the salts thereof, the stereoisomers of the compounds and the salts thereof which are converted into compounds according to the present subject matter, the salts thereof, the stereoisomers of the compounds or the salts thereof in a biological system (bioprecursors or pro-drugs) are covered by the present subject matter. Said biological system is e.g. a mammalian organism, particularly a human subject. The bioprecursor is, for example, converted into the compounds according to the present subject matter, the salts thereof, the stereoisomers of the compounds or the salts thereof by metabolic processes.

The compounds according to the present subject matter can be prepared as follows.

Reaction scheme 1

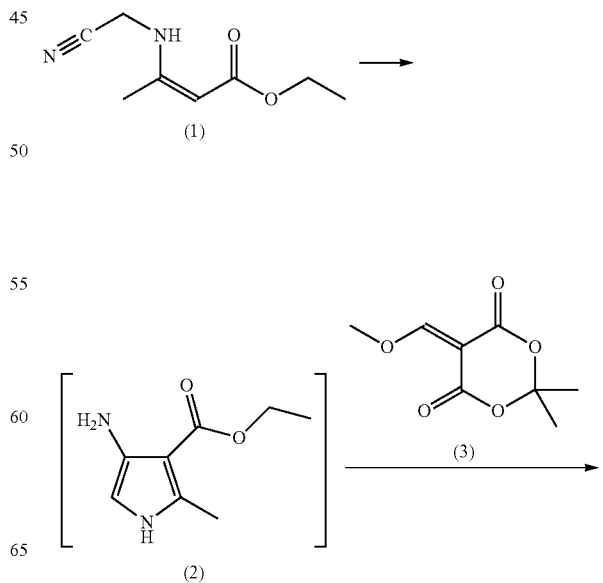

-continued

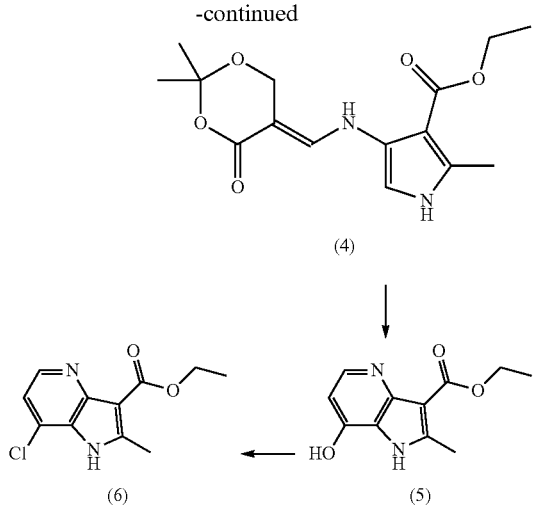

A compound of formula (6) can be obtained as shown in reaction scheme 1. Reaction of a compound of formula (1) according to the procedure described in Birnberg, G. H.; William, J. F.; Gerardo, D. F.; Epstein, J. W. J. Heterocycl. Chem., 1995, 32, 1293 delivers a compound of formula (2) that is in situ reacted with a commercially available compound of formula (3) at a temperature of from 20° C. to 100° C. for 2 to 24 h to get a compound of formula (4). In a second step a compound of formula (4) is treated in a high boiling solvent such as nitrotoluene at a temperature of from 220° C. to 260° C. for 2 to 6 h to give a compound of formula (5). Subsequent reaction of a compound of formula (5) with either neat $POCl_3$ or a solution of $POCl_3$ in an inert organic solvent (preferentially acetonitril) at reflux temperature for 2 h to 24 h delivers a compound of formula (6).

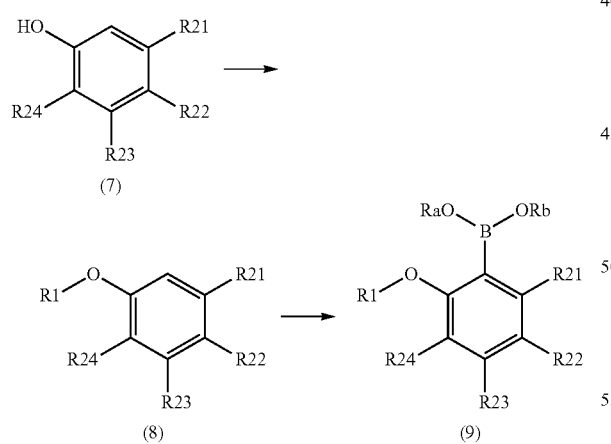

As shown in reaction scheme 2, synthesis of a boronic acid derivative of formula (9) may start from phenols of formula (7) wherein R21, R22, R23 and R24 have the above defined meanings. The phenols of formula (7) are commercially available or can be prepared by methods known to a person skilled in the art. In a first step R1, which has the above defined meaning, may be introduced by alkylation. The alkylation is for example carried out by suspending sodium hydride in an organic solvent, such as dimethylethane (DME) or dimethylsulfoxide (DMSO) or a mixture thereof, adding a solution of compound (7) in an organic solvent, such as DME, at a temperature in the range of from 0 to 40° C., then adding a compound R1-halogen, preferably R1-Br or R1-I, and reacting the mixture at a temperature of from 20 to 80° C. for 1 to 48 h to give a compound of formula (8). In a second step, directed ortho-metalation followed by reaction with a boron electrophile leads to the compounds of formula (9) wherein R1, R21, R22, R23 and R24 have the above defined meanings, and Ra and Rb represent 1-4C-alkyl or hydrogen, preferably Ra and Rb combine to form a straight-chain or branched alkylene group having 2 to 8 carbon atoms, for example without limitation —$C(CH_3)_2$—$C(CH_3)_2$—. In particular, a solution of compound (8) in an organic solvent, such as tetrahydrofuran (THF), can be reacted with n-butyl lithium (n-BuLi) in an organic solvent, such as hexane, at a temperature of from −78 to 0° C. for 0.5 to 4 h. Subsequently, for example commercially available 2-iso-propoxy-4,4,5,5-tetramethyl-[1,3,2]dioxaborolane is added and the reaction is performed at a temperature of from −78 to 0° C. for 0.5 to 3 h to yield a compound of formula (9).

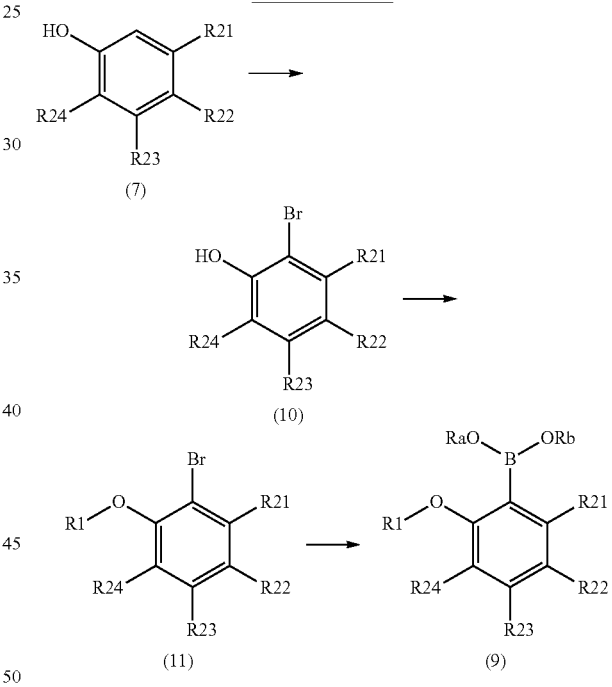

An alternative preparation of compounds of formula (9) is shown in reaction scheme 3. The preparation may start from phenols of formula (7), wherein R21, R22, R23 and R24 have the above defined meanings and which are commercially available or can be prepared by methods known to a person skilled in the art or as for example described in Yamamoto, Y.; Hattori, K.; Ishii, J.-I.; Nishiyama, H. Tetrahedron, 2006, 62, 4294. The phenols of formula (7) are for example reacted with bromine or N-bromosuccinimide in an organic solvent such as dichloromethane (DCM) at a temperature of from −40 to 20° C. for 0.5 to 4 h to give compounds of formula (10). In a second step R1, which has the above defined meaning, may be introduced by alkylation. The alkylation is for example carried out by suspending sodium hydride in an organic solvent, such as dimethylethane (DME) or dimethylsulfoxide (DMSO) or a mixture thereof, adding a solution of compound

(10) in an organic solvent, such as DME, at a temperature in the range of from 0 to 40° C., then adding a compound R1-halogen, preferably R1-Br or R1-I, and reacting the mixture at a temperature of from 20 to 80° C. for 1 to 48 h leading to compounds of formula (11). In a next step, halogen-lithium exchange followed by reaction with a boron electrophile yields the compounds of formula (9), wherein R1, R21, R22, R23 and R24 have the above defined meanings, and Ra and Rb represent 1-4C-alkyl or hydrogen, preferably Ra and Rb combine to form a straight-chain or branched alkylene group having 2 to 8 carbon atoms, for example without limitation —C(CH$_3$)$_2$—C(CH$_3$)$_2$—. In particular, a solution of compound (II) in an organic solvent, such as tert-butylmethylether, can be reacted with n-BuLi (n-butyl lithium) in an organic solvent, such as hexane, at a temperature of from −78 to 0° C. for 0.5 to 3 h. Subsequently, for example commercially available 2-iso-propoxy-4,4,5,5-tetramethyl-[1,3,2]dioxaborolane is added and the reaction is performed at a temperature of from −78 to 0° C. for 0.5 to 3 h to yield a compound of formula (9). Compounds of formula (9), wherein R22 is 1-4C-alkyl-1,3-dioxolane and R1, R21, R23, R24, Ra and Rb have the above defined meanings can be also prepared starting from phenols of formula (7), wherein R22 is —C(O)-1-4C-alkyl and R1, R21, R23 and R24 have the above defined meanings, by acetalisation of compound (11), wherein R22 is —C(O)-1-4C-alkyl and R1, R21, R23 and R24 have the above defined meanings before the halogen-lithium exchange reaction as described above is followed. The acetalisation can be performed by methods known to a person skilled in the art for example by reacting compound (11) in an organic solvent, such as dichloromethane with 1,2-bis (trimethylsilyloxy)-ethane in the presence of a catalytic amount of trimethylsilyl trifluoro-methane sulfonate at a temperature of from 0° C. to 25° C. for 1 to 4 h as for example described in Hwu, J. R.; Wetzel, J. M.; J. Org. Chem. 1985, 50, 3946.

Reaction scheme 4

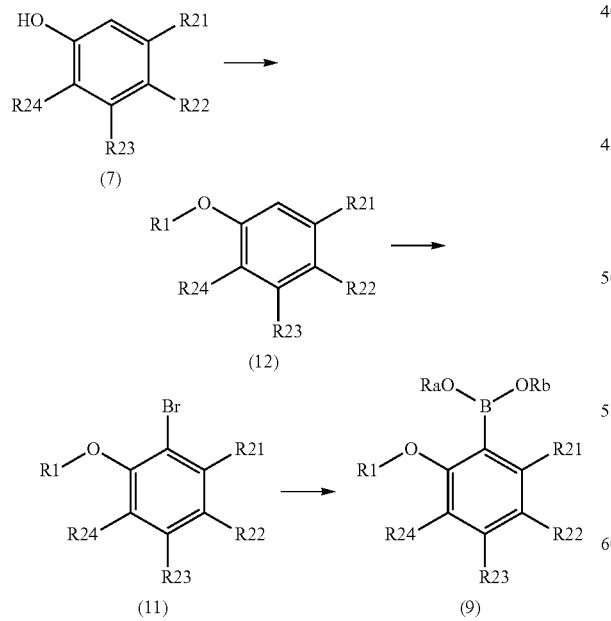

According to a further alternative preparation method shown in reaction scheme 4, synthesis of boronic acid derivatives of formula (9) may start from phenols of formula (7) wherein R21, R22, R23 and R24 have the above defined meanings and which are commercially available or can be prepared by methods known to a person skilled in the art. In a first step R1, which has the above defined meaning, is introduced by alkylation. The alkylation is for example carried out by suspending sodium hydride in an organic solvent, such as dimethylethane (DME) or dimethylsulfoxide (DMSO) or a mixture thereof, adding a solution of compound (7) in an organic solvent, such as DME, at a temperature in the range of from 0 to 40° C., then adding a compound R1-halogen, preferably R1-Br or R1-I, and reacting the mixture at a temperature of from 20 to 80° C. for 1 to 48 h to give a compound of formula (12). In a second step, compound (11) may be prepared for example from compound (12) by reaction with N-bromosuccinimide in an organic solvent, such as dimethylformamide, at a temperature of from 0 to 60° C. for 0.5 to 5 h. In a third step, halogen-lithium exchange followed by reaction with a boron electrophile yields the compounds of formula (9), wherein R1, R21, R22, R23 and R24 have the above defined meanings, and Ra and Rb represent 1-4C-alkyl or hydrogen, preferably Ra and Rb combine to form a straight-chain or branched alkylene group having 2 to 8 carbon atoms, for example without limitation —C(CH$_3$)$_2$—C(CH$_3$)$_2$—. In particular, a solution of compound (11) in an organic solvent, such as tert-butylmethylether, can be reacted with n-BuLi (n-butyl lithium) in an organic solvent, such as hexane, at a temperature of from −78 to 0° C. for 0.5 to 3 h. Subsequently, for example commercially available 2-iso-propoxy-4,4,5,5-tetramethyl-[1,3,2]dioxaborolane is added and the reaction is performed at a temperature of from −78 to 0° C. for 0.5 to 3 h to yield a compound of formula (9). Alternatively, compounds of formula (9) may be synthesized from compounds of formula (11) and an appropriate boron compound, such as bis(pinacolato)diboron, in the presence of a Pd catalyst, such as 1,1'-bis(diphenyl-phosphino)ferrocene palladium-(II)-chloride, and a base, such as potassium acetate, in an organic solvent, such as dioxane, at a temperature of from 20 to 100° C. for 1 to 24 h. The Pd catalyzed preparation of boronic acid derivatives is, for example, described in Murata et al, J Org Chem 2000, 65, 164 and J Org Chem 1997, 62, 6458.

Reaction scheme 5

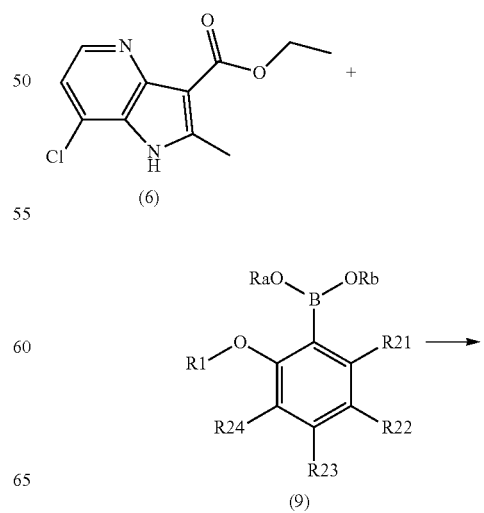

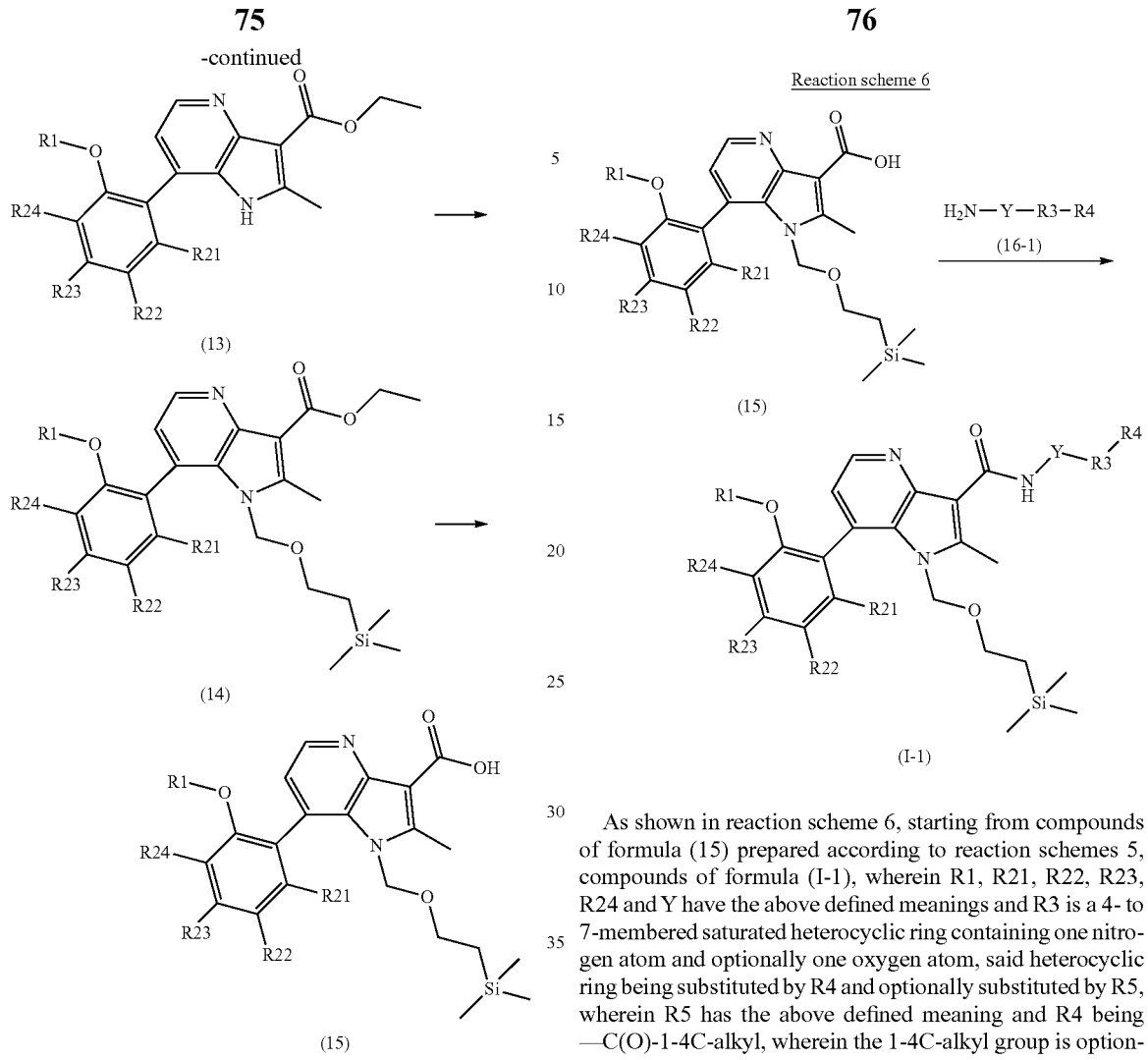

Reaction scheme 5 illustrates the synthesis of compounds of formula (15) wherein R1, R21, R22, R23 and R24 have the above defined meanings. In a first step, compound (6) prepared according to reaction scheme 1 can be reacted with a compound of formula (9) prepared according to any of reaction schemes 2, 3 or 4, wherein R1, R21, R22, R23, R24, Ra and Rb have the above defined meanings, to obtain a compound of formula (13). In particular, the compound of formula (6), a base, such as $K_2CO_3$, $Cs_2CO_3$ or $K_3PO_4$, a solvent, such as dimethoxyethane, dioxane or dimethylformamide, a compound of formula (9) and a Pd catalyst, such as $PdCl_2(PCy_3)_2$ (Cy=cyclohexyl), are preferably heated at a temperature in the range of from 60 to 120° C. for 1 to 16 h. The compound of formula (13) thus obtained can then be protected by reaction with a base such as sodium hydride and (2-chloromethoxy-ethyl)-trimethyl-silane in a organic solvent such as dimethoxyethane, dimethylformamide or dimethylsulfoxide at a temperature of from 0° C. to 25° C. for 1 h to 24 h as for example described in Muchowski, J. M.; Solas, D. R.; J. Org: Chem. 1984, 49, 203 to a compound of formula (14). The compound of formula (14) is reacted with an alkali hydroxide, such as LiOH, in a solvent, preferably a mixture of an organic solvent, such as dioxane, and water, at a temperature in the range of from 20 to 100° C. for 1 to 48 h to yield a compound of formula (15).

As shown in reaction scheme 6, starting from compounds of formula (15) prepared according to reaction schemes 5, compounds of formula (I-1), wherein R1, R21, R22, R23, R24 and Y have the above defined meanings and R3 is a 4- to 7-membered saturated heterocyclic ring containing one nitrogen atom and optionally one oxygen atom, said heterocyclic ring being substituted by R4 and optionally substituted by R5, wherein R5 has the above defined meaning and R4 being —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43, with R41, R42 and R43 having the above defined meanings, can be prepared by reaction with compounds of formula (16-1), wherein Y has the above defined meaning and R3 is a 4- to 7-membered saturated heterocyclic ring containing one nitrogen atom and optionally one oxygen atom, said heterocyclic ring being substituted by R4 and optionally substituted by R5, wherein R5 has the above defined meaning and R4 being —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43, with R41, R42 and R43 having the above defined meanings, under standard amide bond forming conditions. The compounds of formula (16-1) are commercially available or can be prepared by methods known to a person skilled in the art. In particular, a dehydrating agent, such as 1-(3-dimethylaminopropyl)-3-ethylcarbodiimide hydrochloride, a base, such as triethylamine, and a catalyst, such as 1-hydroxybenzotriazole, can be added to a compound of formula (15) which is preferably dissolved or suspended in an organic solvent, e.g. dichloromethane. After stirring the mixture e.g. for 0.3 to 2 h, preferably at ambient temperature (e.g. 20 to 25° C.), a compound of formula (16-1) can be added and the reaction is preferably performed at ambient temperature (e.g. 20 to 25° C.) for 1 to 48 h to yield the compound of formula (I-1).

Reaction scheme 7

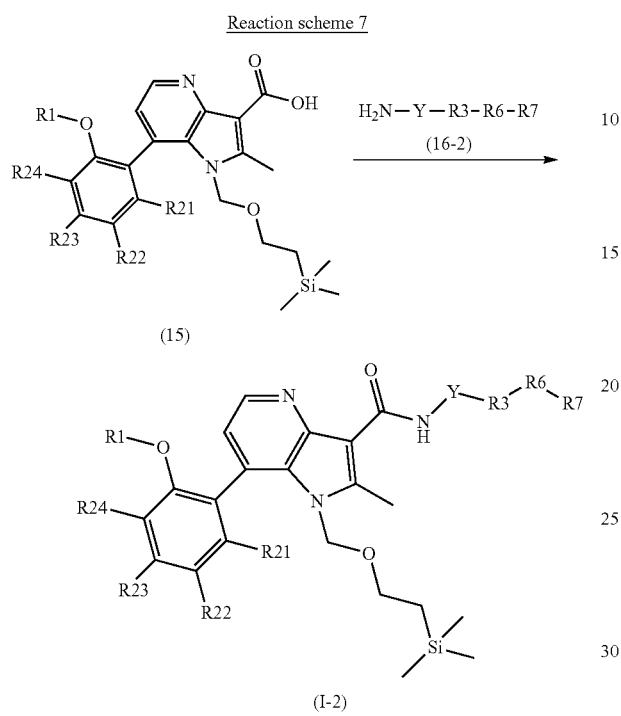

As shown in reaction scheme 7, compounds of formula (I-2), wherein R1, R21, R22, R23, R24 and Y have the above defined meanings and R3 is a 3-6C-cycloalkyl group substituted by R6, with R6 being —NH—C(O)—R7 and R7 being 1-4C-alkyl, which is optionally substituted by R71, 3-6C-cycloalkyl, which is optionally substituted by R72, or 1-4C-alkoxy, which is optionally substituted by R73, with R71, R72 and R73 having the above defined meanings can be synthesized by reaction of compounds of formula (15) prepared according to reaction schemes 5, with compounds of formula (16-2), wherein Y has the above defined meaning and R3 is a 3-6C-cycloalkyl group substituted by R6, with R6 being —NH—C(O)—R7 and R7 being 1-4C-alkyl, which is optionally substituted by R71, 3-6C-cycloalkyl, which is optionally substituted by R72, or 1-4C-alkoxy, which is optionally substituted by R73, with R71, R72 and R73 having the above defined meanings. The compounds of formula (16-2) are commercially available or can be prepared by methods known to a person skilled in the art. In particular, a dehydrating agent, such as 1-(3-dimethylaminopropyl)-3-ethylcarbodiimide hydrochloride, a base, such as triethylamine, and a catalyst, such as 1-hydroxybenzotriazole, can be added to a compound of formula (15) which is preferably dissolved or suspended in an organic solvent, such as dichloromethane. After stirring the mixture e.g. for 0.3 to 2 h preferably at ambient temperature (e.g. 20 to 25° C.), a compound of formula (16-2) can be added and the reaction is preferably performed at ambient temperature (e.g. 20 to 25° C.) for 1 to 48 h to yield the compound of formula (I-2).

Reaction scheme 8

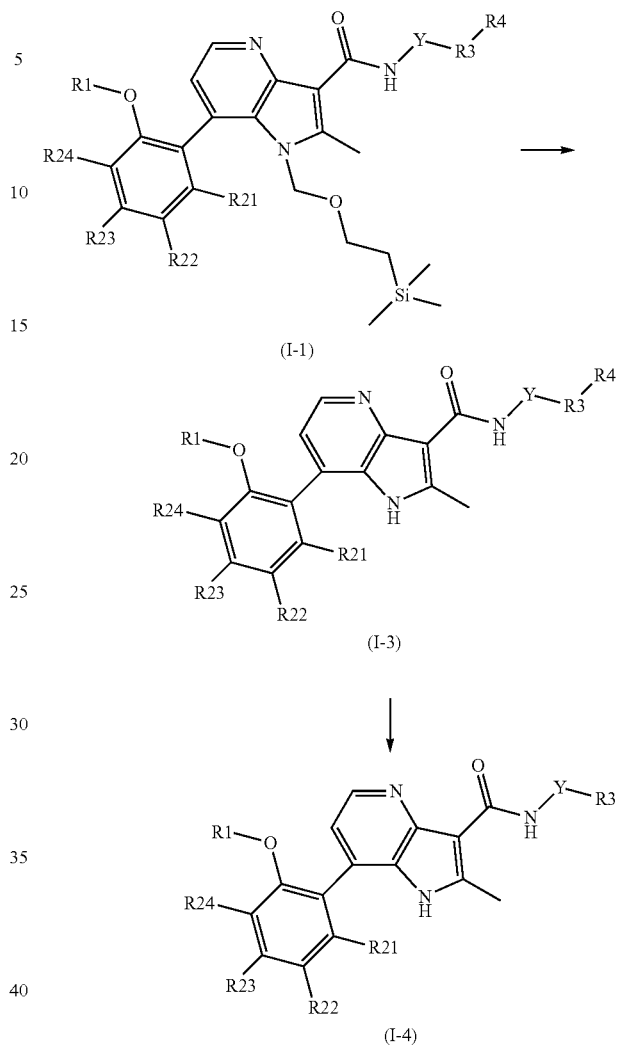

Compounds of formula (I-1), wherein R1, R21, R22, R23, R24 and Y have the above defined meanings and R3 is a 4- to 7-membered saturated heterocyclic ring containing one nitrogen atom and optionally one oxygen atom, said heterocyclic ring being substituted by R4 and optionally substituted by R5, wherein R5 has the above defined meaning and R4 being —C(O)—O—C(CH$_3$)$_3$, prepared according to reaction scheme 6 can be deprotected and converted into compounds of formula (I-4), wherein R1, R21, R22, R23, R24 and Y have the above defined meanings and R3 is a 4- to 7-membered saturated heterocyclic ring containing one nitrogen atom and optionally one oxygen atom, said heterocyclic ring being optionally substituted by R5, wherein R5 has the above defined meaning. In particular, compounds of formula (I-1) are deprotected by methods known to a person skilled in the art for example by reaction with tetrabutylammonium fluoride and 1,2-diamino-ethane in an organic solvent like tetrahydrofurane as for example described in Muchowski, J. M.; Solas, D. R.; J. Org: Chem. 1984, 49, 203.

In the following step HCl preferably dissolved in an organic solvent, such as dioxane, can be added to the compound of formula (I-3) which is preferably dissolved in an organic solvent, such as an alcohol, e.g. 2-propanol. The reaction mixture is then preferably heated at 40 to 80° C. for 1 to 4 h to yield the hydrochloride of the compound of formula (I-4). The compound of formula (I-4) can be prepared from said hydrochloride as known to a person skilled in the art, such as by treatment with a base, e.g. aqueous potassium carbonate or aqueous ammonia.

Reaction scheme 9

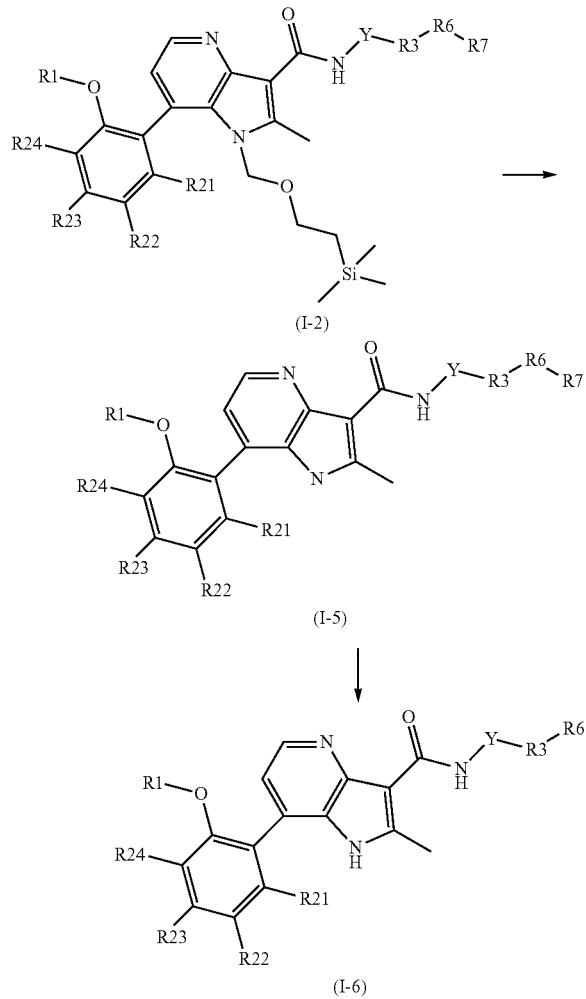

Compounds of formula (I-2), wherein R1, R21, R22, R23, R24 and Y have the above defined meanings and R3 is a 3-6C-cycloalkyl group substituted by R6 with R6 being —NH—C(O)—R7 and R7 being —O—C(CH$_3$)$_3$, prepared according to reaction scheme 7 can be deprotected and converted into compounds of formula (I-6), wherein R1, R21, R22, R23, R24 and Y have the above defined meanings and R3 is a 3-6C-cycloalkyl group substituted by R6 with R6 being —NH$_2$ as shown in reaction scheme 9. In particular, compounds of formula (I-2) are deprotected by methods known to a person skilled in the art for example by reaction with tetrabutylammonium fluoride and 1,2-diamino-ethane in an organic solvent like tetrahydrofurane as for example described in Muchowski, J. M.; Solas, D. R.; J. Org: Chem. 1984, 49, 203.

In the following step HCl preferably dissolved in an organic solvent, such as dioxane, can be added to the compound of formula (I-5) which is preferably dissolved in an organic solvent, such as an alcohol, e.g. 2-propanol. The reaction mixture is then preferably heated at 40 to 80° C. for 1 to 4 h to yield the hydrochloride of the compound of formula (I-6). The compound of formula (I-6) can be prepared from said hydrochloride as known to a person skilled in the art, such as by treatment with a base, e.g. aqueous potassium carbonate or aqueous ammonia.

Reaction scheme 10

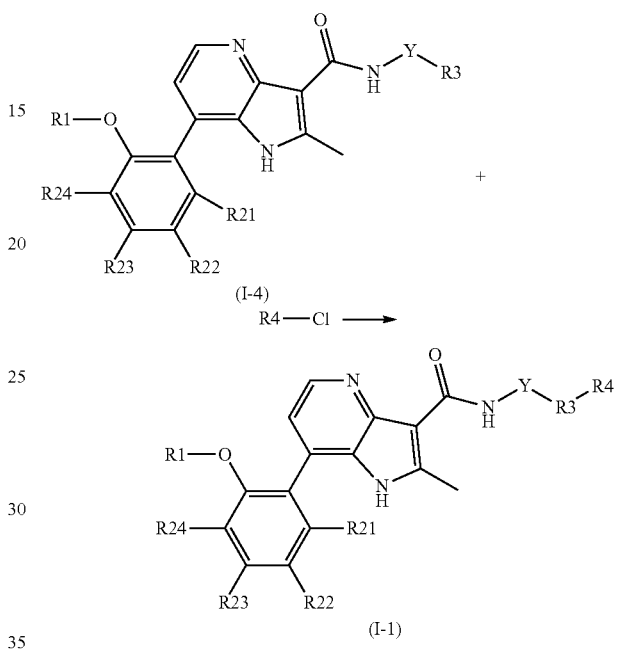

Alternatively, as shown in reaction scheme 10, compounds of formula (I-1), wherein R1, R21, R22, R23, R24 and Y have the above defined meanings and R3 is a 4- to 7-membered saturated heterocyclic ring containing one nitrogen atom and optionally one oxygen atom, said heterocyclic ring being substituted by R4 and optionally substituted by R5, wherein R5 has the above defined meaning and R4 being —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43, and R41, R42 and R43 are as defined above, may be prepared from compounds of formula (I-4), wherein R1, R21, R22, R23, R24 and Y have the above defined meanings and R3 is a 4- to 7-membered saturated heterocyclic ring containing one nitrogen atom and optionally one oxygen atom, said heterocyclic ring being optionally substituted by R5, wherein R5 has the above defined meaning, prepared according to reaction scheme 8. In particular, a compound R4-Cl can be added to the compound of formula (I-4) which is preferably dissolved in an organic solvent, such as dichloromethane, in the presence of a base, such as diazabicycloundecene (DBU). The compound of formula R4-Cl is commercially available or can be prepared by methods known to a person skilled in the art. The addition is preferably carried out at a temperature of from 0 to 20° C. After complete addition, the reaction is preferably continued at ambient temperature (e.g. 20 to 25° C.) for 1 to 24 h. In case R41, R42 or R43 represent hydroxy, it is known to a person skilled in the art that the hydroxy group is preferably to be protected by a suitable protecting group, such as an acetate group or a silyl protective group, e.g. a tert-butyl-dimethylsilyl group or a tert-butyl-diphenylsilyl group. Said protective groups can be removed by methods known to a person skilled in the art with or without prior isolation of the protected intermediate (i.e. the compound of formula (I-1) in its protected form).

suitable protecting group, such as an acetate group or a silyl protective group, e.g. a tert-butyl-dimethylsilyl group or tert-butyl-diphenylsilyl group. Said protective groups can be removed by methods known to a person skilled in the art with or without prior isolation of the protected intermediate (i.e. the compound of formula (I-2) in its protected form).

Reaction scheme 11

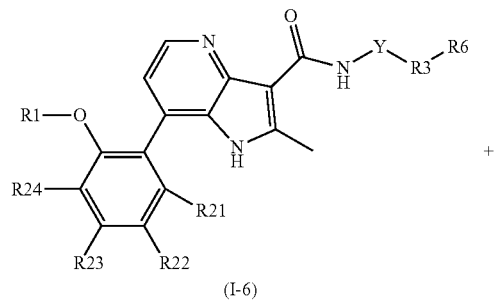

(I-6)

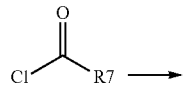

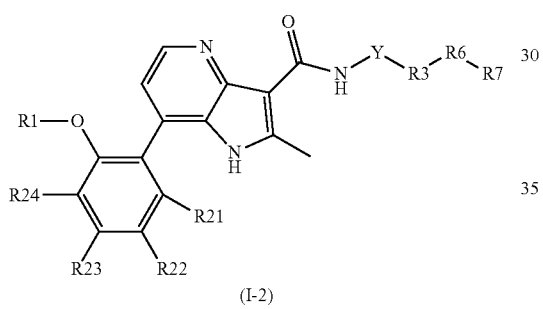

(I-2)

Reaction scheme 12

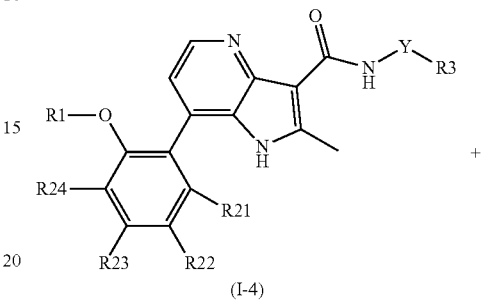

(I-4)

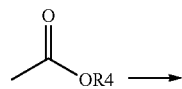

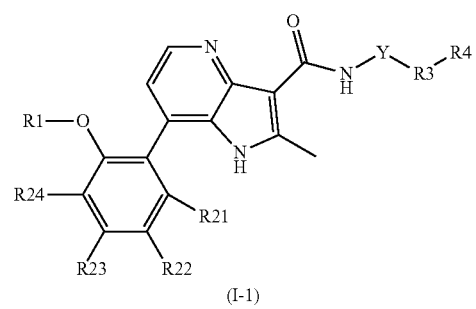

(I-1)

Alternatively, as shown in reaction scheme 11, compounds of formula (I-2), wherein R1, R21, R22, R23, R24 and Y have the above defined meanings and R3 is a 3-6C-cycloalkyl group substituted by R6, with R6 being —NH—C(O)—R7, with R7 being 1-4C-alkyl, which is optionally substituted by R71, 3-6C-cycloalkyl, which is optionally substituted by R72, or 1-4C-alkoxy, which is optionally substituted by R73, and R71, R72 and R73 are as defined above, may be prepared from compounds of formula (I-6), wherein R1, R21, R22, R23, R24 and Y have the above defined meanings and R3 is a 3-6C-cycloalkyl group substituted by R6 with R6 being NH$_2$ prepared according to reaction scheme 9. In particular, a compound R7-C(O)—Cl can be added to the compound of formula (I-6) which is preferably dissolved in an organic solvent, such as dichloromethane, in the presence of a base, such as diazabicycloundecene (DBU). The compound of formula R7-C(O)—Cl is commercially available or can be prepared by methods known to a person skilled in the art. The addition is preferably carried out at a temperature of from 0 to 20° C. After complete addition, the reaction is preferably continued at ambient temperature (e.g. 20 to 25° C.) for 1 to 24 h to yield the compound of formula (I-2). In case R71, R72 or R73 represent hydroxy, it is known to a person skilled in the art that the hydroxy group is preferably to be protected by a As shown in reaction scheme 12, compounds of formula (I-1), wherein R1, R21, R22, R23, R24 and Y have the above defined meanings and R3 is a 4- to 7-membered saturated heterocyclic ring containing one nitrogen atom and optionally one oxygen atom, said heterocyclic ring being substituted by R4 and optionally substituted by R5, wherein R5 has the above defined meaning and R4 being —C(O)—H can be prepared from compounds of formula (I-4), wherein R1, R21, R22, R23, R24 and Y have the above defined meanings and R3 is a 4- to 7-membered saturated heterocyclic ring containing one nitrogen atom and optionally one oxygen atom, said heterocyclic ring being optionally substituted by R5, wherein R5 has the above defined meaning, prepared according to reaction scheme 8. In particular, the compound R4-O—C(O)—CH$_3$, which can be prepared by methods known to a person skilled in the art, can be added to the compound of formula (I-4) which is preferably dissolved in an organic solvent, such as dichloromethane, in the presence of a base, such as diazabicycloundecene (DBU). The addition is preferably carried out at a temperature of from 0 to 20° C. After completion of addition, the reaction is preferably continued at ambient temperature (e.g. 20 to 25° C.) for 1 to 24 h to yield the compound of formula (I-1).

Reaction scheme 13

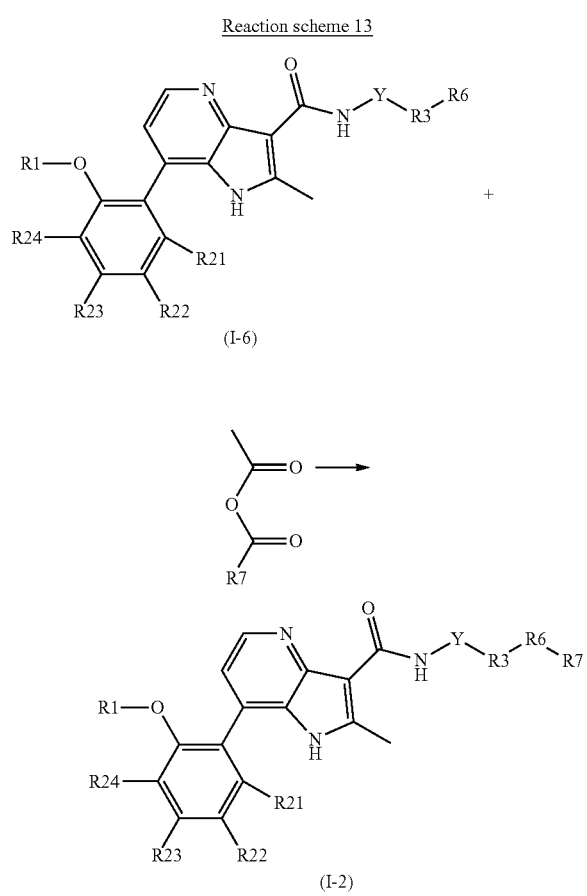

As shown in reaction scheme 13, compounds of formula (I-2), wherein R1, R21, R22, R23, R24 and Y have the above defined meanings and R3 is a 3-6C-cycloalkyl group substituted by R6 with R6 being —NH—C(O)—R7 with R7 being hydrogen can be prepared from compounds of formula (I-6), wherein R1, R21, R22, R23, R24 and Y have the above defined meanings and R3 is a 3-6C-cycloalkyl group substituted by R6 with R6 being —NH$_2$, obtained according to reaction scheme 9. In particular, the compound R7-C(O)—O—C(O)—CH$_3$ with R7 being hydrogen, which can be prepared by methods known to a person skilled in the art, can be added to the compound of formula (I-6) which is preferably dissolved in an organic solvent, such as dichloromethane, in the presence of a base, such as diazabicycloundecene (DBU). The addition is preferably carried out at a temperature of from 0 to 20° C. After completion of addition, the reaction is preferably continued at ambient temperature (e.g. 20 to 25° C.) for 1 to 24 h to yield a compound of formula (I-2).

As shown in reaction scheme 14, compounds of formula (16a) or (16b) can be prepared from known compounds (18a) or (18b) [Zhao, S.; Ghosh, A.; D'Andrea, S. V.; Freeman, P.; VonVoigtlander, P. F.; Carter, D. B.; Smith, M. W.; Heterocycles, 1994, 39, 163 and Erickson, S. D.; Banner, B.; Berthel, S.; Conde-Knape, K.; Falicioni, F.; Hakimi, I.; Hennessy, B.; Kester, R. F.; Kim, K.; Ma, Ch.; McComas, W.; Mennona, F.; Mischke, S.; Orzechowski, L.; Qian, Y.; Salari, H.; Tengi, J.; Thakkar, K.; Taub, R.; Tilley, J. W.; Wang, H.; Bioorg. Med. Chem. Lett. 2008, 18, 1402] by methods known to a person skilled in the art for example by catalytic hydrogenation in an organic solvent like ethanol or methanol in the presence of a precious metal catalyst like palladium on carbon or platinum oxide at a temperature of from 20 to 50° C. and at standard atmospheric pressure (101,325 kPa) to 1050 kPa for 1 h to 48 h.

It is known to the person skilled in the art that, if there are a number of reactive centers on a starting or intermediate compound, it may be necessary to block one or more reactive centers temporarily by protective groups in order to allow a reaction to proceed specifically at the desired reaction center.

The compounds according to the present subject matter are isolated and purified in a manner known per se, e.g. by distilling off the solvent in vacuo and recrystallizing the residue obtained from a suitable solvent or subjecting them to one of the customary purification methods, such as column chromatography on a suitable support material.

Salts of the compounds of formula (I) and the stereoisomers thereof can be obtained by dissolving the free compound in a suitable solvent (for example a ketone such as acetone, methylethylketone or methylisobutylketone, an ether such as diethyl ether, tetrahydrofurane or dioxane, a chlorinated hydrocarbon such as methylene chloride or chloroform, a low molecular weight aliphatic alcohol such as methanol, ethanol or isopropanol, a low molecular weight aliphatic ester such as ethyl acetate or isopropyl acetate, or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the compounds of formula (I) and the salts thereof can be obtained e.g. by asymmetric synthesis, by using chiral starting compounds in synthesis and/or by splitting up enantiomeric and diasteriomeric mixtures obtained in synthesis. Preferably, the pure diastereomeric and pure enantiomeric compounds of the present subject matter are obtainable by using chiral starting compounds in synthesis and/or by splitting up enantiomeric and diasteriomeric mixtures obtained in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated e.g. by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

All patents, patent applications, publications, test methods and other materials cited herein are incorporated by reference in their entireties.

The following examples illustrate the present subject matter in greater detail, without restricting it. Further compounds according to the present subject matter, of which the preparation is not explicitly described, can be prepared in an analogous way.

The compounds, salts and stereoisomers which are mentioned in the examples, and the salts of the compounds which are mentioned in the examples, and the stereoisomers of the compounds mentioned in the examples, the stereoisomers of the salts which are mentioned in the examples and the stereoisomers of the salts of the compounds which are mentioned in the examples represent preferred embodiments of the present subject matter.

EXAMPLES

The following abbreviations are used: min: minutes, h: hour(s), DCM: dichloromethane, DCE: dichloroethane, THF: tetrahydrofuran, EA: ethyl acetate, sesamol: 3,4-methylenedioxyphenol, brine: saturated sodium chloride solution, DBU: 1,8-diazabicyclo[5.4.0]undec-7-ene, Huenigs base: N-ethyl-diisopropylamine, mp.: melting point, bp: boiling point, RT: room temperature (20 to 25° C.), ambient temperature: 20 to 25° C., TLC: thin layer chromatography, HPLC: high performance liquid chromatography, GC-MS (EI): gas chromatography coupled to mass spectrometry with electron impact ionization, MS (ESI): mass spectrometry with electron spray ionization, $^1$H-NMR: $^1$H nuclear magnetic resonance spectroscopy (chemical shifts are reported as ppm against tetramethylsilane as internal standard, coupling constants J are reported in Hz). Epimers and/or racemates are marked herein with a "*" in the chemical name at the corresponding stereogenic center.

Example A1

Ethyl 4-[(2,2-dimethyl-4,6-dioxo-[1,3]dioxan-5-ylidenemethyl)-amino]-2-methyl-1H-pyrrole-3-carboxylate Sodium ethoxide (21% solution in EtOH, 140.0 mL, 1.91 mol) is added to dry EtOH (2900 mL), followed by (E)-3-(cyanomethyl-1-amino)but-2-enoic acid ethyl ester (254.5 g, 1.51 mol) that is prepared according to literature [Birnberg, G. H.; William, J. F.; Gerardo, D. F.; Epstein, J. W. J. Heterocycl. Chem, 1995, 32, 1293]. The stirred suspension is heated to reflux for 3 hours to come to complete transformation as monitored by LC-MS. The resulting solution is cooled to ambient temperature and neutralized to pH 7 by careful addition of acetic acid (about 100 mL).

Commercially available 5-methoxymethylene-2,2-dimethyl-[1,3]dioxane-4,6-dione (337.0 g, 1.81 mol) is added. The mixture is heated to reflux for one hour and stirred at ambient temperature over night. The precipitated product is filtered, washed with several small portions of EtOH and dried in vacuum at 50° C. to yield the title compound as yellow solid.

$^1$H-NMR (300 MHz, CDCl$_3$): 11.84 (d, J=15.0, 1H, —NH); 11.55 (s, 1H, —NH); 8.48 (d, J=15.0, 1H); 7.31 (d, J=2.6, 1H); 4.27 (qu, J=7.1, 2H); 2.39 (s, 3H); 1.65 (s, 6H); 1.31 (t, J=7.1, 3H).

Example A2

Ethyl 7-hydroxy-2-methyl-1H-pyrrolo[3,2-b]pyridine-3-carboxylate

Ethyl 4-[(2,2-dimethyl-4,6-dioxo-[1,3]dioxan-5-ylidenemethyl)-amino]-2-methyl-1H-pyrrole-3-carboxylate from example A1 (110.0 g, 0.34 mol) is suspended in dry nitrotoluene (550 mL). The well stirred suspension is heated to 250° C. for three hours. Formed acetone (about 70 mL) is removed by distillation. From the black reaction mixture nitrobenzene (300 mL) is removed by careful distillation under reduced pressure. The tarry residue is cooled to ambient temperature. After addition of tert.-BuOMe (800 mL) stirring is continued at ambient temperature over night. The crude product is filtered and washed with tert.-BuOMe (2×50 mL).

The black solid is treated with boiling 4N hydrochloric acid (220 mL) for one hour. After cooling to ambient temperature the residue is filtered and again treated with boiling 4N hydrochloric acid (2×150 mL). The combined aqueous filtrates are concentrated under reduced pressure to about 350 mL and extracted with dichloromethane (4×200 mL). The aqueous layer is stripped from dichloromethane under reduced pressure, carefully neutralized to pH 8 by dropwise addition of 6N NaOH at ambient temperature and stirred over night.

The precipitated product is filtered, washed with several small portions of water and dried in vacuum at 60° C. for 24 hours to yield the title compound as off-white solid.

MS (ESI): m/z=221 (MH$^+$, 100%).

$^1$H-NMR (300 MHz, CDCl$_3$): 12.35 (s, 1H, —NH); 11.01 (s, 1H, —NH/—OH); 7.52 (dd, J=7.2, 5.7, 1H); 5.96 (d, J=7.2, 1H); 4.31 (qu, J=7.1, 2H); 2.54 (s, 3H); 1.33 (t, J=7.1, 3H).

Example A3

Ethyl-7-chloro-2-methyl-1H-pyrrolo[3,2-b]pyridine-3-carboxylate

Ethyl 7-hydroxy-2-methyl-1H-pyrrolo[3,2-b]pyridine-3-carboxylate (44.0 g, 0.20 mol) is suspended in dry acetonitrile (400 mL). After addition of $POCl_3$ (47 mL, 0.50 mol) the stirred reaction mixture is heated to reflux for 4 hours. The volatiles are removed under reduced pressure. The residue is suspended in ice-cold water (500 mL) and carefully neutralized to pH 8 by dropwise addition of 6N NaOH. Stirring is continued at ambient temperature over night. The pH is readjusted to 8, the product is filtered, washed with several small portions of water and dried in vacuum at 50° C. for 24 hours to yield the title compound as off-white solid.

MS (ESI): m/z=239 ($MH^+$, 100%).

$^1$H-NMR (300 MHz, $CDCl_3$): 12.39 (s, 1H, —NH); 8.35 (d, J=5.2, 1H); 7.29 (d, J=5.2, 1H); 4.29 (qu, J=7.1, 2H); 2.72 (s, 3H); 1.32 (t, J=7.1, 3H).

Example B.a1

2-Bromo-5-fluoro-4-methoxy-phenol

3-Fluoro-4-methoxy-phenol (21.32 g; 0.15 mol) prepared according to literature [Freedman, J.; Stewart, K. T.; J. Heterocycl. Chem. 1989, 26, 1547-1554] is dissolved in dry dichloromethane (300 mL). The well stirred reaction mixture is cooled to −15° C. (ice/salt). A solution of bromine (23.97 g; 0.15 mol) in dry dichloromethane (75 mL) is dropped into the reaction mixture. After complete addition stirring is continued for one hour. Water (150 mL) containing sodium sulfite (3.0 g) is added to the reaction mixture. Stirring is continued at ambient temperature for 30 min. The organic layer is separated, ished with water (100 mL) and dried over $MgSO_4$ in the presence of decolorizing charcoal. After filtration the solvent is completely removed under reduced pressure. The residue is crystallized from tert-butylmethylether/hexane to yield the title compound as a colorless solid.

GC-MS (EI): m/z=222, 220 ($M^+$); 207, 205 ($M^+$-$CH_3$, 100%); 179, 177.

$^1$H-NMR (300 MHz, DMSO-$d_6$): 10.06 (s, 1H, —OH); 7.28 (d, J=9.2, 1H); 6.81 (d, J=12.6, 1H); 3.76 (s, 3H).

The following compound is obtained analogously to the procedure described in above example B.a1.

Example B.a2

2-Bromo-4-fluoro-5-methoxy-phenol

Starting from 4-fluoro-3-methoxy-phenol prepared according to literature [Belanger, P. C.; Lau, C. K.; Williams, H. W. R.; Dufresne, C.; Scheigetz, J. Can. J. Chem. 1988, 66, 1479-1482] the title compound is obtained as colorless solid.

GC-MS (EI): m/z=222, 220 ($M^+$, 100%); 207, 205 ($M$-$CH_3^+$); 179, 177.

$^1$H-NMR (300 MHz, $CDCl_3$): 7.16 (d, J=10.2, 1H); 6.67 (d, J=7.7, 1H); 5.29 (s, 1H, —OH); 3.85 (s, 3H).

Example B.b1

5-Cyclopropylmethoxy-benzo[1,3]dioxole

Sodium hydride (60 wt % dispersion in mineral oil; 11.0 g; 275.0 mmol) is freed from oil by ishing with hexane (2×50 mL) and suspended in dry DME (375 mL) and dry DMSO (37.5 mL).

Under an atmosphere of nitrogen a solution of commercially available sesamol (3,4-methylenedioxy-phenol) (34.53 g; 250.0 mmol) in dry DME (250 mL) is dropped into the well-stirred suspension at a rate to keep the internal temperature below 40° C. After complete addition stirring is continued at ambient temperature for one hour.

Neat commercially available bromomethyl-cyclopropane (37.13 g; 275.0 mmol) is added in one portion and the reaction mixture is stirred at 80° C. over night. Ice-cold water (125 mL) is drop wise added and the reaction mixture is stirred for 30 min at ambient temperature. After addition of brine (125 mL) the organic layer is separated and concentrated in vacuo. The aqueous layer is extracted with tert-butylmethylether (3×200 mL). All organic phases are combined, washed with brine (200 mL), dried over $MgSO_4$ and filtered through a plug of neutral alumina containing 5 wt % of water.

The product is completely eluted with several portions of tert-butylmethylether. The solvent is removed under reduced pressure. The remaining crude product is purified by short path distillation at $3 \times 10^{-3}$ mbar (117° C.) to give the title compound as colorless oil that solidifies at ambient temperature.

GC-MS (EI): m/z=192 ($M^+$); 138 ($M^+$-$C_4H_6$, 100%).

$^1$H-NMR (200 MHz, DMSO-$d_6$): 6.77 (d, J=8.5, 1H); 6.59 (d, J=2.5, 1H); 6.32 (dd, J=8.5, 2.5, 1H); 5.93 (s, 2H); 3.71 (d, J=6.9, 2H); 1.15 (m, 1H); 0.53 (m, 2H); 0.27 (m, 2H).

The following compounds are obtained analogously to the procedure described in above example B.b1.

Example B.b2

1-Bromo-2-cyclopropylmethoxy-4-fluoro-benzene

Starting from commercially available 2-bromo-5-fluoro-phenol and commercially available bromo-methyl-cyclopropane the title compound is obtained as colorless oil after distillation at $5 \times 10^{-3}$ mbar.

GC-MS (EI): m/z=244, 246 ($M^+$); 190, 192 ($M^+$-$C_4H_6$); 55 (100%).

$^1$H-NMR (300 MHz, DMSO-$d_6$): 7.58 (dd, J=8.7, 6.4, 1H); 7.02 (dd, J=11.2, 2.8, 1H); 6.75 (ddd, J=8.7, 2.8, 1H); 3.93 (d, J=6.8, 2H); 1.24 (m, 1H); 0.56 (m, 2H); 0.38 (m, 2H).

Example B.b3

1-Bromo-2-cyclopropylmethoxy-5-fluoro-benzene

Starting from commercially available 2-bromo-4-fluoro-phenol and commercially available bromo-methyl-cyclopropane the title compound is obtained as colorless oil after distillation at $5 \times 10^{-3}$ mbar.

GC-MS (EI): m/z=244, 246 ($M^+$); 190, 192; ($M^+$-$C_4H_6$); 55 (100%).

$^1$H-NMR (400 MHz, DMSO-$d_6$): 7.52 (dd, $J_1$=8.2, $J_2$=3.1, 1H); 7.19 (ddd, $J_1$=9.1, $J_2$=8.2, $J_3$=3.1, 1H); 7.10 (dd, $J_1$=9.1, $J_2$=5.0, 1H); 3.89 (d, J=6.8, 2H); 1.22 (m, 2H); 0.57 (m, 2H); 0.35 (m, 2H).

Example B.b4

1-Bromo-2-cyclopropylmethoxy-4-methoxy-benzene

Starting from commercially available 2-bromo-5-methoxy-phenol and bromomethyl-cyclopropane the title compound is obtained as colorless solid.

GC-MS (EI): m/z=258, 256 ($M^+$).

¹H-NMR (200 MHz, DMSO-d₆): 7.41 (d, J=7.9, 1H); 6.48 (dd, J₁=7.9, J₂=2.2, 1H); 6.45 (d, J=2.2, 1H); 3.87 (d, J=5.6, 2H); 3.76 (s, 3H); 1.26 (m, 1H); 0.63 (m, 2H); 0.36 (m, 2H).

Example B.b5

1-Bromo-2-cyclopropylmethoxy-5-methoxy-benzene

Starting from commercially available 2-bromo-4-methoxy-phenol and bromomethyl-cyclopropane the title compound is obtained as colorless oil after distillation at $5 \times 10^{-3}$ mbar.

GC-MS (EI): m/z=256, 258 (M⁺); 202, 204 (100%).

¹H-NMR (200 MHz, CDCl₃): 7.11 (d, J=2.8, 1H); 6.86 (d, J=8.9, 1H); 6.78 (dd, J₁=8.9, J₂=2.8, 1H); 3.82 (d, J=6.8, 2H); 3.75 (s, 3H); 1.16 (m, 1H); 0.51 (m, 2H); 0.44 (m, 2H).

Example B.b6

2-Bromo-1-cyclopropylmethoxy-4-methyl-benzene

Starting from commercially available 2-bromo-4-methyl-phenol and bromomethyl-cyclopropane the title compound is obtained as colorless oil after distillation at $5 \times 10^{-3}$ mbar.

GC-MS (EI): m/z=242, 240 (M⁺); 188, 186 (M⁺-C₄H₆); 107; 80, 78; 55 (100%).

¹H-NMR (300 MHz, DMSO-d₆): 7.38 (dd, J=2.2, 0.7, 1H); 7.10 (ddd, J=8.4, 2.2, 0.7, 1H); 6.96 (d, J=8.4, 1H); 3.86 (d, J=6.8, 2H); 2.22 (s, 3H); 1.21 (m, 1H); 0.56 (m, 2H); 0.33 (m, 2H).

Example B.b7

1-Bromo-2-cyclopropylmethoxy-4-fluoro-5-methoxy-benzene

Starting from 2-bromo-5-fluoro-4-methoxy-phenol (example B.e1) and commercially available bromomethyl-cyclopropane the title compound is obtained as colorless solid.

GC-MS (EI): m/z=276, 274 (M⁺); 222, 220 (M⁺-C₄H₆, 100%); 206, 204.

¹H-NMR (400 MHz, DMSO-d₆): 7.38 (d, J=9.2, 1H); 7.13 (d, J=13.1, 1H); 3.85 (d, J=6.9, 2H); 3.80 (s, 3H); 1.20 (m, 1H); 0.57 (m, 2H); 0.33 (m, 2H).

Example B.b8

1-Bromo-2-cyclopropylmethoxy-5-fluoro-4-methoxy-benzene

Starting from 2-bromo-4-fluoro-5-methoxy-phenol (example B.a2) and commercially available bromomethyl-cyclopropane the title compound is obtained as colorless solid.

GC-MS (EI): m/z=276, 274 (M⁺); 222, 220 (M⁺-C₄H₆, 100%).

¹H-NMR (400 MHz, DMSO-d₆): 7.48 (d, J=10.8, 1H); 6.90 (d, J=7.9, 1H); 3.93 (d, J=6.8, 2H); 3.85 (s, 3H); 1.24 (m, 1H); 0.58 (m, 2H); 0.36 (m, 2H).

Example B.c1

5-Cyclopropylmethoxy-4-(4,4,5,5-tetramethyl-[1,3,2]dioxaborolan-2-yl)-benzo[1,3]dioxole The reaction is performed in flame-dried glassware under an atmosphere of argon.

A stirred solution of 5-cyclopropylmethoxy-benzo[1,3]dioxole from example B.b1 (38.44 g; 200.0 mmol) in dry THF (500 mL) is cooled to −40° C. before n-butyl lithium (138.0 mL; 1.6 M solution in hexane; 220 mmol) is slowly added via syringe. After complete addition, stirring is continued at −40° C. for two hours. At −78° C. neat 2-iso-propoxy-4,4,5,5-tetramethyl-[1,3,2]dioxaborolane (40.95 g; 220.0 mmol) is added via syringe and stirring is continued at −78° C. for two hours.

At −15° C. the reaction mixture is quenched with saturated NH₄Cl-solution (200 mL) and stirred at ambient temperature for 30 min. The organic layer is separated and concentrated under reduced pressure. The aqueous layer is extracted with tert. butylmethylether (3×200 mL). All organic phases are combined, washed with saturated NaCl-solution (200 dried over MgSO₄ and filtered through a plug of neutral alumina containing 5 wt % of water. The product is completely eluted with several small portions of tert. butylmethylether.

The solvent is removed under reduced pressure. The crude is treated with ice-cold methanol (50 mL) to deliver the title compound as colorless solid.

GC-MS (EI): m/z=318 (M⁺); 264 (M⁺-C₄H₆); 207; 164 (100%).

¹H-NMR (200 MHz, DMSO-d₆): 6.78 (d, J=8.4, 1H); 6.29 (d, J=8.4; 1H); 5.92 (s, 2H); 3.71 (d, J=6.3, 2H); 1.29 (s, 12H); 1.14 (m, 1H); 0.50 (m, 2H); 0.34 (m, 2H).

Example B.c2

2-(2-Cyclopropylmethoxy-4-fluoro-5-methoxy-phenyl)-4,4,5,5-tetramethyl-[1,3,2]dioxaborolane The reaction is performed in flame-dried glassware under an atmosphere of argon.

A stirred solution of 1-bromo-2-cyclopropylmethoxy-4-fluoro-5-methoxy-benzene from example B.b7 (27.51 g; 0.10 mol) in dry tert. butylmethylether (500 mL) is cooled to −20° C. before addition of n-butyl lithium (1.6 M in hexane; 68.8 mL; 0.11 mol) via syringe. After complete addition stirring is continued for one hour. Neat 2-iso-propoxy-4,4,5,5-tetramethyl-[1,3,2]dioxaborolane is added via syringe into the reaction mixture at −40° C. After 30 min the reaction is quenched with 1M citric acid (200 mL) at 0° C. and stirred for one hour at ambient temperature. The organic layer is separated. The aqueous layer is extracted with tert. butylmethylether (100 mL). The combined organic layers are washed with brine (200 mL) dried over MgSO₄ and filtered through a plug of neutral alumina containing 5 wt % of water. The product is completely eluted with several small portions of tert. butylmethylether. The solvent is removed under reduced pressure. The crude is purified by short path distillation at $3 \times 10^{-3}$ mbar (160° C.) to give the title compound as a colorless oil that solidifies at ambient temperature.

GC-MS (EI): m/z=322 (M⁺, 100%); 211, 168.

¹H-NMR (300 MHz, DMSO-d₆): 7.14 (d, J=10.5, 1H); 6.91 (d, J=13.6, 1H); 3.81 (d, J=6.0, 2H); 3.77 (s, 3H); 1.28 (s, 12H); 1.16 (m, 1H); 0.48 (m, 2H); 0.38 (m, 2H).

The following compounds are obtained analogously to the procedure described in above example B.c2.

Example B.c3

2-(2-Cyclopropylmethoxy-4-fluoro-phenyl)-4,4,5,5-tetramethyl-[1,3,2]dioxaborolane Starting from 1-bromo-2-cyclopropylmethoxy-4-fluoro-benzene (example B.b2) the title compound is obtained as colorless solid after short bath distillation at $3 \times 10^{-3}$ mbar (130° C.).

GC-MS (EI): m/z=292 (M+); 181, 55 (100%).

¹H-NMR (300 MHz, DMSO-d₆): 7.48 (dd, J1=J2=8.0, 1H); 6.80 (dd, J1=12.0, J2=2.2, 1H); 6.71 (ddd, J1=8.4, J2=8.0, J3=2.2, 1H); 3.89 (d, J=5.8, 2H); 1.27 (s, 12H); 1.17 (m, 1H); 0.51 (m, 2H); 0.46 (m, 2H).

Example B.c4

2-(2-Cyclopropylmethoxy-5-fluoro-phenyl)-4,4,5,5-tetramethyl-[1,3,2]dioxaborolane Starting from 1-bromo-2-cyclopropylmethoxy-5-fluoro-benzene (example B.b3) the title compound is obtained as colorless solid after short bath distillation at $3 \times 10^{-3}$ mbar (100° C.).

GC-MS (EI): m/z=292 (M+); 181 (100%); 55.

¹H-NMR (300 MHz, DMSO-d₆): 7.22-7.13 (m, 2H); 6.95 (dd, J1=8.9, J2=4.2, 1H); 3.85 (d, J=6.4, 2H); 1.28 (s, 12H); 1.17 (m, 1H); 0.52 (m, 2H); 0.46 (m, 2H).

Example B.c5

2-(2-Cyclopropylmethoxy-4-methoxy-phenyl)-4,4,5,5-tetramethyl-[1,3,2]dioxaborolane Starting from 1-bromo-2-cyclopropylmethoxy-4-methoxy-benzene (example B.b4) the title compound is prepared as colorless solid after crystallization from hexane.

GC-MS (EI): m/z=304 (M+); 276; 250; 193; 164 (100%); 150.

¹H-NMR (200 MHz, DMSO-d₆): 7.41 (d, J=7.9, 1H); 6.48 (dd, J₁=7.9, J₂=2.2, 1H); 6.45 (d, J=2.2, 1H); 3.87 (d, J=5.6, 2H); 3.75 (s, 3H); 1.25 (s, 12H); 1.16 (m, 1H); 0.49 (m, 2H); 0.44 (m, 2H).

Example B.c6

2-(2-Cyclopropylmethoxy-5-methoxy-phenyl)-4,4,5,5-tetramethyl-[1,3,2]dioxaborolane Starting from 1-bromo-2-cyclopropylmethoxy-5-methoxy-benzene (example B.b5) the title compound is obtained as colorless oil after short bath distillation at $3 \times 10^{-3}$ mbar (160° C.).

GC-MS (EI): m/z=304 (M+); 276; 250; 193 (100%); 150.

¹H-NMR (200 MHz, CDCl₃): 7.15 (d, J=3.1, 1H); 6.90 (dd, J₁=9.0, J₂=3.1, 1H); 6.81 (d, J=9.0, 1H); 3.80 (d, J=6.3, 2H); 3.78 (s, 3H); 1.35 (s, 12H); 1.17 (m, 1H); 0.55 (m, 2H); 0.38 (m, 2H).

Example B.c7

2-(2-Cyclopropylmethoxy-5-methyl-phenyl)-4,4,5,5-tetramethyl-[1,3,2]dioxaborolane Starting from 1-bromo-2-cyclopropylmethoxy-5-methyl-benzene (example B.b6) the title compound is obtained as colorless solid.

GC-MS (EI): m/z=288 (M+); 177 (100%).

¹H-NMR 400 MHz, DMSO-d₆): 7.26 (d, J=2.1, 1H); 7.16 (dd, J₁=8.3, J₂=2.1, 1H); 6.81 (d, J=8.3, 1H); 3.81 (d, J=5.9, 2H); 2.21 (s, 3H); 1.27 (s, 12H); 1.15 (m, 1H); 0.47 (m, 2H); 0.40 (m, 2H).

Example B.c8

2-(2-Cyclopropylmethoxy-5-fluoro-4-methoxy-phenyl)-4,4,5,5-tetramethyl-[1,3,2]dioxaborolane Starting from 1-bromo-2-cyclopropylmethoxy-5-fluoro-4-methoxy-benzene (example B.b8) the title compound is obtained as colorless solid after crystallization from methanol.

GC-MS (EI): m/z=322 (M+); 211; 182; 168 (100%); 55.

¹H-NMR (300 MHz, DMSO-d₆): 7.15 (d, J=11.7, 1H); 6.73 (d, J=7.0, 1H); 3.88 (d, J=6.0, 2H); 3.85 (s, 3H); 1.26 (s, 12H); 1.16 (m, 1H); 0.50 (m, 2H); 0.30 (m, 2H).

Example C1 tert-Butyl-(3R*,4R*)-4-azido-3-hydroxy-piperidine-1-carboxylate (23f) and tert-butyl-(3S*,4S*)-3-azido-4-hydroxy-piperidine-1-carboxylate (23g)

A mixture of tert-butyl 7-oxa-3-azabicyclo[4.1.0]heptane-3-carboxylate (60 g, 0.30 mol), prepared according to literature [Zhao, S.; Ghosh, A.; D'Andrea, S. V.; Freeman, P.; VonVoigtlander, P. F.; Carter, D. B.; Smith, M. W.; Heterocycles, 1994, 39, 163], sodium azide (25.4 g, 0.39 mol) and ammonium chloride (21 g, 0.39 mol) in ethanol (150 mL) and water (150 mL) is heated to gentle reflux overnight. Ethanol is evaporated in vacuo. The residue is distributed between dichloromethane and water. The aqueous layer is separated and extracted with dichloromethane. The combined organic layer is washed with water and brine, dried over Na₂SO₄ and concentrated in vacuo to obtain, the crude as a 4:1 mixture 23f and 23g according to ¹H-NMR in agreement with literature data [Erickson, S. D.; Banner, B.; Berthel, S.; Conde-Knape, K.; Falicioni, F.; Hakimi, I.; Hennessy, B.; Kester, R. F.; Kim, K.; Ma, Ch.; McComas, W.; Mennona, F.; Mischke, S.; Orzechowski, L.; Qian, Y.; Salari, H.; Tengi, J.; Thakkar, K.; Taub, R.; Tilley, J. W.; Wang, H.; Bioorg. Med. Chem. Lett. 2008, 18, 1402].

Separation by column chromatography on silica gel (heptane:ethyl acetate—4:1) yields of faster eluting 23f, of slower eluting 23g and of un-separated 23f and 23g.

tert-Butyl-(3R*,4R*)-4-azido-3-hydroxy-piperidine-1-carboxylate (23f)

MS (ESI): m/z=217 (MH+, 100%).

¹H-NMR (400 MHz, CDCl₃): 4.12 (m, 1H); 3.95 (br.m, 1H); 3.50 (m, 1H); 3.38 (m, 1H); 2.89 (m, 1H); 2.78 (m, 1H); 2.71-2.32 (m, 1H); 2.00 (m, 1H); 1.52 (m, 1H); 1.44 (s, 9H).

tert-Butyl-(3S*,4S*)-3-azido-4-hydroxy-piperidine-1-carboxylate (23g)

MS (ESI): m/z=217 (MH+, 100%).

¹H-NMR (400 MHz, CDCl₃): 4.23 (m, 1H); 4.00 (m, 1H); 3.54 (m, 1H); 3.30 (m, 1H); 2.82 (m, 1H); 2.66 (m, 1H); 2.24 (m, 1H); 1.97 (m, 1H); 1.59 (m, 1H); 1.46 (s, 9H).

Example C2 tert-Butyl (3R*,4R*)-4-amino-3-hydroxy-piperidine-1-carboxylate (21f)

(3S*,4S*)-tert-butyl 4-azido-3-hydroxypiperidine-1-carboxylate from example C1 (47 g, 194 mmol) is dissolved in methanol (1200 mL) under nitrogen. Palladium hydroxide (20% on carbon; 4.7 g) is added. The atmosphere is changed to hydrogen and the stirred reaction mixture is hydrogenated at room temperature and 70 psi for 72 hours. The mixture is filtered through celite. The filtrate is evaporated. The residue is recrystallized from $CH_2Cl_2$ with a small amount of MeOH to obtain the title compound as a white solid.

HR-MS (ESI): m/z=217.1539 ([MH]$^+$, $C_{10}H_{21}N_2O_3^+$, calc. 217.1547).

Example C3 tert-Butyl (3S*,4S*)-3-Amino-4-hydroxy-piperidine-1-carboxylate (21g)

Following the procedure outlined in above example C2 starting from (3S*,4S*)-3-azido-4-hydroxy-piperidine-1-carboxylic acid tert-butyl ester (example C1) the title compound is obtained as white solid HR-MS (ESI): m/z=217.1541 ([MH]$^+$, $C_{10}H_{21}N_2O_3^+$, calc. 217.1547).

Example D.a1

Ethyl-7-(5-cyclopropylmethoxy-benzo[1,3]dioxol-4-yl)-1-methoxymethyl-2-methyl-1H-pyrrolo[3,2-b]pyridine-3-carboxylate Ethyl-7-chloro-2-methyl-1H-pyrrolo[3,2-b]pyridine-3-carboxylate from example A3 (11.98 g; 50.0 mmol), dioxane (200 mL) and $Cs_2CO_3$ (2M aqueous solution; 75.0 mL; 150.0 mmol) is heated to 80° C. under nitrogen before addition of Pd(OAc)$_2$ (247 mg; 1.1 mmol) and tricyclohexylphosphine (617 mg; 2.2 mmol). After 30 min a solution of 5-cyclopropylmethoxy-4-(4,4,5,5-tetramethyl-[1,3,2]dioxaborolan-2-yl)-benzo[1,3]dioxole from example B.c1 (17.50 g; 55.0 mmol) in dioxane (50.0 mL) and the reaction mixture is heated to 100° C. until the starting material is consumed according to LC-MS.

The cooled reaction mixture is diluted with water (250 mL) and acidified to pH=6 by careful addition of 2M aqueous citric acid. The precipitated crude is filtered, dissolved in dioxane and filtered through a short column of neutral alumina (act. 2-3). The column is rinsed with several portions of dioxane. The filtrate is concentrated under reduced pressure and the product is collected with tert-butyl methyl ether to yield the title compound as off-white solid.

MS (ESI): m/z=395 (MH$^+$, 100%).

$^1$H-NMR (300 MHz, DMSO-d$_6$): 11.51 (br.s, 1H, —NH); 8.41 (d, J=4.9, 1H); 7.13 (d, J=4.9, 1H); 6.94 (d, J=8.6, 1H); 6.54 (d, J=8.6, 1H); 5.99 (s, 2H); 4.29 (qu, J=7.1, 2H); 3.74 (d, J=6.7, 2H); 2.68 (s, 3H); 1.32 (t, J=7.1, 3H); 0.93 (m, 1H); 0.35 (m, 2H); 0.14 (m, 2H).

The following compounds were prepared analogously to the procedure described in above example D.a1.

Example D.a2

Ethyl 7-[2-(cyclopropylmethoxy)-4-fluorophenyl]-2-methyl-1H-pyrrolo[3,2-b]pyridine-3-carboxylate Starting from ethyl-7-chloro-2-methyl-1H-pyrrolo[3,2-b]pyridine-3-carboxylate (example A3) and 2-(2-cyclopropylmethoxy-4-fluoro-phenyl)-4,4,5,5-tetramethyl-[1,3,2]dioxaborolane (example B.c3) the title compound is obtained as off-white solid.

MS (ESI): m/z=369 (MH$^+$, 100%).

$^1$H-NMR (300 MHz, DMSO-d$_6$): 11.33 (s, 1H, —NH); 8.42 (d, J=4.9, 1H); 7.40 (dd, J=8.4, 6.9, 1H); 7.05 (dd, J=11.7, 2.5, 1H); 7.03 (d, J=4.9, 1H); 6.91 (ddd, J=8.4, 8.4, 2.5, 1H); 4.29 (qu, J=6.9, 2H); 3.87 (d, J=6.8, 2H); 2.68 (s, 3H); 1.32 (t, J=6.9, 3H); 0.94 (m, 1H); 0.36 (m, 2H); 0.21 (m, 2H).

Example D.a3

Ethyl 7-[2-(cyclopropylmethoxy)-5-fluorophenyl]-2-methyl-1H-pyrrolo[3,2-b]pyridine-3-carboxylate Starting from ethyl-7-chloro-2-methyl-1H-pyrrolo[3,2-b]pyridine-3-carboxylate (example A3) and 2-(2-cyclopropylmethoxy-5-fluoro-phenyl)-4,4,5,5-tetramethyl-[1,3,2]dioxaborolane (example B.c4) the title compound is obtained as off-white solid.

MS (ESI): m/z=369 (MH$^+$, 100%).

$^1$H-NMR (300 MHz, DMSO-d$_6$): 11.48 (s, 1H, —NH); 8.44 (d, J=4.9, 1H); 7.31 (dd, J=8.8, 3.2, 1H); 7.26 (ddd, J=8.9, 8.0, 3.2, 1H); 7.14 (dd, J=8.9, 4.6, 1H); 7.08 (d, J=4.9, 1H); 4.30 (qu, J=7.1, 2H); 3.83 (d, J=6.8, 2H); 2.69 (s, 3H); 1.33 (t, J=7.1, 3H); 0.92 (m, 1H); 0.34 (m, 2H); 0.17 (m, 2H).

Example D.a4

Ethyl 7-[2-(cyclopropylmethoxy)-4-methoxyphenyl]-2-methyl-1H-pyrrolo[3,2-b]pyridine-3-carboxylate Starting from ethyl-7-chloro-2-methyl-1H-pyrrolo[3,2-b]pyridine-3-carboxylate (example A3) and 2-(2-cyclopropylmethoxy-4-methoxy-phenyl)-4,4,5,5-tetramethyl-[1,3,2]dioxaborolane (example B.c5) the title compound is obtained as off-white solid.

MS (ESI): m/z=381 (MH$^+$, 100%).

$^1$H-NMR (300 MHz, DMSO-d$_6$): 11.35 (s, 1H, —NH); 8.39 (d, J=4.9, 1H); 7.29 (d, J=8.8, 1H); 7.00 (d, J=4.9, 1H); 6.68 (dd, J=7.8, 2.3, 1H); 6.67 (d, J=2.3, 1H); 4.29 (qu, J=7.1, 2H); 3.86 (d, J=6.9, 2H); 3.83 (s, 3H); 2.68 (s, 3H); 1.32 (t, J=7.1, 3H); 0.93 (m, 1H); 0.35 (m, 2H); 0.21 (m, 2H).

Example D.a5

Ethyl 7-[2-(cyclopropylmethoxy)-5-methoxyphenyl]-2-methyl-1H-pyrrolo[3,2-b]pyridine-3-carboxylate Starting from ethyl-7-chloro-2-methyl-1H-pyrrolo[3,2-b]pyridine-3-carboxylate (example A3) and 2-(2-cyclopropylmethoxy-5-methoxy-phenyl)-4,4,5,5-tetramethyl-[1,3,2]dioxaborolane (example B.c6) the title compound is obtained as yellow solid.

MS (ESI): m/z=381 (MH$^+$, 100%).

$^1$H-NMR (300 MHz, DMSO-d$_6$): 11.43 (s, 1H, —NH); 8.42 (d, J=4.9, 1H); 7.08 (d, J=8.9, 1H & d, J=4.9, 1H); 7.02 (dd, J=8.9, 2.9, 1H); 6.94 (d, J=2.9, 1H); 4.29 (qu, J=7.1, 2H);

3.78 (d, J=6.8, 2H); 3.76 (s, 3H); 2.69 (s, 3H); 1.33 (t, J=7.1, 3H); 0.91 (m, 1H); 0.33 (m, 2H); 0.14 (m, 2H).

Example D.a6

Ethyl 7-[2-(cyclopropylmethoxy)-5-methylphenyl]-2-methyl-1H-pyrrolo[3,2-b]pyridine-3-carboxylate Starting from ethyl-7-chloro-2-methyl-1H-pyrrolo[3,2-b]pyridine-3-carboxylate (example A3) and 2-(2-cyclopropyl-methoxy-5-methyl-phenyl)-4,4,5,5-tetramethyl-[1,3,2]dioxaborolane (example B.c7) the title compound is obtained as pale yellow solid.

MS (ESI): m/z=365 (MH$^+$, 100%).

$^1$H-NMR (300 MHz, DMSO-d$_6$): 11.39 (s, 1H, —NH); 8.41 (d, J=4.9, 1H); 7.25 (ddd, J=8.6, 2.2, 0.6, 1H); 7.18 (d, J=2.2, 1H); 7.04 (d, J=4.9, 1H); 7.03 (d, J=8.6, 1H); 4.29 (qu, J=7.1, 2H); 3.82 (d, J=6.8, 2H); 2.68 (s, 3H); 2.31 (s, 3H); 1.33 (t, J=7.1, 3H); 0.93 (m, 1H); 0.34 (m, 2H); 0.18 (m, 2H).

Example D.a7

Ethyl 7-[2-(cyclopropylmethoxy)-4-fluoro-5-methoxyphenyl]-2-methyl-1H-pyrrolo[3,2-b]pyridine-3-carboxylate Starting from ethyl-7-chloro-2-methyl-1H-pyrrolo[3,2-b]pyridine-3-carboxylate (example A3) and 2-(2-Cyclopropyl-methoxy-4-fluoro-5-methoxy-phenyl)-4,4,5,5-tetramethyl-[1,3,2]dioxaborolane (example B.c2) the title compound is obtained as off-white solid.

MS (ESI): m/z=399 (MH$^+$, 100%).

$^1$H-NMR (300 MHz, DMSO-d$_6$): 11.43 (s, 1H, —NH); 8.43 (d, J=4.9, 1H); 7.17 (d, J=8.4, 1H); 7.13 (d, J=12.1, 1H); 7.09 (d, J=4.9, 1H); 4.29 (qu, J=7.1, 2H); 3.84 (s, 3H); 3.80 (d, J=6.8, 2H); 2.68 (s, 3H); 1.33 (t, J=7.1, 3H); 0.91 (m, 1H); 0.34 (m, 2H); 0.16 (m, 2H).

Example D.a8

Ethyl 4-[2-(cyclopropylmethoxy)-5-fluoro-4-methoxyphenyl]-6-methyl-5H-pyrrolo[3,2-d]pyrimidine-7-carboxylate Starting from ethyl-7-chloro-2-methyl-1H-pyrrolo[3,2-b]pyridine-3-carboxylate (example A3) and 2-(2-cyclopropyl-methoxy-5-fluoro-4-methoxy-phenyl)-4,4,5,5-tetramethyl-[1,3,2]dioxaborolane (example B.c8) the title compound is obtained as pale yellow solid.

MS (ESI): m/z=399 (MH$^+$, 100%).

$^1$H-NMR (300 MHz, DMSO-d$_6$): 11.42 (s, 1H, —NH); 8.40 (d, J=4.8, 1H); 7.26 (d, J=11.9, 1H); 7.04 (d, J=4.8, 1H); 6.92 (d, J=7.7, 1H); 4.29 (qu, J=7.1, 2H); 3.94 (s, 3H); 3.89 (d, J=6.9, 2H); 2.68 (s, 3H); 1.32 (t, J=7.1, 3H); 0.93 (m, 1H); 0.36 (m, 2H); 0.18 (m, 2H).

Example D.b1

Ethyl 7-[5-(cyclopropylmethoxy)-1,3-benzodioxol-4-yl]-2-methyl-1-{[2-(trimethylsilyl)ethoxy]methyl}-1H-pyrrolo[3,2-b]pyridine-3-carboxylate Sodium hydride (1.77 g; ~60% dispersion in oil) is washed with hexane (2×25) and suspended in dry DMF (150 mL) and dry DMSO (50 mL). Ethyl-7-(5-cyclopropylmethoxy-benzo[1,3]dioxol-4-yl)-1-methoxymethyl-2-methyl-1H-pyrrolo[3,2-b]pyridine-3-carboxylate from example D.a1 (14.55 g; 36.8 mmol) is added to the well stirred suspension in several small portions. After complete addition the reaction mixture is stirred for one hour at 60° C. and cooled to 10° C. before slow addition of (2-chloromethoxy-ethyl)-trimethyl-silane (7.98 g; 47.8 mmol). After stirring over night at ambient temperature the mixture is poured on ice-cold water and repeatedly extracted with dichloromethane.

The combined organic layer is dried over MgSO$_4$. The solvent is evaporated. The cured product is purified by column chromatography on silica gel (ethylacetate/cyclohexane—1:1) to yield the title compound as pale yellow viscous oil.

MS (ESI): m/z=525 (MH$^+$, 100%).

$^1$H-NMR (300 MHz, DMSO-d$_6$): 8.46 (d, J=4.8, 1H); 7.04 (d, J=4.8, 1H); 6.95 (d, J=8.6, 1H); 6.55 (d, J=8.6, 1H); 5.98 (s, 1H); 5.91 (s, 1H); 5.30 (d, J=10.9, 1H); 5.12 (d, J=10.9, 1H); 4.33 (qu, J=7.1, 2H); 3.76 (dd, J=10.2, 6.4, 1H); 3.67 (dd, J=10.2, 6.9, 1H); 3.05-2.85 (m, 2H); 2.78 (s, 3H); 1.34 (t, J=7.1, 3H); 0.86 (m, 1H); 0.60 (m, 2H); 0.31 (m, 2H); 0.01 (m, 2H); −0.14 (s, 9H).

The following compounds were prepared analogously to the procedure described in above example D.b1.

Example D.b2

Ethyl 7-[2-(cyclopropylmethoxy)-4-fluorophenyl]-2-methyl-1-{[2-(trimethylsilyl)ethoxy]methyl}-1H-pyrrolo[3,2-b]pyridine-3-carboxylate Starting from ethyl 7-[2-(cyclopropylmethoxy)-4-fluorophenyl]-2-methyl-1H-pyrrolo[3,2-b]pyridine-3-carboxylate (example D.a2) and commercially available (2-chloromethoxy-ethyl)-trimethyl-silane the title compound is prepared as pale yellow viscous oil.

MS (ESI): m/z=499 (MH$^+$, 100%).

$^1$H-NMR (300 MHz, DMSO-d$_6$): 8.44 (d, J=4.8, 1H); 7.32 (dd, J=8.4, 6.8, 1H); 7.06 (dd, J=11.5, 2.5, 1H); 6.93 (d, J=4.8, 1H); 6.90 (ddd, J=8.4, 8.4, 2.5, 1H); 5.25 (d, J=10.8, 1H); 4.90 (d, J=10.8, 1H); 4.32 (qu, J=6.9, 2H); 3.88 (dd, J=10.4, 6.6, 2H); 3.79 (dd, J=10.4, 6.9, 1H); 3.00-2.78 (m, 2H); 2.74 (s, 3H); 1.33 (t, J=6.9, 3H); 0.92 (m, 1H); 0.57 (m, 2H); 0.33 (m, 2H); 0.07 (m, 2H); −0.14 (s, 9H).

Example D.b3

Ethyl 7-[2-(cyclopropylmethoxy)-5-fluorophenyl]-2-methyl-1-{[2-(trimethylsilyl)ethoxy]methyl}-1H-pyrrolo[3,2-b]pyridine-3-carboxylate Starting from ethyl 7-[2-(cyclopropylmethoxy)-5-fluorophenyl]-2-methyl-1H-pyrrolo[3,2-b]pyridine-3-carboxylate (example D.a3) and commercially available (2-chloromethoxy-ethyl)-trimethyl-silane the title compound is prepared as pale yellow viscous oil.

MS (ESI): m/z=499 (MH$^+$, 100%).

$^1$H-NMR (300 MHz, DMSO-d$_6$): 8.47 (d, J=4.9, 1H); 7.31 (ddd, J=8.9, 8.4, 3.2, 1H); 7.19 (dd, J=8.6, 3.2, 1H); 7.16 (dd, J=8.9, 4.6, 1H); 6.99 (d, J=4.9, 1H); 5.29 (d, J=10.8, 1H); 4.91 (d, J=10.8, 1H); 4.34 (qu, J=7.1, 2H); 3.83 (dd, J=10.4, 6.6, 1H); 3.76 (dd, J=10.4, 6.8, 1H); 3.04-2.80 (m, 2H); 2.76 (s, 3H); 1.34 (t, J=7.1, 3H); 0.90 (m, 1H); 0.59 (m, 2H); 0.32 (m, 2H); 0.04 (m, 2H); −0.13 (s, 9H).

Example D.b4

Ethyl 7-[2-(cyclopropylmethoxy)-4-methoxyphenyl]-2-methyl-1-{[2-(trimethylsilyl)ethoxy]methyl}-1H-pyrrolo[3,2-b]pyridine-3-carboxylate Starting from ethyl 7-[2-(cyclopropylmethoxy)-4-methoxyphenyl]-2-methyl-1H-pyrrolo[3,2-b]pyridine-3-carboxylate (example D.a4) and commercially available (2-chloromethoxy-ethyl)-trimethyl-silane the title compound is prepared as pale yellow viscous oil.

MS (ESI): m/z=511 (MH$^+$, 100%).
$^1$H-NMR (300 MHz, DMSO-d$_6$): 8.43 (d, J=4.8, 1H); 7.22 (d, J=8.6, 1H); 6.92 (d, J=4.9, 1H); 6.69 (d, J=2.3, 1H); 6.67 (dd, J=8.6, 2.3, 1H); 5.30 (d, J=10.9, 1H); 5.00 (d, J=10.9, 1H); 4.33 (qu, J=7.1, 2H); 3.86 (dd, J=10.4, 6.6, 1H); 3.83 (s, 3H); 3.77 (dd, J=10.4, 6.9, 1H); 2.90 (m, 2H); 2.75 (s, 3H); 1.34 (t, J=7.1, 3H); 0.91 (m, 1H); 0.55 (m, 2H); 0.33 (m, 2H); 0.07 (m, 2H); −0.15 (s, 9H).

Example D.b5

Ethyl 7-[2-(cyclopropylmethoxy)-5-methoxyphenyl]-2-methyl-1-{[2-(trimethylsilyl)ethoxy]methyl}-1H-pyrrolo[3,2-b]pyridine-3-carboxylate Starting from ethyl 7-[2-(cyclopropylmethoxy)-5-methoxyphenyl]-2-methyl-1H-pyrrolo[3,2-b]pyridine-3-carboxylate (example D.a5) and commercially available (2-chloromethoxy-ethyl)-trimethyl-silane the title compound is prepared as pale yellow viscous oil.

MS (ESI): m/z=511 (MH$^+$, 100%).
$^1$H-NMR (300 MHz, DMSO-d$_6$): 8.45 (d, J=4.8, 1H); 7.08 (d, J=8.9, 1H); 7.02 (dd, J=8.9, 2.9, 1H); 6.98 (d, J=4.8, 1H); 6.88 (d, J=2.9, 1H); 5.29 (d, J=10.8, 1H); 4.97 (d, J=10.8, 1H); 4.33 (qu, J=7.1, 2H); 3.76 (dd, J=10.4, 6.6, 2H); 3.74 (s, 3H); 3.69 (dd, J=10.4, 6.8, 1H); 2.99-2.78 (m, 2H); 2.75 (s, 3H); 1.34 (t, J=7.1, 3H); 0.87 (m, 1H); 0.56 (m, 2H); 0.31 (m, 2H); 0.01 (m, 2H); −0.15 (s, 9H).

Example D.b6

Ethyl 7-[2-(cyclopropylmethoxy)-5-methylphenyl]-2-methyl-1-{[2-(trimethylsilyl)ethoxy]methyl}-1H-pyrrolo[3,2-b]pyridine-3-carboxylate Starting from ethyl 7-[2-(cyclopropylmethoxy)-5-methylphenyl]-2-methyl-1H-pyrrolo[3,2-b]pyridine-3-carboxylate (example D.a6) and commercially available (2-chloromethoxy-ethyl)-trimethyl-silane the title compound is prepared as pale yellow viscous oil.

MS (ESI): m/z=495 (MH$^+$, 100%).
$^1$H-NMR (300 MHz, DMSO-d$_6$): 8.44 (d, J=4.8, 1H); 7.27 (dd, J=8.4, 1.8, 1H); 7.12 (d, J=1.8, 1H); 7.03 (d, J=8.4, 1H); 6.94 (d, J=4.8, 1H); 5.28 (d, J=10.8, 1H); 4.96 (d, J=10.8, 1H); 4.33 (qu, J=7.1, 2H); 3.81 (dd, J=10.4, 6.6, 1H); 3.73 (dd, J=10.4, 6.8, 1H); 2.96-2.77 (m, 2H); 2.75 (s, 3H); 2.30 (s, 3H); 1.34 (t, J=7.1, 3H); 0.90 (m, 1H); 0.55 (m, 2H); 0.32 (m, 2H); 0.04 (m, 2H); −0.15 (s, 9H).

Example D.b7

Ethyl 7-[2-(cyclopropylmethoxy)-4-fluoro-5-methoxyphenyl]-2-methyl-1-{[2-(trimethylsilyl)ethoxy]methyl}-1H-pyrrolo[3,2-b]pyridine-3-carboxylate Starting from ethyl 7-[2-(cyclopropylmethoxy)-4-fluoro-5-methoxyphenyl]-2-methyl-1H-pyrrolo[3,2-b]pyridine-3-carboxylate (example D.a7) and commercially available (2-chloromethoxy-ethyl)-trimethyl-silane the title compound is prepared as pale yellow viscous oil.

MS (ESI): m/z=529 (MH$^+$, 100%).
$^1$H-NMR (300 MHz, DMSO-d$_6$): 8.46 (d, J=4.8, 1H); 7.16 (d, J=10.0, 1H); 7.12 (d, J=6.4, 1H); 6.99 (d, J=4.8, 1H); 5.27 (d, J=10.6, 1H); 4.96 (d, J=10.6, 1H); 4.33 (qu, J=7.1, 2H); 3.81 (s, 3H & dd, J=10.4, 6.7, 1H); 3.72 (dd, J=10.4, 6.7, 1H); 2.99 (m, 1H); 2.88 (m, 1H); 2.76 (s, 3H); 1.34 (t, J=7.1, 3H); 0.89 (m, 1H); 0.58 (m, 2H); 0.32 (m, 2H); 0.01 (m, 2H); −0.13 (s, 9H).

Example D.b8

Ethyl 7-[2-(cyclopropylmethoxy)-5-fluoro-4-methoxyphenyl]-2-methyl-1-{[2-(trimethylsilyl)ethoxy]methyl}-1H-pyrrolo[3,2-b]pyridine-3-carboxylate Starting from ethyl 4-[2-(cyclopropylmethoxy)-5-fluoro-4-methoxyphenyl]-6-methyl-5H-pyrrolo[3,2-d]pyrimidine-7-carboxylate (example D.a8) and commercially available (2-chloromethoxy-ethyl)-trimethyl-silane the title compound is prepared as pale yellow viscous oil.

MS (ESI): m/z=551 (MNa$^+$, 100%); 529 (MH$^+$).
$^1$H-NMR (300 MHz, DMSO-d$_6$): 8.44 (d, J=4.7, 1H); 7.18 (d, J=11.5, 1H); 6.95 (d, J=4.7, 1H); 6.93 (d, J=7.6, 1H); 5.30 (d, J=10.8, 1H); 4.99 (d, J=10.8, 1H); 4.33 (qu, J=7.1, 2H); 3.93 (s, 3H); 3.87 (dd, J=10.4, 6.6, 1H); 3.80 (dd, J=10.4, 6.9, 1H); 2.98 (m, 1H); 2.90 (m, 1H); 2.75 (s, 3H); 1.34 (t, J=7.1, 3H); 0.90 (m, 1H); 0.59 (m, 2H); 0.33 (m, 2H); 0.05 (m, 2H); −0.14 (s, 9H).

Example D.c1

7-[5-(Cyclopropylmethoxy)-1,3-benzodioxol-4-yl]-2-methyl-1-{[2-(trimethylsilyl)ethoxy]methyl}-1H-pyrrolo[3,2-b]pyridine-3-carboxylic acid Ethyl 7-[5-(cyclopropylmethoxy)-1,3-benzodioxol-4-yl]-2-methyl-1-{[2-(trimethylsilyl)ethoxy]methyl}-1H-pyrrolo[3,2-b]pyridine-3-carboxylate from example D.b1 (15.28 g; 29.0 mmol) is dissolved in 1,4-dioxane (150 mL) and aqueous LiOH (prepared from 1.04 g; 43.5 mmol; and 75 mL of water). The stirred reaction mixture is heated to 80° C. until the starting material is consumed according to LC-MS. The mixture is concentrated under reduced pressure, and diluted with water. The product is precipitated by addition of 2M citric acid to adjust pH to 5, isolated by suction filtration, washed with several small portions of water and dried in high vacuo at 40° C. to yield the title compound as pale yellow solid.

MS (ESI): m/z=497 (MH$^+$, 100%).
$^1$H-NMR (300 MHz, DMSO-d$_6$): 12.69 (br.s, 1H, CO$_2$H); 8.50 (d, J=4.9, 1H); 7.22 (d, J=4.9, 1H); 6.99 (d, J=8.6, 1H); 6.58 (d, J=8.6, 1H); 6.00 (s, 1H); 5.93 (s, 1H); 5.36 (d, J=10.9, 1H); 5.16 (d, J=10.9, 1H); 3.78 (dd, J=10.4, 6.6, 1H); 3.69 (dd, J=10.4, 6.9, 1H); 3.08-2.89 (m, 2H); 2.83 (s, 3H); 0.90 (m, 1H); 0.59 (m, 2H); 0.32 (m, 2H); 0.03 (m, 2H); −0.14 (s, 9H).

The following compounds were prepared analogously to the procedure described in above example D.c1.

Example D.c2

7-[2-(cyclopropylmethoxy)-4-fluorophenyl]-2-methyl-1-{[2-(trimethylsilyl)ethoxy]methyl}-1H-pyrrolo[3,2-b]pyridine-3-carboxylic acid Starting from ethyl 7-[2-(cyclopropylmethoxy)-4-fluorophenyl]-2-methyl-1-{[2-(trimethylsilyl)ethoxy]methyl}-

1H-pyrrolo[3,2-b]pyridine-3-carboxylate (example D.b2) the title compound is obtained as pale yellow solid.

MS (ESI): m/z=471 (MH+, 100%).

¹H-NMR (300 MHz, DMSO-d₆): 12.72 (br.s, 1H, —CO₂H); 8.48 (d, J=4.9, 1H); 7.39 (dd, J=8.4, 6.9, 1H); 7.11 (d, J=4.9, 1H); 7.10 (dd, J=11.5, 2.4, 1H); 6.94 (ddd, J=8.4, 8.4, 2.4, 1H); 5.32 (d, J=10.8, 1H); 4.96 (d, J=10.8, 1H); 3.91 (dd, J=10.5, 6.6, 2H); 3.81 (dd, J=10.5, 6.9, 1H); 3.04-2.85 (m, 2H); 2.82 (s, 3H); 0.94 (m, 1H); 0.57 (m, 2H); 0.35 (m, 2H); 0.08 (m, 2H); −0.14 (s, 9H).

Example D.c3

7-[2-(Cyclopropylmethoxy)-5-fluorophenyl]-2-methyl-1-{[2-(trimethylsilyl)ethoxy]methyl}-1H-pyrrolo[3,2-b]pyridine-3-carboxylic acid Starting from ethyl 7-[2-(cyclopropylmethoxy)-5-fluorophenyl]-2-methyl-1-{[2-(trimethylsilyl)ethoxy]methyl}-1H-pyrrolo[3,2-b]pyridine-3-carboxylate (example D.b3) the title compound is obtained as pale yellow solid.

MS (ESI): m/z=471 (MH+, 100%).

¹H-NMR (300 MHz, DMSO-d₆): 12.80 (br.s, 1H, CO₂H); 8.50 (d, J=4.9, 1H); 7.34 (ddd, J=9.1, 8.8, 3.2, 1H); 7.26 (dd, J=8.8, 3.2, 1H); 7.19 (dd, J=9.1, 4.6, 1H); 7.15 (d, J=4.9, 1H); 5.35 (d, J=10.9, 1H); 4.96 (d, J=10.9, 1H); 3.85 (dd, J=10.4, 6.6, 1H); 3.77 (dd, J=10.4, 6.9, 1H); 3.04-2.85 (m, 2H); 2.83 (s, 3H); 0.91 (m, 1H); 0.59 (m, 2H); 0.33 (m, 2H); 0.04 (m, 2H); −0.14 (s, 9H).

Example D.c4

7-[2-(Cyclopropylmethoxy)-4-methoxyphenyl]-2-methyl-1-{[2-(trimethylsilyl)ethoxy]methyl}-1H-pyrrolo[3,2-b]pyridine-3-carboxylic acid Starting from ethyl 7-[2-(cyclopropylmethoxy)-4-methoxyphenyl]-2-methyl-1-{[2-(trimethylsilyl)ethoxy]methyl}-1H-pyrrolo[3,2-b]pyridine-3-carboxylate (example D.b4) the title compound is obtained as pale yellow solid.

MS (ESI): m/z=483 (MH+, 100%).

Example D.c5

7-[2-(Cyclopropylmethoxy)-5-methoxyphenyl]-2-methyl-1-{[2-(trimethylsilyl)ethoxy]methyl}-1H-pyrrolo[3,2-b]pyridine-3-carboxylic acid Starting from ethyl 7-[2-(cyclopropylmethoxy)-5-methoxyphenyl]-2-methyl-1-{[2-(trimethylsilyl)ethoxy]methyl}-1H-pyrrolo[3,2-b]pyridine-3-carboxylate (example D.b5) the title compound is obtained as pale yellow solid.

MS (ESI): m/z=483 (MH+, 100%).

¹H-NMR (300 MHz, DMSO-d₆): 13.22-12.37 (br.s, 1H, —CO₂H); 8.48 (d, J=4.9, 1H); 7.15 (d, J=4.9, 1H); 7.08 (d, J=8.9, 1H); 7.06 (dd, J=8.9, 2.9, 1H); 6.94 (d, J=2.9, 1H); 5.35 (d, J=10.8, 1H); 5.02 (d, J=10.8, 1H); 3.77 (dd, J=10.4, 6.6, 2H); 3.75 (s, 3H); 3.71 (dd, J=10.4, 6.9, 1H); 2.99-2.85 (m, 2H); 2.82 (s, 3H); 0.88 (m, 1H); 0.56 (m, 2H); 0.31 (m, 2H); 0.01 (m, 2H); −0.15 (s, 9H).

Example D.c6

7-[2-(Cyclopropylmethoxy)-5-methylphenyl]-2-methyl-1-{[2-(trimethylsilyl)ethoxy]methyl}-1H-pyrrolo[3,2-b]pyridine-3-carboxylic acid Starting from ethyl 7-[2-(cyclopropylmethoxy)-5-methylphenyl]-2-methyl-1-{[2-(trimethylsilyl)ethoxy]methyl}-1H-pyrrolo[3,2-b]pyridine-3-carboxylate (example D.b6) the title compound is obtained as pale yellow solid.

MS (ESI): m/z=467 (MH+, 100%).

¹H-NMR (300 MHz, DMSO-d₆): 13.63-11.66 (br.s, 1H, —CO₂H); 8.48 (d, J=4.9, 1H); 7.30 (dd, J=8.4, 1.8, 1H); 7.16 (d, J=1.8, 1H); 7.12 (d, J=4.9, 1H); 7.07 (d, J=8.4, 1H); 5.35 (d, J=10.8, 1H); 5.00 (d, J=10.8, 1H); 3.83 (dd, J=10.4, 6.6, 1H); 3.75 (dd, J=10.4, 6.8, 1H); 2.97-2.83 (m, 2H); 2.82 (s, 3H); 2.31 (s, 3H); 0.91 (m, 1H); 0.55 (m, 2H); 0.33 (m, 2H); 0.05 (m, 2H); −0.15 (s, 9H).

Example D.c7

7-[2-(Cyclopropylmethoxy)-4-fluoro-5-methoxyphenyl]-2-methyl-1-{[2-(trimethylsilyl)ethoxy]methyl}-1H-pyrrolo[3,2-b]pyridine-3-carboxylic acid Starting from ethyl 7-[2-(cyclopropylmethoxy)-4-fluoro-5-methoxyphenyl]-2-methyl-1-{[2-(trimethylsilyl)ethoxy]methyl}-1H-pyrrolo[3,2-b]pyridine-3-carboxylate (example D.b7) the title compound is obtained as pale yellow solid.

MS (ESI): m/z=501 (MH+, 100%).

¹H-NMR (300 MHz, DMSO-d₆): 12.84 (br.s, 1H, CO₂H); 8.49 (d, J=4.9, 1H); 7.24-7.13 (m, 3H); 5.33 (d, J=10.6, 1H); 5.01 (d, J=10.6, 1H); 3.81 (s, 3H & dd, J=10.4, 6.8, 1H); 3.73 (dd, J=10.4, 6.8, 1H); 3.02 (m, 1H); 2.91 (m, 1H); 2.82 (s, 3H); 0.90 (m, 1H); 0.58 (m, 2H); 0.33 (m, 2H); 0.04 (m, 2H); −0.14 (s, 9H).

Example D.c8

7-[2-(Cyclopropylmethoxy)-5-fluoro-4-methoxyphenyl]-2-methyl-1-{[2-(trimethylsilyl)ethoxy]methyl}-1H-pyrrolo[3,2-b]pyridine-3-carboxylic acid Starting from ethyl 7-[2-(cyclopropylmethoxy)-5-fluoro-4-methoxyphenyl]-2-methyl-1-{[2-(trimethylsilyl)ethoxy]methyl}-1H-pyrrolo[3,2-b]pyridine-3-carboxylate (example D.b8) the title compound is obtained as pale yellow solid.

MS (ESI): m/z=501 (MH+, 100%).

¹H-NMR (300 MHz, DMSO-d₆): 12.82 (br.s, 1H, —CO₂H); 8.47 (d, J=4.9, 1H); 7.26 (d, J=11.3, 1H); 7.11 (d, J=4.9, 1H); 6.96 (d, J=7.5, 1H); 5.37 (d, J=10.8, 1H); 5.03 (d, J=10.8, 1H); 3.94 (s, 3H); 3.89 (dd, J=10.4, 6.6, 1H); 3.82 (dd, J=10.4, 6.9, 1H); 3.05-2.98 (m, 2H); 2.82 (s, 3H); 0.91 (m, 1H); 0.58 (m, 2H); 0.33 (m, 2H); 0.05 (m, 2H); −0.15 (s, 9H).

Example D.d1 tert-Butyl 4-{[(7-[5-(cyclopropylmethoxy)-1,3-benzodioxol-4-yl]-2-methyl-1-{[2-(trimethylsilyl)ethoxy]methyl}-1H-pyrrolo[3,2-b]pyridin-3-yl)carbonyl]amino}piperidine-1-carboxylate 7-[5-(Cyclopropylmethoxy)-1,3-benzodioxol-4-yl]-2-methyl-1-{[2-(trimethylsilyl)ethoxy]methyl}-1H-pyrrolo[3,2-b]pyridine-3-carboxylic acid from example D.c1 (3.98 g; 8.0 mmol), triethylamine (2.43 g; 24.0 mmol) and HOBt (1.08 g; 8.0 mmol) is stirred in dry dichloromethane (40 mL) for 30 min, before addition of EDC (1.84 g; 9.6 mmol). The reaction mixture is stirred for one hour at ambient temperature. After addition of tert-butyl 4-amino-piperidine-1-carboxylate hydrochloride (2.27 g; 9.6 mmol) the reaction mixture is stirred at ambient temperature until the starting material is consumed according to LC-MS and chromatographed on silica gel (ethylacetate/cyclohexane—1:1) to yield the title compound as colorless foam.

MS (ESI): m/z=679 (MH+, 100%).

¹H-NMR (300 MHz, DMSO-d$_6$): 9.56 (d, J=7.7, 1H, —NH); 8.45 (d, J=4.9, 1H); 7.10 (d, J=4.9, 1H); 6.96 (d, J=8.6, 1H); 6.56 (d, J=8.6, 1H); 5.99 (s, 1H); 5.92 (s, 1H); 5.29 (d, J=10.9, 1H); 5.11 (d, J=10.9, 1H); 4.08 (m, 1H); 3.84 (m, 2H); 3.76 (dd, J=10.2, 6.6, 1H); 3.67 (dd, J=10.2, 6.8, 1H); 3.06 (m, 2H); 3.03-2.87 (m, 2H); 2.87 (s, 3H); 1.93 (m, 2H); 1.45 (m, 2H); 1.42 (s, 9H); 0.89 (m, 1H); 0.59 (m, 2H); 0.31 (m, 2H); 0.03 (m, 2H); −0.14 (s, 9H).

The following compounds were prepared analogously to the procedure described in above example D.d1.

Example D.d2 tert-Butyl (trans-4-{[(7-[5-(cyclopropylmethoxy)-1,3-benzodioxol-4-yl]-2-methyl-1-{[2-(trimethylsilyl)ethoxy]methyl}-1H-pyrrolo[3,2-b]pyridin-3-yl)carbonyl]amino}cyclohexyl)carbamate Starting from 7-[5-(cyclopropylmethoxy)-1,3-benzodioxol-4-yl]-2-methyl-1-{[2-(trimethylsilyl)ethoxy]methyl}-1H-pyrrolo[3,2-b]pyridine-3-carboxylic acid (example D.c1) and commercially available tert-butyl trans-(4-amino-cyclohexyl)-carbamate the title compound is obtained as pale yellow viscous oil.

MS (ESI): m/z=693 (MH+, 100%).

¹H-NMR (300 MHz, DMSO-d$_6$): 9.38 (d, J=7.7, 1H, —NH); 8.45 (d, J=4.9, 1H); 7.09 (d, J=4.9, 1H); 6.96 (d, J=8.6, 1H); 6.72 (br.d, J ~7.5, 1H, —NH); 6.56 (d, J=8.6, 1H); 5.99 (s, 1H); 5.92 (s, 1H); 5.29 (d, J=10.9, 1H); 5.10 (d, J=10.9, 1H); 3.76 (m, 1H & dd, J=10.2, 6.6, 1H); 3.67 (dd, J=10.2, 6.8, 1H); 3.29 (m, 1H); 3.04-2.83 (m, 2H); 2.86 (s, 3H); 2.00 (m, 2H); 1.85 (m, 2H); 1.39 (s, 9H); 1.35 (m, 4H); 0.88 (m, 1H); 0.59 (m, 2H); 0.31 (m, 2H); 0.03 (m, 2H); −0.14 (s, 9H).

Example D.d3 tert-Butyl (cis-4-{[(7-[5-(cyclopropylmethoxy)-1,3-benzodioxol-4-yl]-2-methyl-1-{[2-(trimethylsilyl)ethoxy]methyl}-1H-pyrrolo[3,2-b]pyridin-3-yl)carbonyl]amino}cyclohexyl)carbamate Starting from 7-[5-(cyclopropylmethoxy)-1,3-benzodioxol-4-yl]-2-methyl-1-{[2-(trimethylsilyl)ethoxy]methyl}-1H-pyrrolo[3,2-b]pyridine-3-carboxylic acid (example D.c1) and commercially available tert-butyl cis-(4-amino-cyclohexyl)-carbamate the title compound is obtained as pale yellow viscous oil.

MS (ESI): m/z=693 (MH+, 100%).

¹H-NMR (300 MHz, DMSO-d$_6$): 9.74 (d, J=7.7, 1H, —NH); 8.51 (d, J=4.9, 1H); 7.11 (d, J=4.9, 1H); 6.97 (d, J=8.6, 1H); 6.92 (br.d, J ~7.5, 1H, —NH); 6.56 (d, J=8.6, 1H); 5.99 (s, 1H); 5.92 (s, 1H); 5.29 (d, J=10.8, 1H); 5.11 (d, J=10.8, 1H); 4.07 (m, 1H); 3.77 (dd, J=10.2, 6.6, 1H); 3.68 (dd, J=10.2, 6.8, 1H); 3.41 (m, 1H); 3.05-2.87 (m, 2H); 2.87 (s, 3H); 1.88-1.52 (m, 8H); 1.40 (s, 9H); 0.90 (m, 1H); 0.59 (m, 2H); 0.32 (m, 2H); 0.05 (m, 2H); −0.14 (s, 9H).

Example D.d4 tert-Butyl 4-{[(7-[2-(cyclopropylmethoxy)-4-fluorophenyl]-2-methyl-1-{[2-(trimethylsilyl)ethoxy]methyl}-1H-pyrrolo[3,2-b]pyridin-3-yl)carbonyl]amino}piperidine-1-carboxylate Starting from 7-[2-(cyclopropylmethoxy)-4-fluorophenyl]-2-methyl-1-{[2-(trimethylsilyl)ethoxy]methyl}-1H-pyrrolo[3,2-b]pyridine-3-carboxylic acid (example D.c2) and commercially available tert-butyl 4-amino-piperidine-1-carboxylate the title compound is obtained as pale yellow viscous oil.

MS (ESI): m/z=653 (MH+, 100%).

¹H-NMR (300 MHz, DMSO-d$_6$): 9.59 (d, J=7.5, 1H, —NH); 8.44 (d, J=4.9, 1H); 7.34 (dd, J=8.4, 6.9, 1H); 7.08 (dd, J=11.5, 2.4, 1H); 7.00 (d, J=4.9, 1H); 6.92 (ddd, J=8.4, 8.4, 2.4, 1H); 5.25 (d, J=10.8, 1H); 4.90 (d, J=10.8, 1H); 4.08 (m, 1H); 3.90 (dd, J=10.4, 6.6, 2H); 3.85 (m, 2H); 3.80 (dd, J=10.4, 6.9, 1H); 3.06 (m, 2H); 3.00-2.78 (m, 2H); 2.86 (s, 3H); 1.93 (m, 2H); 1.42 (s, 9H & m, 2H); 0.93 (m, 1H); 0.57 (m, 2H); 0.35 (m, 2H); 0.08 (m, 2H); −0.14 (s, 9H).

Example D.d5 tert-Butyl (trans-4-{[(7-[2-(cyclopropylmethoxy)-4-fluorophenyl]-2-methyl-1-{[2-(trimethylsilyl)ethoxy]methyl}-1H-pyrrolo[3,2-b]pyridin-3-yl)carbonyl]amino}cyclohexyl)carbamate Starting from 7-[2-(cyclopropylmethoxy)-4-fluorophenyl]-2-methyl-1-{[2-(trimethylsilyl)ethoxy]methyl}-1H-pyrrolo[3,2-b]pyridine-3-carboxylic acid (example D.c2) and commercially available tert-butyl trans-(4-amino-cyclohexyl)-carbamate the title compound is obtained as pale yellow viscous oil.

MS (ESI): m/z=667 (MH+, 100%).

¹H-NMR (300 MHz, DMSO-d$_6$): 9.40 (d, J=7.7, 1H, —NH); 8.44 (d, J=4.9, 1H); 7.34 (dd, J=8.4, 6.9, 1H); 7.08 (dd, J=11.5, 2.4, 1H); 6.99 (d, J=4.9, 1H); 6.92 (ddd, J=8.4, 8.4, 2.4, 1H); 6.72 (br.d, J ~7.3, 1H, —NH); 5.25 (d, J=10.8, 1H); 4.90 (d, J=10.8, 1H); 3.89 (dd, J=10.4, 6.6, 2H); 3.80 (dd, J=10.4, 6.9, 1H & m, 1H); 3.29 (m, 1H); 3.00-2.78 (m, 2H); 2.85 (s, 3H); 2.00 (m, 2H); 1.85 (m, 2H); 1.39 (s, 9H); 1.35 (m, 4H); 0.93 (m, 1H); 0.56 (m, 2H); 0.34 (m, 2H); 0.08 (m, 2H); −0.14 (s, 9H).

Example D.d6 tert-Butyl (cis-4-{[(7-[2-(cyclopropylmethoxy)-4-fluorophenyl]-2-methyl-1-{[2-(trimethylsilyl)ethoxy]methyl}-1H-pyrrolo[3,2-b]pyridin-3-yl)carbonyl]amino}cyclohexyl)carbamate Starting from 7-[2-(cyclopropylmethoxy)-4-fluorophenyl]-2-methyl-1-{[2-(trimethylsilyl)ethoxy]methyl}-1H-pyrrolo[3,2-b]pyridine-3-carboxylic acid (example D.c2) and commercially available tert-butyl cis-(4-amino-cyclohexyl)-carbamate the title compound is obtained as pale yellow viscous oil.

MS (ESI): m/z=667 (MH+, 100%).

¹H-NMR (300 MHz, DMSO-d$_6$): 9.77 (d, J=7.7, 1H, —NH); 8.50 (d, J=4.9, 1H); 7.35 (dd, J=8.4, 6.9, 1H); 7.09 (dd, J=11.5, 2.4, 1H); 7.01 (d, J=4.9, 1H); 6.93 (ddd, J=8.4, 8.4, 2.4, 1H & br.s, 1H, —NH); 5.26 (d, J=10.8, 1H); 4.91 (d, J=10.8, 1H); 4.07 (m, 1H); 3.90 (dd, J=10.4, 6.6, 2H); 3.81 (dd, J=10.4, 6.9, 1H); 3.41 (m, 1H); 3.01-2.78 (m, 2H); 2.86 (s, 3H); 1.85-1.51 (m, 8H); 1.40 (s, 9H); 0.94 (m, 1H); 0.57 (m, 2H); 0.35 (m, 2H); 0.09 (m, 2H); −0.13 (s, 9H).

Example D.d7 tert-Butyl 4-{[(7-[2-(cyclopropylmethoxy)-5-fluorophenyl]-2-methyl-1-{[2-(trimethylsilyl)ethoxy]methyl}-1H-pyrrolo[3,2-b]pyridin-3-yl)carbonyl]amino}piperidine-1-carboxylate Starting from 7-[2-(cyclopropylmethoxy)-5-fluorophenyl]-2-methyl-1-{[2-(trimethylsilyl)ethoxy]methyl}-1H- pyrrolo[3,2-b]pyridine-3-carboxylic acid (example D.c3) and commercially available tert-butyl 4-amino-piperidine-1-carboxylate the title compound is obtained as pale yellow viscous oil.

MS (ESI): m/z=653 (MH$^+$, 100%).

$^1$H-NMR (400 MHz, DMSO-d$_6$): 9.57 (d, J=7.7, 1H, —NH); 8.45 (d, J=4.9, 1H); 7.32 (ddd, J=9.2, 8.8, 3.2, 1H); 7.20 (dd, J=9.1, 3.2, 1H); 7.17 (dd, J=9.2, 4.5, 1H); 7.04 (d, J=4.9, 1H); 5.28 (d, J=10.8, 1H); 4.90 (d, J=10.8, 1H); 4.08 (m, 1H); 3.83 (dd, J=10.3, 6.6, 1H & m, 2H); 3.76 (dd, J=10.3, 6.9, 1H); 3.06 (m, 2H); 3.00-2.82 (m, 2H); 2.86 (s, 3H); 1.93 (m, 2H); 1.42 (s, 9H & m, 2H); 0.90 (m, 1H); 0.58 (m, 2H); 0.32 (m, 2H); 0.05 (m, 2H); −0.14 (s, 9H).

Example D.d8 tert-Butyl (trans-4-{[(7-[2-(cyclopropylmethoxy)-5-fluorophenyl]-2-methyl-1-{[2-(trimethylsilyl)ethoxy]methyl}-1H-pyrrolo[3,2-b]pyridin-3-yl)carbonyl]amino}cyclohexyl)carbamate Starting from 7-[2-(cyclopropylmethoxy)-5-fluorophenyl]-2-methyl-1-{[2-(trimethylsilyl)ethoxy]methyl}-1H-pyrrolo[3,2-b]pyridine-3-carboxylic acid (example D.c3) and commercially available tert-butyl trans-(4-amino-cyclohexyl)-carbamate the title compound is obtained as pale yellow viscous oil.

MS (ESI): m/z=667 (MH$^+$, 100%).

$^1$H-NMR (400 MHz, DMSO-d$_6$): 9.39 (d, J=7.7, 1H, —NH); 8.45 (d, J=4.9, 1H); 7.31 (ddd, J=9.2, 8.8, 3.2, 1H); 7.19 (dd, J=8.8, 3.2, 1H); 7.17 (dd, J=9.2, 4.5, 1H); 7.04 (d, J=4.9, 1H); 6.72 (d, J=7.5, 1H, —NH); 5.27 (d, J=10.9, 1H); 4.90 (d, J=10.9, 1H); 3.83 (dd, J=10.4, 6.6, 1H); 3.76 (dd, J=10.4, 6.9, 1H & m, 1H); 3.29 (m, 1H); 2.96 (m, 1H); 2.86 (s, 3H & m, 1H); 2.00 (m, 2H); 1.85 (m, 2H); 1.39 (s, 9H); 1.34 (m, 4H); 0.89 (m, 1H); 0.58 (m, 2H); 0.32 (m, 2H); 0.04 (m, 2H); −0.14 (s, 9H).

Example D.d9 tert-Butyl (cis-4-{[(7-[2-(cyclopropylmethoxy)-5-fluorophenyl]-2-methyl-1-{[2-(trimethylsilyl)ethoxy]methyl}-1H-pyrrolo[3,2-b]pyridin-3-yl)carbonyl]amino}cyclohexyl)carbamate Starting from 7-[2-(cyclopropylmethoxy)-5-fluorophenyl]-2-methyl-1-{[2-(trimethylsilyl)ethoxy]methyl}-1H-pyrrolo[3,2-b]pyridine-3-carboxylic acid (example D.c3) and commercially available tert-butyl cis-(4-amino-cyclohexyl)-carbamate the title compound is obtained as pale yellow viscous oil.

MS (ESI): m/z=667 (MH$^+$, 100%).

$^1$H-NMR (300 MHz, DMSO-d$_6$): 9.76 (d, J=7.7, 1H, —NH); 8.52 (d, J=4.9, 1H); 7.32 (ddd, J=9.1, 8.8, 3.3, 1H); 7.20 (dd, J=8.7, 3.3, 1H); 7.17 (dd, J=9.1, 4.6, 1H); 7.06 (d, J=4.9, 1H); 6.92 (br.d, J ~6.0, 1H, —NH); 5.28 (d, J=10.8, 1H); 4.90 (d, J=10.8, 1H); 40.8 (m, 1H); 3.84 (dd, J=10.2, 6.6, 1H); 3.76 (dd, J=10.2, 6.9, 1H); 3.42 (m, 1H); 3.02-2.81 (m, 2H); 2.86 (s, 3H); 1.85-1.52 (m, 8H); 1.40 (s, 9H); 0.91 (m, 1H); 0.59 (m, 2H); 0.33 (m, 2H); 0.06 (m, 2H); −0.13 (s, 9H).

Example D.d10 tert-Butyl (3R*,4R*)-4-{[(7-[2-(cyclopropylmethoxy)-5-fluorophenyl]-2-methyl-1-{[2-(trimethylsilyl)ethoxy]methyl}-1H-pyrrolo[3,2-b]pyridin-3-yl)carbonyl]amino}-3-hydroxypiperidine-1-carboxylate Starting from 7-[2-(cyclopropylmethoxy)-5-fluorophenyl]-2-methyl-1-{[2-(trimethylsilyl)ethoxy]methyl}-1H-pyrrolo[3,2-b]pyridine-3-carboxylic acid (example D.c3) and commercially available tert-butyl (3R*,4R*)-4-amino-3-hydroxy-piperidine-1-carboxylate the title compound is obtained as pale yellow viscous oil.

MS (ESI): m/z=669 (MH$^+$, 100%).

$^1$H-NMR (400 MHz, DMSO-d$_6$): 9.62 (d, J=7.3, 1H, —NH); 8.45 (d, J=4.9, 1H); 7.32 (ddd, J=9.1, 8.6, 3.2, 1H); 7.20 (dd, J=8.8, 3.2, 1H); 7.17 (dd, J=9.1, 4.5, 1H); 7.05 (d, J=4.9, 1H); 5.29 (d, J=10.8, 1H); 5.23 (dd, J=4.4, 4.2, 1H, —OH); 4.91 (d, J=10.8, 1H); 3.99-3.70 (m, 5H); 3.43 (m, 1H); 3.08-2.72 (m, 4H); 2.87 (s, 3H); 2.07 (m, 1H); 1.42 (s, 9H & m, 1H); 0.90 (m, 1H); 0.58 (m, 2H); 0.33 (m, 2H); 0.05 (m, 2H); −0.14 (s, 9H).

Example D.d11 tert-Butyl 4-{[(7-[2-(cyclopropylmethoxy)-4-methoxyphenyl]-2-methyl-1-{[2-(trimethylsilyl)ethoxy]methyl}-1H-pyrrolo[3,2-b]pyridin-3-yl)carbonyl]amino}piperidine-1-carboxylate Starting from 7-[2-(cyclopropylmethoxy)-4-methoxyphenyl]-2-methyl-1-{[2-(trimethylsilyl)ethoxy]methyl}-1H-pyrrolo[3,2-b]pyridine-3-carboxylic acid (example D.c4) and commercially available tert-butyl 4-amino-piperidine-1-carboxylate the title compound is obtained as pale yellow viscous oil.

MS (ESI): m/z=665 (MH$^+$, 100%).

Example D.d12 tert-Butyl (trans-4-{[(7-[2-(cyclopropylmethoxy)-4-methoxyphenyl]-2-methyl-1-{[2-(trimethylsilyl)ethoxy]methyl}-1H-pyrrolo[3,2-b]pyridin-3-yl)carbonyl]amino}cyclohexyl)carbamate Starting from 7-[2-(cyclopropylmethoxy)-4-methoxyphenyl]-2-methyl-1-{[2-(trimethylsilyl)ethoxy]methyl}-1H-pyrrolo[3,2-b]pyridine-3-carboxylic acid (example D.c4) and commercially available tert-butyl trans-(4-amino-cyclohexyl)-carbamate the title compound is obtained as pale yellow viscous oil.

MS (ESI): m/z=679 (MH$^+$, 100%).

$^1$H-NMR (300 MHz, DMSO-d$_6$): 9.43 (d, J=7.7, 1H, —NH); 8.41 (d, J=4.9, 1H); 7.22 (d, J=8.8, 1H); 6.97 (d, J=4.9, 1H); 6.72 (br.d, J ~7.5, 1H, —NH); 6.69 (d, J=2.4, 1H); 6.67 (dd, J=8.8, 2.4, 1H); 5.29 (d, J=10.8, 1H); 4.98 (d, J=10.9, 1H); 3.87 (dd, J=10.4, 6.6, 1H); 3.83 (s, 3H); 3.77 (dd, J=10.4, 6.9, 1H & m, 1H); 3.29 (m, 1H); 2.96-2.81 (m, 2H); 2.85 (s, 3H); 2.00 (m, 2H); 1.86 (m, 2H); 1.39 (s, 9H); 1.35 (m, 4H); 0.91 (m, 1H); 0.55 (m, 2H); 0.33 (m, 2H); 0.07 (m, 2H); −0.15 (s, 9H).

Example D.d13 tert-Butyl (cis-4-{[(7-[2-(cyclopropylmethoxy)-4-methoxyphenyl]-2-methyl-1-{[2-(trimethylsilyl)ethoxy]methyl}-1H-pyrrolo[3,2-b]pyridin-3-yl)carbonyl]amino}cyclohexyl)carbamate Starting from 7-[2-(cyclopropylmethoxy)-4-methoxyphenyl]-2-methyl-1-{[2-(trimethylsilyl)ethoxy]methyl}-1H-pyrrolo[3,2-b]pyridine-3-carboxylic acid (example D.c4) and commercially available tert-butyl cis-(4-amino-cyclohexyl)-carbamate the title compound is obtained as pale yellow viscous oil.

MS (ESI): m/z=679 (MH$^+$, 100%).

Example D.d14 tert-Butyl 4-{[(7-[2-(cyclopropylmethoxy)-5-methoxyphenyl]-2-methyl-1-{[2-(trimethylsilyl)ethoxy]methyl}-1H-pyrrolo[3,2-b]pyridin-3-yl)carbonyl]amino}piperidine-1-carboxylate Starting from 7-[2-(cyclopropylmethoxy)-5-methoxyphenyl]-2-methyl-1-{[2-(trimethylsilyl)ethoxy]methyl}-1H-pyrrolo[3,2-b]pyridine-3-carboxylic acid (example D.c5) and commercially available tert-butyl 4-amino-piperidine-1-carboxylate the title compound is obtained as pale yellow viscous oil.

MS (ESI): m/z=665 (MH$^+$, 100%).

$^1$H-NMR (400 MHz, DMSO-d$_6$): 9.59 (d, J=7.6, 1H, —NH); 8.44 (d, J=4.9, 1H); 7.09 (d, J=8.9, 1H); 7.04 (dd, J=8.9, 2.9, 1H & d, J=4.9, 1H); 6.88 (d, J=2.9, 1H); 5.28 (d, J=10.9, 1H); 4.96 (d, J=10.9, 1H); 4.07 (m, 1H); 3.84 (m, 2H); 3.76 (dd, J=10.4, 6.6, 1H); 3.74 (s, 3H); 3.69 (dd, J=10.4, 6.9, 1H); 3.06 (m, 2H); 2.97-2.81 (m, 2H); 2.86 (s, 3H); 1.93 (m, 2H); 1.42 (s, 9H & m, 2H); 0.87 (m, 1H); 0.55 (m, 2H); 0.30 (m, 2H); 0.02 (m, 2H); −0.15 (s, 9H).

Example D.d15 tert-Butyl (trans-4-{[(7-[2-(cyclopropylmethoxy)-5-methoxyphenyl]-2-methyl-1-{[2-(trimethylsilyl)ethoxy]methyl}-1H-pyrrolo[3,2-b]pyridin-3-yl)carbonyl]amino}cyclohexyl)carbamate Starting from 7-[2-(cyclopropylmethoxy)-5-methoxyphenyl]-2-methyl-1-{[2-(trimethylsilyl)ethoxy]methyl}-1H-pyrrolo[3,2-b]pyridine-3-carboxylic acid (example D.c5) and commercially available tert-butyl trans-(4-amino-cyclohexyl)-carbamate the title compound is obtained as pale yellow viscous oil.

MS (ESI): m/z=679 (MH$^+$, 100%).

$^1$H-NMR (400 MHz, DMSO-d$_6$): 9.41 (d, J=7.7, 1H, —NH); 8.43 (d, J=4.9, 1H); 7.09 (d, J=9.0, 1H); 7.04 (dd, J=9.0, 2.9, 1H & d, J=4.9, 1H); 6.88 (d, J=2.9, 1H); 6.72 (d, J=7.5, 1H, —NH); 5.27 (d, J=10.9, 1H); 4.96 (d, J=10.9, 1H); 3.76 (dd, J=10.4, 6.6, 1H & m, 1H); 3.74 (s, 3H); 3.69 (dd, J=10.4, 6.8, 1H); 3.29 (m, 1H); 2.97-2.81 (m, 2H); 2.85 (s, 3H); 2.00 (m, 2H); 1.85 (m, 2H); 1.39 (s, 9H); 1.34 (m, 4H); 0.87 (m, 1H); 0.55 (m, 2H); 0.31 (m, 2H); 0.02 (m, 2H); −0.15 (s, 9H).

Example D.d16 tert-Butyl (cis-4-{[(7-[2-(cyclopropylmethoxy)-5-methoxyphenyl]-2-methyl-1-{[2-(trimethylsilyl)ethoxy]methyl}-1H-pyrrolo[3,2-b]pyridin-3-yl)carbonyl]amino}cyclohexyl)carbamate Starting from 7-[2-(cyclopropylmethoxy)-5-methoxyphenyl]-2-methyl-1-{[2-(trimethylsilyl)ethoxy]methyl}-1H-pyrrolo[3,2-b]pyridine-3-carboxylic acid (example D.c5) and commercially available tert-butyl cis-(4-amino-cyclohexyl)-carbamate the title compound is obtained as pale yellow viscous oil.

MS (ESI): m/z=679 (MH$^+$, 100%).

$^1$H-NMR (400 MHz, DMSO-d$_6$): 9.77 (d, J=7.7, 1H, —NH); 8.50 (d, J=4.9, 1H); 7.10 (d, J=8.9, 1H); 7.05 (dd, J=8.9, 2.8, 1H & d, J=4.9, 1H); 6.92 (br.s, 1H, —NH); 6.89 (d, J=2.8, 1H); 5.28 (d, J=10.8, 1H); 4.96 (d, J=10.8, 1H); 4.07 (m, 1H); 3.77 (dd, J=10.2, 6.6, 1H & m, 1H); 3.75 (s, 3H); 3.70 (dd, J=10.2, 6.9, 1H); 3.42 (m, 1H); 2.89-2.80 (m, 2H); 2.86 (s, 3H); 1.86-1.51 (m, 8H); 1.40 (s, 9H); 0.88 (m, 1H); 0.56 (m, 2H); 0.32 (m, 2H); 0.03 (m, 2H); −0.15 (s, 9H).

Example D.d17 tert-Butyl-(3R*,4R*)-3-{[(7-[2-(cyclopropylmethoxy)-5-methoxyphenyl]-2-methyl-1-{[2-(trimethylsilyl)ethoxy]methyl}-1H-pyrrolo[3,2-b]pyridin-3-yl)carbonyl]amino}-4-hydroxypyrrolidine-1-carboxylate Starting from 7-[2-(cyclopropylmethoxy)-5-methoxyphenyl]-2-methyl-1-{[2-(trimethylsilyl)ethoxy]methyl}-1H-pyrrolo[3,2-b]pyridine-3-carboxylic acid (example D.c5) and commercially available tert-butyl (3R*,4R*)-3-amino-4-hydroxy-pyrrolidine-1-carboxylate the title compound is obtained as pale yellow viscous oil.

MS (ESI): m/z=667 (MH$^+$, 100%).

$^1$H-NMR (300 MHz, DMSO-d$_6$): 9.66 (~t, J ~6.0, 1H, —NH); 8.38 (d, J=4.9, 1H); 7.09 (d, J=8.9, 1H); 7.04 (dd, J=8.9, 2.9, 1H & d, J=4.9, 1H); 6.88 (d, J=2.9, 1H); 5.46 (d, J=3.7, 1H, —OH); 5.29 (d, J=10.8, 1H); 4.96 (d, J=10.8, 1H); 4.26 (m, 1H); 4.19 (m, 1H); 3.77 (dd, J=10.4, 6.6, 1H); 3.74 (s, 3H); 3.69 (dd, J=10.4, 6.8, 1H); 3.66 (m, 12H); 3.55 (m, 1H); 3.36-3.16 (m, 2H); 2.98-2.80 (m, 2H); 2.86 (s, 3H); 1.43 (s, 9H); 0.87 (m, 1H); 0.55 (m, 2H); 0.31 (m, 2H); 0.02 (m, 2H); −0.15 (s, 9H).

Example D.d18 tert-Butyl 4-{[(7-[2-(cyclopropylmethoxy)-5-methylphenyl]-2-methyl-1-{[2-(trimethylsilyl)ethoxy]methyl}-1H-pyrrolo[3,2-b]pyridin-3-yl)carbonyl]amino}piperidine-1-carboxylate Starting from 7-[2-(cyclopropylmethoxy)-5-methylphenyl]-2-methyl-1-{[2-(trimethylsilyl)ethoxy]methyl}-1H-pyrrolo[3,2-b]pyridine-3-carboxylic acid (example D.c6) and commercially available tert-butyl 4-amino-piperidine-1-carboxylate the title compound is obtained as pale yellow viscous oil.

MS (ESI): m/z=649 (MH$^+$, 100%).

$^1$H-NMR (300 MHz, DMSO-d$_6$): 9.61 (d, J=7.7, 1H, —NH); 8.43 (d, J=4.9, 1H); 7.28 (dd, J=8.6, 2.0, 1H); 7.12 (d, J=2.0, 1H); 7.04 (d, J=8.6, 1H); 7.00 (d, J=4.9, 1H); 5.27 (d, J=10.8, 1H); 4.95 (d, J=10.8, 1H); 4.08 (m, 1); 3.82 (dd, J=10.4, 6.6, 1H & m, 2H); 3.73 (dd, J=10.4, 6.8, 1H); 3.07 (m, 2H); 2.94-2.77 (m, 2H); 2.86 (s, 3H); 2.30 (s, 3H); 1.93 (m, 2H); 1.42 (s, 9H & m, 2H); 0.90 (m, 1H); 0.54 (m, 2H); 0.32 (m, 2H); 0.05 (m, 2H); −0.15 (s, 9H).

Example D.d19 tert-Butyl (trans-4-{[(7-[2-(cyclopropylmethoxy)-5-methylphenyl]-2-methyl-1-{[2-(trimethylsilyl)ethoxy]methyl}-1H-pyrrolo[3,2-b]pyridin-3-yl)carbonyl]amino}cyclohexyl)carbamate Starting from 7-[2-(cyclopropylmethoxy)-5-methylphenyl]-2-methyl-1-{[2-(trimethylsilyl)ethoxy]methyl}-1H-pyrrolo[3,2-b]pyridine-3-carboxylic acid (example D.c6) and commercially available tert-butyl trans-(4-amino-cyclohexyl)-carbamate the title compound is obtained as pale yellow viscous oil.

MS (ESI): m/z=663 (MH$^+$, 100%).

¹H-NMR (300 MHz, DMSO-d₆): 9.42 (d, J=7.7, 1H, —NH); 8.42 (d, J=4.9, 1H); 7.28 (dd, J=8.6, 1.8, 1H); 7.12 (d, J=1.8, 1H); 7.04 (d, J=8.6, 1H); 6.99 (d, J=4.9, 1H); 6.72 (br.d, J ~7.3, 1H, —NH); 5.27 (d, J=10.8, 1H); 4.94 (d, J=10.8, 1H); 3.81 (dd, J=10.4, 6.6, 1H); 3.73 (dd, J=10.4, 6.8, 1H & m, 1H); 3.27 (m, 1H); 2.85 (s, 3H & m, 2H); 2.30 (s, 3H); 2.00 (m, 2H); 1.86 (m, 2H); 1.39 (s, 9H); 1.36 (m, 4H); 0.90 (m, 1H); 0.54 (m, 2H); 0.32 (m, 2H); 0.04 (m, 2H); −0.15 (s, 9H).

Example D.d20 tert-Butyl (cis-4-{[(7-[2-(cyclopropylmethoxy)-5-methylphenyl]-2-methyl-1-{[2-(trimethylsilyl)ethoxy]methyl}-1H-pyrrolo[3,2-b]pyridin-3-yl)carbonyl]amino}cyclohexyl)carbamate Starting from 7-[2-(cyclopropylmethoxy)-5-methylphenyl]-2-methyl-1-{[2-(trimethylsilyl)ethoxy]methyl}-1H-pyrrolo[3,2-b]pyridine-3-carboxylic acid (example D.c6) and commercially available tert-butyl cis-(4-amino-cyclohexyl)-carbamate the title compound is obtained as pale yellow viscous oil.
MS (ESI): m/z=663 (MH⁺, 100%).
¹H-NMR (300 MHz, DMSO-d₆): 9.78 (d, J=7.7, 1H, —NH); 8.49 (d, J=4.9, 1H); 7.28 (dd, J=8.4, 2.0, 1H); 7.13 (d, J=2.0, 1H); 7.05 (d, J=8.4, 1H); 7.01 (d, J=4.9, 1H); 6.92 (br.d, J ~6.4, 1H, —NH); 5.27 (d, J=10.8, 1H); 4.95 (d, J=10.8, 1H); 4.07 (m, 1H); 3.82 (dd, J=10.4, 6.6, 1H); 3.74 (dd, J=10.4, 6.8, 1H & m, 1H); 3.42 (m, 1H); 2.96-2.76 (m, 2H); 2.85 (s, 3H); 2.31 (s, 3H); 1.87-1.50 (m, 8H); 1.40 (s, 9H); 0.91 (m, 1H); 0.55 (m, 2H); 0.33 (m, 2H); 0.05 (m, 2H); −0.15 (s, 9H).

Example D.d21 tert-Butyl 4-{[(7-[2-(cyclopropylmethoxy)-4-fluoro-5-methoxyphenyl]-2-methyl-1-{[2-(trimethylsilyl)ethoxy]methyl}-1H-pyrrolo[3,2-b]pyridin-3-yl)carbonyl]amino}piperidine-1-carboxylate Starting from 7-[2-(cyclopropylmethoxy)-4-fluoro-5-methoxyphenyl]-2-methyl-1-{[2-(trimethylsilyl)ethoxy]methyl}-1H-pyrrolo[3,2-b]pyridine-3-carboxylic acid (example D.c7) and commercially available tert-butyl 4-amino-piperidine-1-carboxylate the title compound is obtained as pale yellow viscous oil.
MS (ESI): m/z=683 (MH⁺, 100%).
¹H-NMR (300 MHz, DMSO-d₆): 9.60 (d, J=7.7, 1H, —NH); 8.45 (d, J=4.9, 1H); 7.18 (d, J=13.3, 1H); 7.14 (d, J=9.7, 1H); 7.06 (d, J=4.9, 1H); 5.28 (d, J=10.6, 1H); 4.95 (d, J=10.6, 1H); 4.07 (m, 1H); 3.83 (dd, J=10.4, 6.6, 1H & m, 1H); 3.81 (s, 3H); 3.71 (dd, J=10.4, 6.9, 1H); 3.06 (m, 2H); 2.98 (m, 1H); 2.87 (s, 3H & m, 1H); 1.94 (m, 2H); 1.42 (s, 9H & m, 2H); 0.89 (m, 1H); 0.57 (m, 2H); 0.33 (m, 2H); 0.05 (m, 2H); −0.14 (s, 9H).

Example D.d22 tert-Butyl (trans-4-{[(7-[2-(cyclopropylmethoxy)-4-fluoro-5-methoxyphenyl]-2-methyl-1-{[2-(trimethylsilyl)ethoxy]methyl}-1H-pyrrolo[3,2-b]pyridin-3-yl)carbonyl]amino}cyclohexyl)carbamate Starting from 7-[2-(cyclopropylmethoxy)-4-fluoro-5-methoxyphenyl]-2-methyl-1-{[2-(trimethylsilyl)ethoxy]methyl}-1H-pyrrolo[3,2-b]pyridine-3-carboxylic acid (example D.c7) and commercially available tert-butyl trans-(4-aminocyclohexyl)-carbamate the title compound is obtained as pale yellow viscous oil.
MS (ESI): m/z=697 (MH⁺, 100%).
¹H-NMR (300 MHz, DMSO-d₆): 9.42 (d, J=7.5, 1H, —NH); 8.45 (d, J=4.9, 1H); 7.17 (d, J=12.4, 1H); 7.14 (d, J=9.5, 1H); 7.05 (d, J=4.9, 1H); 6.77 (d, J=7.9, 1H, —NH); 5.27 (d, J=10.6, 1H); 4.94 (d, J=10.6, 1H); 3.81 (dd, J=10.4, 6.6, 1H & s, 3H & m, 1H); 3.71 (dd, J=10.4, 6.9, 1H); 3.31 (m, 1H); 3.04-2.79 (m, 2H); 2.86 (s, 3H); 2.00 (m, 2H); 1.85 (m, 2H); 1.39 (s, 9H); 0.88 (m, 1H); 0.57 (m, 2H); 0.32 (m, 2H); 0.04 (m, 2H); −0.14 (s, 9H).

Example D.d23 tert-Butyl (cis-4-{[(7-[2-(cyclopropylmethoxy)-4-fluoro-5-methoxyphenyl]-2-methyl-1-{[2-(trimethylsilyl)ethoxy]methyl}-1H-pyrrolo[3,2-b]pyridin-3-yl)carbonyl]amino}cyclohexyl)carbamate Starting from 7-[2-(cyclopropylmethoxy)-4-fluoro-5-methoxyphenyl]-2-methyl-1-{[2-(trimethylsilyl)ethoxy]methyl}-1H-pyrrolo[3,2-b]pyridine-3-carboxylic acid (example D.c7) and commercially available tert-butyl cis-(4-aminocyclohexyl)-carbamate the title compound is obtained as pale yellow viscous oil.
MS (ESI): m/z=697 (MH⁺, 100%).
¹H-NMR (300 MHz, DMSO-d₆): 9.76 (d, J=7.7, 1H, —NH); 8.51 (d, J=4.9, 1H); 7.17 (d, J=13.4, 1H); 7.14 (d, J=9.7, 1H); 7.06 (d, J=4.9, 1H); 6.92 (br.d, J ~5.0, 1H, —NH); 5.26 (d, J=10.8, 1H); 4.94 (d, J=10.8, 1H); 4.07 (m, 1H); 3.82 (dd, J=10.4, 6.9, 1H); 3.81 (s, 3H); 3.73 (dd, J=10.4, 6.9, 1H); 3.42 (m, 1H); 2.99 (m, 1H); 2.88 (m, 1H); 2.86 (s, 3H); 1.84-1.53 (m, 8H); 1.40 (s, 9H); 0.90 (m, 1H); 0.58 (m, 2H); 0.33 (m, 2H); 0.05 (m, 2H); −0.13 (s, 9H).

Example D.d24 tert-Butyl (3R*,4R*)-3-{[(7-[2-(cyclopropylmethoxy)-4-fluoro-5-methoxyphenyl]-2-methyl-1-{[2-(trimethylsilyl)ethoxy]methyl}-1H-pyrrolo[3,2-b]pyridin-3-yl)carbonyl]amino}-4-hydroxypyrrolidine-1-carboxylate Starting from 7-[2-(cyclopropylmethoxy)-4-fluoro-5-methoxyphenyl]-2-methyl-1-{[2-(trimethylsilyl)ethoxy]methyl}-1H-pyrrolo[3,2-b]pyridine-3-carboxylic acid (example D.c7) and commercially available tert-butyl (3R*,4R*)-3-amino-4-hydroxy-pyrrolidine-1-carboxylate the title compound is obtained as pale yellow viscous oil.
MS (ESI): m/z=685 (MH⁺, 100%).
¹H-NMR (300 MHz, DMSO-d₆): 9.66 (dd, J=6.6, 6.0, 1H, —NH); 8.40 (d, J=4.9, 1H); 7.18 (d, J=13.3, 1H); 7.13 (d, J=10.0, 1H); 7.06 (d, J=4.9, 1H); 5.49 (d, J=3.8, 1H, —OH); 5.28 (d, J=10.6, 1H); 4.95 (d, J=10.6, 1H); 4.26 (m, 1H); 4.19 (m, 1H); 3.81 (dd, J=10.4, 6.7, 1H); 3.80 (s, 3H); 3.71 (dd, J=10.4, 7.1, 1H); 3.65 (m, 1H); 3.54 (m, 1H); 3.36-3.17 (m, 2H); 2.97 (m, 1H); 2.86 (s, 3H & m, 1H); 1.43 (s, 9H); 0.88 (m, 1H); 0.57 (m, 2H); 0.32 (m, 2H); 0.05 (m, 2H); −0.14 (s, 9H).

Example D.d25 tert-Butyl (3R*,4R*)-4-{[(7-[2-(cyclopropylmethoxy)-4-fluoro-5-methoxyphenyl]-2-methyl-1-{[2-(trimethylsilyl)ethoxy]methyl}-1H-pyrrolo[3,2-b]pyridin-3-yl)carbonyl]amino}-3-hydroxypiperidine-1-carboxylate Starting from 7-[2-(cyclopropylmethoxy)-4-fluoro-5-methoxyphenyl]-2-methyl-1-{[2-(trimethylsilyl)ethoxy]methyl}-1H-pyrrolo[3,2-b]pyridine-3-carboxylic acid (example D.c7) and commercially available: tert-butyl (3R*,4R*)-4-amino-3-hydroxy-piperidine-1-carboxylate the title compound is obtained as pale yellow viscous oil.

MS (ESI): m/z=699 (MH+, 100%).

$^1$H-NMR (300 MHz, DMSO-d$_6$): 9.64 (d, J=7.3, 1H, —NH); 8.44 (d, J=4.9, 1H); 7.17 (d, J=12.4, 1H); 7.13 (d, J=9.5, 1H); 7.05 (d, J=4.9, 1H); 5.27 (d, J=10.7, 1H); 5.22 (dd, J=4.9, 2.9, 1H, —OH); 4.96 (d, J=10.7, 1H); 3.99-3.67 (m, 5H); 3.81 (s, 3H); 3.44 (m, 1H); 3.08-2.72 (m, 4H); 2.87 (s, 3H); 2.07 (m, 1H); 1.42 (s, 9H); 1.37 (m, 1H); 0.89 (m, 1H); 0.58 (m, 2H); 0.33 (m, 2H); 0.04 (m, 2H); −0.13 (s, 9H).

Example D.d26 tert-Butyl 4-{[(7-[2-(cyclopropylmethoxy)-5-fluoro-4-methoxyphenyl]-1-(methoxymethyl)-2-{[2-(trimethylsilyl)ethoxy]methyl}-1H-pyrrolo[3,2-b]pyridin-3-yl)carbonyl]amino}piperidine-1-carboxylate Starting from 7-[2-(cyclopropylmethoxy)-5-fluoro-4-methoxyphenyl]-2-methyl-1-{[2-(trimethylsilyl)ethoxy]methyl}-1H-pyrrolo[3,2-b]pyridine-3-carboxylic acid (example D.c8) and commercially available tert-butyl 4-amino-piperidine-1-carboxylate the title compound is obtained as pale yellow viscous oil.

MS (ESI): m/z=683 (MH+, 100%); 627 (MH+—C$_4$H$_8$).

$^1$H-NMR (300 MHz, DMSO-d$_6$): 9.59 (d, J=7.7, 1H, —NH); 8.42 (d, J=4.9, 1H); 7.19 (d, J=11.5, 1H); 7.01 (d, J=4.9, 1H); 6.94 (d, J=7.5, 1H); 5.30 (d, J=10.8, 1H); 4.97 (d, J=10.8, 1H); 4.07 (m, 1H); 3.94 (s, 3H); 3.88 (dd, J=10.4, 6.7, 1H); 3.80 (dd, J=10.4, 7.0, 1H); 3.06 (m, 2H); 3.03-2.88 (m, 2H); 2.86 (s, 3H); 1.93 (m, 2H); 1.42 (s, 9H & m, 2H); 0.90 (m, 1H); 0.58 (m, 2H); 0.33 (m, 2H); 0.06 (m, 2H); −0.14 (s, 9H).

Example D.d27 tert-Butyl (trans-4-{[(7-[2-(cyclopropylmethoxy)-5-fluoro-4-methoxyphenyl]-2-methyl-1-{[2-(trimethylsilyl)ethoxy]methyl}-1H-pyrrolo[3,2-b]pyridin-3-yl)carbonyl]amino}cyclohexyl)carbamate Starting from 7-[2-(cyclopropylmethoxy)-5-fluoro-4-methoxyphenyl]-2-methyl-1-{[2-(trimethylsilyl)ethoxy]methyl}-1H-pyrrolo[3,2-b]pyridine-3-carboxylic acid (example D.c8) and commercially available tert-butyl trans-(4-aminocyclohexyl)-carbamate the title compound is obtained as pale yellow viscous oil.

MS (ESI): m/z=697 (MH+, 100%).

$^1$H-NMR (300 MHz, DMSO-d$_6$): 9.40 (d, J=7.7, 1H, —NH); 8.42 (d, J=4.9, 1H); 7.19 (d, J=11.5, 1H); 6.99 (d, J=4.9, 1H); 6.93 (d, J=7.5, 1H); 6.71 (d, J=7.3, 1H, —NH); 5.29 (d, J=10.9, 1H); 4.96 (d, J=10.9, 1H); 3.94 (s, 3H); 3.88 (dd, J=10.4, 6.7, 1H); 3.80 (dd, J=10.4, 6.9, 1H); 3.76 (m, 1H); 3.27 (m, 1H); 3.02-2.87 (m, 2H); 2.86 (s, 3H); 1.99 (m, 2H); 1.85 (m, 2H); 1.39 (s, 9H); 1.33 (m, 4H); 0.90 (m, 1H); 0.58 (m, 2H); 0.33 (m, 2H); 0.05 (m, 2H); −0.15 (s, 9H).

Example D.d28 tert-Butyl (cis-4-{[(7-[2-(cyclopropylmethoxy)-5-fluoro-4-methoxyphenyl]-2-methyl-1-{[2-(trimethylsilyl)ethoxy]methyl}-1H-pyrrolo[3,2-b]pyridin-3-yl)carbonyl]amino}cyclohexyl)carbamate Starting from 7-[2-(cyclopropylmethoxy)-5-fluoro-4-methoxyphenyl]-2-methyl-1-{[2-(trimethylsilyl)ethoxy]methyl}-1H-pyrrolo[3,2-b]pyridine-3-carboxylic acid (example D.c8) and commercially available tert-butyl cis-(4-aminocyclohexyl)-carbamate the title compound is obtained as pale yellow viscous oil.

MS (ESI): m/z=719 (MNa+); 697 (MH+, 100%); 641 (MH+—C$_4$H$_8$).

$^1$H-NMR (300 MHz, DMSO-d$_6$): 9.77 (d, J=7.7, 1H, —NH); 8.49 (d, J=4.9, 1H); 7.19 (d, J=11.5, 1H); 7.02 (d, J=4.9, 1H); 6.95 (d, J=7.5, 1H); 6.92 (br.s, 1H, —NH); 5.30 (d, J=10.8, 1H); 4.98 (d, J=10.8, 1H); 4.07 (m, 1H); 3.94 (s, 3H); 3.89 (dd, J=10.4, 6.7, 1H); 3.81 (dd, J=10.4, 7.0, 1H); 3.42 (m, 1H); 3.04-2.87 (m, 2H); 2.87 (s, 3H); 1.76 (m, 2H); 1.65 (m, 6H); 1.40 (s, 9H); 0.91 (m, 1H); 0.58 (m, 2H); 0.34 (m, 2H); 0.07 (m, 2H); −0.14 (s, 9H).

Example D.e1 tert-Butyl 4-[({7-[5-(cyclopropylmethoxy)-1,3-benzodioxol-4-yl]-2-methyl-1H-pyrrolo[3,2-b]pyridin-3-yl}carbonyl)amino]piperidine-1-carboxylate A solution of tert-butyl 4-{[(7-[5-(cyclopropylmethoxy)-1,3-benzodioxol-4-yl]-2-methyl-1-{[2-(trimethylsilyl)ethoxy]methyl}-1H-pyrrolo[3,2-b]pyridin-3-yl)carbonyl]amino}piperidine-1-carboxylate from example D.d1 (3.74 g; 5.5 mmol), tetrabutylammonium fluoride trihydrate (5.21 g; 16.5 mmol) and ethane-1,2-diamine (0.50 g; 8.25 mmol) in tetrahydrofurane (40 mL) is heated to gentle reflux until the starting material is completely consumed according to LC-MS. The crude is purified by column chromatography on silica gel (ethyl acetate/cyclohexane—1:1 to 2:1) to yield the title compound as colorless solid.

MS (ESI): m/z=549 (MH+, 100%).

$^1$H-NMR (300 MHz, DMSO-d$_6$): 11.43 (s, 1H, —NH); 9.24 (d, J=7.7, 1H, —NH); 8.39 (d, J=5.1, 1H); 7.18 (d, J=5.1, 1H); 6.95 (d, J=8.5, 1H); 6.55 (d, J=8.5, 1H); 6.00 (s, 2H); 4.06 (m, 1H); 3.84 (m, 2H); 3.74 (d, J=6.8, 2H); 3.06 (m, 2H); 2.73 (s, 3H); 1.92 (m, 2H); 1.42 (m, 2H & s, 9H); 0.93 (m, 1H); 0.35 (m, 2H); 0.15 (m, 2H).

The following compounds were prepared analogously to the procedure described in above example D.e1.

Example D.e2 tert-Butyl {trans-4-[({7-[5-(cyclopropylmethoxy)-1,3-benzodioxol-4-yl]-2-methyl-1H-pyrrolo[3,2-b]pyridin-3-yl}carbonyl)amino]cyclohexyl}carbamate Starting from tert-butyl (trans-4-{[(7-[5-(cyclopropylmethoxy)-1,3-benzodioxol-4-yl]-2-methyl-1-{[2-(trimethylsilyl)ethoxy]methyl}-1H-pyrrolo[3,2-b]pyridin-3-yl)carbonyl]amino}cyclohexyl)carbamate (example D.d2) the title compound is obtained as colorless solid.

MS (ESI): m/z=563 (MH+, 100%).

$^1$H-NMR (300 MHz, DMSO-d$_6$): 11.39 (s, 1H, —NH); 9.05 (d, J=7.7, 1H, —NH); 8.39 (d, J=4.9, 1H); 7.17 (d, J=4.9, 1H); 6.95 (d, J=8.6, 1H); 6.71 (br.d, J ~7.7, 1H, —NH); 6.55 (d, J=8.6, 1H); 6.00 (s, 2H); 3.74 (m, 1H & d, J=6.8, 2H); 3.29 (m, 1H); 2.72 (s, 3H); 1.99 (m, 2H); 1.85 (m, 2H); 1.39 (s, 9H); 1.36 (m, 4H); 0.92 (m, 1H); 0.35 (m, 2H); 0.15 (m, 2H).

Example D.e3 tert-Butyl {cis-4-[({7-[5-(cyclopropylmethoxy)-1,3-benzodioxol-4-yl]-2-methyl-1H-pyrrolo[3,2-b]pyridin-3-yl}carbonyl)amino]cyclohexyl}carbamate Starting from tert-butyl (cis-4-{[(7-[5-(cyclopropylmethoxy)-1,3-benzodioxol-4-yl]-2-methyl-1-{[2-(trimethylsilyl)ethoxy]methyl}-1H-pyrrolo[3,2-b]pyridin-3-yl)carbonyl]amino}cyclohexyl)carbamate (example D.d3) the title compound is obtained as colorless solid.

MS (ESI): m/z=563 (MH+, 100%).

$^1$H-NMR (300 MHz, DMSO-d$_6$): 11.39 (s, 1H, —NH); 9.39 (d, J=7.7, 1H, —NH); 8.44 (d, J=5.1, 1H); 7.19 (d, J=5.1, 1H); 6.95 (d, J=8.7, 1H); 6.92 (br.d, J ~5.0, 1H, —NH); 6.55 (d, J=8.6, 1H); 6.00 (s, 2H); 4.03 (m, 1H); 3.75 (d, J=6.8, 2H); 3.41 (m, 1H); 2.73 (s, 3H); 1.85-1.51 (m, 8H); 1.40 (s, 9H); 0.94 (m, 1H); 0.34 (m, 2H); 0.16 (m, 2H).

Example D.e4 tert-Butyl 4-{[(7-[2-(cyclopropylmethoxy)-4-fluorophenyl]-2-methyl-1-{[2-(trimethylsilyl)ethoxy]methyl}-1H-pyrrolo[3,2-b]pyridin-3-yl)carbonyl]amino}piperidine-1-carboxylate Starting from tert-butyl 4-{[(7-[2-(cyclopropylmethoxy)-4-fluorophenyl]-2-methyl-1-{[2-(trimethylsilyl)ethoxy]methyl}-1H-pyrrolo[3,2-b]pyridin-3-yl)carbonyl]amino}piperidine-1-carboxylate (example D.d4) the title compound is obtained as colorless solid.

MS (ESI): m/z=523 (MH+, 100%).

$^1$H-NMR (300 MHz, DMSO-d$_6$): 11.35 (s, 1H; —NH); 9.27 (d, J=7.7, 1H, —NH); 8.40 (d, J=4.9, 1H); 7.42 (dd, J=8.4, 6.9, 1H); 7.08 (d, J=4.9, 1H); 7.05 (dd, J=11.5, 2.4, 1H); 6.92 (ddd, J=8.4, 8.4, 2.4, 1H); 4.07 (m, 1H); 3.88 (d, J=6.9, 2H); 3.84 (m, 2H); 3.06 (m, 2H); 2.73 (s, 3H); 1.92 (m, 2H); 1.42 (s, 9H & m, 2H); 0.94 (m, 1H); 0.36 (m, 2H); 0.21 (m, 2H).

Example D.e5 tert-Butyl {trans-4-[({7-[2-(cyclopropylmethoxy)-4-fluorophenyl]-2-methyl-1H-pyrrolo[3,2-b]pyridin-3-yl}carbonyl)amino]cyclohexyl}carbamate Starting from: tert-butyl (trans-4-{[(7-[2-(cyclopropylmethoxy)-4-fluorophenyl]-2-methyl-1-{[2-(trimethylsilyl)ethoxy]methyl}-1H-pyrrolo[3,2-b]pyridin-3-yl)carbonyl]amino}cyclohexyl)carbamate (example D.d5) the title compound is obtained as colorless solid.

MS (ESI): m/z=537 (MH+, 100%).

$^1$H-NMR (300 MHz, DMSO-d$_6$): 11.32 (s, 1H; —NH); 9.08 (d, J=7.7, 1H, —NH); 8.40 (d, J=4.9, 1H); 7.41 (dd, J=8.4, 6.9, 1H); 7.07 (d, J=4.9, 1H); 7.05 (dd, J=11.6, 2.4, 1H); 6.92 (ddd, J=8.4, 8.4, 2.4, 1H); 6.71 (br.d, J ~7.5, 1H, —NH); 3.88 (d, J=6.8, 2H); 3.75 (m, 1H); 3.28 (m, 1H); 2.72 (s, 3H); 1.99 (m, 2H); 1.85 (m, 2H); 1.39 (s, 9H); 1.33 (m, 4H); 0.94 (m, 1H); 0.36 (m, 2H); 0.21 (m, 2H).

Example D.e6 tert-Butyl {cis-4-[({7-[2-(cyclopropylmethoxy)-4-fluorophenyl]-2-methyl-1H-pyrrolo[3,2-b]pyridin-3-yl}carbonyl)amino]cyclohexyl}carbamate Starting from tert-butyl (cis-4-{[(7-[2-(cyclopropylmethoxy)-4-fluorophenyl]-2-methyl-1-{[2-(trimethylsilyl)ethoxy]methyl}-1H-pyrrolo[3,2-b]pyridin-3-yl)carbonyl]amino}cyclohexyl)carbamate (example D.d6) the title compound is obtained as colorless solid.

MS (ESI): m/z=537 (MH+, 100%).

$^1$H-NMR (300 MHz, DMSO-d$_6$): 11.31 (s, 1H; —NH); 9.42 (d, J=7.7, 1H, —NH); 8.44 (d, J=4.9, 1H); 7.42 (dd, J=8.4, 6.9, 1H); 7.09 (d, J=4.9, 1H); 7.06 (dd, J=11.5, 2.4, 1H); 6.93 (ddd, J=8.4, 8.4, 2.4, 1H & br.s, 1H, —NH); 4.04 (m, 1H); 3.89 (d, J=6.8, 2H); 3.42 (m, 1H); 2.73 (s, 3H); 1.85-1.52 (m, 8H); 1.40 (s, 9H); 0.95 (m, 1H); 0.37 (m, 2H); 0.22 (m, 2H).

Example D.e7 tert-Butyl 4-[({7-[2-(cyclopropylmethoxy)-5-fluorophenyl]-2-methyl-1H-pyrrolo[3,2-b]pyridin-3-yl}carbonyl)amino]piperidine-1-carboxylate Starting from tert-butyl 4-{[(7-[2-(cyclopropylmethoxy)-5-fluorophenyl]-2-methyl-1-{[2-(trimethylsilyl)ethoxy]methyl}-1H-pyrrolo[3,2-b]pyridin-3-yl)carbonyl]amino}piperidine-1-carboxylate (example D.d7) the title compound is obtained as colorless solid.

MS (ESI): m/z=523 (MH+, 100%).

$^1$H-NMR (300 MHz, DMSO-d$_6$): 11.40 (s, 1H, —NH); 9.27 (d, J=7.7, 1H, —NH); 8.41 (d, J=4.9, 1H); 7.32 (dd, J=8.6, 3.2, 1H); 7.27 (ddd, J=9.1, 8.7, 3.2, 1H); 7.15 (dd, J=9.1, 4.6, 1H); 7.13 (d, J=4.9, 1H); 4.06 (m, 1H); 3.84 (d, J=6.9, 2H & m, 2H); 3.06 (m, 2H); 2.74 (s, 3H); 1.92 (m, 2H); 1.42 (s, 9H & m, 2H); 0.93 (m, 1H); 0.35 (m, 2H); 0.19 (m, 2H).

Example D.e8 tert-Butyl {trans-4-[({7-[2-(cyclopropylmethoxy)-5-fluorophenyl]-2-methyl-1H-pyrrolo[3,2-b]pyridin-3-yl}carbonyl)amino]cyclohexyl}carbamate Starting from tert-butyl (trans-4-{[(7-[2-(cyclopropylmethoxy)-5-fluorophenyl]-2-methyl-1-{[2-(trimethylsilyl)ethoxy]methyl}-1H-pyrrolo[3,2-b]pyridin-3-yl)carbonyl]amino}cyclohexyl)carbamate (example D.d8) the title compound is obtained as colorless solid.

MS (ESI): m/z=537 (MH+, 100%).

$^1$H-NMR (300 MHz, DMSO-d$_6$): 11.37 (s, 1H, —NH); 9.07 (d, J=7.7, 1H, —NH); 8.41 (d, J=4.9, 1H); 7.31 (dd, J=8.6, 3.2, 1H); 7.26 (ddd, J=8.9, 8.6, 3.2, 1H); 7.15 (dd, J=8.9, 4.6, 1H); 7.12 (d, J=4.9, 1H); 6.71 (d, J=7.7, 1H, —NH); 3.83 (d, J=6.9, 2H); 3.75 (m, 1H); 3.30 (m, 1H); 2.73 (s, 3H); 1.99 (m, 2H); 1.85 (m, 2H); 1.39 (s, 9H); 1.33 (m, 4H); 0.91 (m, 1H); 0.34 (m, 2H); 0.18 (m, 2H).

Example D.e9 tert-Butyl {cis-4-[({7-[2-(cyclopropylmethoxy)-5-fluorophenyl]-2-methyl-1H-pyrrolo[3,2-b]pyridin-3-yl}carbonyl)amino]cyclohexyl}carbamate Starting from tert-butyl (cis-4-{[(7-[2-(cyclopropylmethoxy)-5-fluorophenyl]-2-methyl-1-{[2-(trimethylsilyl)ethoxy]ethyl}-1H-pyrrolo[3,2-b]pyridin-3-yl)carbonyl]amino}cyclohexyl)carbamate (example D.d9) the title compound is obtained as colorless solid.

MS (ESI): m/z=537 (MH+, 100%).

$^1$H-NMR (300 MHz, DMSO-d$_6$): 11.36 (s, 1H, —NH); 9.42 (d, J=7.7, 1H, —NH); 8.46 (d, J=4.9, 1H); 7.32 (dd, J=8.4, 3.3, 1H); 7.27 (ddd, J=8.9, 8.9, 3.3, 1H); 7.16 (dd, J=8.9, 4.6, 1H); 7.14 (d, J=4.9, 1H); 6.92 (br.d, J ~5.8, 1H, —NH); 4.04 (m, 1H); 3.84 (d, J=6.8, 2H); 3.41 (m, 1H); 2.74 (s, 3H); 1.85-1.54 (m, 8H); 1.40 (s, 9H); 0.93 (m, 1H); 0.35 (m, 2H); 0.19 (m, 2H).

Example D.e10 tert-Butyl (3R*,4R*)-4-[({7-[2-(cyclopropylmethoxy)-5-fluorophenyl]-2-methyl-1H-pyrrolo[3,2-b]pyridin-3-yl}carbonyl)amino]-3-hydroxypiperidine-1-carboxylate Starting from tert-butyl (3R*,4R*)-4-{[(7-[2-(cyclopropylmethoxy)-5-fluorophenyl]-2-methyl-1-{[2-(trimethylsilyl)ethoxy]methyl}-1H-pyrrolo[3,2-b]pyridin-3-yl)carbonyl]amino}-3-hydroxypiperidine-1-carboxylate (example D.d10) the title compound is obtained as colorless solid.

MS (ESI): m/z=539 (MH$^+$, 100%).

$^1$H-NMR (400 MHz, DMSO-d$_6$): 11.40 (s, 1H, —NH); 9.31 (d, J=7.3, 1H, —NH); 8.42 (d, J=4.9, 1H); 7.32 (dd, J=8.6, 3.2, 1H); 7.26 (ddd, J=9.1, 8.7, 3.2, 1H); 7.15 (dd, J=9.1, 4.5, 1H); 7.14 (d, J=4.9, 1H); 5.25 (d, J=4.8, 1H, —OH); 3.98-3.72 (m, 3H); 3.84 (d, J=6.9, 2H); 3.43 (m, 1H); 3.00 (m, 1H); 2.82 (m, 1H); 2.74 (s, 3H); 2.32 (m, 1H); 2.06 (m, 1H); 1.42 (s, 9H); 0.93 (m, 1H); 0.35 (m, 2H); 0.19 (m, 2H).

Example D.e11 tert-Butyl 4-[({7-[2-(cyclopropylmethoxy)-4-methoxyphenyl]-2-methyl-1H-pyrrolo[3,2-b]pyridin-3-yl}carbonyl)amino]piperidine-1-carboxylate Starting from tert-butyl 4-{[(7-[2-(cyclopropylmethoxy)-4-methoxyphenyl]-2-methyl-1-{[2-(trimethylsilyl)ethoxy]methyl}-1H-pyrrolo[3,2-b]pyridin-3-yl)carbonyl]amino}piperidine-1-carboxylate (example D.d11) the title compound is obtained as colorless solid.

MS (ESI): m/z=535 (MH$^+$, 100%).

$^1$H-NMR (300 MHz, DMSO-d$_6$): 11.27 (s, 1H; —NH); 9.30 (d, J=7.7, 1H, —NH); 8.37 (d, J=4.9, 1H); 7.31 (d, J=8.9, 1H); 7.06 (d, J=4.9, 1H); 6.69 (dd, J=8.9, 2.4, 1H); 6.67 (d, J=2.4, 1H); 4.06 (m, 1H); 3.87 (d, J=6.8, 2H); 3.84 (s, 3H); 3.82 (m, 2H); 3.06 (m, 2H); 2.73 (s, 3H); 1.92 (m, 2H); 1.42 (s, 9H & m, 2H); 0.94 (m, 1H); 0.36 (m, 2H); 0.22 (m, 2H).

Example D.e12 tert-Butyl {trans-4-[({7-[2-(cyclopropylmethoxy)-4-methoxyphenyl]-2-methyl-1H-pyrrolo[3,2-b]pyridin-3-yl}carbonyl)amino]cyclohexyl}carbamate Starting from tert-butyl (trans-4-{[(7-[2-(cyclopropylmethoxy)-4-methoxyphenyl]-2-methyl-1-{[2-(trimethylsilyl)ethoxy]methyl}-1H-pyrrolo[3,2-b]pyridin-3-yl)carbonyl]amino}cyclohexyl)carbamate (example D.d12) the title compound is obtained as colorless solid.

MS (ESI): m/z=549 (MH$^+$, 100%).

$^1$H-NMR (300 MHz, DMSO-d$_6$): 11.24 (s, 1H; —NH); 9.11 (d, J=7.9, 1H, —NH); 8.36 (d, J=4.9, 1H); 7.31 (d, J=9.1, 1H); 7.06 (d, J=4.9, 1H); 6.72 (br.s, 1H, —NH); 6.69 (dd, J=9.1, 2.2, 1H); 6.66 (d, J=2.2, 1H); 3.87 (d, J=6.8, 2H); 3.83 (s, 3H); 3.76 (m, 1H); 3.27 (m, 1H); 2.72 (s, 3H); 1.98 (m, 2H); 1.84 (m, 2H); 1.39 (s, 9H); 1.29 (m, 4H); 0.94 (m, 1H); 0.35 (m, 2H); 0.21 (m, 2H).

Example D.e13 tert-Butyl {cis-4-[({7-[2-(cyclopropylmethoxy)-4-methoxyphenyl]-2-methyl-1H-pyrrolo[3,2-b]pyridin-3-yl}carbonyl)amino]cyclohexyl}carbamate Starting from tert-butyl (cis-4-{[(7-[2-(cyclopropylmethoxy)-4-methoxyphenyl]-2-methyl-1-{[2-(trimethylsilyl)ethoxy]methyl}-1H-pyrrolo[3,2-b]pyridin-3-yl)carbonyl]amino}cyclohexyl)carbamate (example D.d13) the title compound is obtained as colorless solid.

MS (ESI): m/z=549 (MH$^+$, 100%).

$^1$H-NMR (300 MHz, DMSO-d$_6$): 11.24 (s, 1H; —NH); 9.45 (d, J=7.9, 1H, —NH); 8.42 (d, J=5.0, 1H); 7.31 (d, J=8.9, 1H); 7.06 (d, J=5.0, 1H); 6.91 (br.d, J ~5.0, 1H, —NH); 6.69 (dd, J=8.9, 2.4, 1H); 6.68 (d, J=2.4, 1H); 4.04 (m, 1H); 3.88 (d, J=6.9, 2H); 3.84 (s, 3H); 3.41 (m, 1H); 2.72 (s, 3H); 1.83-1.52 (m, 8H); 1.40 (s, 9H); 0.95 (m, 1H); 0.36 (m, 2H); 0.23 (m, 2H).

Example D.e14 tert-Butyl 4-[({7-[2-(cyclopropylmethoxy)-5-methoxyphenyl]-2-methyl-1H-pyrrolo[3,2-b]pyridin-3-yl}carbonyl)amino]piperidine-1-carboxylate Starting from tert-butyl 4-{[(7-[2-(cyclopropylmethoxy)-5-methoxyphenyl]-2-methyl-1-{[2-(trimethylsilyl)ethoxy]methyl}-1H-pyrrolo[3,2-b]pyridin-3-yl)carbonyl]amino}piperidine-1-carboxylate (example D.d14) the title compound is obtained as colorless solid.

MS (ESI): m/z=535 (MH$^+$, 100%).

$^1$H-NMR (400 MHz, DMSO-d$_6$): 11.35 (s, 1H; —NH); 9.28 (d, J=7.6, 1H, —NH); 8.40 (d, J=4.9, 1H); 7.09 (d, J=8.9, 1H); 7.03 (dd, J=8.9, 2.9, 1H); 6.95 (d, J=2.9, 1H); 4.06 (m, 1H); 3.84 (m, 2H); 3.78 (d, J=6.8, 2H); 3.76 (s, 3H); 3.06 (m, 2H); 2.73 (s, 3H); 1.92 (m, 2H); 1.42 (s, 9H & m, 2H); 0.91 (m, 1H); 0.34 (m, 2H); 0.16 (m, 2H).

Example D.e15 tert-Butyl {trans-4-[({7-[2-(cyclopropylmethoxy)-5-methoxyphenyl]-2-methyl-1H-pyrrolo[3,2-b]pyridin-3-yl}carbonyl)amino]cyclohexyl}carbamate Starting from tert-butyl (trans-4-{[(7-[2-(cyclopropylmethoxy)-5-methoxyphenyl]-2-methyl-1-{[2-(trimethylsilyl)ethoxy]methyl}-1H-pyrrolo[3,2-b]pyridin-3-yl)carbonyl]amino}cyclohexyl)carbamate (example D.d15) the title compound is obtained as colorless solid.

MS (ESI): m/z=549 (MH$^+$, 100%).

$^1$H-NMR (300 MHz, DMSO-d$_6$): 11.32 (s, 1H; —NH); 9.10 (d, J=7.7, 1H, —NH); 8.40 (d, J=4.9, 1H); 7.12 (d, J=4.9, 1H); 7.09 (d, J=9.1, 1H); 7.03 (dd, J=9.1, 2.9, 1H); 6.95 (d, J=2.9, 1H); 6.72 (d, J=7.5, 1H, —NH); 3.79 (d, J=6.9, 2H); 3.77 (s, 3H & m, 1H); 3.30 (m, 1H); 2.73 (s, 3H); 1.99 (m, 2H); 1.86 (m, 2H); 1.42 (s, 9H); 1.33 (m, 4H); 0.89 (m, 1H); 0.34 (m, 2H); 0.16 (m, 2H).

Example D.e16 tert-Butyl {cis-4-[({7-[2-(cyclopropylmethoxy)-5-methoxyphenyl]-2-methyl-1H-pyrrolo[3,2-b]pyridin-3-yl}carbonyl)amino]cyclohexyl}carbamate Starting from: tert-butyl (cis-4-{[(7-[2-(cyclopropylmethoxy)-5-methoxyphenyl]-2-methyl-1-{[2-(trimethylsilyl)ethoxy]methyl}-1H-pyrrolo[3,2-b]pyridin-3-yl)carbonyl]amino}cyclohexyl)carbamate (example D.d16) the title compound is obtained as colorless solid.

MS (ESI): m/z=549 (MH$^+$, 100%).
$^1$H-NMR (400 MHz, DMSO-d$_6$): 11.31 (s, 1H, —NH); 9.43 (d, J=7.9, 1H, —NH); 8.45 (d, J=4.9, 1H); 7.14 (d, J=4.9, 1H); 7.09 (d, J=9.1, 1H); 7.03 (dd, J=9.1, 2.9, 1H); 6.96 (d, J=2.9, 1H); 6.92 (br.s, 1H, —NH); 4.04 (m, 1H); 3.79 (d, J=6.8, 2H); 3.77 (s, 3H); 3.42 (m, 1H); 2.73 (s, 3H); 1.85-1.54 (m, 8H); 1.40 (s, 9H); 0.92 (m, 1H); 0.34 (m, 2H); 0.16 (m, 2H).

Example D.e17 tert-Butyl-(3R*,4R*)-3-[({7-[2-(cyclopropylmethoxy)-5-methoxyphenyl]-2-methyl-1H-pyrrolo[3,2-b]pyridin-3-yl}carbonyl)amino]-4-hydroxypyrrolidine-1-carboxylate Starting from tert-butyl-(3R*,4R*)-3-{[(7-[2-(cyclopropylmethoxy)-5-methoxyphenyl]-2-methyl-1-{[2-(trimethylsilyl)ethoxy]methyl}-1H-pyrrolo[3,2-b]pyridin-3-yl)carbonyl]amino}-4-hydroxypyrrolidine-1-carboxylate (example D.d17) the title compound is obtained as colorless solid.

MS (ESI): m/z=537 (MH$^+$, 100%).
$^1$H-NMR (400 MHz, DMSO-d$_6$): 11.40 (s, 1H, —NH); 9.35 (~t, J ~6.7, 1H, —NH); 8.36 (d, J=4.9, 1H); 7.13 (d, J=4.9, 1H); 7.09 (d, J=9.0, 1H); 7.04 (dd, J=9.0, 3.0, 1H); 6.95 (d, J=3.0, 1H); 5.44 (d, J=3.8, 1H, —OH); 4.26 (m, 1H); 4.18 (m, 1H); 3.78 (d, J=6.9, 2H); 3.76 (s, 3H); 3.67 (m, 1H); 3.54 (m, 1H); 3.34-3.17 (m, 2H); 2.74 (s, 3H); 1.43 (s, 9H); 0.91 (m, 1H); 0.33 (m, 2H); 0.15 (m, 2H).

Example D.e18 tert-Butyl 4-[({7-[2-(cyclopropylmethoxy)-5-methylphenyl]-2-methyl-1H-pyrrolo[3,2-b]pyridin-3-yl}carbonyl)amino]piperidine-1-carboxylate Starting from tert-butyl 4-{[(7-[2-(cyclopropylmethoxy)-5-methylphenyl]-2-methyl-1-{[2-(trimethylsilyl)ethoxy]methyl}-1H-pyrrolo[3,2-b]pyridin-3-yl)carbonyl]amino}piperidine-1-carboxylate (example D.d18) the title compound is obtained as colorless solid.

MS (ESI): m/z=519 (MH$^+$, 100%).
$^1$H-NMR (300 MHz, DMSO-d$_6$): 11.31 (s, 1H, —NH); 9.29 (d, J=7.7, 1H, —NH); 8.39 (d, J=4.9, 1H); 7.26 (dd, J=8.4, 1.8, 1H); 7.19 (d, J=1.8, 1H); 7.09 (d, J=4.9, 1H); 7.03 (d, J=8.4, 1H); 4.07 (m, 1); 3.87 (m, 2H); 3.83 (d, J=6.8, 2H); 3.06 (m, 2H); 2.73 (s, 3H); 2.32 (s, 3H); 1.92 (m, 2H); 1.42 (s, 9H & m, 2H); 0.93 (m, 1H); 0.34 (m, 2H); 0.19 (m, 2H).

Example D.e19 tert-Butyl {trans-4-[({7-[2-(cyclopropylmethoxy)-5-methylphenyl]-2-methyl-1H-pyrrolo[3,2-b]pyridin-3-yl}carbonyl)amino]cyclohexyl}carbamate Starting from tert-butyl (trans-4-{[(7-[2-(cyclopropylmethoxy)-5-methylphenyl]-2-methyl-1-{[2-(trimethylsilyl)ethoxy]methyl}-1H-pyrrolo[3,2-b]pyridin-3-yl)carbonyl]amino}cyclohexyl)carbamate (example D.d19) the title compound is obtained as colorless solid.

MS (ESI): m/z=533 (MH$^+$, 100%).
$^1$H-NMR (300 MHz, DMSO-d$_6$): 11.28 (s, 1H, —NH); 9.10 (d, J=7.7, 1H, —NH); 8.39 (d, J=4.9, 1H); 7.26 (dd, J=8.4, 2.0, 1H); 7.19 (d, J=2.0, 1H); 7.08 (d, J=4.9, 1H); 7.03 (d, J=8.4, 1H); 6.71 (br.d, J ~7.9, 1H, —NH); 3.82 (d, J=6.8, 2H); 3.76 (m, 1H); 3.27 (m, 1H); 2.72 (s, 3H); 2.31 (s, 3H); 1.99 (m, 2H); 1.85 (m, 2H); 1.39 (s, 9H); 1.33 (m, 4H); 0.93 (m, 1H); 0.34 (m, 2H); 0.18 (m, 2H).

Example D.e20 tert-Butyl {cis-4-[({7-[2-(cyclopropylmethoxy)-5-methylphenyl]-2-methyl-1H-pyrrolo[3,2-b]pyridin-3-yl}carbonyl)amino]cyclohexyl}carbamate Starting from tert-butyl (cis-4-{[(7-[2-(cyclopropylmethoxy)-5-methylphenyl]-2-methyl-1-{[2-(trimethylsilyl)ethoxy]methyl}-1H-pyrrolo[3,2-b]pyridin-3-yl)carbonyl]amino}cyclohexyl)carbamate (example D.d20) the title compound is obtained as colorless solid.

MS (ESI): m/z=533 (MH$^+$, 100%).
$^1$H-NMR (300 MHz, DMSO-d$_6$): 11.27 (s, 1H, —NH); 9.44 (d, J=7.9, 1H, —NH); 8.44 (d, J=5.0, 1H); 7.26 (dd, J=8.4, 2.0, 1H); 7.20 (d, J=2.0, 1H); 7.10 (d, J=5.0, 1H); 7.04 (d, J=8.4, 1H); 6.92 (br.d, J ~5.5, 1H, —NH); 4.04 (m, 1H); 3.83 (d, J=6.8, 2H); 3.42 (m, 1H); 2.73 (s, 3H); 2.32 (s, 3H); 1.86-1.51 (m, 8H); 1.40 (s, 9H); 0.94 (m, 1H); 0.35 (m, 2H); 0.198 (m, 2H).

Example D.e21 tert-Butyl 4-[({7-[2-(cyclopropylmethoxy)-4-fluoro-5-methoxyphenyl]-2-methyl-1H-pyrrolo[3,2-b]pyridin-3-yl}carbonyl)amino]piperidine-1-carboxylate Starting from tert-butyl 4-{[(7-[2-(cyclopropylmethoxy)-4-fluoro-5-methoxyphenyl]-2-methyl-1-{[2-(trimethylsilyl)ethoxy]methyl}-1H-pyrrolo[3,2-b]pyridin-3-yl)carbonyl]amino}piperidine-1-carboxylate (example D.d21) the title compound is obtained as colorless solid.

MS (ESI): m/z=553 (MH$^+$, 100%).
$^1$H-NMR (300 MHz, DMSO-d$_6$): 11.35 (s, 1H, —NH); 9.27 (d, J=7.7, 1H, —NH); 8.41 (d, J=5.1, 1H); 7.18 (d, J=7.9, 1H); 7.16 (d, J=11.5, 1H & d, J=5.1, 1H); 4.06 (m, 1H); 3.86 (m, 2H); 3.84 (s, 3H); 3.81 (d, J=6.8, 2H); 3.06 (m, 2H); 2.73 (s, 3H); 1.92 (m, 2H); 1.42 (s, 9H & m, 2H); 0.92 (m, 1H); 0.35 (m, 2H); 0.17 (m, 2H).

Example D.e22 tert-Butyl {trans-4-[({7-[2-(cyclopropylmethoxy)-4-fluoro-5-methoxyphenyl]-2-methyl-1H-pyrrolo[3,2-b]pyridin-3-yl}carbonyl)amino]cyclohexyl}carbamate Starting from tert-butyl (trans-4-{[(7-[2-(cyclopropylmethoxy)-4-fluoro-5-methoxyphenyl]-2-methyl-1-{[2-(trimethylsilyl)ethoxy]methyl}-1H-pyrrolo[3,2-b]pyridin-3-yl)carbonyl]amino}cyclohexyl)carbamate (example D.d22) the title compound is obtained as colorless solid.

MS (ESI): m/z=567 (MH$^+$, 100%).
$^1$H-NMR (300 MHz, DMSO-d$_6$): 11.32 (s, 1H, —NH); 9.08 (d, J=7.7, 1H, —NH); 8.40 (d, J=4.9, 1H); 7.18 (d, J=7.9, 1H); 7.14 (d, J=11.6, 1H & d, J=4.9, 1H); 6.71 (d, J=7.7, 1H,

—NH); 3.84 (s, 3H); 3.80 (d, J=6.8, 2H); 3.77 (m, 1H); 3.30 (m, 1H); 2.72 (s, 3H); 1.99 (m, 2H); 1.85 (m, 2H); 1.39 (s, 9H); 1.33 (m, 4H); 0.91 (m, 1H); 0.34 (m, 2H); 0.16 (m, 2H).

Example D.e23 tert-Butyl {cis-4-[({7-[2-(cyclopropylmethoxy)-4-fluoro-5-methoxyphenyl]-2-methyl-1H-pyrrolo[3,2-b]pyridin-3-yl}carbonyl)amino]cyclohexyl}carbamate Starting from tert-butyl (cis-4-{[(7-[2-(cyclopropylmethoxy)-4-fluoro-5-methoxyphenyl]-2-methyl-1-{[2-(trimethylsilyl)ethoxy]methyl}-1H-pyrrolo[3,2-b]pyridin-3-yl)carbonyl]amino}cyclohexyl)carbamate (example D.d23) the title compound is obtained as colorless solid.
MS (ESI): m/z=567 (MH$^+$, 100%).
$^1$H-NMR (300 MHz, DMSO-d$_6$): 11.32 (s, 1H, —NH); 9.42 (d, J=7.7, 1H, —NH); 8.46 (d, J=4.9, 1H); 7.19 (d, J=7.9, 1H); 7.15 (d, J=4.9, 1H); 7.14 (d, J=11.5, 1H); 6.92 (br.d, J ~5.8, 1H, —NH); 4.04 (m, 1H); 3.84 (s, 3H); 3.81 (d, J=6.8, 2H); 3.42 (m, 1H); 2.73 (s, 3H); 1.85-1.52 (m, 8H); 1.40 (s, 9H); 0.92 (m, 1H); 0.35 (m, 2H); 0.18 (m, 2H).

Example D.e24 tert-Butyl (3R*,4R*)-3-[({7-[2-(cyclopropylmethoxy)-4-fluoro-5-methoxyphenyl]-2-methyl-1H-pyrrolo[3,2-b]pyridin-3-yl}carbonyl)amino]-4-hydroxypyrrolidine-1-carboxylate Starting from tert-butyl (3R*,4R*)-3-{[(7-[2-(cyclopropylmethoxy)-4-fluoro-5-methoxyphenyl]-2-methyl-1-{[2-(trimethylsilyl)ethoxy]methyl}-1H-pyrrolo[3,2-b]pyridin-3-yl)carbonyl]amino}-4-hydroxypyrrolidine-1-carboxylate (example D.d24) the title compound is obtained as colorless solid.
MS (ESI): m/z=555 (MH$^+$, 100%).
$^1$H-NMR (300 MHz, DMSO-d$_6$): 11.41 (s, 1H, —NH); 9.33 (dd, J=6.0, 4.8, 1H, —NH); 8.36 (d, J=4.9, 1H); 7.18 (d, J=6.6, 1H); 7.15 (d, J=4.9, 1H); 7.14 (d, J=10.2, 1H); 5.45 (d, J=3.8, 1H, —OH); 4.25 (m, 1H); 4.18 (m, 1H); 3.84 (s, 3H); 3.81 (d, J=6.9, 2H); 3.67 (m, 1H); 3.54 (m, 1H); 3.33-3.17 (m, 2H); 2.73 (s, 3H); 1.43 (s, 9H); 0.90 (m, 1H); 0.35 (m, 2H); 0.17 (m, 2H).

Example D.e25 tert-Butyl (3R*,4R*)-4-[({7-[2-(cyclopropylmethoxy)-4-fluoro-5-methoxyphenyl]-2-methyl-1H-pyrrolo[3,2-b]pyridin-3-yl}carbonyl)amino]-3-hydroxypiperidine-1-carboxylate Starting from tert-butyl (3R*,4R*)-4-{[(7-[2-(cyclopropylmethoxy)-4-fluoro-5-methoxyphenyl]-2-methyl-1-{[2-(trimethylsilyl)ethoxy]methyl}-1H-pyrrolo[3,2-b]pyridin-3-yl)carbonyl]amino}-3-hydroxypiperidine-1-carboxylate (example D.d25) the title compound is obtained as colorless solid.
MS (ESI): m/z=569 (MH$^+$, 100%).
$^1$H-NMR (300 MHz, DMSO-d$_6$): 11.35 (s, 1H, —NH); 9.32 (d, J=7.3, 1H, —NH); 8.41 (d, J=5.1, 1H); 7.18 (d, J=8.2, 1H); 7.15 (d, J=12.1, 1H & d, J=5.1, 1H); 5.25 (d, J=4.9, 1H, —OH); 3.97-3.73 (m, 3H); 3.84 (s, 3H); 3.81 (d, J=6.8, 2H); 3.42 (m, 1H); 3.00 (m, 1H); 2.81 (m, 1H); 2.74 (s, 3H); 2.06 (m, 1H); 1.42 (s, 9H); 1.38 (m, 1H); 0.92 (m, 1H); 0.35 (m, 2H); 0.17 (m, 2H).

Example D.e26 tert-Butyl 4-[({7-[2-(cyclopropylmethoxy)-5-fluoro-4-methoxyphenyl]-2-methyl-1H-pyrrolo[3,2-b]pyridin-3-yl}carbonyl)amino]piperidine-1-carboxylate Starting from tert-butyl 4-{[(7-[2-(cyclopropylmethoxy)-5-fluoro-4-methoxyphenyl]-1-(methoxymethyl)-2-{[2-(trimethylsilyl)ethoxy]methyl}-1H-pyrrolo[3,2-b]pyridin-3-yl)carbonyl]amino}piperidine-1-carboxylate (example D.d-26) the title compound is obtained as colorless solid.
MS (ESI): m/z=553 (MH$^+$, 100%); 497 (MH$^+$—C$_4$H$_8$).
$^1$H-NMR (300 MHz, DMSO-d$_6$): 11.33 (s, 1H, —NH); 9.27 (d, J=7.8, 1H, —NH); 8.38 (d, J=4.9, 1H); 7.27 (d, J=11.7, 1H); 7.09 (d, J=4.9, 1H); 6.93 (d, J=7.7, 1H); 4.06 (m, 1H); 3.95 (s, 3H); 3.90 (d, J=6.9, 2H); 3.84 (m, 2H); 3.05 (m, 2H); 2.73 (s, 3H); 1.92 (m, 2H); 1.42 (s, 9H & m, 2H); 0.94 (m, 1H); 0.36 (m, 2H); 0.20 (m, 2H).

Example D.e27 tert-Butyl {trans-4-[({7-[2-(cyclopropylmethoxy)-5-fluoro-4-methoxyphenyl]-2-methyl-1H-pyrrolo[3,2-b]pyridin-3-yl}carbonyl)amino]cyclohexyl}carbamate Starting from tert-butyl (trans-4-{[(7-[2-(cyclopropylmethoxy)-5-fluoro-4-methoxyphenyl]-2-methyl-1-{[2-(trimethylsilyl)ethoxy]methyl}-1H-pyrrolo[3,2-b]pyridin-3-yl)carbonyl]amino}cyclohexyl)carbamate (example D.d27) the title compound is obtained as colorless solid.
MS (ESI): m/z=567 (MH$^+$, 100%); 511 (MH$^+$—C$_4$H$_8$).
$^1$H-NMR (300 MHz, DMSO-d$_6$): 11.30 (s, 1H, —NH); 9.08 (d, J=7.8, 1H, —NH); 8.38 (d, J=4.9, 1H); 7.27 (d, J=11.7, 1H); 7.08 (d, J=4.9, 1H); 6.92 (d, J=7.7, 1H); 6.71 (d, J=6.9, 1H, —NH); 3.94 (s, 3H); 3.89 (d, J=6.9, 2H); 3.75 (m, 1H); 3.28 (m, 1H); 2.72 (s, 3H); 1.98 (m, 2H); 1.85 (m, 2H); 1.39 (s, 9H); 1.32 (m, 4H); 0.93 (m, 1H); 0.36 (m, 2H); 0.20 (m, 2H).

Example D.e28 tert-Butyl {cis-4-[({7-[2-(cyclopropylmethoxy)-5-fluoro-4-methoxyphenyl]-2-methyl-1H-pyrrolo[3,2-b]pyridin-3-yl}carbonyl)amino]cyclohexyl}carbamate Starting from tert-butyl (cis-4-{[(7-[2-(cyclopropylmethoxy)-5-fluoro-4-methoxyphenyl]-2-methyl-1-{[2-(trimethylsilyl)ethoxy]methyl}-1H-pyrrolo[3,2-b]pyridin-3-yl)carbonyl]amino}cyclohexyl)carbamate (example D.d28) the title compound is obtained as colorless solid.
MS (ESI): m/z=567 (MH$^+$, 100%); 511 (MH$^+$—C$_4$H$_8$).
$^1$H-NMR (300 MHz, DMSO-d$_6$): 11.29 (s, 1H, —NH); 9.437 (d, J=7.7, 1H, —NH); 8.43 (d, J=4.9, 1H); 7.28 (d, J=11.7, 1H); 7.10 (d, J=4.9, 1H); 6.93 (d, J=7.7, 1H); 6.92 (br.s, 1H, —NH); 4.03 (m, 1H); 3.95 (s, 3H); 3.90 (d, J=6.9, 2H); 3.41 (m, 1H); 2.73 (s, 3H); 1.74 (m, 2H); 1.63 (m, 6H); 1.40 (s, 9H); 0.94 (m, 1H); 0.37 (m, 2H); 0.21 (m, 2H).

Example D.f1

7-[5-(Cyclopropylmethoxy)-1,3-benzodioxol-4-yl]-2-methyl-N-piperidin-4-yl-1H-pyrrolo[3,2-b]pyridine-3-carboxamide hydrochloride tert-Butyl 4-[({7-[5-(cyclopropylmethoxy)-1,3-benzodioxol-4-yl]-2-methyl-1H-pyrrolo[3,2-b]pyridin-3- yl}carbonyl)amino]piperidine-1-carboxylate from example D.e1 (2.72 g; 4.95 mmol) is dissolved in dry 2-propanol (50 mL). After addition of 4M HCl in dioxane (5.0 mL) the stirred reaction mixture is heated to 80° C. for two hours. At ambient temperature tert.-butyl methyl ether (100 mL) is added. The precipitated product is isolated by suction filtration, washed with several portions of tert.-butyl methyl ether and dried in high vacuo at 40° C. to yield of the title compound as yellow solid.

MS (ESI): m/z=449 (MH$^+$, 100%).

$^1$H-NMR (300 MHz, DMSO-d$_6$, MeOH-d$_4$): 8.50 (d, J=5.8, 1H); 7.55 (br.d, J ~5.8, 1H); 7.03 (d, J=8.6, 1H); 6.61 (d, J=8.6, 1H); 6.06 (s, 2H); 4.15 (m, 1H); 3.80 (d, J=6.9, 2H); 3.55 (m, 2H); 3.08 (m, 2H); 2.77 (s, 3H); 2.12 (m, 2H); 1.86 (m, 2H); 0.96 (m, 1H); 0.39 (m, 2H); 0.19 (m, 2H).

The following compounds were prepared analogously to the procedure described in above example D.f1.

Example D.f2

N-(trans-4-aminocyclohexyl)-7-[5-(cyclopropyl-methoxy)-1,3-benzodioxol-4-yl]-2-methyl-1H-pyrrolo[3,2-b]pyridine-3-carboxamide hydrochloride Starting from tert-butyl {trans-4-[({7-[5-(cyclopropyl-methoxy)-1,3-benzodioxol-4-yl]-2-methyl-1H-pyrrolo[3,2-b]pyridin-3-yl}carbonyl)amino]cyclohexyl}carbamate (example D.e2) the title compound is obtained as yellow solid.

MS (ESI): m/z=463 (MH$^+$, 100%).

$^1$H-NMR (300 MHz, DMSO-d$_6$, MeOH-d$_4$): 8.47 (d, J=5.7, 1H); 7.53 (br.d, J ~5.7, 1H); 7.03 (d, J=8.6, 1H); 6.60 (d, J=8.6, 1H); 6.05 (s, 2H); 3.79 (m, 1H & d, J=6.9, 2H); 3.05 (m, 1H); 2.76 (s, 3H); 2.05 (m, 4H); 1.49 (m, 4H); 0.95 (m, 1H); 0.38 (m, 2H); 0.18 (m, 2H).

Example D.f3

N-(cis-4-aminocyclohexyl)-7-[5-(cyclopropyl-methoxy)-1,3-benzodioxol-4-yl]-2-methyl-1H-pyrrolo[3,2-b]pyridine-3-carboxamide hydrochloride Starting from tert-butyl {cis-4-[({7-[5-(cyclopropyl-methoxy)-1,3-benzodioxol-4-yl]-2-methyl-1H-pyrrolo[3,2-b]pyridin-3-yl}carbonyl)amino]cyclohexyl}carbamate (example D.e3) the title compound is obtained as yellow solid.

MS (ESI): m/z=463 (MH$^+$, 100%).

Example D.f4

7-[2-(Cyclopropylmethoxy)-4-fluorophenyl]-2-methyl-N-(piperidin-4-yl)-1H-pyrrolo[3,2-b]pyridine-3-carboxamide hydrochloride Starting from tert-butyl 4-{[(7-[2-(cyclopropylmethoxy)-4-fluorophenyl]-2-methyl-1-{[2-(trimethylsilyl)ethoxy]methyl}-1H-pyrrolo[3,2-b]pyridin-3-yl)carbonyl]amino}piperidine-1-carboxylate (example D.e4) the title compound is obtained as yellow solid.

MS (ESI): m/z=422 (MH$^+$, 100%).

$^1$H-NMR (300 MHz, DMSO-d$_6$): 8.50 (d, J=5.8, 1H); 7.54 (dd, J=8.4, 6.9, 1H); 7.46 (br.d, J ~5.8, 1H); 7.13 (dd, J=11.5, 2.4, 1H); 7.00 (ddd, J=8.4, 8.4, 2.4, 1H); 4.12 (m, 1H); 3.92 (d, J=7.1, 2H); 3.35 (m, 2H); 3.06 (m, 2H); 2.78 (s, 3H); 2.10 (m, 2H); 1.88 (m, 2H); 0.95 (m, 1H); 0.40 (m, 2H); 0.24 (m, 2H).

Example D.f5

N-(trans-4-aminocyclohexyl)-7-[2-(cyclopropyl-methoxy)-4-fluorophenyl]-2-methyl-1H-pyrrolo[3,2-b]pyridine-3-carboxamide Starting from tert-butyl {trans-4-[({7-[2-(cyclopropyl-methoxy)-4-fluorophenyl]-2-methyl-1H-pyrrolo[3,2-b]pyridin-3-yl}carbonyl)amino]cyclohexyl}carbamate (example D.e5) the title compound is obtained as yellow solid.

MS (ESI): m/z=437 (MH$^+$, 100%).

$^1$H-NMR (300 MHz, DMSO-d$_6$): 8.48 (d, J=5.8, 1H); 7.53 (dd, J=8.4, 6.9, 1H); 7.45 (br.s, 1H); 7.13 (dd, J=11.5, 2.2, 1H); 7.00 (ddd, J=8.4, 8.4, 2.2, 1H); 3.92 (d, J=6.9, 2H); 3.81 (m, 1H); 3.06 (m, 1H); 2.77 (s, 3H); 2.05 (m, 4H); 1.51 (m, 4H); 0.95 (m, 1H); 0.40 (m, 2H); 0.24 (m, 2H).

Example D.f6

N-(Cis-4-aminocyclohexyl)-7-[2-(cyclopropyl-methoxy)-4-fluorophenyl]-2-methyl-1H-pyrrolo[3,2-b]pyridine-3-carboxamide hydrochloride Starting from tert-butyl {cis-4-[({7-[2-(cyclopropyl-methoxy)-4-fluorophenyl]-2-methyl-1H-pyrrolo[3,2-b]pyridin-3-yl}carbonyl)amino]cyclohexyl}carbamate (example D.e6) the title compound is obtained as yellow solid.

MS (ESI): m/z=437 (MH$^+$, 100%).

$^1$H-NMR (300 MHz, DMSO-d$_6$): 8.51 (d, J=5.7, 1H); 7.54 (dd, J=8.4, 6.9, 1H); 7.45 (br.s, 1H); 7.13 (dd, J=11.5, 2.4, 1H); 7.00 (ddd, J=8.4, 8.4, 2.4, 1H); 4.09 (m, 1H); 3.93 (d, J=6.9, 2H); 3.18 (m, 1H); 2.84 (s, 3H); 2.06-1.64 (m, 8H); 0.97 (m, 1H); 0.42 (m, 2H); 0.26 (m, 2H).

Example D.f7

7-[2-(Cyclopropylmethoxy)-5-fluorophenyl]-2-methyl-N-(piperidin-4-yl)-1H-pyrrolo[3,2-b]pyridine-3-carboxamide hydrochloride Starting from tert-butyl 4-[({7-[2-(cyclopropylmethoxy)-5-fluorophenyl]-2-methyl-1H-pyrrolo[3,2-b]pyridin-3-yl}carbonyl)amino]piperidine-1-carboxylate (example D.e7) the title compound is obtained as yellow solid.

MS (ESI): m/z=423 (MH$^+$, 100%).

$^1$H-NMR (300 MHz, DMSO-d$_6$, MeOH-d$_4$): 8.52 (d, J=4.9, 1H); 7.49 (br.s, 1H); 7.43-7.34 (m, 2H); 7.27-7.18 (m, 1H); 7.14 (m, 1H); 3.88 (d, J=6.8, 2H); 3.34 (m, 2H); 3.06 (m, 2H); 2.78 (s, 3H); 2.10 (m, 2H); 1.88 (m, 2H); 0.93 (m, 1H); 0.38 (m, 2H); 0.21 (m, 2H).

Example D.f8

N-(trans-4-Aminocyclohexyl)-7-[2-(cyclopropyl-methoxy)-5-fluorophenyl]-2-methyl-1H-pyrrolo[3,2-b]pyridine-3-carboxamide hydrochloride Starting from tert-butyl {trans-4-[({7-[2-(cyclopropyl-methoxy)-5-fluorophenyl]-2-methyl-1H-pyrrolo[3,2-b]pyri-din-3-yl}carbonyl)amino]cyclohexyl}carbamate (example D.e8) the title compound is obtained as yellow solid.

MS (ESI): m/z=437 (MH$^+$, 100%).

$^1$H-NMR (300 MHz, DMSO-d$_6$, MeOH-d$_4$): 8.50 (d, J=5.7, 1H); 7.49 (br.d, J=5.7, 1H); 7.43-7.34 (m, 2H); 7.27-7.18 (m, 1H); 3.88 (d, J=6.8, 2H); 3.82 (m, 1H); 3.05 (m, 1H); 2.77 (s, 3H); 2.06 (m, 4H); 1.51 (m, 4H); 0.94 (m, 1H); 0.38 (m, 2H); 0.21 (m, 2H).

Example D.f9

N-(cis-4-Aminocyclohexyl)-7-[2-(cyclopropylmethoxy)-5-fluorophenyl]-2-methyl-1H-pyrrolo[3,2-b]pyridine-3-carboxamide hydrochloride Starting from tert-butyl {cis-4-[({7-[2-(cyclopropylmethoxy)-5-fluorophenyl]-2-methyl-1H-pyrrolo[3,2-b]pyridin-3-yl}carbonyl)amino]cyclohexyl}carbamate (example D.e9) the title compound is obtained as yellow solid.

MS (ESI): m/z=437 (MH$^+$, 100%).
$^1$H-NMR (300 MHz, DMSO-d$_6$, MeOH-d$_4$): 8.53 (d, J=5.7, 1H); 7.49 (br.s, 1H); 7.43-7.33 (m, 2H); 7.27-7.18 (m, 1H); 4.09 (m, 1H); 3.88 (d, J=6.8, 2H); 3.17 (m, 1H); 2.84 (s, 3H); 2.08-1.63 (m, 8H); 0.94 (m, 1H); 0.39 (m, 2H); 0.21 (m, 2H).

Example D.f10

7-[2-(Cyclopropylmethoxy)-5-fluorophenyl]-N-[(3R*,4R*)-3-hydroxypiperidin-4-yl]-2-methyl-1H-pyrrolo[3,2-b]pyridine-3-carboxamide hydrochloride Starting from tert-butyl (3R*,4R*)-4-[({7-[2-(cyclopropylmethoxy)-5-fluorophenyl]-2-methyl-1H-pyrrolo[3,2-b]pyridin-3-yl}carbonyl)amino]-3-hydroxypiperidine-1-carboxylate (example D.e10) the title compound is obtained as yellow solid.

MS (ESI): m/z=439 (MH$^+$, 100%).
$^1$H-NMR (300 MHz, DMSO-d$_6$, MeOH-d$_4$): 8.52 (d, J=5.7, 1H); 7.48 (br.s, 1H); 7.43-7.33 (m, 2H); 7.27-7.19 (m, 1H); 4.01-3.92 (m, 2H); 3.88 (d, J=6.9, 2H); 3.32 (m, 2H); 3.06 (m, 1H); 2.89 (m, 1H); 2.80 (s, 3H); 2.20 (m, 1H); 1.83 (m, 1H); 0.94 (m, 1H); 0.38 (m, 2H); 0.21 (m, 2H).

Example D.f11

7-[2-(Cyclopropylmethoxy)-4-methoxyphenyl]-2-methyl-N-(piperidin-4-yl)-1H-pyrrolo[3,2-b]pyridine-3-carboxamide hydrochloride Starting from tert-butyl 4-[({7-[2-(cyclopropylmethoxy)-4-methoxyphenyl]-2-methyl-1H-pyrrolo[3,2-b]pyridin-3-yl}carbonyl)amino]piperidine-1-carboxylate (example D.e11) the title compound is obtained as yellow solid.

MS (ESI): m/z=435 (MH$^+$, 100%).
$^1$H-NMR (300 MHz, DMSO-d$_6$, MeOH-d$_4$): 8.46 (d, J=5.8, 1H); 7.46 (br.s, 1H); 7.44 (d, J=8.2, 1H); 6.76 (dd, J=8.2, 2.2, 1H); 6.75 (d, J=2.2, 1H); 4.14 (m, 1H); 3.92 (d, J=6.9, 2H); 3.87 (s, 3H); 3.34 (m, 2H); 3.06 (m, 2H); 2.78 (s, 3H); 2.09 (m, 2H); 1.88 (m, 2H); 0.96 (m, 1H); 0.40 (m, 2H); 0.25 (m, 2H).

Example D.f12

N-(Trans-4-aminocyclohexyl)-7-[2-(cyclopropylmethoxy)-4-methoxyphenyl]-2-methyl-1H-pyrrolo[3,2-b]pyridine-3-carboxamide hydrochloride Starting from tert-butyl {trans-4-[({7-[2-(cyclopropylmethoxy)-4-methoxyphenyl]-2-methyl-1H-pyrrolo[3,2-b]pyridin-3-yl}carbonyl)amino]cyclohexyl}carbamate (example D.e12) the title compound is obtained as yellow solid.

MS (ESI): m/z=449 (MH$^+$, 100%).
$^1$H-NMR (300 MHz, DMSO-d$_6$, MeOH-d$_4$): 8.45 (d, J=5.8, 1H); 7.46 (br.s, 1H); 7.45 (d, J=8.2, 1H); 6.76 (dd, J=8.2, 2.4, 1H); 6.75 (d, J=2.4, 1H); 3.92 (d, J=6.9, 2H); 3.87 (s, 3H); 3.82 (m, 1H); 3.04 (m, 1H); 2.77 (s, 3H); 2.05 (m, 4H); 1.51 (m, 4H); 0.96 (m, 1H); 0.40 (m, 2H); 0.26 (m, 2H).

Example D.f13

N-(Cis-4-aminocyclohexyl)-7-[2-(cyclopropylmethoxy)-4-methoxyphenyl]-2-methyl-1H-pyrrolo[3,2-b]pyridine-3-carboxamide hydrochloride Starting from tert-butyl {cis-4-[({7-[2-(cyclopropylmethoxy)-4-methoxyphenyl]-2-methyl-1H-pyrrolo[3,2-b]pyridin-3-yl}carbonyl)amino]cyclohexyl}carbamate (example D.e13) the title compound is obtained as yellow solid.

MS (ESI): m/z=449 (MH$^+$, 100%).
$^1$H-NMR (300 MHz, DMSO-d$_6$, MeOH-d$_4$): 8.47 (d, J=5.8, 1H); 8.22 (br.s, 1H); 7.43 (d, J=8.4, 1H); 6.76 (dd, J=8.4, 2.4, 1H); 6.77 (d, J=2.4, 1H); 4.08 (m, 1H); 3.92 (d, J=6.9, 2H); 3.87 (s, 3H); 3.17 (m, 1H); 2.83 (s, 3H); 2.07-1.61 (m, 8H); 0.96 (m, 1H); 0.41 (m, 2H); 0.26 (m, 2H).

Example D.f14

7-[2-(Cyclopropylmethoxy)-5-methoxyphenyl]-2-methyl-N-(piperidin-4-yl)-1H-pyrrolo[3,2-b]pyridine-3-carboxamide hydrochloride Starting from tert-butyl 4-[({7-[2-(cyclopropylmethoxy)-5-methoxyphenyl]-2-methyl-1H-pyrrolo[3,2-b]pyridin-3-yl}carbonyl)amino]piperidine-1-carboxylate (example D.e14) the title compound is obtained as yellow solid.

MS (ESI): m/z=435 (MH$^+$, 100%).
$^1$H-NMR (400 MHz, DMSO-d$_6$, MeOH-d$_4$): 8.50 (d, J=5.8, 1H); 7.50 (br.s, 1H); 7.17 (d, J=9.0, 1H); 7.13 (dd, J=9.0, 2.1, 1H); 7.06 (d, J=2.1, 1H); 4.15 (m, 1H); 3.83 (d, J=6.8, 2H); 3.79 (s, 3H); 3.36 (m, 2H); 3.08 (m, 2H); 2.78 (s, 3H); 2.12 (m, 2H); 1.86 (m, 2H); 0.93 (m, 1H); 0.37 (m, 2H); 0.19 (m, 2H).

Example D.f15

N-(Trans-4-aminocyclohexyl)-7-[2-(cyclopropylmethoxy)-5-methoxyphenyl]-2-methyl-1H-pyrrolo[3,2-b]pyridine-3-carboxamide hydrochloride Starting from tert-butyl {trans-4-[({7-[2-(cyclopropylmethoxy)-5-methoxyphenyl]-2-methyl-1H-pyrrolo[3,2-b]pyridin-3-yl}carbonyl)amino]cyclohexyl}carbamate (example D.e15) the title compound is obtained as yellow solid.

MS (ESI): m/z=449 (MH$^+$, 100%).
$^1$H-NMR (400 MHz, DMSO-d$_6$, MeOH-d$_4$): 8.48 (d, J=5.9, 1H); 7.52 (br.s, 1H); 7.17 (d, J=9.1, 1H); 7.14 (dd, J=9.1, 2.2, 1H); 7.06 (d, J=2.2, 1H); 3.83 (d, J=6.9, 2H); 3.79 (s, 3H & m, 1H); 3.05 (m, 1H); 2.77 (s, 3H); 2.06 (m, 4H); 1.51 (m, 4H); 0.93 (m, 1H); 0.37 (m, 2H); 0.19 (m, 2H).

Example D.f16

N-(Cis-4-aminocyclohexyl)-7-[2-(cyclopropylmethoxy)-5-methoxyphenyl]-2-methyl-1H-pyrrolo[3,2-b]pyridine-3-carboxamide hydrochloride Starting from tert-butyl {cis-4-[({7-[2-(cyclopropylmethoxy)-5-methoxyphenyl]-2-methyl-1H-pyrrolo[3,2-b]pyridin-3-yl}carbonyl)amino]cyclohexyl}carbamate (example D.e16) the title compound is obtained as yellow solid.

MS (ESI): m/z=449 (MH$^+$, 100%).

¹H-NMR (400 MHz, DMSO-d₆, MeOH-d₄): 8.51 (d, J=5.7, 1H); 7.47 (br.s, 1H); 7.17 (d, J=9.1, 1H); 7.12 (dd, J=9.1, 2.2, 1H); 7.05 (d, J=2.2, 1H); 4.07 (m, 1H); 3.83 (d, J=6.9, 2H); 3.79 (s, 3H); 3.17 (m, 1H); 2.83 (s, 3H); 2.07-1.64 (m, 8H); 1.51 (m, 4H); 0.93 (m, 1H); 0.37 (m, 2H); 0.19 (m, 2H).

Example D.f17

7-[2-(Cyclopropylmethoxy)-5-methoxyphenyl]-N-[(3R*,4R*)-4-hydroxypyrrolidin-3-yl]-2-methyl-1H-pyrrolo[3,2-b]pyridine-3-carboxamide hydrochloride Starting from tert-butyl-(3R*,4R*)-3-[({7-[2-(cyclopropylmethoxy)-5-methoxyphenyl]-2-methyl-1H-pyrrolo[3,2-b]pyridin-3-yl}carbonyl)amino]-4-hydroxypyrrolidine-1-carboxylate (example D.e17) the title compound is obtained as yellow solid.
MS (ESI): m/z=437 (MH⁺, 100%).
¹H-NMR (400 MHz, DMSO-d₆): 8.53 (d, J=6.0, 1H); 7.57 (br.s, 1H); 7.18 (d, J=9.0, 1H); 7.14 (dd, J=9.0, 2.0, 1H); 7.08 (d, J=2.0, 1H); 4.47 (m, 1H); 4.42 (m, 1H); 3.83 (d, J=6.9, 2H); 3.80 (s, 3H); 3.62 (m, 1H); 3.56 (m, 1H); 3.43 (m, 1H); 3.18 (m, 1H); 2.83 (s, 3H); 0.92 (m, 1H); 0.38 (m, 2H); 0.19 (m, 2H).

Example D.f18

7-[2-(Cyclopropylmethoxy)-5-methylphenyl]-2-methyl-N-(piperidin-4-yl)-1H-pyrrolo[3,2-b]pyridine-3-carboxamide hydrochloride Starting from tert-butyl 4-[({7-[2-(cyclopropylmethoxy)-5-methylphenyl]-2-methyl-1H-pyrrolo[3,2-b]pyridin-3-yl}carbonyl)amino]piperidine-1-carboxylate (example D.e18) the title compound is obtained as yellow solid.
MS (ESI): $^m/_z$=419 (MH⁺, 100%).
¹H-NMR (300 MHz, DMSO-d₆, MeOH-d₄): 8.50 (d, J=5.8, 1H); 7.51 (br.d, J ~5.8, 1H); 7.38 (dd, J=8.4, 1.8, 1H); 7.30 (d, J=1.8, 1H); 7.12 (d, J=8.4, 1H); 4.15 (m, 1H); 3.88 (d, J=6.8, 2H); 3.37 (m, 2H); 3.08 (m, 2H); 2.78 (s, 3H); 2.35 (s, 3H); 2.12 (m, 2H); 1.87 (m, 2H); 0.95 (m, 1H); 0.39 (m, 2H); 0.22 (m, 2H).

Example D.f19

N-(Trans-4-aminocyclohexyl)-7-[2-(cyclopropylmethoxy)-5-methylphenyl]-2-methyl-1H-pyrrolo[3,2-b]pyridine-3-carboxamide hydrochloride Starting from tert-butyl {trans-4-[({7-[2-(cyclopropylmethoxy)-5-methylphenyl]-2-methyl-1H-pyrrolo[3,2-b]pyridin-3-yl}carbonyl)amino]cyclohexyl}carbamate (example D.e19) the title compound is obtained as yellow solid.
MS (ESI): m/z=433 (MH⁺, 100%).

Example D.f20

N-(Cis-4-aminocyclohexyl)-7-[2-(cyclopropylmethoxy)-5-methylphenyl]-2-methyl-1H-pyrrolo[3,2-b]pyridine-3-carboxamide hydrochloride Starting from tert-butyl {cis-4-[({7-[2-(cyclopropylmethoxy)-5-methylphenyl]-2-methyl-1H-pyrrolo[3,2-b]pyridin-3-yl}carbonyl)amino]cyclohexyl}carbamate (example D.e20) the title compound is obtained as yellow solid.
MS (ESI): m/z=433 (MH⁺, 100%).

Example D.f21

7-[2-(Cyclopropylmethoxy)-4-fluoro-5-methoxyphenyl]-2-methyl-N-(piperidin-4-yl)-1H-pyrrolo[3,2-b]pyridine-3-carboxamide hydrochloride Starting from tert-butyl 4-[({7-[2-(cyclopropylmethoxy)-4-fluoro-5-methoxyphenyl]-2-methyl-1H-pyrrolo[3,2-b]pyridin-3-yl}carbonyl)amino]piperidine-1-carboxylate (example D.e21) the title compound is obtained as yellow solid.
MS (ESI): m/z=453 (MH⁺, 100%).
¹H-NMR (400 MHz, DMSO-d₆, MeOH-d₄): 8.50 (d, J=5.8, 1H); 7.46 (br.s, 1H); 7.28 (d, J=9.5, 1H); 7.22 (d, J=13.5, 1H); 4.13 (m, 1H); 3.86 (s, 3H); 3.85 (d, J=6.8, 2H); 3.32 (m, 2H); 3.05 (m, 2H); 2.78 (s, 3H); 2.10 (m, 2H); 1.88 (m, 2H); 0.93 (m, 1H); 0.38 (m, 2H); 0.20 (m, 2H).

Example D.f22

N-(Trans-4-aminocyclohexyl)-7-[2-(cyclopropylmethoxy)-4-fluoro-5-methoxyphenyl]-2-methyl-1H-pyrrolo[3,2-b]pyridine-3-carboxamide hydrochloride Starting from tert-butyl {trans-4-[({7-[2-(cyclopropylmethoxy)-4-fluoro-5-methoxyphenyl]-2-methyl-1H-pyrrolo[3,2-b]pyridin-3-yl}carbonyl)amino]cyclohexyl}carbamate (example D.e22) the title compound is obtained as yellow solid.
MS (ESI): m/z=467 (MH⁺, 100%).
¹H-NMR (400 MHz, DMSO-d₆, MeOH-d₄): 8.48 (d, J=5.8, 1H); 7.49 (br.s, 1H); 7.28 (d, J=9.5, 1H); 7.22 (d, J=13.5, 1H); 3.86 (s, 3H); 3.85 (d, J=6.8, 2H); 3.81 (m, 1H); 3.02 (m, 1H); 2.78 (s, 3H); 2.04 (m, 2H); 1.52 (m, 2H); 0.91 (m, 1H); 0.37 (m, 2H); 0.19 (m, 2H).

Example D.f23

N-(Cis-4-aminocyclohexyl)-7-[2-(cyclopropylmethoxy)-4-fluoro-5-methoxyphenyl]-2-methyl-1H-pyrrolo[3,2-b]pyridine-3-carboxamide hydrochloride Starting from tert-butyl {cis-4-[({7-[2-(cyclopropylmethoxy)-4-fluoro-5-methoxyphenyl]-2-methyl-1H-pyrrolo[3,2-b]pyridin-3-yl}carbonyl)amino]cyclohexyl}carbamate (example D.e23) the title compound is obtained as yellow solid.
MS (ESI): m/z=467 (MH⁺, 100%).
¹H-NMR (300 MHz, DMSO-d₆, MeOH-d₄): 8.51 (d, J=5.7, 1H); 7.42 (br.s, 1H); 7.26 (d, J=9.7, 1H); 7.21 (d, J=13.5, 1H); 4.09 (m, 1H); 3.86 (s, 3H); 3.84 (d, J=6.8, 2H); 3.16 (m, 1H); 2.72 (s, 3H); 2.05-1.60 (m, 8H); 0.93 (m, 1H); 0.38 (m, 2H); 0.20 (m, 2H).

Example D.f24

7-[2-(Cyclopropylmethoxy)-4-fluoro-5-methoxyphenyl]-N-[(3R*,4R*)-4-hydroxypyrrolidin-3-yl]-2-methyl-1H-pyrrolo[3,2-b]pyridine-3-carboxamide hydrochloride Starting from tert-butyl (3R*,4R*)-3-[({7-[2-(cyclopropylmethoxy)-4-fluoro-5-methoxyphenyl]-2-methyl-1H-pyrrolo[3,2-b]pyridin-3-yl}carbonyl)amino]-4-hydroxypyrrolidine-1-carboxylate (example D.e24) the title compound is obtained as yellow solid.

MS (ESI): m/z=455 (MH+, 100%).
¹H-NMR (300 MHz, DMSO-d₆, MeOH-d₄): 8.53 (d, J=5.9, 1H); 7.58 (br.d, J ~5.9, 1H); 7.31 (d, J=9.5, 1H); 7.23 (d, J=13.3, 1H); 4.48 (m, 1H); 4.42 (m, 1H); 3.87 (s, 3H); 3.85 (d, J=6.9, 2H); 3.66-3.51 (m, 2H); 3.43 (m, 1H); 3.19 (m, 1H); 2.83 (s, 3H); 0.93 (m, 1H); 0.39 (m, 2H); 0.20 (m, 2H).

Example D.f25

7-[2-(Cyclopropylmethoxy)-4-fluoro-5-methoxyphenyl]-N-[(3R*,4R*)-3-hydroxypiperidin-4-yl]-2-methyl-1H-pyrrolo[3,2-b]pyridine-3-carboxamide hydrochloride Starting from tert-butyl (3R*,4R*)-4-[({7-[2-(cyclopropylmethoxy)-4-fluoro-5-methoxyphenyl]-2-methyl-1H-pyrrolo[3,2-b]pyridin-3-yl}carbonyl)amino]-3-hydroxypiperidine-1-carboxylate (example D.e25) the title compound is obtained as yellow solid.
MS (ESI): m/z=469 (MH+, 100%).
¹H-NMR (300 MHz, DMSO-d₆, MeOH-d₄): 8.51 (d, J=5.8, 1H); 7.52 (br.s, 1H); 7.29 (d, J=9.7, 1H); 7.22 (d, J=13.3, 1H); 3.96 (m, 1H); 3.87 (s, 3H); 3.85 (d, J=6.9, 2H); 3.41-3.24 (m, 2H); 3.06 (m, 1H); 2.90 (m, 1H); 2.80 (s, 3H); 2.20 (m, 1H); 1.83 (m, 1H); 0.94 (m, 1H); 0.39 (m, 2H); 0.21 (m, 2H).

Example D.f26

7-[2-(Cyclopropylmethoxy)-5-fluoro-4-methoxyphenyl]-2-methyl-N-piperidin-4-yl-1H-pyrrolo[3,2-b]pyridine-3-carboxamide hydrochloride Starting from tert-butyl 4-[({7-[2-(cyclopropylmethoxy)-5-fluoro-4-methoxyphenyl]-2-methyl-1H-pyrrolo[3,2-b]pyridin-3-yl}carbonyl)amino]piperidine-1-carboxylate (example D.e26) the title compound is obtained as yellow solid.
MS (ESI): m/z=453 (MH+, 100%).
¹H-NMR (300 MHz, DMSO-d₆, MeOH-d₄): 8.47 (d, J=6.0, 1H); 7.49 (br.d, J ~6.0, 1H); 7.42 (d, J=11.5, 1H); 6.98 (d, J=7.5, 1H); 4.15 (m, 1H); 3.98 (s, 3H); 3.95 (d, J=6.9, 2H); 3.36 (m, 2H); 3.08 (m, 2H); 2.78 (s, 3H); 2.11 (m, 2H); 1.87 (m, 2H); 0.96 (m, 1H); 0.41 (m, 2H); 0.24 (m, 2H).

Example D.f27

N-(Trans-4-aminocyclohexyl)-7-[2-(cyclopropylmethoxy)-5-fluoro-4-methoxyphenyl]-2-methyl-1H-pyrrolo[3,2-b]pyridine-3-carboxamide hydrochloride Starting from tert-butyl {trans-4-[({7-[2-(cyclopropylmethoxy)-5-fluoro-4-methoxyphenyl]-2-methyl-1H-pyrrolo[3,2-b]pyridin-3-yl}carbonyl)amino]cyclohexyl}carbamate (example D.e27) the title compound is obtained as yellow solid.
MS (ESI): m/z=467 (MH+, 100%).

Example D.f28

N-(Cis-4-aminocyclohexyl)-7-[2-(cyclopropylmethoxy)-5-fluoro-4-methoxyphenyl]-2-methyl-1H-pyrrolo[3,2-b]pyridine-3-carboxamide hydrochloride Starting from tert-butyl {cis-4-[({7-[2-(cyclopropylmethoxy)-5-fluoro-4-methoxyphenyl]-2-methyl-1H-pyrrolo[3,2-b]pyridin-3-yl}carbonyl)amino]cyclohexyl}carbamate (example D.e28) the title compound is obtained as yellow solid.
MS (ESI): m/z=467 (MH+, 100%).
¹H-NMR (300 MHz, DMSO-d₆, MeOH-d₄): 8.47 (d, J=5.7, 1H); 7.42 (br.s, 1H); 7.39 (d, J=11.7, 1H); 6.97 (d, J=7.5, 1H); 4.10 (m, 1H); 3.98 (s, 3H); 3.94 (d, J=6.9, 2H); 3.19 (m, 1H); 2.82 (s, 3H); 2.05-1.65 (m, 8H); 0.96 (m, 1H); 0.41 (m, 2H); 0.24 (m, 2H).

Example E1

N-(1-Acetylpiperidin-4-yl)-7-[5-(cyclopropylmethoxy)-1,3-benzodioxol-4-yl]-2-methyl-1H-pyrrolo[3,2-b]pyridine-3-carboxamide 7-[5-(Cyclopropylmethoxy)-1,3-benzodioxol-4-yl]-2-methyl-N-piperidin-4-yl-1H-pyrrolo[3,2-b]pyridine-3-carboxamide hydrochloride from example D.f1 (485 mg; 1.0 mmol) and DBU (2.5 mmol) is dissolved in dry dichloromethane (5 mL). Acetyl chloride (1.1 mmol) is syringed into the reaction mixture at ice bath temperature. After addition the mixture is stirring at ambient temperature over night. Methanol (1 mL) is added and stirring is continued for two hours. The volatiles are evaporated. The residue is purified by reversed phase preparative HPLC. The collected product fraction is freeze-dried to yield the title compound as colorless solid.
MS (ESI): m/z=491 (MH+, 100%).
¹H-NMR (300 MHz, DMSO-d₆): 11.43 (s, 1H, —NH); 9.25 (d, J=7.8, 1H, —NH); 8.38 (d, J=5.0, 1H); 7.18 (d, J=5.0, 1H); 6.95 (d, J=8.6, 1H); 6.55 (d, J=8.6, 1H); 6.00 (s, 2H); 4.22-4.04 (m, 2H); 3.80 (m, 1H); 3.75 (d, J=6.8, 2H); 3.27 (m, 1H); 2.97 (m, 1H); 2.73 (s, 3H); 2.04 (s, 3H); 1.95 (m, 2H); 1.52 (m, 1H); 1.37 (m, 1H); 0.93 (m, 1H); 0.34 (m, 2H); 0.15 (m, 2H).

The following compounds are prepared analogously to the procedure described in above example E1.

Example E2

7-[5-(Cyclopropylmethoxy)-1,3-benzodioxol-4-yl]-2-methyl-N-(1-propionylpiperidin-4-yl)-1H-pyrrolo[3,2-b]pyridine-3-carboxamide Starting from 7-[5-(cyclopropylmethoxy)-1,3-benzodioxol-4-yl]-2-methyl-N-piperidin-4-yl-1H-pyrrolo[3,2-b]pyridine-3-carboxamide hydrochloride (example D.f1) and commercially available propionyl chloride the title compound is obtained as colorless solid.
MS (ESI): m/z=506 (MH+, 100%).
¹H-NMR (300 MHz, DMSO-d₆): 12.00 (s, 1H, —NH); 8.93 (s, 1H); 8.75 (d, J=7.7, 1H, —NH); 7.00 (d, J=8.6, 1H); 6.56 (d, J=8.6, 1H); 6.00 (s, 2H); 4.25-4.03 (m, 2H); 3.79 (m, 1H); 3.76 (d, J=6.8, 2H); 3.25 (m, 1H); 2.95 (m, 1H); 2.77 (s, 3H); 2.36 (qu, J=7.5, 2H); 1.96 (m, 2H); 1.52 (m, 1H); 1.39 (m, 1H); 1.01 (t, J=7.5, 3H); 0.88 (m, 1H); 0.31 (m, 2H); 0.13 (m, 2H).

Example E3

7-[5-(Cyclopropylmethoxy)-1,3-benzodioxol-4-yl]-N-[1-(methoxyacetyl)piperidin-4-yl]-2-methyl-1H-pyrrolo[3,2-b]pyridine-3-carboxamide Starting from 7-[5-(cyclopropylmethoxy)-1,3-benzodioxol-4-yl]-2-methyl-N-piperidin-4-yl-1H-pyrrolo[3,2-b]

pyridine-3-carboxamide hydrochloride (example D.f1) and commercially available methoxy-acetyl chloride the title compound is obtained as colorless solid.

MS (ESI): m/z=521 (MH+, 100%).

$^1$H-NMR (300 MHz, DMSO-d$_6$): 11.43 (s, 1H, —NH); 9.25 (d, J=7.7, 1H, —NH); 8.38 (d, J=5.0, 1H); 7.18 (d, J=5.0, 1H); 6.95 (d, J=8.6, 1H); 6.55 (d, J=8.6, 1H); 6.00 (s, 2H); 4.20-4.03 (m, 2H); 4.11 (s, 2H); 3.75 (d, J=6.8, 2H); 3.72 (m, 1H); 3.29 (m, 3H); 3.22 (m, 1H); 2.99 (m, 1H); 2.73 (s, 3H); 1.96 (m, 2H); 1.52 (m, 1H); 1.39 (m, 1H); 0.93 (m, 1H); 0.34 (m, 2H); 0.15 (m, 2H).

Example E4

Ethyl 4-[({7-[5-(cyclopropylmethoxy)-1,3-benzo-dioxol-4-yl]-2-methyl-1H-pyrrolo[3,2-b]pyridin-3-yl}carbonyl)amino]piperidine-1-carboxylate Starting from 7-[5-(cyclopropylmethoxy)-1,3-benzodioxol-4-yl]-2-methyl-N-piperidin-4-yl-1H-pyrrolo[3,2-b]pyridine-3-carboxamide hydrochloride (example D.f1) and commercially available ethyl chloroformate the title compound is obtained as colorless solid.

MS (ESI): m/z=521 (MH+, 100%).

$^1$H-NMR (300 MHz, DMSO-d$_6$): 11.43 (s, 1H, —NH); 9.25 (d, J=7.7, 1H, —NH); 8.38 (d, J=5.0, 1H); 7.18 (d, J=5.0, 1H); 6.95 (d, J=8.6, 1H); 6.55 (d, J=8.6, 1H); 6.00 (s, 2H); 4.14-4.01 (m, 1H & qu, J=6.9, 2H); 3.89 (m, 1H); 3.85 (m, 1H); 3.75 (d, J=6.8, 2H); 3.12 (m, 2H); 2.73 (s, 3H); 1.94 (m, 2H); 1.44 (m, 2H); 1.20 (t, J=6.9, 3H); 0.93 (m, 1H); 0.34 (m, 2H); 0.15 (m, 2H).

Example E5

N-(trans-4-Acetamidocyclohexyl)-7-[5-(cyclopropylmethoxy)-1,3-benzodioxol-4-yl]-2-methyl-1H-pyrrolo[3,2-b]pyridine-3-carboxamide Starting from N-(trans-4-aminocyclohexyl)-7-[5-(cyclopropylmethoxy)-1,3-benzodioxol-4-yl]-2-methyl-1H-pyrrolo[3,2-b]pyridine-3-carboxamide hydrochloride (example D.f2) and commercially available acetyl chloride the title compound is obtained as colorless solid.

MS (ESI): m/z=505 (MH+, 100%).

$^1$H-NMR (300 MHz, DMSO-d$_6$): 11.40 (s, 1H, —NH); 9.07 (d, J=7.9, 1H, —NH); 8.39 (d, J=5.0, 1H); 7.72 (d, J=7.7, 1H, —NH); 7.17 (d, J=5.0, 1H); 6.94 (d, J=8.6, 1H); 6.55 (d, J=8.6, 1H); 6.00 (s, 2H); 3.81 (m, 1H); 3.75 (d, J=6.8, 2H); 3.58 (m, 1H); 2.72 (s, 3H); 2.01 (m, 2H); 1.86 (m, 2H); 1.79 (s, 3H); 1.34 (m, 4H); 0.93 (m, 1H); 0.34 (m, 2H); 0.15 (m, 2H).

Example E6

N-(cis-4-acetamidocyclohexyl)-7-[5-(cyclopropylmethoxy)-1,3-benzodioxol-4-yl]-2-methyl-1H-pyrrolo[3,2-b]pyridine-3-carboxamide Starting from N-(cis-4-aminocyclohexyl)-7-[5-(cyclopropylmethoxy)-1,3-benzodioxol-4-yl]-2-methyl-1H-pyrrolo[3,2-b]pyridine-3-carboxamide hydrochloride (example D.f3) and commercially available acetyl chloride the title compound is obtained as colorless solid.

MS (ESI): m/z=505 (MH+, 100%).

$^1$H-NMR (300 MHz, DMSO-d$_6$): 11.40 (s, 1H, —NH); 9.35 (d, J=7.5, 1H, —NH); 8.43 (d, J=4.9, 1H); 7.84 (d, J=7.5, 1H, —NH); 7.19 (d, J=4.9, 1H); 6.95 (d, J=8.5, 1H); 6.55 (d, J=8.5, 1H); 6.01 (s, 2H); 4.02 (m, 1H); 3.75 (m, 1H & d, J=6.8, 2H); 2.73 (s, 3H); 1.83 (s, 3H); 1.83-1.49 (m, 8H); 0.93 (m, 1H); 0.35 (m, 2H); 0.16 (m, 2H).

Example E7

7-[5-(Cyclopropylmethoxy)-1,3-benzodioxol-4-yl]-2-methyl-N-[cis-4-(propionylamino)cyclohexyl]-1H-pyrrolo[3,2-b]pyridine-3-carboxamide Starting from N-(cis-4-aminocyclohexyl)-7-[5-(cyclopropylmethoxy)-1,3-benzodioxol-4-yl]-2-methyl-1H-pyrrolo[3,2-b]pyridine-3-carboxamide hydrochloride (example D.f3) and commercially available propionyl chloride the title compound is obtained as colorless solid.

MS (ESI): m/z=519 (MH+, 100%).

$^1$H-NMR (300 MHz, DMSO-d$_6$): 11.40 (s, 1H, —NH); 9.35 (d, J=7.5, 1H, —NH); 8.43 (d, J=4.9, 1H); 7.75 (d, J=7.5, 1H, —NH); 7.19 (d, J=4.9, 1H); 6.95 (d, J=8.6, 1H); 6.56 (d, J=8.6, 1H); 6.01 (s, 2H); 4.02 (m, 1H); 3.75 (m, 1H & d, J=6.8, 2H); 2.73 (s, 3H); 2.11 (qu, J=7.7, 2H); 1.85-1.50 (m, 8H); 1.00 (t, J=7.7, 3H); 0.93 (m, 1H); 0.35 (m, 2H); 0.15 (m, 2H).

Example E8

7-[5-(Cyclopropylmethoxy)-1,3-benzodioxol-4-yl]-N-{cis-4-[(methoxyacetyl)amino]cyclohexyl}-2-methyl-1H-pyrrolo[3,2-b]pyridine-3-carboxamide Starting from N-(cis-4-aminocyclohexyl)-7-[5-(cyclopropylmethoxy)-1,3-benzodioxol-4-yl]-2-methyl-1H-pyrrolo[3,2-b]pyridine-3-carboxamide hydrochloride (example D.f3) and commercially available methoxy-acetyl chloride the title compound is obtained as colorless solid.

MS (ESI): m/z=535 (MH+, 100%).

$^1$H-NMR (300 MHz, DMSO-d$_6$): 11.40 (s, 1H, —NH); 9.39 (d, J=7.5, 1H, —NH); 8.43 (d, J=5.0, 1H); 7.64 (d, J=7.7, 1H, —NH); 7.19 (d, J=5.0, 1H); 6.95 (d, J=8.6, 1H); 6.55 (d, J=8.6, 1H); 6.01 (s, 2H); 4.06 (m, 1H); 3.81 (s, 2H); 3.75 (m, 1H & d, J=6.8, 2H); 3.31 (s, 3H); 2.73 (s, 3H); 1.85-1.59 (m, 8H); 0.93 (m, 1H); 0.35 (m, 2H); 0.16 (m, 2H).

Example E9

Ethyl {cis-4-[({7-[5-(cyclopropylmethoxy)-1,3-benzodioxol-4-yl]-2-methyl-1H-pyrrolo[3,2-b]pyridin-3-yl}carbonyl)amino]cyclohexyl}carbamate Starting from N-(cis-4-aminocyclohexyl)-7-[5-(cyclopropylmethoxy)-1,3-benzodioxol-4-yl]-2-methyl-1H-pyrrolo[3,2-b]pyridine-3-carboxamide hydrochloride (example D.f3) and commercially available ethyl chloroformate the title compound is obtained as colorless solid.

MS (ESI): m/z=535 (MH+, 100%).

$^1$H-NMR (300 MHz, DMSO-d$_6$): 11.39 (s, 1H, —NH); 9.39 (d, J=7.7, 1H, —NH); 8.44 (d, J=5.0, 1H); 7.21 (br.s, 1H, —NH); 7.19 (d, J=5.0, 1H); 6.95 (d, J=8.6, 1H); 6.55 (d, J=8.6, 1H); 6.00 (s, 2H); 4.03 (m, 1H); 3.99 (qu, J=7.1, 2H); 3.75 (d, J=6.8, 2H); 3.74 (m, 1H); 2.73 (s, 3H); 1.87-1.55 (m, 8H); 1.17 (t, J=7.1, 3H); 0.94 (m, 1H); 0.35 (m, 2H); 0.15 (m, 2H).

Example E10

N-(1-Acetylpiperidin-4-yl)-7-[2-(cyclopropylmethoxy)-4-fluorophenyl]-2-methyl-1H-pyrrolo[3,2-b]pyridine-3-carboxamide Starting from 7-[2-(cyclopropylmethoxy)-4-fluorophenyl]-2-methyl-N-(piperidin-4-yl)-1H-pyrrolo[3,2-b]pyridine-3-carboxamide hydrochloride (example D.f4) and commercially available acetyl chloride the title compound is obtained as colorless solid.

MS (ESI): m/z=465 (MH$^+$, 100%).
$^1$H-NMR (300 MHz, DMSO-d$_6$): 11.35 (s, 1H, —NH); 9.28 (d, J=7.9, 1H, —NH); 8.40 (d, J=4.9, 1H); 7.41 (dd, J=8.4, 6.9, 1H); 7.08 (d, J=4.9, 1H); 7.05 (dd, J=11.5, 2.4, 1H); 6.92 (ddd, J=8.4, 8.4, 2.4, 1H); 4.23-4.05 (m, 2H); 3.88 (d, J=6.8, 2H); 3.78 (m, 1H); 3.28 (m, 1H); 2.96 (m, 1H); 2.73 (s, 3H); 2.04 (s, 3H); 1.95 (m, 2H); 1.52 (m, 1H); 1.37 (m, 1H); 0.94 (m, 1H); 0.36 (m, 2H); 0.22 (m, 2H).

Example E11

7-[2-(Cyclopropylmethoxy)-4-fluorophenyl]-2-methyl-N-(1-propanoylpiperidin-4-yl)-1H-pyrrolo[3,2-b]pyridine-3-carboxamide Starting from 7-[2-(cyclopropylmethoxy)-4-fluorophenyl]-2-methyl-N-(piperidin-4-yl)-1H-pyrrolo[3,2-b]pyridine-3-carboxamide hydrochloride (example D.f4) and commercially available propionyl chloride the title compound is obtained as colorless solid.

MS (ESI): m/z=479 (MH$^+$, 100%).
$^1$H-NMR (300 MHz, DMSO-d$_6$): 11.34 (s, 1H, —NH); 9.28 (d, J=7.7, 1H, —NH); 8.39 (d, J=4.9, 1H); 7.42 (dd, J=8.4, 6.9, 1H); 7.08 (d, J=4.9, 1H); 7.05 (dd, J=11.5, 2.4, 1H); 6.92 (ddd, J=8.4, 8.4, 2.4, 1H); 4.24-4.05 (m, 2H); 3.88 (d, J=6.8, 2H); 3.81 (m, 1H); 3.25 (m, 1H); 2.97 (m, 1H); 2.73 (s, 3H); 2.36 (qu, J=7.3, 2H); 1.95 (m, 2H); 1.50 (m, 1H); 1.37 (m, 1H); 1.01 (t, J=7.3, 2H); 0.94 (m, 1H); 0.36 (m, 2H); 0.22 (m, 2H).

Example E12

7-[2-(Cyclopropylmethoxy)-4-fluorophenyl]-N-[1-(methoxyacetyl)piperidin-4-yl]-2-methyl-1H-pyrrolo[3,2-b]pyridine-3-carboxamide Starting from 7-[2-(cyclopropylmethoxy)-4-fluorophenyl]-2-methyl-N-(piperidin-4-yl)-1H-pyrrolo[3,2-b]pyridine-3-carboxamide hydrochloride (example D.f4) and commercially available methoxy-acetyl chloride the title compound is obtained as colorless solid.

MS (ESI): m/z=495 (MH$^+$, 100%).
$^1$H-NMR (300 MHz, DMSO-d$_6$): 11.35 (s, 1H, —NH); 9.28 (d, J=7.7, 1H, —NH); 8.40 (d, J=4.9, 1H); 7.41 (dd, J=8.4, 6.9, 1H); 7.08 (d, J=4.9, 1H); 7.06 (dd, J=11.5, 2.4, 1H); 6.92 (ddd, J=8.4, 8.4, 2.4, 1H); 4.22-4.04 (m, 2H); 4.12 (d, J=1.3, 2H); 3.88 (d, J=6.8, 2H); 3.74 (m, 1H); 3.31 (s, 3H); 3.22 (m, 1H); 2.99 (m, 1H); 2.74 (s, 3H); 1.96 (m, 2H); 1.53 (m, 1H); 1.40 (m, 1H); 0.94 (m, 1H); 0.37 (m, 2H); 0.21 (m, 2H).

Example E13

N-[trans-4-(Acetylamino)cyclohexyl]-7-[2-(cyclopropylmethoxy)-4-fluorophenyl]-2-methyl-1H-pyrrolo[3,2-b]pyridine-3-carboxamide Starting from N-(trans-4-aminocyclohexyl)-7-[2-(cyclopropylmethoxy)-4-fluorophenyl]-2-methyl-1H-pyrrolo[3,2-b]pyridine-3-carboxamide (example D.f5) and commercially available acetyl chloride the title compound is obtained as colorless solid.

MS (ESI): m/z=479 (MH$^+$, 100%).
$^1$H-NMR (300 MHz, DMSO-d$_6$): 11.32 (s, 1H, —NH); 9.11 (d, J=7.9, 1H, —NH); 8.40 (d, J=5.1, 1H); 7.73 (d, J=7.7, 1H, —NH); 7.41 (dd, J=8.4, 6.9, 1H); 7.08 (d, J=4.9, 1H); 7.05 (dd, J=11.5, 2.4, 1H); 6.92 (ddd, J=8.4, 8.4, 2.4, 1H); 3.88 (d, J=6.8, 2H); 3.80 (m, 1H); 3.58 (m, 1H); 2.73 (s, 3H); 2.01 (m, 2H); 1.86 (m, 2H); 1.79 (s, 3H); 1.34 (m, 4H); 0.94 (m, 1H); 0.36 (m, 2H); 0.21 (m, 2H).

Example E14

7-[2-(Cyclopropylmethoxy)-4-fluorophenyl]-2-methyl-N-[trans-4-(propanoylamino)cyclohexyl]-1H-pyrrolo[3,2-b]pyridine-3-carboxamide Starting from N-(trans-4-aminocyclohexyl)-7-[2-(cyclopropylmethoxy)-4-fluorophenyl]-2-methyl-1H-pyrrolo[3,2-b]pyridine-3-carboxamide (example D.f5) and commercially available propionyl chloride the title compound is obtained as colorless solid.

MS (ESI): m/z=493 (MH$^+$, 100%).
$^1$H-NMR (300 MHz, DMSO-d$_6$): 11.33 (s, 1H, —NH); 9.11 (d, J=7.9, 1H, —NH); 8.40 (d, J=5.1, 1H); 7.63 (d, J=7.7, 1H, —NH); 7.42 (dd, J=8.4, 6.9, 1H); 7.08 (d, J=4.9, 1H); 7.05 (dd, J=11.5, 2.4, 1H); 6.92 (ddd, J=8.4, 8.4, 2.4, 1H); 3.88 (d, J=6.8, 2H); 3.79 (m, 1H); 3.59 (m, 1H); 2.73 (s, 3H); 2.06 (qu, J=7.7, 2H); 2.00 (m, 2H); 1.85 (m, 2H); 1.34 (m, 4H); 1.00 (t, J=7.7, 3H); 0.94 (m, 1H); 0.36 (m, 2H); 0.21 (m, 2H).

Example E15

7-[2-(Cyclopropylmethoxy)-4-fluorophenyl]-N-{trans-4-[(methoxyacetyl)amino]cyclohexyl}-2-methyl-1H-pyrrolo[3,2-b]pyridine-3-carboxamide Starting from N-(trans-4-aminocyclohexyl)-7-[2-(cyclopropylmethoxy)-4-fluorophenyl]-2-methyl-1H-pyrrolo[3,2-b]pyridine-3-carboxamide (example D.f5) and commercially available methoxy-acetyl chloride the title compound is obtained as colorless solid.

MS (ESI): m/z=509 (MH$^+$, 100%).
$^1$H-NMR (300 MHz, DMSO-d$_6$): 11.33 (s, 1H, —NH); 9.10 (d, J=7.7, 1H, —NH); 8.40 (d, J=4.9, 1H); 7.57 (d, J=8.2, 1H, —NH); 7.41 (dd, J=8.4, 6.9, 1H); 7.08 (d, J=4.9, 1H); 7.05 (dd, J=11.5, 2.4, 1H); 6.92 (ddd, J=8.4, 8.4, 2.4, 1H); 3.88 (d, J=6.9, 2H); 3.79 (s, 2H & m, 1H); 3.69 (m, 1H); 3.31 (s, 3H); 2.73 (s, 3H); 2.01 (m, 2H); 1.82 (m, 2H); 1.42 (m, 4H); 0.94 (m, 1H); 0.36 (m, 2H); 0.21 (m, 2H).

Example E16

N-[cis-4-(Acetylamino)cyclohexyl]-7-[2-(cyclopropylmethoxy)-4-fluorophenyl]-2-methyl-1H-pyrrolo[3,2-b]pyridine-3-carboxamide Starting from N-(cis-4-aminocyclohexyl)-7-[2-(cyclopropylmethoxy)-4-fluorophenyl]-2-methyl-1H-pyrrolo[3,2-b]pyridine-3-carboxamide (example D.f6) and commercially available acetyl chloride the title compound is obtained as colorless solid.

MS (ESI): m/z=479 (MH$^+$, 100%).
$^1$H-NMR (300 MHz, DMSO-d$_6$): 11.33 (s, 1H, —NH); 9.39 (d, J=7.7, 1H, —NH); 8.44 (d, J=5.1, 1H); 7.84 (d, J=7.3,

1H, —NH); 7.42 (dd, J=8.4, 6.9, 1H); 7.10 (d, J=5.1, 1H); 7.06 (dd, J=11.5, 2.4, 1H); 6.93 (ddd, J=8.4, 8.4, 2.4, 1H); 4.03 (m, 1H); 3.89 (d, J=6.8, 2H); 3.74 (m, 1H); 2.73 (s, 3H); 1.83 (s, 3H); 1.83-1.51 (m, 8H); 0.95 (m, 1H); 0.37 (m, 2H); 0.22 (m, 2H).

Example E17

7-[2-(Cyclopropylmethoxy)-5-fluorophenyl]-2-methyl-N-[cis-4-(propanoylamino)cyclohexyl]-1H-pyrrolo[3,2-b]pyridine-3-carboxamide Starting from N-(cis-4-aminocyclohexyl)-7-[2-(cyclopropylmethoxy)-4-fluorophenyl]-2-methyl-1H-pyrrolo[3,2-b]pyridine-3-carboxamide (example D.f6) and commercially available propionyl chloride the title compound is obtained as colorless solid.

MS (ESI): m/z=493 (MH$^+$, 100%).

$^1$H-NMR (300 MHz, DMSO-d$_6$): 11.33 (s, 1H, —NH); 9.39 (d, J=7.7, 1H, —NH); 8.44 (d, J=4.9, 1H); 7.75 (d, J=7.5, 1H, —NH); 7.42 (dd, J=8.4, 6.9, 1H); 7.10 (d, J=4.9, 1H); 7.06 (dd, J=11.6, 2.4, 1H); 6.93 (ddd, J=8.4, 8.4, 2.4, 1H); 4.03 (m, 1H); 3.89 (d, J=6.9, 2H); 3.74 (m, 1H); 2.74 (s, 3H); 2.11 (qu, J=7.7, 2H); 1.85-1.50 (m, 8H); 1.00 (t, J=7.7, 3H); 0.95 (m, 1H); 0.37 (m, 2H); 0.22 (m, 2H).

Example E18

7-[2-(Cyclopropylmethoxy)-4-fluorophenyl]-N-{cis-4-[(methoxyacetyl)amino]cyclohexyl}-2-methyl-1H-pyrrolo[3,2-b]pyridine-3-carboxamide Starting from N-(cis-4-aminocyclohexyl)-7-[2-(cyclopropylmethoxy)-4-fluorophenyl]-2-methyl-1H-pyrrolo[3,2-b]pyridine-3-carboxamide (example D.f6) and commercially available methoxy-acetyl chloride the title compound is obtained as colorless solid.

MS (ESI): m/z=509 (MH$^+$, 100%).

$^1$H-NMR (300 MHz, DMSO-d$_6$): 11.33 (s, 1H, —NH); 9.42 (d, J=7.5, 1H, —NH); 8.44 (d, J=4.9, 1H); 7.64 (d, J=7.7, 1H, —NH); 7.42 (dd, J=8.4, 6.9, 1H); 7.09 (d, J=4.9, 1H); 7.06 (dd, J=11.6, 2.4, 1H); 6.93 (ddd, J=8.4, 8.4, 2.4, 1H); 4.05 (m, 1H); 3.89 (d, J=6.9, 2H); 3.82 (s, 2H); 3.71 (m, 1H); 3.31 (s, 3H); 2.73 (s, 3H); 1.89-1.57 (m, 8H); 0.95 (m, 1H); 0.36 (m, 2H); 0.22 (m, 2H).

Example E19

N-(1-Acetylpiperidin-4-yl)-7-[2-(cyclopropylmethoxy)-5-fluorophenyl]-2-methyl-1H-pyrrolo[3,2-b]pyridine-3-carboxamide Starting from 7-[2-(cyclopropylmethoxy)-5-fluorophenyl]-2-methyl-N-(piperidin-4-yl)-1H-pyrrolo[3,2-b]pyridine-3-carboxamide hydrochloride (example D.f7) and commercially acetyl chloride the title compound is obtained as colorless solid.

MS (ESI): m/z=465 (MH$^+$, 100%).

$^1$H-NMR (400 MHz, DMSO-d$_6$): 11.39 (s, 1H, —NH); 9.27 (d, J=7.7, 1H, —NH); 8.40 (d, J=4.9, 1H); 7.30 (dd, J=8.8, 3.2, 1H); 7.25 (ddd, J=9.1, 8.9, 3.2, 1H); 7.14 (dd, J=9.1, 4.5, 1H); 7.12 (d, J=4.9, 1H); 4.20-4.06 (m, 2H); 3.83 (d, J=6.8, 2H); 3.77 (m, 1H); 3.27 (m, 1H); 2.96 (m, 1H); 2.73 (s, 3H); 2.03 (s, 3H); 1.94 (m, 2H); 1.52 (m, 1H); 1.36 (m, 1H); 0.92 (m, 1H); 0.34 (m, 2H); 0.17 (m, 2H).

Example E20

7-[2-(Cyclopropylmethoxy)-5-fluorophenyl]-2-methyl-N-(1-propanoylpiperidin-4-yl)-1H-pyrrolo[3,2-b]pyridine-3-carboxamide Starting from 7-[2-(cyclopropylmethoxy)-5-fluorophenyl]-2-methyl-N-(piperidin-4-yl)-1H-pyrrolo[3,2-b]pyridine-3-carboxamide hydrochloride (example D.f7) and commercially propionyl chloride the title compound is obtained as colorless solid.

MS (ESI): m/z=479 (MH$^+$, 100%).

$^1$H-NMR (400 MHz, DMSO-d$_6$): 11.40 (s, 1H, —NH); 9.27 (d, J=7.7, 1H, —NH); 8.40 (d, J=5.0, 1H); 7.31 (dd, J=8.8, 3.2, 1H); 7.26 (ddd, J=9.1, 8.9, 3.2, 1H); 7.15 (dd, J=9.1, 4.5, 1H); 7.13 (d, J=5.0, 1H); 4.23-4.06 (m, 2H); 3.83 (d, J=6.9, 2H); 3.80 (m, 1H); 3.25 (m, 1H); 2.96 (m, 1H); 2.74 (s, 3H); 2.35 (qu, J=7.5, 2H); 1.94 (m, 2H); 1.50 (m, 1H); 1.37 (m, 1H); 1.01 (t, J=7.5, 3H); 0.92 (m, 1H); 0.34 (m, 2H); 0.18 (m, 2H).

Example E21

7-[2-(Cyclopropylmethoxy)-5-fluorophenyl]-N-[1-(methoxyacetyl)piperidin-4-yl]-2-methyl-1H-pyrrolo[3,2-b]pyridine-3-carboxamide Starting from 7-[2-(cyclopropylmethoxy)-5-fluorophenyl]-2-methyl-N-(piperidin-4-yl)-1H-pyrrolo[3,2-b]pyridine-3-carboxamide hydrochloride (example D.f7) and commercially methoxy-acetyl chloride the title compound is obtained as colorless solid.

MS (ESI): m/z=495 (MH$^+$, 100%).

$^1$H-NMR (400 MHz, DMSO-d$_6$): 11.42 (s, 1H, —NH); 9.27 (d, J=7.7, 1H, —NH); 8.41 (d, J=4.9, 1H); 7.31 (dd, J=8.8, 3.2, 1H); 7.26 (ddd, J=9.1, 8.8, 3.2, 1H); 7.15 (dd, J=9.1, 4.5, 1H); 7.13 (d, J=4.9, 1H); 4.21-4.07 (m, 2H); 4.12 (d, J=2.5, 2H); 3.84 (d, J=6.8, 2H); 3.74 (m, 1H); 3.31 (s, 3H); 3.22 (m, 1H); 2.99 (m, 1H); 2.74 (s, 3H); 1.96 (m, 2H); 1.53 (m, 1H); 1.40 (m, 1H); 0.92 (m, 1H); 0.35 (m, 2H); 0.18 (m, 2H).

Example E22

N-[trans-4-(Acetylamino)cyclohexyl]-7-[2-(cyclopropylmethoxy)-5-fluorophenyl]-2-methyl-1H-pyrrolo[3,2-b]pyridine-3-carboxamide Starting from N-(trans-4-aminocyclohexyl)-7-[2-(cyclopropylmethoxy)-5-fluorophenyl]-2-methyl-1H-pyrrolo[3,2-b]pyridine-3-carboxamide hydrochloride (example D.f8) and commercially acetyl chloride the title compound is obtained as colorless solid.

MS (ESI): m/z=479 (MH$^+$, 100%).

$^1$H-NMR (400 MHz, DMSO-d$_6$): 11.37 (s, 1H, —NH); 9.09 (d, J=7.7, 1H, —NH); 8.41 (d, J=4.9, 1H); 7.72 (d, J=7.7, 1H, —NH); 7.31 (dd, J=8.7, 3.2, 1H); 7.26 (ddd, J=9.1, 8.6, 3.2, 1H); 7.15 (dd, J=9.1, 4.5, 1H); 7.13 (d, J=4.9, 1H); 3.84 (d, J=6.9, 2H); 3.80 (m, 1H); 3.58 (m, 1H); 2.73 (s, 3H); 2.01 (m, 2H); 1.86 (m, 2H); 1.79 (s, 3H); 1.34 (m, 4H); 0.92 (m, 1H); 0.34 (m, 2H); 0.18 (m, 2H).

Example E23

7-[2-(Cyclopropylmethoxy)-5-fluorophenyl]-2-methyl-N-[trans-4-(propanoylamino)cyclohexyl]-1H-pyrrolo[3,2-b]pyridine-3-carboxamide Starting from N-(trans-4-aminocyclohexyl)-7-[2-(cyclopropylmethoxy)-5-fluorophenyl]-2-methyl-1H-pyrrolo[3,2- b]pyridine-3-carboxamide hydrochloride (example D.f8) and commercially propionyl chloride the title compound is obtained as colorless solid.

MS (ESI): m/z=493 (MH+, 100%).

$^1$H-NMR (400 MHz, DMSO-d$_6$): 11.37 (s, 1H, —NH); 9.09 (d, J=7.7, 1H, —NH); 8.42 (d, J=5.0, 1H); 7.62 (d, J=7.7, 1H, —NH); 7.31 (dd, J=8.8, 3.2, 1H); 7.26 (ddd, J=9.1, 8.8, 3.2, 1H); 7.15 (dd, J=9.1, 4.5, 1H); 7.13 (d, J=5.0, 1H); 3.84 (d, J=6.8, 2H); 3.80 (m, 1H); 3.59 (m, 1H); 2.73 (s, 3H); 2.06 (qu, J=7.6, 2H); 2.01 (m, 2H); 1.86 (m, 2H); 1.34 (m, 4H); 0.99 (t, J=7.6, 3H); 0.93 (m, 1H); 0.35 (m, 2H); 0.18 (m, 2H).

Example E24

7-[2-(Cyclopropylmethoxy)-5-fluorophenyl]-N-{trans-4-[(methoxyacetyl)amino]cyclohexyl}-2-methyl-1H-pyrrolo[3,2-b]pyridine-3-carboxamide Starting from N-(trans-4-aminocyclohexyl)-7-[2-(cyclopropylmethoxy)-5-fluorophenyl]-2-methyl-1H-pyrrolo[3,2-b]pyridine-3-carboxamide hydrochloride (example D.f8) and commercially methoxy-acetyl chloride the title compound is obtained as colorless solid.

MS (ESI): m/z=509 (MH+, 100%).

$^1$H-NMR (400 MHz, DMSO-d$_6$): 11.37 (s, 1H, —NH); 9.08 (d, J=7.7, 1H, —NH); 8.41 (d, J=4.9, 1H); 7.56 (d, J=8.2, 1H, —NH); 7.31 (dd, J=8.8, 3.2, 1H); 7.26 (ddd, J=9.1, 8.7, 3.2, 1H); 7.15 (dd, J=9.1, 4.5, 1H); 7.13 (d, J=4.9, 1H); 3.84 (d, J=6.9, 2H); 3.81 (m, 1H); 3.78 (s, 2H); 3.69 (m, 1H); 3.31 (s, 3H); 2.73 (s, 3H); 2.01 (m, 2H); 1.82 (m, 2H); 1.42 (m, 4H); 0.92 (m, 1H); 0.35 (m, 2H); 0.18 (m, 2H).

Example E25

N-[cis-4-(Acetylamino)cyclohexyl]-7-[2-(cyclopropylmethoxy)-5-fluorophenyl]-2-methyl-1H-pyrrolo[3,2-b]pyridine-3-carboxamide Starting from N-(cis-4-aminocyclohexyl)-7-[2-(cyclopropylmethoxy)-5-fluorophenyl]-2-methyl-1H-pyrrolo[3,2-b]pyridine-3-carboxamide hydrochloride (example D.f9) and commercially acetyl chloride the title compound is obtained as colorless solid.

MS (ESI): m/z=479 (MH+, 100%).

$^1$H-NMR (300 MHz, DMSO-d$_6$): 11.38 (s, 1H, —NH); 9.38 (d, J=7.5, 1H, —NH); 8.45 (d, J=4.9, 1H); 7.84 (d, J=7.5, 1H, —NH); 7.32 (dd, J=8.6, 3.2, 1H); 7.28 (ddd, J=8.9, 8.9, 3.2, 1H); 7.16 (dd, J=8.9, 4.5, 1H); 7.15 (d, J=4.9, 1H); 4.03 (m, 1H); 3.85 (d, J=6.8, 2H); 3.74 (m, 1H); 2.74 (s, 3H); 1.83 (s, 3H); 1.83-1.51 (m, 8H); 0.93 (m, 1H); 0.35 (m, 2H); 0.19 (m, 2H).

Example E26

7-[2-(Cyclopropylmethoxy)-5-fluorophenyl]-2-methyl-N-[cis-4-(propanoylamino)cyclohexyl]-1H-pyrrolo[3,2-b]pyridine-3-carboxamide Starting from N-(cis-4-aminocyclohexyl)-7-[2-(cyclopropylmethoxy)-5-fluorophenyl]-2-methyl-1H-pyrrolo[3,2-b]pyridine-3-carboxamide hydrochloride (example D.f9) and commercially propionyl chloride the title compound is obtained as colorless solid.

MS (ESI): m/z=493 (MH+, 100%).

$^1$H-NMR (300 MHz, DMSO-d$_6$): 11.38 (s, 1H, —NH); 9.38 (d, J=7.5, 1H, —NH); 8.45 (d, J=4.9, 1H); 7.75 (d, J=7.3, 1H, —NH); 7.32 (dd, J=8.4, 3.2, 1H); 7.27 (ddd, J=8.9, 8.9, 3.2, 1H); 7.16 (dd, J=8.9, 4.5, 1H); 7.14 (d, J=4.9, 1H); 4.03 (m, 1H); 3.84 (d, J=6.9, 2H); 3.74 (m, 1H); 2.74 (s, 3H); 2.11 (qu, J=7.7, 2H); 1.91-1.51 (m, 8H); 1.00 (t, J=7.7, 3H); 0.93 (m, 1H); 0.35 (m, 2H); 0.19 (m, 2H).

Example E27

7-[2-(Cyclopropylmethoxy)-5-fluorophenyl]-N-{cis-4-[(methoxyacetyl)amino]cyclohexyl}-2-methyl-1H-pyrrolo[3,2-b]pyridine-3-carboxamide Starting from N-(cis-4-aminocyclohexyl)-7-[2-(cyclopropylmethoxy)-5-fluorophenyl]-2-methyl-1H-pyrrolo[3,2-b]pyridine-3-carboxamide hydrochloride (example D.f9) and commercially methoxy-acetyl chloride the title compound is obtained as colorless solid.

MS (ESI): m/z=509 (MH+, 100%).

$^1$H-NMR (300 MHz, DMSO-d$_6$): 11.37 (s, 1H, —NH); 9.41 (d, J=7.5, 1H, —NH); 8.46 (d, J=4.9, 1H); 7.64 (d, J=7.7, 1H, —NH); 7.32 (dd, J=8.4, 3.2, 1H); 7.27 (ddd, J=8.9, 8.9, 3.2, 1H); 7.16 (dd, J=8.9, 4.5, 1H); 7.14 (d, J=4.9, 1H); 4.06 (m, 1H); 3.85 (d, J=6.8, 2H); 3.82 (s, 2H); 3.78 (m, 1H); 3.31 (s, 3H); 2.74 (s, 3H); 1.88-1.56 (m, 8H); 0.93 (m, 1H); 0.35 (m, 2H); 0.19 (m, 2H).

Example E28

N-[(3R*,4R*)-1-Acetyl-3-hydroxypiperidin-4-yl]-7-[2-(cyclopropylmethoxy)-5-fluorophenyl]-2-methyl-1H-pyrrolo[3,2-b]pyridine-3-carboxamide Starting from 7-[2-(cyclopropylmethoxy)-5-fluorophenyl]-N-[(3R*,4R*)-3-hydroxypiperidin-4-yl]-2-methyl-1H-pyrrolo[3,2-b]pyridine-3-carboxamide hydrochloride (example D.f10) and commercially acetyl chloride the title compound is obtained as colorless solid.

HR-MS (ESI): m/z=481.2243 ([MH]+, $C_{26}H_{30}FN_4O_4^+$, calc. 481.2246).

Example E29

7-[2-(Cyclopropylmethoxy)-5-fluorophenyl]-N-[(3R*,4R*)-3-hydroxy-1-propanoylpiperidin-4-yl]-2-methyl-1H-pyrrolo[3,2-b]pyridine-3-carboxamide Starting from 7-[2-(cyclopropylmethoxy)-5-fluorophenyl]-N-[(3R*,4R*)-3-hydroxypiperidin-4-yl]-2-methyl-1H-pyrrolo[3,2-b]pyridine-3-carboxamide hydrochloride (example D.f10) and commercially propionyl chloride the title compound is obtained as colorless solid.

HR-MS (ESI): m/z=495.2399 ([MH]+, $C_{27}H_{32}FN_4O_4^+$, calc. 495.2402).

Example E30

7-[2-(Cyclopropylmethoxy)-5-fluorophenyl]-N-[(3R*,4R*)-3-hydroxy-1-(methoxyacetyl)piperidin-4-yl]-2-methyl-1H-pyrrolo[3,2-b]pyridine-3-carboxamide Starting from 7-[2-(cyclopropylmethoxy)-5-fluorophenyl]-N-[(3R*,4R*)-3-hydroxypiperidin-4-yl]-2-methyl-1H-pyrrolo[3,2-b]pyridine-3-carboxamide hydrochloride (example D.f10) and commercially methoxy-acetyl chloride the title compound is obtained as colorless solid.

HR-MS (ESI): m/z=511.2342 ([MH]$^+$, $C_{27}H_{32}FN_4O_6^+$, calc. 511.2351).

Example E31

N-(1-Acetylpiperidin-4-yl)-7-[2-(cyclopropylmethoxy)-4-methoxyphenyl]-2-methyl-1H-pyrrolo[3,2-b]pyridine-3-carboxamide Starting from 7-[2-(cyclopropylmethoxy)-4-methoxyphenyl]-2-methyl-N-(piperidin-4-yl)-1H-pyrrolo[3,2-b]pyridine-3-carboxamide hydrochloride (example D.f11) and commercially acetyl chloride the title compound is obtained as colorless solid.

MS (ESI): m/z=477 (MH$^+$, 100%).

$^1$H-NMR (300 MHz, DMSO-d$_6$): 11.28 (s, 1H; —NH); 9.31 (d, J=7.7, 1H, —NH); 8.37 (d, J=4.9, 1H); 7.31 (d, J=9.1, 1H); 7.08 (d, J=4.9, 1H); 6.69 (dd, J=9.1, 2.4, 1H); 6.68 (d, J=2.4, 1H); 4.21-4.04 (m, 2H); 3.87 (d, J=6.9, 2H); 3.84 (s, 3H); 3.77 (m, 1H); 3.27 (m, 1H); 2.96 (m, 1H); 2.73 (s, 3H); 2.04 (s, 3H); 1.95 (m, 2H); 1.52 (m, 1H); 1.37 (m, 1H); 0.94 (m, 1H); 0.36 (m, 2H); 0.22 (m, 2H).

Example E32

7-[2-(Cyclopropylmethoxy)-4-methoxyphenyl]-2-methyl-N-(1-propanoylpiperidin-4-yl)-1H-pyrrolo[3,2-b]pyridine-3-carboxamide Starting from 7-[2-(cyclopropylmethoxy)-4-methoxyphenyl]-2-methyl-N-(piperidin-4-yl)-1H-pyrrolo[3,2-b]pyridine-3-carboxamide hydrochloride (example D.f11) and commercially propionyl chloride the title compound is obtained as colorless solid.

MS (ESI): m/z=491 (MH$^+$, 100%).

$^1$H-NMR (300 MHz, DMSO-d$_6$): 11.28 (s, 1H; —NH); 9.31 (d, J=7.7, 1H, —NH); 8.36 (d, J=4.9, 1H); 7.31 (d, J=9.1, 1H); 7.05 (d, J=4.9, 1H); 6.68 (dd, J=9.1, 2.4, 1H); 6.67 (d, J=2.4, 1H); 4.25-4.04 (m, 2H); 3.87 (d, J=6.9, 2H); 3.84 (s, 3H); 3.80 (m, 1H); 3.25 (m, 1H); 2.97 (m, 1H); 2.73 (s, 3H); 2.36 (qu, J=7.3, 2H); 1.94 (m, 2H); 1.50 (m, 1H); 1.37 (m, 1H); 1.01 (t, J=7.3, 3H); 0.94 (m, 1H); 0.36 (m, 2H); 0.22 (m, 2H).

Example E33

7-[2-(Cyclopropylmethoxy)-4-methoxyphenyl]-N-[1-(methoxyacetyl)piperidin-4-yl]-2-methyl-1H-pyrrolo[3,2-b]pyridine-3-carboxamide Starting from 7-[2-(cyclopropylmethoxy)-4-methoxyphenyl]-2-methyl-N-(piperidin-4-yl)-1H-pyrrolo[3,2-b]pyridine-3-carboxamide hydrochloride (example D.f11) and commercially methoxy-acetyl chloride the title compound is obtained as colorless solid.

MS (ESI): m/z=507 (MH$^+$, 100%).

$^1$H-NMR (300 MHz, DMSO-d$_6$): 11.28 (s, 1H; —NH); 9.31 (d, J=7.9, 1H, —NH); 8.36 (d, J=4.9, 1H); 7.31 (d, J=8.9, 1H); 7.06 (d, J=4.9, 1H); 6.69 (dd, J=8.9, 2.4, 1H); 6.68 (d, J=2.4, 1H); 4.20-4.05 (m, 2H); 4.11 (d, J=1.3, 2H); 3.87 (d, J=6.9, 2H); 3.84 (s, 3H); 3.74 (m, 1H); 3.31 (s, 3H); 3.22 (m, 1H); 2.99 (m, 1H); 2.73 (s, 3H); 1.96 (m, 2H); 1.52 (m, 1H); 1.39 (m, 1H); 0.94 (m, 1H); 0.36 (m, 2H); 0.22 (m, 2H).

Example E34

N-[trans-4-(Acetylamino)cyclohexyl]-7-[2-(cyclopropylmethoxy)-4-methoxyphenyl]-2-methyl-1H-pyrrolo[3,2-b]pyridine-3-carboxamide Starting from N-(trans-4-aminocyclohexyl)-7-[2-(cyclopropylmethoxy)-4-methoxyphenyl]-2-methyl-1H-pyrrolo[3,2-b]pyridine-3-carboxamide hydrochloride (example D.f12) and commercially acetyl chloride the title compound is obtained as colorless solid.

MS (ESI): m/z=491 (MH$^+$, 100%).

$^1$H-NMR (300 MHz, DMSO-d$_6$): 11.24 (s, 1H; —NH); 9.12 (d, J=7.7, 1H, —NH); 8.37 (d, J=4.9, 1H); 7.72 (d, J=7.7, 1H, —NH); 7.31 (d, J=9.1, 1H); 7.05 (d, J=4.9, 1H); 6.69 (dd, J=9.1, 2.4, 1H); 6.68 (d, J=2.4, 1H); 3.87 (d, J=6.8, 2H); 3.84 (s, 3H); 3.80 (m, 1H); 3.58 (m, 1H); 2.72 (s, 3H); 2.00 (m, 2H); 1.86 (m, 2H); 1.79 (s, 3H); 1.34 (m, 4H); 0.94 (m, 1H); 0.36 (m, 2H); 0.22 (m, 2H).

Example E35

7-[2-(Cyclopropylmethoxy)-4-methoxyphenyl]-2-methyl-N-[trans-4-(propanoylamino)cyclohexyl]-1H-pyrrolo[3,2-b]pyridine-3-carboxamide Starting from N-(trans-4-aminocyclohexyl)-7-[2-(cyclopropylmethoxy)-4-methoxyphenyl]-2-methyl-1H-pyrrolo[3,2-b]pyridine-3-carboxamide hydrochloride (example D.f12) and commercially propionyl chloride the title compound is obtained as colorless solid.

MS (ESI): m/z=505 (MH$^+$, 100%).

$^1$H-NMR (300 MHz, DMSO-d$_6$): 11.24 (s, 1H; —NH); 9.13 (d, J=7.7, 1H, —NH); 8.37 (d, J=4.9, 1H); 7.62 (d, J=7.7, 1H, —NH); 7.31 (d, J=8.9, 1H); 7.05 (d, J=4.9, 1H); 6.68 (dd, J=8.9, 2.4, 1H); 6.67 (d, J=2.4, 1H); 3.87 (d, J=6.8, 2H); 3.84 (s, 3H); 3.80 (m, 1H); 3.58 (m, 1H); 2.72 (s, 3H); 2.06 (qu, J=7.7, 2H); 2.00 (m, 2H); 1.85 (m, 2H); 1.34 (m, 4H); 0.99 (t, J=7.7, 3H); 0.94 (m, 1H); 0.36 (m, 2H); 0.22 (m, 2H).

Example E36

7-[2-(Cyclopropylmethoxy)-4-methoxyphenyl]-N-{trans-4-[(methoxyacetyl)amino]cyclohexyl}-2-methyl-1H-pyrrolo[3,2-b]pyridine-3-carboxamide Starting from N-(trans-4-aminocyclohexyl)-7-[2-(cyclopropylmethoxy)-4-methoxyphenyl]-2-methyl-1H-pyrrolo[3,2-b]pyridine-3-carboxamide hydrochloride (example D.f12) and commercially methoxy-acetyl chloride the title compound is obtained as colorless solid.

MS (ESI): m/z=521 (MH$^+$, 100%).

$^1$H-NMR (300 MHz, DMSO-d$_6$): 11.24 (s, 1H; —NH); 9.12 (d, J=7.7, 1H, —NH); 8.37 (d, J=4.9, 1H); 7.56 (d, J=8.2, 1H, —NH); 7.31 (d, J=8.9, 1H); 7.05 (d, J=4.9, 1H); 6.68 (dd, J=8.9, 2.4, 1H); 6.67 (d, J=2.4, 1H); 3.87 (d, J=6.9, 2H); 3.84 (s, 3H); 3.78 (s, 2H & m, 1H); 3.69 (m, 1H); 3.31 (s, 3H); 2.72 (s, 3H); 2.00 (m, 2H); 1.82 (m, 2H); 1.42 (m, 4H); 0.94 (m, 1H); 0.36 (m, 2H); 0.22 (m, 2H).

Example E37

N-[cis-4-(Acetylamino)cyclohexyl]-7-[2-(cyclopropylmethoxy)-4-methoxyphenyl]-2-methyl-1H-pyrrolo[3,2-b]pyridine-3-carboxamide Starting from N-(cis-4-aminocyclohexyl)-7-[2-(cyclopropylmethoxy)-4-methoxyphenyl]-2-methyl-1H-pyrrolo[3,2-b]pyridine-3-carboxamide hydrochloride (example D.f13) and commercially acetyl chloride the title compound is obtained as colorless solid.

MS (ESI): m/z=491 (MH$^+$, 100%).
$^1$H-NMR (300 MHz, DMSO-d$_6$): 11.25 (s, 1H; —NH); 9.41 (d, J=7.5, 1H, —NH); 8.41 (d, J=5.0, 1H); 7.84 (d, J=7.5, 1H, —NH); 7.32 (d, J=8.9, 1H); 7.07 (d, J=5.0, 1H); 6.69 (dd, J=8.9, 2.4, 1H); 6.68 (d, J=2.4, 1H); 4.02 (m, 1H); 3.88 (d, J=6.8, 2H); 3.84 (s, 3H); 3.72 (m, 1H); 2.73 (s, 3H); 1.83 (s, 3H); 1.82-1.52 (m, 8H); 0.94 (m, 1H); 0.36 (m, 2H); 0.22 (m, 2H).

Example E38

7-[2-(Cyclopropylmethoxy)-4-methoxyphenyl]-2-methyl-N-[cis-4-(propanoylamino)cyclohexyl]-1H-pyrrolo[3,2-b]pyridine-3-carboxamide Starting from N-(cis-4-aminocyclohexyl)-7-[2-(cyclopropylmethoxy)-4-methoxyphenyl]-2-methyl-1H-pyrrolo[3,2-b]pyridine-3-carboxamide hydrochloride (example D.f13) and commercially propionyl chloride the title compound is obtained as colorless solid.

MS (ESI): m/z=505 (MH$^+$, 100%).
$^1$H-NMR (300 MHz, DMSO-d$_6$): 11.25 (s, 1H; —NH); 9.41 (d, J=7.5, 1H, —NH); 8.41 (d, J=5.0, 1H); 7.75 (d, J=7.5, 1H, —NH); 7.32 (d, J=9.1, 1H); 7.07 (d, J=5.0, 1H); 6.69 (dd, J=9.1, 2.4, 1H); 6.68 (d, J=2.4, 1H); 4.03 (m, 1H); 3.88 (d, J=6.8, 2H); 3.84 (s, 3H); 3.73 (m, 1H); 2.73 (s, 3H); 2.11 (qu, J=7.5, 2H); 1.86-1.50 (m, 8H); 1.00 (t, J=7.5, 3H); 0.94 (m, 1H); 0.36 (m, 2H); 0.22 (m, 2H).

Example E39

7-[2-(Cyclopropylmethoxy)-4-methoxyphenyl]-N-{cis-4-[(methoxyacetyl)amino]cyclohexyl}-2-methyl-1H-pyrrolo[3,2-b]pyridine-3-carboxamide Starting from N-(cis-4-aminocyclohexyl)-7-[2-(cyclopropylmethoxy)-4-methoxyphenyl]-2-methyl-1H-pyrrolo[3,2-b]pyridine-3-carboxamide hydrochloride (example D.f13) and commercially methoxy-acetyl chloride the title compound is obtained as colorless solid.

MS (ESI): m/z=521 (MH$^+$, 100%).
$^1$H-NMR (300 MHz, DMSO-d$_6$): 11.25 (s, 1H; —NH); 9.45 (d, J=7.3, 1H, —NH); 8.40 (d, J=5.0, 1H); 7.64 (d, J=7.5, 1H, —NH); 7.32 (d, J=8.9, 1H); 7.07 (d, J=5.0, 1H); 6.69 (dd, J=8.9, 2.4, 1H); 6.68 (d, J=2.4, 1H); 4.05 (m, 1H); 3.88 (d, J=6.8, 2H); 3.84 (s, 3H); 3.82 (s, 2H); 3.78 (m, 1H); 3.31 (s, 3H); 2.73 (s, 3H); 1.85-1.58 (m, 8H); 0.94 (m, 1H); 0.36 (m, 2H); 0.22 (m, 2H).

Example E40

N-(1-Acetylpiperidin-4-yl)-7-[2-(cyclopropylmethoxy)-5-methoxyphenyl]-2-methyl-1H-pyrrolo[3,2-b]pyridine-3-carboxamide Starting from 7-[2-(cyclopropylmethoxy)-5-methoxyphenyl]-2-methyl-N-(piperidin-4-yl)-1H-pyrrolo[3,2-b]pyridine-3-carboxamide hydrochloride (example D.f14) and commercially available acetyl chloride the title compound is obtained as colorless solid.

MS (ESI): m/z=477 (MH$^+$, 100%).
$^1$H-NMR (300 MHz, DMSO-d$_6$): 11.36 (s, 1H, —NH); 9.30 (d, J=7.7, 1H, —NH); 8.40 (d, J=4.9, 1H); 7.13 (d, J=4.9, 1H); 7.09 (d, J=8.9, 1H); 7.03 (dd, J=8.9, 2.9, 1H); 6.96 (d, J=2.9, 1H); 4.21-4.05 (m, 2H); 3.79 (d, J=6.9, 2H); 3.77 (s, 3H & m, 1H); 3.27 (m, 1H); 2.96 (m, 1H); 2.74 (s, 3H); 2.04 (s, 3H); 1.95 (m, 2H); 1.53 (m, 1H); 1.38 (m, 1H); 0.91 (m, 1H); 0.34 (m, 2H); 0.16 (m, 2H).

Example E41

7-[2-(cyclopropylmethoxy)-5-methoxyphenyl]-2-methyl-N-(1-propanoylpiperidin-4-yl)-1H-pyrrolo[3,2-b]pyridine-3-carboxamide Starting from 7-[2-(cyclopropylmethoxy)-5-methoxyphenyl]-2-methyl-N-(piperidin-4-yl)-1H-pyrrolo[3,2-b]pyridine-3-carboxamide hydrochloride (example D.f14) and commercially available propionyl chloride the title compound is obtained as colorless solid.

MS (ESI): m/z=491 (MH$^+$, 100%).
$^1$H-NMR (300 MHz, DMSO-d$_6$): 11.36 (s, 1H, —NH); 9.30 (d, J=7.7, 1H, —NH); 8.40 (d, J=4.9, 1H); 7.13 (d, J=4.9, 1H); 7.09 (d, J=8.9, 1H); 7.03 (dd, J=8.9, 2.9, 1H); 6.96 (d, J=2.9, 1H); 4.25-4.06 (m, 2H); 3.79 (d, J=6.9, 2H & m, 1H); 3.77 (s, 3H); 3.25 (m, 1H); 2.97 (m, 1H); 2.74 (s, 3H); 2.36 (qu, J=7.4, 2H); 1.95 (m, 2H); 1.50 (m, 1H); 1.38 (m, 1H); 1.01 (t, J=7.4, 3H); 0.90 (m, 1H); 0.34 (m, 2H); 0.16 (m, 2H).

Example E42

7-[2-(cyclopropylmethoxy)-5-methoxyphenyl]-N-[1-(methoxyacetyl)piperidin-4-yl]-2-methyl-1H-pyrrolo[3,2-b]pyridine-3-carboxamide Starting from 7-[2-(cyclopropylmethoxy)-5-methoxyphenyl]-2-methyl-N-(piperidin-4-yl)-1H-pyrrolo[3,2-b]pyridine-3-carboxamide hydrochloride (example D.f14) and commercially available methoxy-acetyl chloride the title compound is obtained as colorless solid.

MS (ESI): m/z=507 (MH$^+$, 100%).
$^1$H-NMR (300 MHz, DMSO-d$_6$): 11.36 (s, 1H, —NH); 9.30 (d, J=7.7, 1H, —NH); 8.40 (d, J=4.9, 1H); 7.13 (d, J=4.9, 1H); 7.09 (d, J=8.9, 1H); 7.03 (dd, J=8.9, 2.9, 1H); 6.96 (d, J=2.9, 1H); 4.22-4.05 (m, 2H); 4.12 (d, J=1.3, 2H); 3.79 (d, J=6.9, 2H); 3.77 (s, 3H); 3.74 (m, 1H); 3.31 (s, 3H); 3.22 (m, 1H); 3.00 (m, 1H); 2.74 (s, 3H); 1.97 (m, 2H); 1.53 (m, 1H); 1.40 (m, 1H); 0.91 (m, 1H); 0.34 (m, 2H); 0.16 (m, 2H).

Example E43

N-[trans-4-(Acetylamino)cyclohexyl]-7-[2-(cyclopropylmethoxy)-5-methoxyphenyl]-2-methyl-1H-pyrrolo[3,2-b]pyridine-3-carboxamide Starting from N-(trans-4-aminocyclohexyl)-7-[2-(cyclopropylmethoxy)-5-methoxyphenyl]-2-methyl-1H-pyrrolo[3,2-b]pyridine-3-carboxamide hydrochloride (example D.f15) and commercially available acetyl chloride the title compound is obtained as colorless solid.

MS (ESI): m/z=491 (MH$^+$, 100%).
$^1$H-NMR (300 MHz, DMSO-d$_6$): 11.34 (s, 1H, —NH); 9.09 (d, J=7.9, 1H, —NH); 8.40 (d, J=4.9, 1H); 7.72 (d, J=7.9, 1H, —NH); 7.13 (d, J=4.9, 1H); 7.09 (d, J=9.1, 1H); 7.03 (dd,

J=9.1, 2.9, 1H); 6.95 (d, J=2.9, 1H); 3.78 (d, J=6.8, 2H & m, 1H); 3.76 (s, 3H); 3.58 (m, 1H); 2.73 (s, 3H); 2.01 (s, 3H); 1.86 (m, 2H); 1.79 (s, 3H); 1.34 (m, 4H); 0.91 (m, 1H); 0.33 (m, 2H); 0.16 (m, 2H).

Example E44

7-[2-(Cyclopropylmethoxy)-5-methoxyphenyl]-2-methyl-N-[trans-4-(propanoylamino)cyclohexyl]-1H-pyrrolo[3,2-b]pyridine-3-carboxamide Starting from N-(trans-4-aminocyclohexyl)-7-[2-(cyclopropylmethoxy)-5-methoxyphenyl]-2-methyl-1H-pyrrolo[3,2-b]pyridine-3-carboxamide hydrochloride (example D.f15) and commercially available propionyl chloride the title compound is obtained as colorless solid.

MS (ESI): m/z=505 (MH$^+$, 100%).

$^1$H-NMR (300 MHz, DMSO-d$_6$): 11.32 (s, 1H, —NH); 9.11 (d, J=7.7, 1H, —NH); 8.40 (d, J=4.9, 1H); 7.62 (d, J=7.9, 1H, —NH); 7.12 (d, J=4.9, 1H); 7.08 (d, J=8.9, 1H); 7.02 (dd, J=8.9, 2.8, 1H); 6.94 (d, J=2.8, 1H); 3.78 (d, J=6.9, 2H & m, 1H); 3.76 (s, 3H); 3.59 (m, 1H); 2.72 (s, 3H); 2.05 (qu, J=7.7, 2H); 2.00 (m, 2H); 1.85 (m, 2H); 1.34 (m, 4H); 0.99 (t, J=7.7, 3H); 0.90 (m, 1H); 0.33 (m, 2H); 0.15 (m, 2H).

Example E45

7-[2-(Cyclopropylmethoxy)-5-methoxyphenyl]-N-{trans-4-[(methoxyacetyl)amino]cyclohexyl}-2-methyl-1H-pyrrolo[3,2-b]pyridine-3-carboxamide Starting from N-(trans-4-aminocyclohexyl)-7-[2-(cyclopropylmethoxy)-5-methoxyphenyl]-2-methyl-1H-pyrrolo[3,2-b]pyridine-3-carboxamide hydrochloride (example D.f15) and commercially available methoxy-acetyl chloride the title compound is obtained as colorless solid.

MS (ESI): m/z=521 (MH$^+$, 100%).

$^1$H-NMR (300 MHz, DMSO-d$_6$): 11.32 (s, 1H, —NH); 9.10 (d, J=7.9, 1H, —NH); 8.40 (d, J=4.9, 1H); 7.56 (d, J=8.2, 1H, —NH); 7.12 (d, J=4.9, 1H); 7.09 (d, J=8.9, 1H); 7.02 (dd, J=8.9, 2.9, 1H); 6.95 (d, J=2.9, 1H); 3.78 (d, J=6.8, 2H & s, 2H & m, 1H); 3.76 (s, 3H); 3.70 (m, 1H); 3.31 (s, 3H); 2.73 (s, 3H); 2.01 (m, 2H); 1.82 (m, 2H); 1.42 (m, 4H); 0.91 (m, 1H); 0.33 (m, 2H); 0.16 (m, 2H).

Example E46

N-[cis-4-(Acetylamino)cyclohexyl]-7-[2-(cyclopropylmethoxy)-5-methoxyphenyl]-2-methyl-1H-pyrrolo[3,2-b]pyridine-3-carboxamide Starting from N-(cis-4-aminocyclohexyl)-7-[2-(cyclopropylmethoxy)-5-methoxyphenyl]-2-methyl-1H-pyrrolo[3,2-b]pyridine-3-carboxamide hydrochloride (example D.f16) and commercially available acetyl chloride the title compound is obtained as colorless solid.

MS (ESI): m/z=491 (MH$^+$, 100%).

$^1$H-NMR (300 MHz, DMSO-d$_6$): 11.33 (s, 1H, —NH); 9.40 (d, J=7.7, 1H, —NH); 8.44 (d, J=4.9, 1H); 7.85 (d, J=7.5, 1H, —NH); 7.14 (d, J=4.9, 1H); 7.09 (d, J=8.9, 1H); 7.03 (dd, J=8.9, 2.9, 1H); 6.96 (d, J=2.9, 1H); 4.02 (m, 1H); 3.79 (d, J=6.8, 2H); 3.77 (s, 3H); 3.74 (m, 1H); 2.73 (s, 3H); 1.83 (s, 3H); 1.83-1.52 (m, 8H); 0.91 (m, 1H); 0.34 (m, 2H); 0.16 (m, 2H).

Example E47

7-[2-(Cyclopropylmethoxy)-5-methoxyphenyl]-2-methyl-N-[cis-4-(propanoylamino)cyclohexyl]-1H-pyrrolo[3,2-b]pyridine-3-carboxamide Starting from N-(cis-4-aminocyclohexyl)-7-[2-(cyclopropylmethoxy)-5-methoxyphenyl]-2-methyl-1H-pyrrolo[3,2-b]pyridine-3-carboxamide hydrochloride (example D.f16) and commercially available propionyl chloride the title compound is obtained as colorless solid.

MS (ESI): m/z=505 (MH$^+$, 100%).

$^1$H-NMR (300 MHz, DMSO-d$_6$): 11.33 (s, 1H, —NH); 9.39 (d, J=7.5, 1H, —NH); 8.44 (d, J=4.9, 1H); 7.75 (d, J=7.3, 1H, —NH); 7.14 (d, J=4.9, 1H); 7.09 (d, J=9.1, 1H); 7.03 (dd, J=9.1, 2.9, 1H); 6.96 (d, J=2.9, 1H); 4.03 (m, 1H); 3.79 (d, J=6.8, 2H); 3.77 (s, 3H); 3.74 (m, 1H); 2.73 (s, 3H); 2.11 (qu, J=7.5, 2H); 1.85-1.51 (m, 8H); 1.00 (t, J=7.5, 3H); 0.91 (m, 1H); 0.34 (m, 2H); 0.16 (m, 2H).

Example E48

7-[2-(Cyclopropylmethoxy)-5-methoxyphenyl]-N-{cis-4-[(methoxyacetyl)amino]cyclohexyl}-2-methyl-1H-pyrrolo[3,2-b]pyridine-3-carboxamide Starting from N-(cis-4-aminocyclohexyl)-7-[2-(cyclopropylmethoxy)-5-methoxyphenyl]-2-methyl-1H-pyrrolo[3,2-b]pyridine-3-carboxamide hydrochloride (example D.f16) and commercially available methoxy-acetyl chloride the title compound is obtained as colorless solid.

MS (ESI): m/z=521 (MH$^+$, 100%).

$^1$H-NMR (300 MHz, DMSO-d$_6$): 11.32 (s, 1H, —NH); 9.43 (d, J=7.3, 1H, —NH); 8.44 (d, J=4.9, 1H); 7.65 (d, J=7.7, 1H, —NH); 7.14 (d, J=4.9, 1H); 7.09 (d, J=9.1, 1H); 7.03 (dd, J=9.1, 2.9, 1H); 6.96 (d, J=2.9, 1H); 4.06 (m, 1H); 3.82 (s, 2H); 3.79 (d, J=6.8, 2H); 3.77 (s, 3H & m, 1H); 3.31 (s, 3H); 2.74 (s, 3H); 1.85-1.59 (m, 8H); 0.92 (m, 1H); 0.34 (m, 2H); 0.16 (m, 2H).

Example E49

N-[(3R*,4R*)-1-Acetyl-4-hydroxypyrrolidin-3-yl]-7-[2-(cyclopropylmethoxy)-5-methoxyphenyl]-2-methyl-1H-pyrrolo[3,2-b]pyridine-3-carboxamide Starting from 7-[2-(cyclopropylmethoxy)-5-methoxyphenyl]-N-[(3R*,4R*)-4-hydroxypyrrolidin-3-yl]-2-methyl-1H-pyrrolo[3,2-b]pyridine-3-carboxamide hydrochloride (example D.f17) and commercially available acetyl chloride the title compound is obtained as colorless solid.

HR-MS (ESI): m/z=479.22871 ([MH]$^+$, C$_{26}$H$_{31}$N$_4$O$_5^+$, calc. 479.289).

Example E50

7-[2-(Cyclopropylmethoxy)-5-methoxyphenyl]-N-[(3R*,4R*)-4-hydroxy-1-propanoylpyrrolidin-3-yl]-2-methyl-1H-pyrrolo[3,2-b]pyridine-3-carboxamide Starting from 7-[2-(cyclopropylmethoxy)-5-methoxyphenyl]-N-[(3R*,4R*)-4-hydroxypyrrolidin-3-yl]-2-methyl-1H-pyrrolo[3,2-b]pyridine-3-carboxamide hydrochloride (example D.f17) and commercially available propionyl chloride the title compound is obtained as colorless solid.
HR-MS (ESI): m/z=493.2443 ([MH]$^+$, $C_{27}H_{33}N_4O_6^+$, calc. 493.2445).

Example E51

7-[2-(Cyclopropylmethoxy)-5-methoxyphenyl]-N-[(3R*,4R*)-4-hydroxy-1-(methoxyacetyl)pyrrolidin-3-yl]-2-methyl-1H-pyrrolo[3,2-b]pyridine-3-carboxamide Starting from 7-[2-(cyclopropylmethoxy)-5-methoxyphenyl]-N-[(3R*,4R*)-4-hydroxypyrrolidin-3-yl]-2-methyl-1H-pyrrolo[3,2-b]pyridine-3-carboxamide hydrochloride (example D.f17) and commercially available methoxy-acetyl chloride the title compound is obtained as colorless solid.
HR-MS (ESI): m/z=509.2394 ([MH]$^+$, $C_{27}H_{33}N_4O_6^+$, calc. 509.2395).

Example E52

N-(1-Acetylpiperidin-4-yl)-7-[2-(cyclopropylmethoxy)-5-methylphenyl]-2-methyl-1H-pyrrolo[3,2-b]pyridine-3-carboxamide Starting from 7-[2-(cyclopropylmethoxy)-5-methylphenyl]-2-methyl-N-(piperidin-4-yl)-1H-pyrrolo[3,2-b]pyridine-3-carboxamide hydrochloride (example D.f18) and commercially available acetyl chloride the title compound is obtained as colorless solid.
MS (ESI): m/z=461 (MH$^+$, 100%).
$^1$H-NMR (300 MHz, DMSO-d$_6$): 11.31 (br.s, 1H, —NH); 9.30 (d, J=7.7, 1H, —NH); 8.39 (d, J=4.9, 1H); 7.26 (dd, J=8.4, 2.0, 1H); 7.19 (d, J=2.0, 1H); 7.09 (d, J=4.9, 1H); 7.03 (d, J=8.4, 1H); 4.21-4.04 (m, 2H); 3.83 (d, J=6.8, 2H); 3.78 (m, 1H); 3.27 (m, 1H); 2.96 (m, 1H); 2.73 (s, 3H); 2.32 (s, 3H); 2.04 (s, 3H); 1.95 (m, 2H); 1.52 (m, 1H); 1.37 (m 1H); 0.93 (m, 1H); 0.34 (m, 2H); 0.19 (m, 2H).

Example E53

7-[2-(Cyclopropylmethoxy)-5-methylphenyl]-2-methyl-N-(1-propanoylpiperidin-4-yl)-1H-pyrrolo[3,2-b]pyridine-3-carboxamide Starting from 7-[2-(cyclopropylmethoxy)-5-methylphenyl]-2-methyl-N-(piperidin-4-yl)-1H-pyrrolo[3,2-b]pyridine-3-carboxamide hydrochloride (example D.f18) and commercially available propionyl chloride the title compound is obtained as colorless solid.
MS (ESI): $^m/_z$=475 (MH$^+$, 100%).
$^1$H-NMR (300 MHz, DMSO-d$_6$): 11.31 (br.s, 1H, —NH); 9.30 (d, J=7.7, 1H, —NH); 8.38 (d, J=4.9, 1H); 7.26 (dd, J=8.4, 2.0, 1H); 7.19 (d, J=2.0, 1H); 7.09 (d, J=4.9, 1H); 7.03 (d, J=8.4, 1H); 4.24-4.04 (m, 2H); 3.82 (d, J=6.8, 2H); 3.78 (m, 1H); 3.25 (m, 1H); 2.97 (m, 1H); 2.73 (s, 3H); 2.36 (qu, J=7.5, 2H); 2.31 (s, 3H); 1.94 (m, 2H); 1.50 (m, 1H); 1.37 (m 1H); 1.01 (t, J=7.5, 3H); 0.93 (m, 1H); 0.34 (m, 2H); 0.19 (m, 2H).

Example E54

7-[2-(Cyclopropylmethoxy)-5-methylphenyl]-N-[1-(methoxyacetyl)piperidin-4-yl]-2-methyl-1H-pyrrolo[3,2-b]pyridine-3-carboxamide Starting from 7-[2-(cyclopropylmethoxy)-5-methylphenyl]-2-methyl-N-(piperidin-4-yl)-1H-pyrrolo[3,2-b]pyridine-3-carboxamide hydrochloride (example D.f18) and commercially available methoxy-acetyl chloride the title compound is obtained as colorless solid.
MS (ESI): m/z=491 (MH$^+$, 100%).
$^1$H-NMR (300 MHz, DMSO-d$_6$): 11.31 (br.s, 1H, —NH); 9.30 (d, J=7.9, 1H, —NH); 8.39 (d, J=4.9, 1H); 7.26 (dd, J=8.6, 1.8, 1H); 7.20 (d, J=1.8, 1H); 7.09 (d, J=4.9, 1H); 7.03 (d, J=8.6, 1H); 4.22-4.05 (m, 2H); 4.12 (d, J=1.3, 2H); 3.82 (d, J=6.8, 2H); 3.75 (m, 1H); 3.31 (s, 3H); 3.23 (m, 1H); 3.00 (m, 1H); 2.74 (s, 3H); 2.32 (s, 3H); 1.96 (m, 2H); 1.53 (m, 1H); 1.40 (m 1H); 0.93 (m, 1H); 0.35 (m, 2H); 0.19 (m, 2H).

Example E55

N-[trans-4-(Acetylamino)cyclohexyl]-7-[2-(cyclopropylmethoxy)-5-methylphenyl]-2-methyl-1H-pyrrolo[3,2-b]pyridine-3-carboxamide Starting from N-(trans-4-aminocyclohexyl)-7-[2-(cyclopropylmethoxy)-5-methylphenyl]-2-methyl-1H-pyrrolo[3,2-b]pyridine-3-carboxamide hydrochloride (example D.f19) and commercially available acetyl chloride the title compound is obtained as colorless solid.
MS (ESI): m/z=475 (MH$^+$, 100%).
$^1$H-NMR (300 MHz, DMSO-d$_6$): 11.25 (br.s, 1H, —NH); 9.12 (d, J=7.8, 1H, —NH); 8.39 (d, J=4.9, 1H); 7.72 (d, J=7.7, 1H, —NH); 7.26 (dd, J=8.4, 2.0, 1H); 7.19 (d, J=2.0, 1H); 7.08 (d, J=4.9, 1H); 7.03 (d, J=8.4, 1H); 3.82 (d, J=6.8, 2H); 3.79 (m, 1H); 3.58 (m, 1H); 2.72 (s, 3H); 2.32 (s, 3H); 2.00 (m, 2H); 1.86 (m, 2H); 1.79 (s, 3H); 1.34 (m 4H); 0.93 (m, 1H); 0.34 (m, 2H); 0.18 (m, 2H).

Example E56

7-[2-(Cyclopropylmethoxy)-5-methylphenyl]-2-methyl-N-[trans-4-(propanoylamino)cyclohexyl]-1H-pyrrolo[3,2-b]pyridine-3-carboxamide Starting from N-(trans-4-aminocyclohexyl)-7-[2-(cyclopropylmethoxy)-5-methylphenyl]-2-methyl-1H-pyrrolo[3,2-b]pyridine-3-carboxamide hydrochloride (example D.f19) and commercially available propionyl chloride the title compound is obtained as colorless solid.
MS (ESI): m/z=489 (MH$^+$, 100%).
$^1$H-NMR (300 MHz, DMSO-d$_6$): 11.27 (br.s, 1H, —NH); 9.12 (d, J=7.7, 1H, —NH); 8.39 (d, J=4.9, 1H); 7.62 (d, J=7.9, 1H, —NH); 7.26 (dd, J=8.6, 1.8, 1H); 7.19 (d, J=1.8, 1H); 7.08 (d, J=4.9, 1H); 7.03 (d, J=8.6, 1H); 3.82 (d, J=6.9, 2H); 3.78 (m, 1H); 3.59 (m, 1H); 2.72 (s, 3H); 2.31 (s, 3H); 2.06 (qu, J=7.5, 2H); 2.01 (m, 2H); 1.85 (m, 2H); 1.34 (m 4H); 0.99 (t, J=7.5, 3H); 0.93 (m, 1H); 0.34 (m, 2H); 0.18 (m, 2H).

Example E57

7-[2-(Cyclopropylmethoxy)-5-methylphenyl]-N-{trans-4-[(methoxyacetyl)amino]cyclohexyl}-2-methyl-1H-pyrrolo[3,2-b]pyridine-3-carboxamide Starting from N-(trans-4-aminocyclohexyl)-7-[2-(cyclopropylmethoxy)-5-methylphenyl]-2-methyl-1H-pyrrolo[3,2-b]pyridine-3-carboxamide hydrochloride (example D.f19) and commercially available methoxy-acetyl chloride the title compound is obtained as colorless solid.
MS (ESI): m/z=505 (MH$^+$, 100%).
$^1$H-NMR (300 MHz, DMSO-d$_6$): 11.27 (br.s, 1H, —NH); 9.12 (d, J=7.7, 1H, —NH); 8.39 (d, J=4.9, 1H); 7.57 (d, J=8.2, 1H, —NH); 7.26 (dd, J=8.4, 2.0, 1H); 7.19 (d, J=2.0, 1H);

7.08 (d, J=4.9, 1H); 7.03 (d, J=8.4, 1H); 3.83 (d, J=6.8, 2H); 3.78 (s, 2H); 3.75 (m, 1H); 3.70 (m, 1H); 3.30 (s, 3H); 2.73 (s, 3H); 2.32 (s, 3H); 2.01 (m, 2H); 1.82 (m, 2H); 1.42 (m 4H); 0.93 (m, 1H); 0.34 (m, 2H); 0.19 (m, 2H).

Example E58

N-[cis-4-(Acetylamino)cyclohexyl]-7-[2-(cyclopropylmethoxy)-5-methylphenyl]-2-methyl-1H-pyrrolo[3,2-b]pyridine-3-carboxamide Starting from N-(cis-4-aminocyclohexyl)-7-[2-(cyclopropylmethoxy)-5-methylphenyl]-2-methyl-1H-pyrrolo[3,2-b]pyridine-3-carboxamide hydrochloride (example D.f20) and commercially available acetyl chloride the title compound is obtained as colorless solid.

MS (ESI): m/z=475 (MH$^+$, 100%).

$^1$H-NMR (300 MHz, DMSO-d$_6$): 11.29 (br.s, 1H, —NH); 9.41 (d, J=7.5, 1H, —NH); 8.43 (d, J=4.9, 1H); 7.84 (d, J=7.5, 1H, —NH); 7.26 (dd, J=8.4, 2.0, 1H); 7.20 (d, J=2.0, 1H); 7.10 (d, J=4.9, 1H); 7.04 (d, J=8.4, 1H); 4.03 (m, 1H); 3.83 (d, J=6.9, 2H); 3.74 (m, 1H); 2.73 (s, 3H); 2.32 (s, 3H); 1.84 (s, 3H); 1.84-1.45 (m 8H); 0.93 (m, 1H); 0.35 (m, 2H); 0.19 (m, 2H).

Example E59

7-[2-(Cyclopropylmethoxy)-5-methylphenyl]-2-methyl-N-[cis-4-(propanoylamino)cyclohexyl]-1H-pyrrolo[3,2-b]pyridine-3-carboxamide Starting from N-(cis-4-aminocyclohexyl)-7-[2-(cyclopropylmethoxy)-5-methylphenyl]-2-methyl-1H-pyrrolo[3,2-b]pyridine-3-carboxamide hydrochloride (example D.f20) and commercially available propionyl chloride the title compound is obtained as colorless solid.

MS (ESI): m/z=489 (MH$^+$, 100%).

$^1$H-NMR (300 MHz, DMSO-d$_6$): 11.29 (br.s, 1H, —NH); 9.41 (d, J=7.7, 1H, —NH); 8.43 (d, J=5.0, 1H); 7.84 (d, J=7.5, 1H, —NH); 7.26 (dd, J=8.4, 2.0, 1H); 7.20 (d, J=2.0, 1H); 7.10 (d, J=5.0, 1H); 7.04 (d, J=8.4, 1H); 4.03 (m, 1H); 3.83 (d, J=6.8, 2H); 3.74 (m, 1H); 2.73 (s, 3H); 2.32 (s, 3H); 2.11 (qu, J=7.7, 2H); 1.87-1.49 (m 8H); 1.00 (t, J=7.7, 3H); 0.93 (m, 1H); 0.35 (m, 2H); 0.19 (m, 2H).

Example E60

7-[2-(Cyclopropylmethoxy)-5-methylphenyl]-N-{cis-4-[(methoxyacetyl)amino]cyclohexyl}-2-methyl-1H-pyrrolo[3,2-b]pyridine-3-carboxamide Starting from N-(cis-4-aminocyclohexyl)-7-[2-(cyclopropylmethoxy)-5-methylphenyl]-2-methyl-1H-pyrrolo[3,2-b]pyridine-3-carboxamide hydrochloride (example D.f20) and commercially available methoxy-acetyl chloride the title compound is obtained as colorless solid.

MS (ESI): m/z=505 (MH$^+$, 100%).

$^1$H-NMR (300 MHz, DMSO-d$_6$): 11.29 (br.s, 1H, —NH); 9.45 (d, J=7.3, 1H, —NH); 8.44 (d, J=4.9, 1H); 7.65 (d, J=7.7, 1H, —NH); 7.26 (dd, J=8.4, 2.0, 1H); 7.20 (d, J=2.0, 1H); 7.10 (d, J=4.9, 1H); 7.04 (d, J=8.4, 1H); 4.06 (m, 1H); 3.83 (d, J=6.9, 2H); 3.82 (s, 2H); 3.79 (m, 1H); 3.31 (s, 3H); 2.73 (s, 3H); 2.32 (s, 3H); 1.87-1.56 (m 8H); 0.93 (m, 1H); 0.35 (m, 2H); 0.19 (m, 2H).

Example E61

N-(1-Acetylpiperidin-4-yl)-7-[2-(cyclopropylmethoxy)-4-fluoro-5-methoxyphenyl]-2-methyl-1H-pyrrolo[3,2-b]pyridine-3-carboxamide Starting from 7-[2-(cyclopropylmethoxy)-4-fluoro-5-methoxyphenyl]-2-methyl-N-(piperidin-4-yl)-1H-pyrrolo[3,2-b]pyridine-3-carboxamide hydrochloride (example D.f21) and commercially available acetyl chloride the title compound is obtained as colorless solid.

MS (ESI): m/z=495 (MH$^+$, 100%).

$^1$H-NMR (300 MHz, DMSO-d$_6$): 11.35 (s, 1H, —NH); 9.28 (d, J=7.7, 1H, —NH); 8.40 (d, J=5.1, 1H); 7.18 (d, J=7.3, 1H); 7.15 (d, J=11.1, 1H & d, J=5.1, 1H); 4.21-4.05 (m, 2H); 3.84 (s, 3H); 3.81 (d, J=6.8, 2H); 3.75 (m, 1H); 3.28 (m, 1H); 2.96 (m, 1H); 2.73 (s, 3H); 2.04 (s, 3H); 1.95 (m, 2H); 1.53 (m, 1H); 1.37 (m, 1H); 0.92 (m, 1H); 0.35 (m, 2H); 0.17 (m, 2H).

Example E62

7-[2-(Cyclopropylmethoxy)-4-fluoro-5-methoxyphenyl]-2-methyl-N-(1-propanoylpiperidin-4-yl)-1H-pyrrolo[3,2-b]pyridine-3-carboxamide Starting from 7-[2-(cyclopropylmethoxy)-4-fluoro-5-methoxyphenyl]-2-methyl-N-(piperidin-4-yl)-1H-pyrrolo[3,2-b]pyridine-3-carboxamide hydrochloride (example D.f21) and commercially available propionyl chloride the title compound is obtained as colorless solid.

MS (ESI): m/z=509 (MH$^+$, 100%).

$^1$H-NMR (300 MHz, DMSO-d$_6$): 11.35 (s, 1H, —NH); 9.28 (d, J=7.7, 1H, —NH); 8.40 (d, J=5.1, 1H); 7.18 (d, J=7.3, 1H); 7.14 (d, J=11.1, 1H & d, J=5.0, 1H); 4.24-4.04 (m, 2H); 3.84 (s, 3H); 3.81 (d, J=6.8, 2H); 3.78 (m, 1H); 3.25 (m, 1H); 2.97 (m, 1H); 2.74 (s, 3H); 2.36 (qu, J=7.5, 2H); 1.95 (m, 2H); 1.50 (m, 1H); 1.37 (m, 1H); 1.01 (t, J=7.5, 3H); 0.92 (m, 1H); 0.35 (m, 2H); 0.17 (m, 2H).

Example E63

7-[2-(Cyclopropylmethoxy)-4-fluoro-5-methoxyphenyl]-N-[1-(methoxyacetyl)piperidin-4-yl]-2-methyl-1H-pyrrolo[3,2-b]pyridine-3-carboxamide Starting from 7-[2-(cyclopropylmethoxy)-4-fluoro-5-methoxyphenyl]-2-methyl-N-(piperidin-4-yl)-1H-pyrrolo[3,2-b]pyridine-3-carboxamide hydrochloride (example D.f21) and commercially available methoxy-acetyl chloride the title compound is obtained as colorless solid.

MS (ESI): m/z=525 (MH$^+$, 100%).

$^1$H-NMR (300 MHz, DMSO-d$_6$): 11.36 (s, 1H, —NH); 9.28 (d, J=7.7, 1H, —NH); 8.40 (d, J=5.0, 1H); 7.18 (d, J=7.5, 1H); 7.15 (d, J=11.3, 1H & d, J=5.0, 1H); 4.21-4.04 (m, 2H); 4.12 (d, J=1.3, 2H); 3.84 (s, 3H); 3.81 (d, J=6.9, 2H); 3.76 (m, 1H); 3.31 (s, 3H); 3.22 (m, 1H); 2.99 (m, 1H); 2.74 (s, 3H); 1.96 (m, 2H); 1.52 (m, 1H); 1.40 (m, 1H); 0.92 (m, 1H); 0.35 (m, 2H); 0.17 (m, 2H).

Example E64

N-[trans-4-(Acetylamino)cyclohexyl]-7-[2-(cyclopropylmethoxy)-4-fluoro-5-methoxyphenyl]-2-methyl-1H-pyrrolo[3,2-b]pyridine-3-carboxamide Starting from N-(trans-4-aminocyclohexyl)-7-[2-(cyclopropylmethoxy)-4-fluoro-5-methoxyphenyl]-2-methyl-1H-pyrrolo[3,2-b]pyridine-3-carboxamide hydrochloride (example D.f22) and commercially available acetyl chloride the title compound is obtained as colorless solid.

MS (ESI): m/z=509 (MH$^+$, 100%).
$^1$H-NMR (300 MHz, DMSO-d$_6$): 11.34 (s, 1H, —NH); 9.08 (d, J=7.7, 1H, —NH); 8.41 (d, J=5.0, 1H); 7.72 (d, J=7.7, 1H, —NH); 7.18 (d, J=7.7, 1H); 7.15 (d, J=5.0, 1H); 7.14 (d, J=11.5, 1H); 3.84 (s, 3H); 3.80 (d, J=6.8, 2H); 3.79 (m, 1H); 3.58 (m, 1H); 2.73 (s, 3H); 2.00 (m, 2H); 1.86 (m, 2H); 1.79 (s, 3H); 1.34 (m, 4H); 0.91 (m, 1H); 0.34 (m, 2H); 0.17 (m, 2H).

Example E65

7-[2-(Cyclopropylmethoxy)-4-fluoro-5-methoxyphenyl]-2-methyl-N-[trans-4-(propanoylamino)cyclohexyl]-1H-pyrrolo[3,2-b]pyridine-3-carboxamide Starting from N-(trans-4-aminocyclohexyl)-7-[2-(cyclopropylmethoxy)-4-fluoro-5-methoxyphenyl]-2-methyl-1H-pyrrolo[3,2-b]pyridine-3-carboxamide hydrochloride (example D.f22) and commercially available propionyl chloride the title compound is obtained as colorless solid.

MS (ESI): m/z=523 (MH$^+$, 100%).
$^1$H-NMR (300 MHz, DMSO-d$_6$): 11.32 (s, 1H, —NH); 9.10 (d, J=7.9, 1H, —NH); 8.41 (d, J=5.0, 1H); 7.62 (d, J=7.7, 1H, —NH); 7.18 (d, J=7.9, 1H); 7.14 (d, J=5.0, 1H & d, J=11.7, 1H); 3.84 (s, 3H); 3.80 (d, J=6.8, 2H); 3.77 (m, 1H); 3.59 (m, 1H); 2.73 (s, 3H); 2.06 (qu, J=7.7, 2H); 2.00 (m, 2H); 1.86 (m, 2H); 1.34 (m, 4H); 0.99 (t, J=7.7, 3H); 0.91 (m, 1H); 0.35 (m, 2H); 0.17 (m, 2H).

Example E66

7-[2-(Cyclopropylmethoxy)-4-fluoro-5-methoxyphenyl]-N-{trans-4-[(methoxyacetyl)amino]cyclohexyl}-2-methyl-1H-pyrrolo[3,2-b]pyridine-3-carboxamide Starting from N-(trans-4-aminocyclohexyl)-7-[2-(cyclopropylmethoxy)-4-fluoro-5-methoxyphenyl]-2-methyl-1H-pyrrolo[3,2-b]pyridine-3-carboxamide hydrochloride (example D.f22) and commercially available methoxy-acetyl chloride the title compound is obtained as colorless solid.

MS (ESI): m/z=539 (MH$^+$, 100%).
$^1$H-NMR (300 MHz, DMSO-d$_6$): 11.32 (s, 1H, —NH); 9.09 (d, J=7.7, 1H, —NH); 8.40 (d, J=5.0, 1H); 7.56 (d, J=8.2, 1H, —NH); 7.18 (d, J=7.7, 1H); 7.14 (d, J=5.0, 1H & d, J=11.5, 1H); 3.84 (s, 3H); 3.80 (d, J=6.8, 2H); 3.78 (m, 1H); 3.68 (m, 2H); 3.31 (s, 3H); 2.73 (s, 3H); 2.01 (m, 2H); 1.81 (m, 2H); 1.43 (m, 4H); 0.91 (m, 1H); 0.35 (m, 2H); 0.17 (m, 2H).

Example E67

N-[cis-4-(Acetylamino)cyclohexyl]-7-[2-(cyclopropylmethoxy)-4-fluoro-5-methoxyphenyl]-2-methyl-1H-pyrrolo[3,2-b]pyridine-3-carboxamide Starting from N-(cis-4-aminocyclohexyl)-7-[2-(cyclopropylmethoxy)-4-fluoro-5-methoxyphenyl]-2-methyl-1H-pyrrolo[3,2-b]pyridine-3-carboxamide hydrochloride (example D.f23) and commercially available acetyl chloride the title compound is obtained as colorless solid.

MS (ESI): m/z=509 (MH$^+$, 100%).
$^1$H-NMR (300 MHz, DMSO-d$_6$): 11.33 (s, 1H, —NH); 9.38 (d, J=7.7, 1H, —NH); 8.44 (d, J=4.9, 1H); 7.84 (d, J=7.5, 1H, —NH); 7.19 (d, J=6.8, 1H); 7.16 (d, J=4.9, 1H); 7.14 (d, J=10.4, 1H); 4.02 (m, 1H); 3.84 (s, 3H); 3.81 (d, J=6.8, 2H); 3.74 (m, 1H); 2.73 (s, 3H); 1.83 (s, 3H); 1.83-1.50 (m, 8H); 0.92 (m, 1H); 0.35 (m, 2H); 0.17 (m, 2H).

Example E68

7-[2-(Cyclopropylmethoxy)-4-fluoro-5-methoxyphenyl]-2-methyl-N-[cis-4-(propanoylamino)cyclohexyl]-1H-pyrrolo[3,2-b]pyridine-3-carboxamide Starting from N-(cis-4-aminocyclohexyl)-7-[2-(cyclopropylmethoxy)-4-fluoro-5-methoxyphenyl]-2-methyl-1H-pyrrolo[3,2-b]pyridine-3-carboxamide hydrochloride (example D.f23) and commercially available propionyl chloride the title compound is obtained as colorless solid.

MS (ESI): m/z=523 (MH$^+$, 100%).
$^1$H-NMR (300 MHz, DMSO-d$_6$): 11.33 (s, 1H, —NH); 9.38 (d, J=7.5, 1H, —NH); 8.44 (d, J=5.1, 1H); 7.75 (d, J=7.5, 1H, —NH); 7.19 (d, J=6.6, 1H); 7.16 (d, J=5.1, 1H); 7.15 (d, J=10.4, 1H); 4.02 (m, 1H); 3.84 (s, 3H); 3.81 (d, J=6.8, 2H); 3.74 (m, 1H); 2.73 (s, 3H); 2.11 (qu, J=7.5, 2H); 1.86-1.50 (m, 8H); 1.00 (t, J=7.5, 3H); 0.92 (m, 1H); 0.35 (m, 2H); 0.17 (m, 2H).

Example E69

7-[2-(Cyclopropylmethoxy)-4-fluoro-5-methoxyphenyl]-N-{cis-4-[(methoxyacetyl)amino]cyclohexyl}-2-methyl-1H-pyrrolo[3,2-b]pyridine-3-carboxamide Starting from N-(cis-4-aminocyclohexyl)-7-[2-(cyclopropylmethoxy)-4-fluoro-5-methoxyphenyl]-2-methyl-1H-pyrrolo[3,2-b]pyridine-3-carboxamide hydrochloride (example D.f23) and commercially available methoxyl-acetyl chloride the title compound is obtained as colorless solid.

MS (ESI): m/z=539 (MH$^+$, 100%).
$^1$H-NMR (300 MHz, DMSO-d$_6$): 11.33 (s, 1H, —NH); 9.41 (d, J=7.5, 1H, —NH); 8.44 (d, J=4.9, 1H); 7.64 (d, J=7.7, 1H, —NH); 7.19 (d, J=6.7, 1H); 7.16 (d, J=4.9, 1H); 7.15 (d, J=10.2, 1H); 4.05 (m, 1H); 3.84 (s, 3H); 3.82 (s, 2H); 3.81 (d, J=6.8, 2H); 3.77 (m, 1H); 3.31 (s, 3H); 2.73 (s, 3H); 1.86-1.58 (m, 8H); 0.92 (m, 1H); 0.35 (m, 2H); 0.17 (m, 2H).

Example E70

N-[(3R*,4R*)-1-Acetyl-4-hydroxypyrrolidin-3-yl]-7-[2-(cyclopropylmethoxy)-4-fluoro-5-methoxyphenyl]-2-methyl-1H-pyrrolo[3,2-b]pyridine-3-carboxamide Starting from 7-[2-(cyclopropylmethoxy)-4-fluoro-5-methoxyphenyl]-N-[(3R*,4R*)-4-hydroxypyrrolidin-3-yl]-2-methyl-1H-pyrrolo[3,2-b]pyridine-3-carboxamide hydrochloride (example D.f24) and commercially available acetyl chloride the title compound is obtained as colorless solid.

HR-MS (ESI): m/z=497.2201 ([MH]$^+$, $C_{26}H_{30}FN_4O_5^+$, calc. 497.2195).

Example E71

7-[2-(Cyclopropylmethoxy)-4-fluoro-5-methoxyphenyl]-N-[(3R*,4R*)-4-hydroxy-1-propanoylpyrrolidin-3-yl]-2-methyl-1H-pyrrolo[3,2-b]pyridine-3-carboxamide Starting from 7-[2-(cyclopropylmethoxy)-4-fluoro-5-methoxyphenyl]-N-[(3R*,4R*)-4-hydroxypyrrolidin-3-yl]-2-methyl-1H-pyrrolo[3,2-b]pyridine-3-carboxamide hydrochloride (example D.f24) and commercially available propionyl chloride the title compound is obtained as colorless solid.
HR-MS (ESI): m/z=511.2347 ([MH]$^+$, $C_{27}H_{32}FN_4O_5^+$, calc. 511.2351).

Example E72

7-[2-(Cyclopropylmethoxy)-4-fluoro-5-methoxyphenyl]-N-[(3R*,4R*)-4-hydroxy-1-(methoxyacetyl)pyrrolidin-3-yl]-2-methyl-1H-pyrrolo[3,2-b]pyridine-3-carboxamide Starting from 7-[2-(cyclopropylmethoxy)-4-fluoro-5-methoxyphenyl]-N-[(3R*,4R*)-4-hydroxypyrrolidin-3-yl]-2-methyl-1H-pyrrolo[3,2-b]pyridine-3-carboxamide hydrochloride (example D.f24) and commercially available methoxy-acetyl chloride the title compound is obtained as colorless solid.
HR-MS (ESI): m/z=527.2303 ([MH]$^+$, $C_{27}H_{32}FN_4O_6^+$, calc. 527.2300).

Example E73

N-[(3R*,4R*)-1-Acetyl-3-hydroxypiperidin-4-yl]-7-[2-(cyclopropylmethoxy)-4-fluoro-5-methoxyphenyl]-2-methyl-1H-pyrrolo[3,2-b]pyridine-3-carboxamide Starting from 7-[2-(cyclopropylmethoxy)-4-fluoro-5-methoxyphenyl]-N-[(3R*,4R*)-3-hydroxypiperidin-4-yl]-2-methyl-1H-pyrrolo[3,2-b]pyridine-3-carboxamide hydrochloride (example D.f25) and commercially available acetyl chloride the title compound is obtained as colorless solid.
HR-MS (ESI): m/z=511.2353 ([MH]$^+$, $C_{27}H_{32}FN_4O_5^+$, calc. 511.2351).

Example E74

7-[2-(Cyclopropylmethoxy)-4-fluoro-5-methoxyphenyl]-N-[(3R*,4R*)-3-hydroxy-1-propanoylpiperidin-4-yl]-2-methyl-1H-pyrrolo[3,2-b]pyridine-3-carboxamide Starting from 7-[2-(cyclopropylmethoxy)-4-fluoro-5-methoxyphenyl]-N-[(3R*,4R*)-3-hydroxypiperidin-4-yl]-2-methyl-1H-pyrrolo[3,2-b]pyridine-3-carboxamide hydrochloride (example D.f25) and commercially available propionyl chloride the title compound is obtained as colorless solid.
HR-MS (ESI): m/z=525.2506 ([MH]$^+$, $C_{28}H_{34}FN_4O_5^+$, calc. 525.2508).

Example E75

7-[2-(Cyclopropylmethoxy)-4-fluoro-5-methoxyphenyl]-N-[(3R*,4R*)-3-hydroxy-1-(methoxyacetyl)piperidin-4-yl]-2-methyl-1H-pyrrolo[3,2-b]pyridine-3-carboxamide Starting from 7-[2-(cyclopropylmethoxy)-4-fluoro-5-methoxyphenyl]-N-[(3R*,4R*)-3-hydroxypiperidin-4-yl]-2-methyl-1H-pyrrolo[3,2-b]pyridine-3-carboxamide hydrochloride (example D.f25) and commercially available methoxy-acetyl chloride the title compound is obtained as colorless solid.
HR-MS (ESI): m/z=541.2458 ([MH]$^+$, $C_{28}H_{34}FN_4O_6^+$, calc. 541.2457).

Example E76

N-(1-Acetylpiperidin-4-yl)-7-[2-(cyclopropylmethoxy)-5-fluoro-4-methoxyphenyl]-2-methyl-1H-pyrrolo[3,2-b]pyridine-3-carboxamide Starting from 7-[2-(cyclopropylmethoxy)-5-fluoro-4-methoxyphenyl]-2-methyl-N-piperidin-4-yl-1H-pyrrolo[3,2-b]pyridine-3-carboxamide hydrochloride (example D.f26) and commercially available acetyl chloride the title compound is obtained as colorless solid.
MS (ESI): m/z=495 (MH$^+$, 100%).
$^1$H-NMR (300 MHz, DMSO-$d_6$): 11.33 (s, 1H, —NH); 9.28 (d, J=7.7, 1H, —NH); 8.37 (d, J=5.0, 1H); 7.27 (d, J=11.7, 1H); 7.09 (d, J=5.0, 1H); 6.93 (d, J=7.5, 1H); 4.17 (m, 1H); 4.13 (m, 1H); 3.95 (s, 3H); 3.90 (d, J=6.8, 2H); 3.77 (m, 1H); 3.27 (m, 1H); 2.96 (m, 1H); 2.74 (s, 3H); 2.04 (s, 3H); 1.95 (m, 2H); 1.52 (m, 1H); 1.37 (m, 1H); 0.94 (m, 1H); 0.36 (m, 2H); 0.20 (m, 2H).

Example E77

7-[2-(Cyclopropylmethoxy)-5-fluoro-4-methoxyphenyl]-2-methyl-N-(1-propionylpiperidin-4-yl)-1H-pyrrolo[3,2-b]pyridine-3-carboxamide Starting from 7-[2-(cyclopropylmethoxy)-5-fluoro-4-methoxyphenyl]-2-methyl-N-piperidin-4-yl-1H-pyrrolo[3,2-b]pyridine-3-carboxamide hydrochloride (example D.f26) and commercially available propionyl chloride the title compound is obtained as colorless solid.
MS (ESI): m/z=509 (MH$^+$, 100%).
$^1$H-NMR (300 MHz, DMSO-$d_6$): 11.33 (s, 1H, —NH); 9.28 (d, J=7.9, 1H, —NH); 8.37 (d, J=5.0, 1H); 7.27 (d, J=11.7, 1H); 7.09 (d, J=5.0, 1H); 6.93 (d, J=7.5, 1H); 4.20 (m, 1H); 4.15 (m, 1H); 3.94 (s, 3H); 3.90 (d, J=6.9, 2H); 3.80 (m, 1H); 3.25 (m, 1H); 2.97 (m, 1H); 2.78 (s, 3H); 2.36 (qu, J=7.5, 2H); 1.95 (m, 2H); 1.49 (m, 1H); 1.37 (m, 1H); 1.01 (t, J=7.5, 3H); 0.94 (m, 1H); 0.36 (m, 2H); 0.20 (m, 2H).

Example E78

7-[2-(Cyclopropylmethoxy)-5-fluoro-4-methoxyphenyl]-N-[1-(methoxyacetyl)piperidin-4-yl]-2-methyl-1H-pyrrolo[3,2-b]pyridine-3-carboxamide Starting from 7-[2-(cyclopropylmethoxy)-5-fluoro-4-methoxyphenyl]-2-methyl-N-piperidin-4-yl-1H-pyrrolo[3,2-b]pyridine-3-carboxamide hydrochloride (example D.f26) and commercially available methoxy-acetyl chloride the title compound is obtained as colorless solid.

MS (ESI): m/z=525 (MH+, 100%).
¹H-NMR (300 MHz, DMSO-d₆): 11.33 (s, 1H, —NH); 9.28 (d, J=7.9, 1H, —NH); 8.37 (d, J=5.0, 1H); 7.28 (d, J=11.7, 1H); 7.09 (d, J=5.0, 1H); 6.92 (d, J=7.5, 1H); 4.21-4.05 (m, 2H & s, 2H); 3.94 (s, 3H); 3.90 (d, J=6.9, 2H); 3.74 (m, 1H); 3.31 (s, 3H); 3.22 (m, 1H); 2.99 (m, 1H); 2.73 (s, 3H); 1.93 (m, 2H); 1.51 (m, 1H); 1.39 (m, 1H); 0.94 (m, 1H); 0.36 (m, 2H); 0.20 (m, 2H).

Example E79

N-(trans-4-Acetamidocyclohexyl)-7-[2-(cyclopropylmethoxy)-5-fluoro-4-methoxyphenyl]-2-methyl-1H-pyrrolo[3,2-b]pyridine-3-carboxamide Starting from N-(trans-4-aminocyclohexyl)-7-[2-(cyclopropylmethoxy)-5-fluoro-4-methoxyphenyl]-2-methyl-1H-pyrrolo[3,2-b]pyridine-3-carboxamide hydrochloride (example D.f27) and commercially available acetyl chloride the title compound is obtained as colorless solid.
MS (ESI): m/z=509 (MH+, 100%).
¹H-NMR (300 MHz, DMSO-d₆): 11.30 (s, 1H, —NH); 9.10 (d, J=7.7, 1H, —NH); 8.38 (d, J=4.9, 1H); 7.72 (d, J=7.7, 1H, —NH); 7.28 (d, J=11.7, 1H); 7.08 (d, J=4.9, 1H); 6.92 (d, J=7.5, 1H); 3.94 (s, 3H); 3.89 (d, J=6.8, 2H); 3.79 (m, 1H); 3.58 (m, 1H); 2.73 (s, 3H); 2.00 (m, 2H); 1.86 (m, 2H); 1.79 (s, 3H); 1.33 (m, 4H); 0.93 (m, 1H); 0.36 (m, 2H); 0.19 (m, 2H).

Example E80

7-[2-(Cyclopropylmethoxy)-5-fluoro-4-methoxyphenyl]-2-methyl-N-[trans-4-(propionylamino)cyclohexyl]-1H-pyrrolo[3,2-b]pyridine-3-carboxamide Starting from N-(trans-4-aminocyclohexyl)-7-[2-(cyclopropylmethoxy)-5-fluoro-4-methoxyphenyl]-2-methyl-1H-pyrrolo[3,2-b]pyridine-3-carboxamide hydrochloride (example D.f27) and commercially available propionyl chloride the title compound is obtained as colorless solid.
MS (ESI): m/z=523 (MH+, 100%).
¹H-NMR (300 MHz, DMSO-d₆): 11.30 (s, 1H, —NH); 9.10 (d, J=7.9, 1H, —NH); 8.38 (d, J=4.9, 1H); 7.62 (d, J=7.9, 1H, —NH); 7.27 (d, J=11.9, 1H); 7.08 (d, J=4.9, 1H); 6.93 (d, J=7.5, 1H); 3.94 (s, 3H); 3.89 (d, J=6.9, 2H); 3.79 (m, 1H); 3.59 (m, 1H); 2.73 (s, 3H); 2.06 (qu, J=7.7, 2H); 2.00 (m, 2H); 1.85 (m, 2H); 1.34 (m, 4H); 0.99 (t, J=7.7, 3H); 0.93 (m, 1H); 0.36 (m, 2H); 0.20 (m, 2H).

Example E81

7-[2-(Cyclopropylmethoxy)-5-fluoro-4-methoxyphenyl]-N-{trans-4-[(methoxyacetyl)amino]cyclohexyl}-2-methyl-1H-pyrrolo[3,2-b]pyridine-3-carboxamide Starting from N-(trans-4-aminocyclohexyl)-7-[2-(cyclopropylmethoxy)-5-fluoro-4-methoxyphenyl]-2-methyl-1H-pyrrolo[3,2-b]pyridine-3-carboxamide hydrochloride (example D.f27) and commercially available methoxy-acetyl chloride the title compound is obtained as colorless solid.
MS (ESI): m/z=539 (MH+, 100%).
¹H-NMR (300 MHz, DMSO-d₆): 11.30 (s, 1H, —NH); 9.09 (d, J=7.9, 1H, —NH); 8.38 (d, J=4.9, 1H); 7.56 (d, J=8.2, 1H, —NH); 7.27 (d, J=11.7, 1H); 7.08 (d, J=4.9, 1H); 6.93 (d, J=7.5, 1H); 3.94 (s, 3H); 3.89 (d, J=6.9, 2H); 3.78 (m, 1H & s, 2H); 3.69 (m, 1H); 3.31 (s, 3H); 2.73 (s, 3H); 2.00 (m, 2H); 1.81 (m, 2H); 1.42 (m, 4H); 0.94 (m, 1H); 0.36 (m, 2H); 0.20 (m, 2H).

Example E82

N-(cis-4-Acetamidocyclohexyl)-7-[2-(cyclopropylmethoxy)-5-fluoro-4-methoxyphenyl]-2-methyl-1H-pyrrolo[3,2-b]pyridine-3-carboxamide Starting from N-(cis-4-aminocyclohexyl)-7-[2-(cyclopropylmethoxy)-5-fluoro-4-methoxyphenyl]-2-methyl-1H-pyrrolo[3,2-b]pyridine-3-carboxamide hydrochloride (example D.f28) and commercially available acetyl chloride the title compound is obtained as colorless solid.
MS (ESI): m/z=509 (MH+, 100%).
¹H-NMR (300 MHz, DMSO-d₆): 11.31 (s, 1H, —NH); 9.39 (d, J=7.7, 1H, —NH); 8.41 (d, J=4.9, 1H); 7.83 (d, J=7.5, 1H, —NH); 7.28 (d, J=11.7, 1H); 7.10 (d, J=4.9, 1H); 6.93 (d, J=7.7, 1H); 4.02 (m, 1H); 3.95 (s, 3H); 3.90 (d, J=6.8, 2H); 3.72 (m, 1H); 2.73 (s, 3H); 1.83 (s, 3H); 1.83-1.51 (m, 8H); 0.94 (m, 1H); 0.37 (m, 2H); 0.20 (m, 2H).

Example E83

7-[2-(Cyclopropylmethoxy)-5-fluoro-4-methoxyphenyl]-2-methyl-N-[cis-4-(propionylamino)cyclohexyl]-1H-pyrrolo[3,2-b]pyridine-3-carboxamide Starting from N-(cis-4-aminocyclohexyl)-7-[2-(cyclopropylmethoxy)-5-fluoro-4-methoxyphenyl]-2-methyl-1H-pyrrolo[3,2-b]pyridine-3-carboxamide hydrochloride (example D.f28) and commercially available propionyl chloride the title compound is obtained as colorless solid.
MS (ESI): m/z=523 (MH+, 100%).
¹H-NMR (300 MHz, DMSO-d₆): 11.31 (s, 1H, —NH); 9.39 (d, J=7.5, 1H, —NH); 8.41 (d, J=5.1, 1H); 7.74 (d, J=7.7, 1H, —NH); 7.28 (d, J=11.7, 1H); 7.10 (d, J=5.1, 1H); 6.93 (d, J=7.5, 1H); 4.02 (m, 1H); 3.95 (s, 3H); 3.90 (d, J=6.8, 2H); 3.73 (m, 1H); 2.73 (s, 3H); 2.11 (qu, J=7.7, 2H); 1.84-1.47 (m, 8H); 1.00 (t, J=7.7, 3H); 0.94 (m, 1H); 0.37 (m, 2H); 0.20 (m, 2H).

Example E84

7-[2-(Cyclopropylmethoxy)-5-fluoro-4-methoxyphenyl]-N-{cis-4-[(methoxyacetyl)amino]cyclohexyl}-2-methyl-1H-pyrrolo[3,2-b]pyridine-3-carboxamide Starting from N-(cis-4-aminocyclohexyl)-7-[2-(cyclopropylmethoxy)-5-fluoro-4-methoxyphenyl]-2-methyl-1H-pyrrolo[3,2-b]pyridine-3-carboxamide hydrochloride (example D.f28) and commercially available methoxy-acetyl chloride the title compound is obtained as colorless solid.
MS (ESI): m/z=539 (MH+, 100%).
¹H-NMR (300 MHz, DMSO-d₆): 11.30 (s, 1H, —NH); 9.44 (d, J=7.5, 1H, —NH); 8.42 (d, J=5.1, 1H); 7.63 (d, J=7.7, 1H, —NH); 7.28 (d, J=11.9, 1H); 7.10 (d, J=5.1, 1H); 6.93 (d, J=7.5, 1H); 4.06 (m, 1H); 3.95 (s, 3H); 3.90 (d, J=6.9, 2H); 3.82 (s, 2H); 3.78 (m, 1H); 3.31 (s, 3H); 2.74 (s, 3H); 1.86-1.57 (m, 8H); 0.94 (m, 1H); 0.37 (m, 2H); 0.20 (m, 2H).

Example F1

4-[5-(Cyclopropylmethoxy)-1,3-benzodioxol-4-yl]-N-(1-glycoloylpiperidin-4-yl)-6-methyl-5H-pyrrolo[3,2-d]pyrimidine-7-carboxamide 7-[5-(Cyclopropylmethoxy)-1,3-benzodioxol-4-yl]-2-methyl-N-piperidin-4-yl-1H-pyrrolo[3,2-b]pyridine-3-carboxamide hydrochloride from example D.f1 (485 mg; 1.0 mmol) is dissolved in dry dichloromethane (5 mL) and DBU (2.5 mmol). Commercially available 2-chloro-2-oxoethyl acetate (1.1 mmol) is syringed into the reaction mixture at ice bath temperature. After addition stirring is continued at ambient temperature overnight. Methanol (1 mL) is added and stirring is continued for two hours. The volatiles are evaporated.

The residue is dissolved in methanol (5 mL), treated with 5M KOH (1.5 mmol) and stirred overnight at ambient temperature. The pH of the reaction mixture is adjusted to 6-7 by addition of 2M citric acid. The volatiles are evaporated. The residue is purified by reversed phase preparative HPLC. The collected product fraction is freeze-dried to yield the title compound as colorless solid.

MS (ESI): m/z=507 (MH$^+$, 100%).
$^1$H-NMR (300 MHz, DMSO-d$_6$): 11.43 (s, 1H, —NH); 9.25 (d, J=7.8, 1H, —NH); 8.38 (d, J=5.0, 1H); 7.18 (d, J=5.0, 1H); 6.95 (d, J=8.6, 1H); 6.55 (d, J=8.6, 1H); 6.00 (s, 2H); 4.49 (t, J=5.5, 1H, —OH); 4.25-4.04 (m, 4H); 3.75 (d, J=6.8, 2H); 3.67 (m, 1H); 3.20 (m, 1H); 3.03 (m, 1H); 2.73 (s, 3H); 1.96 (m, 2H); 1.52 (m, 1H); 1.41 (m, 1H); 0.93 (m, 1H); 0.34 (m, 2H); 0.15 (m, 2H).

The following compounds are prepared analogously to the procedure described in above example F1.

Example F2

7-[5-(Cyclopropylmethoxy)-1,3-benzodioxol-4-yl]-N-{1-[(2S)-2-hydroxypropanoyl]piperidin-4-yl}-2-methyl-1H-pyrrolo[3,2-b]pyridine-3-carboxamide Starting from 7-[5-(cyclopropylmethoxy)-1,3-benzodioxol-4-yl]-2-methyl-N-piperidin-4-yl-1H-pyrrolo[3,2-b]pyridine-3-carboxamide hydrochloride (example D.f1) and commercially available (2S)-1-chloro-1-oxopropan-2-yl acetate the title compound is obtained as colorless solid.

MS (ESI): m/z=521 (MH$^+$, 100%).
$^1$H-NMR (300 MHz, DMSO-d$_6$): 11.43 (s, 1H, —NH); 9.25 (d, J=7.5, 1H, —NH); 8.39 (d, J=5.0, 1H); 7.18 (d, J=5.0, 1H); 6.95 (d, J=8.5, 1H); 6.55 (d, J=8.5, 1H); 6.00 (s, 2H); 4.85 (d, J=6.8, 1H, —OH); 4.46 (m, 1H); 4.28-4.06 (m, 2H); 3.94 (m, 1H); 3.75 (d, J=6.8, 2H); 3.27 (m, 1H); 3.00 (m, 1H); 2.73 (s, 3H); 1.98 (m, 2H); 1.51 (m, 1H); 1.41 (m, 1H); 1.21 (d, J=4.8, 3H); 0.93 (m, 1H); 0.34 (m, 2H); 0.15 (m, 2H).

Example F3

7-[5-(Cyclopropylmethoxy)-1,3-benzodioxol-4-yl]-N-[1-(methoxyacetyl)piperidin-4-yl]-2-methyl-1H-pyrrolo[3,2-b]pyridine-3-carboxamide Starting from N-(trans-4-aminocyclohexyl)-7-[5-(cyclopropylmethoxy)-1,3-benzodioxol-4-yl]-2-methyl-1H-pyrrolo[3,2-b]pyridine-3-carboxamide hydrochloride (example D.f2) and commercially available 2-chloro-2-oxoethyl acetate the title compound is obtained as colorless solid.

MS (ESI): m/z=535 (MH$^+$, 100%).
$^1$H-NMR (300 MHz, DMSO-d$_6$): 11.40 (s, 1H, —NH); 9.07 (d, J=7.7, 1H, —NH); 8.39 (d, J=5.0, 1H); 7.42 (d, J=8.4, 1H, —NH); 7.18 (d, J=5.0, 1H); 6.95 (d, J=8.6, 1H); 6.55 (d, J=8.6, 1H); 6.00 (s, 2H); 5.40 (br.d, J 2.4, 1H, —OH); 3.94 (m, 1H); 3.80 (m, 1H); 3.75 (d, J=6.8, 2H); 3.62 (m, 1H); 2.73 (s, 3H); 2.00 (m, 2H); 1.82 (m, 2H); 1.41 (m, 4H); 1.21 (d, J=6.7, 3H); 0.93 (m, 1H); 0.34 (m, 2H); 0.15 (m, 2H).

Example F4

7-[5-(Cyclopropylmethoxy)-1,3-benzodioxol-4-yl]-N-[cis-4-(glycoloylamino)cyclohexyl]-2-methyl-1H-pyrrolo[3,2-b]pyridine-3-carboxamide Starting from N-(cis-4-aminocyclohexyl)-7-[5-(cyclopropylmethoxy)-1,3-benzodioxol-4-yl]-2-methyl-1H-pyrrolo[3,2-b]pyridine-3-carboxamide hydrochloride (example D.f3) and commercially available 2-chloro-2-oxoethyl acetate the title compound is obtained as colorless solid.

MS (ESI): m/z=521 (MH$^+$, 100%).
$^1$H-NMR (300 MHz, DMSO-d$_6$): 11.40 (s, 1H, —NH); 9.39 (d, J=7.5, 1H, —NH); 8.43 (d, J=4.9, 1H); 7.50 (d, J=7.9, 1H, —NH); 7.19 (d, J=4.9, 1H); 6.95 (d, J=8.6, 1H); 6.56 (d, J=8.6, 1H); 6.00 (s, 2H); 5.32 (t, J=5.8, 1H, —OH); 4.06 (m, 1H); 3.82 (d, J=5.8, 2H); 3.75 (m, 1H & d, J=6.8, 2H); 2.73 (s, 3H); 1.84-1.57 (m, 8H); 0.93 (m, 1H); 0.35 (m, 2H); 0.16 (m, 2H).

Example F5

7-[5-(Cyclopropylmethoxy)-1,3-benzodioxol-4-yl]-N-(cis-4-{[(2S)-2-hydroxypropanoyl]amino}cyclohexyl)-2-methyl-1H-pyrrolo[3,2-b]pyridine-3-carboxamide Starting from N-(cis-4-aminocyclohexyl)-7-[5-(cyclopropylmethoxy)-1,3-benzodioxol-4-yl]-2-methyl-1H-pyrrolo[3,2-b]pyridine-3-carboxamide hydrochloride (example D.f3) and commercially available (2S)-1-chloro-1-oxopropan-2-yl acetate the title compound is obtained as colorless solid.

MS (ESI): m/z=535 (MH$^+$, 100%).
$^1$H-NMR (300 MHz, DMSO-d$_6$): 11.41 (s, 1H, —NH); 9.38 (d, J=7.5, 1H, —NH); 8.43 (d, J=5.0, 1H); 7.45 (d, J=7.7, 1H, —NH); 7.19 (d, J=5.0, 1H); 6.95 (d, J=8.6, 1H); 6.55 (d, J=8.6, 1H); 6.00 (s, 2H); 5.35 (d, J=5.5, 1H, —OH); 4.05 (m, 1H); 3.99 (dqu, J=6.7, 5.5, 1H); 3.75 (d, J=6.8, 2H); 3.74 (m, 1H); 2.73 (s, 3H); 1.82-1.56 (m, 8H); 0.93 (m, 1H); 0.35 (m, 2H); 0.16 (m, 2H).

Example F6

7-[2-(Cyclopropylmethoxy)-4-fluorophenyl]-N-[1-(methoxyacetyl)piperidin-4-yl]-2-methyl-1H-pyrrolo[3,2-b]pyridine-3-carboxamide Starting from 7-[2-(cyclopropylmethoxy)-4-fluorophenyl]-2-methyl-N-(piperidin-4-yl)-1H-pyrrolo[3,2-b]pyridine-3-carboxamide hydrochloride (example D.f4) and commercially available 2-chloro-2-oxoethyl acetate the title compound is obtained as colorless solid.

MS (ESI): m/z=481 (MH$^+$, 100%).
$^1$H-NMR (300 MHz, DMSO-d$_6$): 11.36 (s, 1H, —NH); 9.28 (d, J=7.7, 1H, —NH); 8.40 (d, J=4.9, 1H); 7.41 (dd, J=8.4, 6.9, 1H); 7.09 (d, J=4.9, 1H); 7.06 (dd, J=11.5, 2.4, 1H); 6.92 (ddd, J=8.4, 8.4, 2.4, 1H); 4.50 (t, J=5.3, 1H, —OH); 4.23-4.04 (m, 2H); 4.13 (d, J=5.3, 2H); 3.88 (d, J=6.8, 2H); 3.67 (m, 1H); 3.20 (m, 1H); 3.03 (m, 1H); 2.74 (s, 3H); 1.96 (m, 2H); 1.53 (m, 1H); 1.41 (m, 1H); 0.94 (m, 1H); 0.36 (m, 2H); 0.21 (m, 2H).

Example F7

7-[2-(Cyclopropylmethoxy)-4-fluorophenyl]-N-{1-[(2S)-2-hydroxypropanoyl]piperidin-4-yl}-2-methyl-1H-pyrrolo[3,2-b]pyridine-3-carboxamide Starting from 7-[2-(cyclopropylmethoxy)-4-fluorophenyl]-2-methyl-N-(piperidin-4-yl)-1H-pyrrolo[3,2-b]pyridine-3-carboxamide hydrochloride (example D.f4) and commercially available (2S)-1-chloro-1-oxopropan-2-yl acetate the title compound is obtained as colorless solid.

MS (ESI): m/z=495 (MH$^+$, 100%).

$^1$H-NMR (300 MHz, DMSO-d$_6$): 11.36 (s, 1H, —NH); 9.28 (d, J=7.7, 1H, —NH); 8.40 (d, J=4.9, 1H); 7.41 (dd, J=8.4, 6.9, 1H); 7.08 (d, J=4.9, 1H); 7.06 (dd, J=11.5, 2.4, 1H); 6.92 (ddd, J=8.4, 8.4, 2.4, 1H); 4.86 (d, J=6.9, 1H, —OH); 4.47 (m, 1H); 4.28-4.06 (m, 2H); 3.92 (m, 1H); 3.88 (d, J=6.8, 2H); 3.28 (m, 1H); 3.01 (m, 1H); 2.74 (s, 3H); 1.97 (m, 2H); 1.65-1.30 (m, 2H); 1.21 (br.s, 3H); 0.94 (m, 1H); 0.36 (m, 2H); 0.21 (m, 2H).

Example F8

7-[2-(Cyclopropylmethoxy)-4-fluorophenyl]-N-{trans-4-[(hydroxyacetyl)amino]cyclohexyl}-2-methyl-1H-pyrrolo[3,2-b]pyridine-3-carboxamide Starting from N-(trans-4-aminocyclohexyl)-7-[2-(cyclopropylmethoxy)-4-fluorophenyl]-2-methyl-1H-pyrrolo[3,2-b]pyridine-3-carboxamide hydrochloride (example D.f5) and commercially available 2-chloro-2-oxoethyl acetate the title compound is obtained as colorless solid.

MS (ESI): m/z=495 (MH$^+$, 100%).

$^1$H-NMR (300 MHz, DMSO-d$_6$): 11.33 (s, 1H, —NH); 9.10 (d, J=7.7, 1H, —NH); 8.40 (d, J=4.9, 1H); 7.48 (d, J=8.2, 1H, —NH); 7.41 (dd, J=8.4, 6.9, 1H); 7.08 (d, J=4.9, 1H); 7.05 (dd, J=11.5, 2.4, 1H); 6.92 (ddd, J=8.4, 8.4, 2.4, 1H); 5.40 (t, J=5.7, 1H, —OH); 3.88 (d, J=6.9, 2H); 3.79 (d, J=5.7, 2H & m, 1H); 3.69 (m, 1H); 2.73 (s, 3H); 2.01 (m, 2H); 1.83 (m, 2H); 1.43 (m, 4H); 0.94 (m, 1H); 0.36 (m, 2H); 0.21 (m, 2H).

Example F9

7-[2-(Cyclopropylmethoxy)-4-fluorophenyl]-N-(trans-4-{[(2S)-2-hydroxypropanoyl]amino}cyclohexyl)-2-methyl-1H-pyrrolo[3,2-b]pyridine-3-carboxamide Starting from N-(trans-4-aminocyclohexyl)-7-[2-(cyclopropylmethoxy)-4-fluorophenyl]-2-methyl-1H-pyrrolo[3,2-b]pyridine-3-carboxamide hydrochloride (example D.f5) and commercially available (2S)-1-chloro-1-oxopropan-2-yl acetate the title compound is obtained as colorless solid.

MS (ESI): m/z=509 (MH$^+$, 100%).

$^1$H-NMR (300 MHz, DMSO-d$_6$): 11.33 (s, 1H, —NH); 9.09 (d, J=7.9, 1H, —NH); 8.40 (d, J=4.9, 1H); 7.43 (d, J=7.6, 1H, —NH); 7.41 (dd, J=8.4, 6.9, 1H); 7.08 (d, J=4.9, 1H); 7.05 (dd, J=11.5, 2.4, 1H); 6.92 (ddd, J=8.4, 8.4, 2.4, 1H); 5.40 (d, J=5.1, 1H, —OH); 3.94 (dqu, J=6.8, 5.1, 2H); 3.88 (d, J=6.9, 2H); 3.81 (m, 2H); 3.63 (m, 1H); 2.73 (s, 3H); 2.00 (m, 2H); 1.82 (m, 2H); 1.42 (m, 4H); 1.21 (d, J=6.8, 3H); 0.94 (m, 1H); 0.36 (m, 2H); 0.21 (m, 2H).

Example F10

7-[2-(Cyclopropylmethoxy)-4-fluorophenyl]-N-{cis-4-[(hydroxyacetyl)amino]cyclohexyl}-2-methyl-1H-pyrrolo[3,2-b]pyridine-3-carboxamide Starting from N-(cis-4-aminocyclohexyl)-7-[2-(cyclopropylmethoxy)-4-fluorophenyl]-2-methyl-1H-pyrrolo[3,2-b]pyridine-3-carboxamide hydrochloride (example D.f6) and commercially available 2-chloro-2-oxoethyl acetate the title compound is obtained as colorless solid.

MS (ESI): m/z=495 (MH$^+$, 100%).

$^1$H-NMR (300 MHz, DMSO-d$_6$): 11.33 (s, 1H, —NH); 9.43 (d, J=7.7, 1H, —NH); 8.43 (d, J=4.9, 1H); 7.49 (d, J=7.9, 1H, —NH); 7.42 (dd, J=8.4, 6.9, 1H); 7.09 (d, J=4.9, 1H); 7.06 (dd, J=11.6, 2.4, 1H); 6.92 (ddd, J=8.4, 8.4, 2.4, 1H); 5.32 (t, J=5.8, 1H, —OH); 4.06 (m, 1H); 3.89 (d, J=6.8, 2H); 3.82 (d, J=5.8, 2H); 3.78 (m, 1H); 2.73 (s, 3H); 1.84-1.57 (m, 8H); 0.94 (m, 1H); 0.37 (m, 2H); 0.22 (m, 2H).

Example F11

7-[2-(Cyclopropylmethoxy)-4-fluorophenyl]-N-(cis-4-{[(2S)-2-hydroxypropanoyl]amino}cyclohexyl)-2-methyl-1H-pyrrolo[3,2-b]pyridine-3-carboxamide Starting from N-(cis-4-aminocyclohexyl)-7-[2-(cyclopropylmethoxy)-4-fluorophenyl]-2-methyl-1H-pyrrolo[3,2-b]pyridine-3-carboxamide hydrochloride (example D.f6) and commercially available (2S)-1-chloro-1-oxopropan-2-yl acetate the title compound is obtained as colorless solid.

MS (ESI): m/z=509 (MH$^+$, 100%).

$^1$H-NMR (300 MHz, DMSO-d$_6$): 11.33 (s, 1H, —NH); 9.42 (d, J=7.5, 1H, —NH); 8.43 (d, J=4.9, 1H); 7.45 (d, J=7.8, 1H, —NH); 7.42 (dd, J=8.4, 6.9, 1H); 7.09 (d, J=4.9, 1H); 7.06 (dd, J=11.6, 2.4, 1H); 6.93 (ddd, J=8.4, 8.4, 2.4, 1H); 5.37 (br.s, 1H, —OH); 4.06 (m, 1H); 3.99 (~qu, J ~6.8, 1H); 3.89 (d, J=6.9, 2H); 3.74 (m, 1H); 2.73 (s, 3H); 1.83-1.57 (m, 8H); 1.22 (d, J=6.8, 3H); 0.95 (m, 1H); 0.36 (m, 2H); 0.22 (m, 2H).

Example F12

7-[2-(Cyclopropylmethoxy)-5-fluorophenyl]-N-[1-(hydroxyacetyl)piperidin-4-yl]-2-methyl-1H-pyrrolo[3,2-b]pyridine-3-carboxamide Starting from 7-[2-(cyclopropylmethoxy)-5-fluorophenyl]-2-methyl-N-(piperidin-4-yl)-1H-pyrrolo[3,2-b]pyridine-3-carboxamide hydrochloride (example D.f7) and commercially available 2-chloro-2-oxoethyl acetate the title compound is obtained as colorless solid.

MS (ESI): m/z=481 (MH$^+$, 100%).

$^1$H-NMR (400 MHz, DMSO-d$_6$): 11.41 (s, 1H, —NH); 9.27 (d, J=7.7, 1H, —NH); 8.41 (d, J=4.9, 1H); 7.31 (dd, J=8.8, 3.2, 1H); 7.26 (ddd, J=9.1, 8.6, 3.2, 1H); 7.15 (dd, J=9.1, 4.6, 1H); 7.13 (d, J=4.9, 1H); 4.50 (br.t, J ~4.8, 1H, —OH); 4.23-4.05 (m, 2H); 4.14 (br.s, 2H); 3.84 (d, J=6.8, 2H); 3.68 (m, 1H); 3.20 (m, 1H); 3.03 (m, 1H); 2.74 (s, 3H); 1.96 (m, 2H); 1.53 (m, 1H); 1.41 (m, 1H); 0.93 (m, 1H); 0.35 (m, 2H); 0.19 (m, 2H).

Example F13

7-[2-(Cyclopropylmethoxy)-5-fluorophenyl]-N-{1-[(2S)-2-hydroxypropanoyl]piperidin-4-yl}-2-methyl-1H-pyrrolo[3,2-b]pyridine-3-carboxamide Starting from 7-[2-(cyclopropylmethoxy)-5-fluorophenyl]-2-methyl-N-(piperidin-4-yl)-1H-pyrrolo[3,2-b]pyridine-3-carboxamide hydrochloride (example D.f7) and commercially available (2S)-1-chloro-1-oxopropan-2-yl acetate the title compound is obtained as colorless solid.

MS (ESI): m/z=495 (MH$^+$, 100%).

$^1$H-NMR (400 MHz, DMSO-d$_6$): 11.41 (s, 1H, —NH); 9.27 (br.s, 1H, —NH); 8.41 (d, J=5.0, 1H); 7.31 (dd, J=8.8, 3.2, 1H); 7.26 (ddd, J=9.1, 8.8, 3.2, 1H); 7.15 (dd, J=9.1, 4.5, 1H); 7.13 (d, J=5.0, 1H); 4.86 (br.d, J ~5.8, 1H, —OH); 4.74 (br.s, 1H); 4.28-4.08 (m, 2H); 3.94 (m, 1H); 3.84 (d, J=6.8, 2H); 3.27 (m, 1H); 3.01 (m, 1H); 2.73 (s, 3H); 1.97 (m, 2H); 1.53 (m, 1H); 1.40 (m, 1H); 1.20 (br.s, 3H); 0.92 (m, 1H); 0.34 (m, 2H); 0.18 (m, 2H).

Example F14

7-[2-(Cyclopropylmethoxy)-5-fluorophenyl]-N-{trans-4-[(hydroxyacetyl)amino]cyclohexyl}-2-methyl-1H-pyrrolo[3,2-b]pyridine-3-carboxamide Starting from N-(trans-4-aminocyclohexyl)-7-[2-(cyclopropylmethoxy)-5-fluorophenyl]-2-methyl-1H-pyrrolo[3,2-b]pyridine-3-carboxamide hydrochloride (example D.f8) and commercially available 2-chloro-2-oxoethyl acetate the title compound is obtained as colorless solid.

MS (ESI): m/z=495 (MH$^+$, 100%).

$^1$H-NMR (400 MHz, DMSO-d$_6$): 11.37 (s, 1H, —NH); 9.09 (d, J=7.7, 1H, —NH); 8.41 (d, J=5.0, 1H); 7.47 (d, J=8.2, 1H, —NH); 7.31 (dd, J=8.7, 3.2, 1H); 7.26 (ddd, J=9.1, 8.7, 3.2, 1H); 7.15 (dd, J=9.1, 4.5, 1H); 7.13 (d, J=5.0, 1H); 5.40 (t, J=5.9, 1H, —OH); 3.84 (d, J=6.9, 2H); 3.79 (d, J=5.9, 2H & m, 1H); 3.69 (m, 1H); 2.73 (s, 3H); 2.01 (m, 2H); 1.83 (m, 2H); 1.43 (m, 4H); 0.93 (m, 1H); 0.35 (m, 2H); 0.18 (m, 2H).

Example F15

7-[2-(Cyclopropylmethoxy)-5-fluorophenyl]-N-(trans-4-{[(2S)-2-hydroxypropanoyl]amino}cyclohexyl)-2-methyl-1H-pyrrolo[3,2-b]pyridine-3-carboxamide Starting from N-(trans-4-aminocyclohexyl)-7-[2-(cyclopropylmethoxy)-5-fluorophenyl]-2-methyl-1H-pyrrolo[3,2-b]pyridine-3-carboxamide hydrochloride (example D.f8) and commercially available (2S)-1-chloro-1-oxopropan-2-yl acetate the title compound is obtained as colorless solid.

MS (ESI): m/z=509 (MH$^+$, 100%).

$^1$H-NMR (400 MHz, DMSO-d$_6$): 11.37 (s, 1H, —NH); 9.09 (d, J=7.7, 1H, —NH); 8.41 (d, J=4.9, 1H); 7.42 (d, J=8.2, 1H, —NH); 7.31 (dd, J=8.7, 3.2, 1H); 7.26 (ddd, J=9.1, 8.7, 3.2, 1H); 7.15 (dd, J=9.1, 4.5, 1H); 7.13 (d, J=4.9, 1H); 5.40 (d, J=5.1, 1H, —OH); 3.94 (dqu, J=6.9, 5.1, 1H); 3.84 (d, J=6.9, 2H); 3.81 (m, 1H); 3.63 (m, 1H); 2.73 (s, 3H); 2.01 (m, 2H); 1.82 (m, 2H); 1.42 (m, 4H); 1.21 (d, J=6.9, 3H); 0.93 (m, 1H); 0.35 (m, 2H); 0.18 (m, 2H).

Example F16

7-[2-(Cyclopropylmethoxy)-5-fluorophenyl]-N-{cis-4-[(hydroxyacetyl)amino]cyclohexyl}-2-methyl-1H-pyrrolo[3,2-b]pyridine-3-carboxamide Starting from N-(cis-4-aminocyclohexyl)-7-[2-(cyclopropylmethoxy)-5-fluorophenyl]-2-methyl-1H-pyrrolo[3,2-b]pyridine-3-carboxamide hydrochloride (example D.f9) and commercially available 2-chloro-2-oxoethyl acetate the title compound is obtained as colorless solid.

MS (ESI): m/z=495 (MH$^+$, 100%).

$^1$H-NMR (300 MHz, DMSO-d$_6$): 11.38 (s, 1H, —NH); 9.42 (d, J=7.5, 1H, —NH); 8.45 (d, J=4.9, 1H); 7.50 (d, J=7.9, 1H, —NH); 7.32 (dd, J=8.4, 3.2, 1H); 7.27 (ddd, J=8.9, 8.9, 3.2, 1H); 7.16 (dd, J=8.9, 4.5, 1H); 7.14 (d, J=4.9, 1H); 5.32 (t, J=5.8, 1H, —OH); 4.06 (m, 1H); 3.85 (d, J=6.8, 2H); 3.82 (d, J=5.8, 2H); 3.79 (m, 1H); 2.74 (s, 3H); 1.82-1.57 (m, 8H); 0.93 (m, 1H); 0.35 (m, 2H); 0.19 (m, 2H).

Example F17

7-[2-(Cyclopropylmethoxy)-5-fluorophenyl]-N-(cis-4-{[abs.(2S)-2-hydroxypropanoyl]amino}cyclohexyl)-2-methyl-1H-pyrrolo[3,2-b]pyridine-3-carboxamide Starting from N-(cis-4-aminocyclohexyl)-7-[2-(cyclopropylmethoxy)-5-fluorophenyl]-2-methyl-1H-pyrrolo[3,2-b]pyridine-3-carboxamide hydrochloride (example D.f9) and commercially available (2S)-1-chloro-1-oxopropan-2-yl acetate the title compound is obtained as colorless solid.

MS (ESI): m/z=509 (MH$^+$, 100%).

$^1$H-NMR (300 MHz, DMSO-d$_6$): 11.38 (s, 1H, —NH); 9.41 (d, J=7.5, 1H, —NH); 8.45 (d, J=4.9, 1H); 7.45 (d, J=7.9, 1H, —NH); 7.32 (dd, J=8.4, 3.2, 1H); 7.27 (ddd, J=8.9, 8.9, 3.2, 1H); 7.16 (dd, J=8.9, 4.5, 1H); 7.14 (d, J=4.9, 1H); 5.36 (d, J=5.5, 1H, —OH); 4.06 (m, 1H); 3.99 (dqu, J=6.8, 5.5, 1H); 3.85 (d, J=5.8, 2H); 3.74 (m, 1H); 2.74 (s, 3H); 1.84-1.56 (m, 8H); 1.22 (d, J=6.8, 3H); 0.93 (m, 1H); 0.35 (m, 2H); 0.19 (m, 2H).

Example F18

7-[2-(Cyclopropylmethoxy)-5-fluorophenyl]-N-[rel.(3R,4R)-3-hydroxy-1-(hydroxyacetyl)piperidin-4-yl]-2-methyl-1H-pyrrolo[3,2-b]pyridine-3-carboxamide Starting from 7-[2-(cyclopropylmethoxy)-5-fluorophenyl]-N-[(3R*,4R*)-3-hydroxypiperidin-4-yl]-2-methyl-1H-pyrrolo[3,2-b]pyridine-3-carboxamide hydrochloride (example D.f10) and commercially available 2-chloro-2-oxoethyl acetate the title compound is obtained as colorless solid.

HR-MS (ESI): m/z=497.2197 ([MH]$^+$, C$_{26}$H$_{30}$FN$_4$O$_6$$^+$, calc. 497.2195).

Example F19

Diastereomeric mixture of 7-[2-(Cyclopropylmethoxy)-5-fluorophenyl]-N-{(3R,4R)-3-hydroxy-1-[(2S)-2-hydroxypropanoyl]piperidin-4-yl}-2-methyl-1H-pyrrolo[3,2-b]pyridine-3-carboxamide and 7-[2-(cyclopropylmethoxy)-5-fluorophenyl]-N-{(3S,4S)-3-hydroxy-1-[(2S)-2-hydroxypropanoyl]piperidin-4-yl}-2-methyl-1H-pyrrolo[3,2-b]pyridine-3-carboxamide Starting from 7-[2-(cyclopropylmethoxy)-5-fluorophenyl]-N-[(3R*,4R*)-3-hydroxypiperidin-4-yl]-2-methyl-1H-pyrrolo[3,2-b]pyridine-3-carboxamide hydrochloride (example D.f10) and commercially available (2S)-1-chloro-1-oxopropan-2-yl acetate the title compound is obtained as colorless solid.

HR-MS (ESI): m/z=511.2351 ([MH]$^+$, C$_{27}$H$_{32}$FN$_4$O$_6$$^+$, calc. 511.2351).

Example F20

7-[2-(Cyclopropylmethoxy)-4-methoxyphenyl]-N-[1-(hydroxyacetyl)piperidin-4-yl]-2-methyl-1H-pyrrolo[3,2-b]pyridine-3-carboxamide Starting from 7-[2-(cyclopropylmethoxy)-4-methoxyphenyl]-2-methyl-N-(piperidin-4-yl)-1H-pyrrolo[3,2-b]pyridine-3-carboxamide hydrochloride (example D.f11) and commercially available 2-chloro-2-oxoethyl acetate the title compound is obtained as colorless solid.

MS (ESI): m/z=493 (MH$^+$, 100%).

$^1$H-NMR (300 MHz, DMSO-d$_6$): 11.28 (s, 1H; —NH); 9.32 (d, J=7.7, 1H, —NH); 8.36 (d, J=4.9, 1H); 7.31 (d, J=9.1, 1H); 7.06 (d, J=4.9, 1H); 6.69 (dd, J=9.1, 2.4, 1H); 6.68 (d, J=2.4, 1H); 4.49 (t, J=5.5, 1H, —OH); 4.23-4.04 (m, 2H); 4.13 (m, 2H); 3.87 (d, J=6.9, 2H); 3.84 (s, 3H); 3.68 (m, 1H); 3.20 (m, 1H); 3.03 (m, 1H); 2.73 (s, 3H); 1.96 (m, 2H); 1.53 (m, 1H); 1.40 (m, 1H); 0.94 (m, 1H); 0.35 (m, 2H); 0.22 (m, 2H).

Example F21

7-[2-(Cyclopropylmethoxy)-4-methoxyphenyl]-N-{1-[(2S)-2-hydroxypropanoyl]piperidin-4-yl}-2-methyl-1H-pyrrolo[3,2-b]pyridine-3-carboxamide Starting from 7-[2-(cyclopropylmethoxy)-4-methoxyphenyl]-2-methyl-N-(piperidin-4-yl)-1H-pyrrolo[3,2-b]pyridine-3-carboxamide hydrochloride (example D.f11) and commercially available (2S)-1-chloro-1-oxopropan-2-yl acetate the title compound is obtained as colorless solid.

MS (ESI): m/z=507 (MH$^+$, 100%).

$^1$H-NMR (300 MHz, DMSO-d$_6$): 11.28 (s, 1H; —NH); 9.31 (d, J=7.5, 1H, —NH); 8.36 (d, J=5.1, 1H); 7.31 (d, J=8.9, 1H); 7.06 (d, J=5.1, 1H); 6.69 (dd, J=8.9, 2.4, 1H); 6.68 (d, J=2.2, 1H); 4.86 (d, J=6.9, 1H, —OH); 4.47 (m, 1H); 4.28-4.07 (m, 2H); 3.92 (m, 1H); 3.87 (d, J=6.9, 2H); 3.84 (s, 3H); 3.30 (m, 1H); 3.01 (m, 1H); 2.73 (s, 3H); 1.97 (m, 2H); 1.62-1.31 (m, 2H); 1.21 (br.s, 3H); 0.94 (m, 1H); 0.36 (m, 2H); 0.22 (m, 2H).

Example F22

7-[2-(Cyclopropylmethoxy)-4-methoxyphenyl]-N-{trans-4-[(hydroxyacetyl)amino]cyclohexyl}-2-methyl-1H-pyrrolo[3,2-b]pyridine-3-carboxamide Starting from N-(trans-4-aminocyclohexyl)-7-[2-(cyclopropylmethoxy)-4-methoxyphenyl]-2-methyl-1H-pyrrolo[3,2-b]pyridine-3-carboxamide hydrochloride (example D.f12) and commercially available 2-chloro-2-oxoethyl acetate the title compound is obtained as colorless solid.

MS (ESI): m/z=507 (MH$^+$, 100%).

$^1$H-NMR (300 MHz, DMSO-d$_6$): 11.25 (s, 1H; —NH); 9.12 (d, J=7.7, 1H, —NH); 8.37 (d, J=4.9, 1H); 7.47 (d, J=8.2, 1H, —NH); 7.31 (d, J=8.9, 1H); 7.05 (d, J=4.9, 1H); 6.69 (dd, J=8.9, 2.2, 1H); 6.68 (d, J=2.2, 1H); 5.40 (t, J=5.7, 1H, —OH); 3.87 (d, J=6.9, 2H); 3.84 (s, 3H); 3.79 (d, J=5.7, 2H & m, 1H); 3.69 (m, 1H); 2.72 (s, 3H); 2.00 (m, 2H); 1.82 (m, 2H); 1.42 (m, 4H); 0.94 (m, 1H); 0.36 (m, 2H); 0.22 (m, 2H).

Example F23

7-[2-(Cyclopropylmethoxy)-4-methoxyphenyl]-N-(trans-4-{[(2S)-2-hydroxypropanoyl]amino}cyclohexyl)-2-methyl-1H-pyrrolo[3,2-b]pyridine-3-carboxamide Starting from N-(trans-4-aminocyclohexyl)-7-[2-(cyclopropylmethoxy)-4-methoxyphenyl]-2-methyl-1H-pyrrolo[3,2-b]pyridine-3-carboxamide hydrochloride (example D.f12) and commercially available (2S)-1-chloro-1-oxopropan-2-yl acetate the title compound is obtained as colorless solid.

MS (ESI): m/z=521 (MH$^+$, 100%).

$^1$H-NMR (300 MHz, DMSO-d$_6$): 11.25 (s, 1H; —NH); 9.12 (d, J=7.9, 1H, —NH); 8.37 (d, J=4.9, 1H); 7.42 (d, J=8.4, 1H, —NH); 7.31 (d, J=8.9, 1H); 7.05 (d, J=4.9, 1H); 6.68 (dd, J=8.9, 2.4, 1H); 6.67 (d, J=2.4, 1H); 5.40 (d, J=5.1, 1H, —OH); 3.94 (dqu, J=6.8, 5.1, 1H); 3.87 (d, J=6.9, 2H); 3.84 (s, 3H); 3.80 (m, 1H); 3.62 (m, 1H); 2.72 (s, 3H); 2.00 (m, 2H); 1.83 (m, 2H); 1.41 (m, 4H); 1.21 (d, J=6.8, 3H); 0.94 (m, 1H); 0.36 (m, 2H); 0.22 (m, 2H).

Example F24

7-[2-(Cyclopropylmethoxy)-4-methoxyphenyl]-N-{cis-4-[(hydroxyacetyl)amino]cyclohexyl}-2-methyl-1H-pyrrolo[3,2-b]pyridine-3-carboxamide Starting from N-(cis-4-aminocyclohexyl)-7-[2-(cyclopropylmethoxy)-4-methoxyphenyl]-2-methyl-1H-pyrrolo[3,2-b]pyridine-3-carboxamide hydrochloride (example D.f13) and commercially available 2-chloro-2-oxoethyl acetate the title compound is obtained as colorless solid.

MS (ESI): m/z=507 (MH$^+$, 100%).

$^1$H-NMR (300 MHz, DMSO-d$_6$): 11.25 (s, 1H; —NH); 9.45 (d, J=7.3, 1H, —NH); 8.40 (d, J=5.0, 1H); 7.49 (d, J=7.7, 1H, —NH); 7.32 (d, J=8.9, 1H); 7.07 (d, J=5.0, 1H); 6.69 (dd, J=8.9, 2.2, 1H); 6.68 (d, J=2.2, 1H); 5.32 (t, J=5.8, 1H, —OH); 4.06 (m, 1H); 3.88 (d, J=6.8, 2H); 3.84 (s, 3H); 3.82 (d, J=5.8, 2H); 3.79 (m, 1H); 2.73 (s, 3H); 1.86-1.58 (m, 8H); 0.94 (m, 1H); 0.36 (m, 2H); 0.22 (m, 2H).

Example F25

7-[2-(Cyclopropylmethoxy)-4-methoxyphenyl]-N-(cis-4-{[(2S)-2-hydroxypropanoyl]amino}cyclohexyl)-2-methyl-1H-pyrrolo[3,2-b]pyridine-3-carboxamide Starting from N-(cis-4-aminocyclohexyl)-7-[2-(cyclopropylmethoxy)-4-methoxyphenyl]-2-methyl-1H-pyrrolo[3,2-b]pyridine-3-carboxamide hydrochloride (example D.f13) and commercially available (2S)-1-chloro-1-oxopropan-2-yl acetate the title compound is obtained as colorless solid.

MS (ESI): m/z=521 (MH$^+$, 100%).

$^1$H-NMR (300 MHz, DMSO-d$_6$): 11.26 (s, 1H; —NH); 9.44 (d, J=7.5, 1H, —NH); 8.40 (d, J=5.1, 1H); 7.44 (d, J=7.7, 1H, —NH); 7.32 (d, J=8.9, 1H); 7.07 (d, J=5.1, 1H); 6.69 (dd, J=8.9, 2.4, 1H); 6.68 (d, J=2.4, 1H); 5.36 (d, J=5.5, 1H, —OH); 4.05 (m, 1H); 3.99 (dqu, J=6.8, 5.5, 1H); 3.88 (d, J=6.8, 2H); 3.84 (s, 3H); 3.73 (m, 1H); 2.73 (s, 3H); 1.83-1.58 (m, 8H); 1.22 (d, J=6.8, 3H); 0.95 (m, 1H); 0.36 (m, 2H); 0.22 (m, 2H).

Example F26

7-[2-(Cyclopropylmethoxy)-5-methoxyphenyl]-N-[1-(hydroxyacetyl)piperidin-4-yl]-2-methyl-1H-pyrrolo[3,2-b]pyridine-3-carboxamide Starting from 7-[2-(cyclopropylmethoxy)-5-methoxyphenyl]-2-methyl-N-(piperidin-4-yl)-1H-pyrrolo[3,2-b]pyridine-3-carboxamide hydrochloride (example D.f14) and commercially available 2-chloro-2-oxoethyl acetate the title compound is obtained as colorless solid.

MS (ESI): m/z=493 (MH$^+$, 100%).
$^1$H-NMR (300 MHz, DMSO-d$_6$): 11.36 (s, 1H, —NH); 9.30 (d, J=7.7, 1H, —NH); 8.40 (d, J=4.9, 1H); 7.13 (d, J=4.9, 1H); 7.09 (d, J=8.9, 1H); 7.03 (dd, J=8.9, 2.8, 1H); 6.96 (d, J=2.8, 1H); 4.50 (t, J=5.5, 1H, —OH); 4.25-4.05 (m, 4H); 3.79 (d, J=6.9, 2H); 3.77 (s, 3H); 3.68 (m, 1H); 3.20 (m, 1H); 3.04 (m, 1H); 2.74 (s, 3H); 1.97 (m, 2H); 1.53 (m, 1H); 1.42 (m, 1H); 0.91 (m, 1H); 0.34 (m, 2H); 0.16 (m, 2H).

Example F27

7-[2-(Cyclopropylmethoxy)-5-methoxyphenyl]-N-{1-[(2S)-2-hydroxypropanoyl]piperidin-4-yl}-2-methyl-1H-pyrrolo[3,2-b]pyridine-3-carboxamide Starting from 7-[2-(cyclopropylmethoxy)-5-methoxyphenyl]-2-methyl-N-(piperidin-4-yl)-1H-pyrrolo[3,2-b]pyridine-3-carboxamide hydrochloride (example D.f14) and commercially available (2S)-1-chloro-1-oxopropan-2-yl acetate the title compound is obtained as colorless solid.

MS (ESI): m/z=507 (MH$^+$, 100%).
$^1$H-NMR (300 MHz, DMSO-d$_6$): 11.36 (s, 1H, —NH); 9.30 (d, J=7.5, 1H, —NH); 8.40 (d, J=4.9, 1H); 7.13 (d, J=4.9, 1H); 7.09 (d, J=9.1, 1H); 7.03 (dd, J=9.1, 2.9, 1H); 6.96 (d, J=2.9, 1H); 4.86 (d, J=6.9, 1H, —OH); 4.47 (m, 1H); 4.28-4.08 (m, 2H); 3.94 (m, 1H); 3.79 (d, J=6.9, 2H); 3.77 (s, 3H); 3.28 (m, 1H); 3.02 (m, 1H); 2.74 (s, 3H); 1.98 (m, 2H); 1.63-1.31 (m, 2H); 1.22 (br.s, 3H); 0.91 (m, 1H); 0.34 (m, 2H); 0.16 (m, 2H).

Example F28

7-[2-(Cyclopropylmethoxy)-5-methoxyphenyl]-N-{trans-4-[(hydroxyacetyl)amino]cyclohexyl}-2-methyl-1H-pyrrolo[3,2-b]pyridine-3-carboxamide Starting from N-(trans-4-aminocyclohexyl)-7-[2-(cyclopropylmethoxy)-5-methoxyphenyl]-2-methyl-1H-pyrrolo[3,2-b]pyridine-3-carboxamide hydrochloride (example D.f15) and commercially available 2-chloro-2-oxoethyl acetate the title compound is obtained as colorless solid.

MS (ESI): m/z=507 (MH$^+$, 100%).
$^1$H-NMR (300 MHz, DMSO-d$_6$): 11.35 (s, 1H, —NH); 9.11 (d, J=7.7, 1H, —NH); 8.40 (d, J=4.9, 1H); 7.51 (d, J=8.2, 1H, —NH); 7.12 (d, J=4.9, 1H); 7.09 (d, J=9.1, 1H); 7.02 (dd, J=9.1, 2.9, 1H); 6.95 (d, J=2.9, 1H); 5.44 (t, J=5.8, 1H, —OH); 3.79 (d, J=6.8, 2H & d, J=5.8, 2H & m, 1H); 3.76 (s, 3H); 3.70 (m, 1H); 2.73 (s, 3H); 2.01 (m, 2H); 1.82 (m, 2H); 1.43 (m, 4H); 0.91 (m, 1H); 0.33 (m, 2H); 0.16 (m, 2H).

Example F29

7-[2-(Cyclopropylmethoxy)-5-methoxyphenyl]-N-(trans-4-{[abs.(2S)-2-hydroxypropanoyl]amino}cyclohexyl)-2-methyl-1H-pyrrolo[3,2-b]pyridine-3-carboxamide Starting from N-(trans-4-aminocyclohexyl)-7-[2-(cyclopropylmethoxy)-5-methoxyphenyl]-2-methyl-1H-pyrrolo[3,2-b]pyridine-3-carboxamide hydrochloride (example D.f15) and commercially available (2S)-1-chloro-1-oxopropan-2-yl acetate the title compound is obtained as colorless solid.

MS (ESI): m/z=521 (MH$^+$, 100%).
$^1$H-NMR (300 MHz, DMSO-d$_6$): 11.35 (s, 1H, —NH); 9.11 (d, J=7.7, 1H, —NH); 8.41 (d, J=4.9, 1H); 7.46 (d, J=8.4, 1H, —NH); 7.13 (d, J=4.9, 1H); 7.09 (d, J=9.1, 1H); 7.03 (dd, J=9.1, 2.9, 1H); 6.95 (d, J=2.9, 1H); 5.45 (d, J=5.1, 1H, —OH); 3.94 (dqu, J=6.8, 5.1, 1H); 3.79 (d, J=6.8, 2H & m, 1H); 3.76 (s, 3H); 3.63 (m, 1H); 2.73 (s, 3H); 2.01 (m, 2H); 1.81 (m, 2H); 1.42 (m, 4H); 1.21 (d, J=6.8, 3H); 0.91 (m, 1H); 0.33 (m, 2H); 0.16 (m, 2H).

Example F30

7-[2-(Cyclopropylmethoxy)-5-methoxyphenyl]-N-{cis-4-[(hydroxyacetyl)amino]cyclohexyl}-2-methyl-1H-pyrrolo[3,2-b]pyridine-3-carboxamide Starting from N-(cis-4-aminocyclohexyl)-7-[2-(cyclopropylmethoxy)-5-methoxyphenyl]-2-methyl-1H-pyrrolo[3,2-b]pyridine-3-carboxamide hydrochloride (example D.f16) and commercially available 2-chloro-2-oxoethyl acetate the title compound is obtained as colorless solid.

MS (ESI): m/z=507 (MH$^+$, 100%).
$^1$H-NMR (300 MHz, DMSO-d$_6$): 11.33 (s, 1H, —NH); 9.43 (d, J=7.5, 1H, —NH); 8.44 (d, J=4.9, 1H); 7.49 (d, J=7.7, 1H, —NH); 7.14 (d, J=4.9, 1H); 7.09 (d, J=9.1, 1H); 7.03 (dd, J=9.1, 2.9, 1H); 6.96 (d, J=2.9, 1H); 5.33 (t, J=5.8, 1H, —OH); 4.06 (m, 1H); 3.82 (d, J=5.8, 2H); 3.79 (d, J=6.9, 2H); 3.77 (s, 3H & m, 1H); 2.74 (s, 3H); 1.82-1.59 (m, 8H); 0.91 (m, 1H); 0.34 (m, 2H); 0.16 (m, 2H).

Example F31

7-[2-(Cyclopropylmethoxy)-5-methoxyphenyl]-N-(cis-4-{[(2S)-2-hydroxypropanoyl]amino}cyclohexyl)-2-methyl-1H-pyrrolo[3,2-b]pyridine-3-carboxamide Starting from N-(cis-4-aminocyclohexyl)-7-[2-(cyclopropylmethoxy)-5-methoxyphenyl]-2-methyl-1H-pyrrolo[3,2-b]pyridine-3-carboxamide hydrochloride (example D.f16) and commercially available (2S)-1-chloro-1-oxopropan-2-yl acetate the title compound is obtained as colorless solid.

MS (ESI): m/z=521 (MH$^+$, 100%).
$^1$H-NMR (300 MHz, DMSO-d$_6$): 11.33 (s, 1H, —NH); 9.42 (d, J=7.5, 1H, —NH); 8.44 (d, J=4.9, 1H); 7.44 (d, J=7.7, 1H, —NH); 7.14 (d, J=4.9, 1H); 7.09 (d, J=8.9, 1H); 7.03 (dd, J=8.9, 2.9, 1H); 6.95 (d, J=2.9, 1H); 5.36 (d, J=5.5, 1H, —OH); 4.06 (m, 1H); 3.99 (dqu, J=6.8, 5.5, 1H); 3.79 (d, J=6.8, 2H); 3.77 (s, 3H); 3.74 (m, 1H); 2.73 (s, 3H); 1.85-1.57 (m, 8H); 1.22 (d, J=6.8, 3H); 0.91 (m, 1H); 0.34 (m, 2H); 0.16 (m, 2H).

Example F32

7-[2-(Cyclopropylmethoxy)-5-methoxyphenyl]-N-[(3R*,4R*)-4-hydroxy-1-(hydroxyacetyl)pyrrolidin-3-yl]-2-methyl-1H-pyrrolo[3,2-b]pyridine-3-carboxamide Starting from 7-[2-(cyclopropylmethoxy)-5-methoxyphenyl]-N-[(3R*,4R*)-4-hydroxypyrrolidin-3-yl]-2-methyl-1H-pyrrolo[3,2-b]pyridine-3-carboxamide hydrochloride (example D.f17) and commercially available 2-chloro-2-oxoethyl acetate the title compound is obtained as colorless solid.

HR-MS (ESI): m/z=495.2231 ([MH]$^+$, $C_{26}H_{31}N_4O_6^+$, calc. 495.2238).

Example F33

Diastereomeric mixture of 7-[2-(Cyclopropyl-methoxy)-5-methoxyphenyl]-N-{(3R*,4R*)-4-hydroxy-1-[(2S)-2-hydroxypropanoyl]pyrrolidin-3-yl}-2-methyl-1H-pyrrolo[3,2-b]pyridine-3-carboxamide and Diastereomeric mixture of 7-[2-(cyclopropyl-methoxy)-5-methoxyphenyl]-N-{(3S*,4S*)-4-hydroxy-1-[(2S)-2-hydroxypropanoyl]pyrrolidin-3-yl}-2-methyl-1H-pyrrolo[3,2-b]pyridine-3-carboxamide Starting from 7-[2-(cyclopropylmethoxy)-5-methoxyphenyl]-N-[(3R*,4R*)-4-hydroxypyrrolidin-3-yl]-2-methyl-1H-pyrrolo[3,2-b]pyridine-3-carboxamide hydrochloride (example D.f17) and commercially available (2S)-1-chloro-1-oxopropan-2-yl acetate the title compound is obtained as colorless solid.

HR-MS (ESI): m/z=509.2388 ([MH]$^+$, $C_{27}H_{33}N_4O_6^+$, calc. 509.2395).

Example F34

7-[2-(Cyclopropylmethoxy)-5-methylphenyl]-N-[1-(hydroxyacetyl)piperidin-4-yl]-2-methyl-1H-pyrrolo[3,2-b]pyridine-3-carboxamide Starting from 7-[2-(cyclopropylmethoxy)-5-methylphenyl]-2-methyl-N-(piperidin-4-yl)-1H-pyrrolo[3,2-b]pyridine-3-carboxamide hydrochloride (example D.f18) and commercially available 2-chloro-2-oxoethyl acetate the title compound is obtained as colorless solid.

MS (ESI): m/z=477 (MH$^+$, 100%).

$^1$H-NMR (300 MHz, DMSO-d$_6$): 11.31 (br.s, 1H, —NH); 9.30 (d, J=7.7, 1H, —NH); 8.38 (d, J=4.9, 1H); 7.26 (dd, J=8.4, 2.0, 1H); 7.19 (d, J=2.0, 1H); 7.09 (d, J=4.9, 1H); 7.03 (d, J=8.4, 1H); 4.49 (t, J=5.3, 1H, —OH); 4.24-4.04 (m, 2H); 4.12 (m, 2H); 3.83 (d, J=6.8, 2H); 3.67 (m, 1H); 3.19 (m, 1H); 3.03 (m, 1H); 2.73 (s, 3H); 2.31 (s, 3H); 1.96 (m, 2H); 1.52 (m, 1H); 1.41 (m 1H); 0.92 (m, 1H); 0.34 (m, 2H); 0.18 (m, 2H).

Example F35

7-[2-(cyclopropylmethoxy)-5-methylphenyl]-N-{1-[abs.(2S)-2-hydroxypropanoyl]piperidin-4-yl}-2-methyl-1H-pyrrolo[3,2-b]pyridine-3-carboxamide Starting from 7-[2-(cyclopropylmethoxy)-5-methylphenyl]-2-methyl-N-(piperidin-4-yl)-1H-pyrrolo[3,2-b]pyridine-3-carboxamide hydrochloride (example D.f18) and commercially available (2S)-1-chloro-1-oxopropan-2-yl acetate the title compound is obtained as colorless solid.

MS (ESI): m/z=491 (MH$^+$, 100%).

$^1$H-NMR (300 MHz, DMSO-d$_6$): 11.32 (br.s, 1H, —NH); 9.30 (d, J=7.5, 1H, —NH); 8.38 (d, J=4.9, 1H); 7.26 (dd, J=8.4, 2.0, 1H); 7.20 (d, J=2.0, 1H); 7.09 (d, J=4.9, 1H); 7.04 (d, J=8.4, 1H); 4.86 (d, J=6.8, 1H, —OH); 4.47 (m, 1H); 4.28-4.07 (m, 2H); 3.95 (m, 1H); 3.83 (d, J=6.8, 2H); 3.27 (m, 1H); 3.01 (m, 1H); 2.74 (s, 3H); 2.32 (s, 3H); 1.97 (m, 2H); 1.52 (m, 1H); 1.41 (m 1H); 1.21 (br.s, 3H); 0.93 (m, 1H); 0.35 (m, 2H); 0.19 (m, 2H).

Example F36

7-[2-(Cyclopropylmethoxy)-5-methylphenyl]-N-{trans-4-[(hydroxyacetyl)amino]cyclohexyl}-2-methyl-1H-pyrrolo[3,2-b]pyridine-3-carboxamide Starting from N-(trans-4-aminocyclohexyl)-7-[2-(cyclopropylmethoxy)-5-methylphenyl]-2-methyl-1H-pyrrolo[3,2-b]pyridine-3-carboxamide hydrochloride (example D.f19) and commercially available 2-chloro-2-oxoethyl acetate the title compound is obtained as colorless solid.

MS (ESI): m/z=491 (MH$^+$, 100%).

$^1$H-NMR (300 MHz, DMSO-d$_6$): 11.28 (s, 1H, —NH); 9.12 (d, J=7.7, 1H, —NH); 8.39 (d, J=5.0, 1H); 7.47 (d, J=8.2, 1H, —NH); 7.26 (dd, J=8.4, 2.0, 1H); 7.19 (d, J=2.0, 1H); 7.08 (d, J=5.0, 1H); 7.03 (d, J=8.4, 1H); 5.40 (t, J=5.8, 1H, —OH); 3.83 (d, J=6.8, 2H); 3.79 (m, 1H & d, J=5.8, 2H); 3.69 (m, 1H); 2.73 (s, 3H); 2.32 (s, 3H); 2.01 (m, 2H); 1.83 (m, 2H); 1.43 (m 4H); 0.93 (m, 1H); 0.34 (m, 2H); 0.18 (m, 2H).

Example F37

7-[2-(Cyclopropylmethoxy)-5-methylphenyl]-N-(trans-4-{[(2S)-2-hydroxypropanoyl]amino}cyclohexyl)-2-methyl-1H-pyrrolo[3,2-b]pyridine-3-carboxamide Starting from N-(trans-4-aminocyclohexyl)-7-[2-(cyclopropylmethoxy)-5-methylphenyl]-2-methyl-1H-pyrrolo[3,2-b]pyridine-3-carboxamide hydrochloride (example D.f19) and commercially available (2S)-1-chloro-1-oxopropan-2-yl acetate the title compound is obtained as colorless solid.

MS (ESI): m/z=491 (MH$^+$, 100%).

$^1$H-NMR (300 MHz, DMSO-d$_6$): 11.28 (s, 1H, —NH); 9.11 (d, J=7.7, 1H, —NH); 8.39 (d, J=4.9, 1H); 7.42 (d, J=8.2, 1H, —NH); 7.26 (dd, J=8.4, 2.0, 1H); 7.19 (d, J=2.0, 1H); 7.08 (d, J=4.9, 1H); 7.04 (d, J=8.4, 1H); 5.40 (d, J=5.1, 1H, —OH); 3.95 (qud, J=6.8, 5.1, 1H); 3.83 (d, J=5.8, 2H); 3.80 (m, 1H); 3.63 (m, 1H); 2.73 (s, 3H); 2.32 (s, 3H); 2.00 (m, 2H); 1.83 (m, 2H); 1.42 (m 4H); 1.21 (d, J=6.8, 3H); 0.93 (m, 1H); 0.34 (m, 2H); 0.18 (m, 2H).

Example F38

7-[2-(Cyclopropylmethoxy)-5-methylphenyl]-N-{cis-4-[(hydroxyacetyl)amino]cyclohexyl}-2-methyl-1H-pyrrolo[3,2-b]pyridine-3-carboxamide Starting from N-(cis-4-aminocyclohexyl)-7-[2-(cyclopropylmethoxy)-5-methylphenyl]-2-methyl-1H-pyrrolo[3,2-b]pyridine-3-carboxamide hydrochloride (example D.f20) and commercially available 2-chloro-2-oxoethyl acetate the title compound is obtained as colorless solid.

MS (ESI): m/z=491 (MH$^+$, 100%).

$^1$H-NMR (300 MHz, DMSO-d$_6$): 11.29 (br.s, 1H, —NH); 9.45 (d, J=7.5, 1H, —NH); 8.44 (d, J=5.0, 1H); 7.50 (d, J=7.9, 1H, —NH); 7.26 (dd, J=8.4, 2.0, 1H); 7.20 (d, J=2.0, 1H); 7.10 (d, J=5.0, 1H); 7.04 (d, J=8.4, 1H); 5.33 (br.s, 1H, —OH); 4.06 (m, 1H); 3.84 (d, J=6.8, 2H); 3.82 (s, 2H); 3.79 (m, 1H); 2.73 (s, 3H); 2.32 (s, 3H); 1.84-1.57 (m 8H); 0.93 (m, 1H); 0.35 (m, 2H); 0.19 (m, 2H).

Example F39

7-[2-(Cyclopropylmethoxy)-5-methylphenyl]-N-(cis-4-{[(2S)-2-hydroxypropanoyl]amino}cyclohexyl)-2-methyl-1H-pyrrolo[3,2-b]pyridine-3-carboxamide Starting from N-(cis-4-aminocyclohexyl)-7-[2-(cyclopropylmethoxy)-5-methylphenyl]-2-methyl-1H-pyrrolo[3,2-b]

pyridine-3-carboxamide hydrochloride (example D.f20) and commercially available (2S)-1-chloro-1-oxopropan-2-yl acetate the title compound is obtained as colorless solid.

MS (ESI): m/z=505 (MH⁺, 100%).

¹H-NMR (300 MHz, DMSO-d₆): 11.29 (br.s, 1H, —NH); 9.44 (d, J=7.5, 1H, —NH); 8.43 (d, J=4.9, 1H); 7.45 (d, J=7.7, 1H, —NH); 7.26 (dd, J=8.4, 2.0, 1H); 7.20 (d, J=2.0, 1H); 7.10 (d, J=4.9, 1H); 7.04 (d, J=8.4, 1H); 5.36 (br.d, J ~2.7, 1H, —OH); 4.05 (m, 1H); 4.00 (~dd, J ~6.8, 2.7, 1H); 3.83 (d, J=6.8, 2H); 3.74 (m, 1H); 2.73 (s, 3H); 2.32 (s, 3H); 1.84-1.56 (m 8H); 1.22 (d, J=6.8, 3H); 0.93 (m, 1H); 0.35 (m, 2H); 0.19 (m, 2H).

Example F40

7-[2-(Cyclopropylmethoxy)-4-fluoro-5-methoxyphenyl]-N-[1-(hydroxyacetyl)piperidin-4-yl]-2-methyl-1H-pyrrolo[3,2-b]pyridine-3-carboxamide Starting from 7-[2-(cyclopropylmethoxy)-4-fluoro-5-methoxyphenyl]-2-methyl-N-(piperidin-4-yl)-1H-pyrrolo[3,2-b]pyridine-3-carboxamide hydrochloride (example D.f21) and commercially available 2-chloro-2-oxoethyl acetate the title compound is obtained as colorless solid.

MS (ESI): m/z=511 (MH⁺, 100%).

¹H-NMR (300 MHz, DMSO-d₆): 11.36 (s, 1H, —NH); 9.28 (d, J=7.7, 1H, —NH); 8.40 (d, J=5.0, 1H); 7.18 (d, J=7.3, 1H); 7.15 (d, J=11.1, 1H & d, J=5.0, 1H); 4.50 (br.s, 1H, —OH); 4.15-4.03 (m, 2H); 4.13 (d, J=3.8, 2H); 3.84 (s, 3H); 3.81 (d, J=6.8, 2H); 3.67 (m, 1H); 3.20 (m, 1H); 3.03 (m, 1H); 2.74 (s, 3H); 1.96 (m, 2H); 1.53 (m, 1H); 1.41 (m, 1H); 0.92 (m, 1H); 0.35 (m, 2H); 0.17 (m, 2H).

Example F41

7-[2-(Cyclopropylmethoxy)-4-fluoro-5-methoxyphenyl]-N-{1-[(2S)-2-hydroxypropanoyl]piperidin-4-yl}-2-methyl-1H-pyrrolo[3,2-b]pyridine-3-carboxamide Starting from 7-[2-(cyclopropylmethoxy)-4-fluoro-5-methoxyphenyl]-2-methyl-N-(piperidin-4-yl)-1H-pyrrolo[3,2-b]pyridine-3-carboxamide hydrochloride (example D.f21) and commercially available (2S)-1-chloro-1-oxopropan-2-yl acetate the title compound is obtained as colorless solid.

MS (ESI): m/z=525 (MH⁺, 100%).

¹H-NMR (300 MHz, DMSO-d₆): 11.36 (s, 1H, —NH); 9.28 (d, J=7.7, 1H, —NH); 8.41 (d, J=5.1, 1H); 7.19 (d, J=7.5, 1H); 7.15 (d, J=11.3, 1H & d, J=5.1, 1H); 4.86 (d, J=6.8, 1H, —OH); 4.47 (m, 1H); 4.29-4.07 (m, 2H); 3.94 (m, 1H); 3.84 (s, 3H); 3.81 (d, J=6.9, 2H); 3.27 (m, 1H); 3.01 (m, 1H); 2.74 (s, 3H); 1.97 (m, 2H); 1.61-1.31 (m, 2H); 1.21 (br.d, J ~3.3, 3H); 0.92 (m, 1H); 0.35 (m, 2H); 0.17 (m, 2H).

Example F42

7-[2-(Cyclopropylmethoxy)-4-fluoro-5-methoxyphenyl]-N-{trans-4-[(hydroxyacetyl)amino]cyclohexyl}-2-methyl-1H-pyrrolo[3,2-b]pyridine-3-carboxamide Starting from N-(trans-4-aminocyclohexyl)-7-[2-(cyclopropylmethoxy)-4-fluoro-5-methoxyphenyl]-2-methyl-1H-pyrrolo[3,2-b]pyridine-3-carboxamide hydrochloride (example D.f22) and commercially available 2-chloro-2-oxoethyl acetate the title compound is obtained as colorless solid.

MS (ESI): m/z=525 (MH⁺, 100%).

¹H-NMR (300 MHz, DMSO-d₆): 11.33 (s, 1H, —NH); 9.10 (d, J=7.7, 1H, —NH); 8.41 (d, J=4.9, 1H); 7.47 (d, J=8.2, 1H, —NH); 7.18 (d, J=7.9, 1H); 7.14 (d, J=4.9, 1H & d, J=11.5, 1H); 5.40 (br.t, J=5.1, 1H, —OH); 3.84 (s, 3H); 3.81 (d, J=6.8, 2H); 3.79 (br.s, 2H); 3.68 (m, 2H); 2.73 (s, 3H); 2.01 (m, 2H); 1.83 (m, 2H); 1.43 (m, 4H); 0.92 (m, 1H); 0.35 (m, 2H); 0.17 (m, 2H).

Example F43

7-[2-(Cyclopropylmethoxy)-4-fluoro-5-methoxyphenyl]-N-(trans-4-{[(2S)-2-hydroxypropanoyl]amino}cyclohexyl)-2-methyl-1H-pyrrolo[3,2-b]pyridine-3-carboxamide Starting from N-(trans-4-aminocyclohexyl)-7-[2-(cyclopropylmethoxy)-4-fluoro-5-methoxyphenyl]-2-methyl-1H-pyrrolo[3,2-b]pyridine-3-carboxamide hydrochloride (example D.f22) and commercially available (2S)-1-chloro-1-oxopropan-2-yl acetate the title compound is obtained as colorless solid.

MS (ESI): m/z=539 (MH⁺, 100%).

¹H-NMR (300 MHz, DMSO-d₆): 11.32 (s, 1H, —NH); 9.10 (d, J=7.7, 1H, —NH); 8.41 (d, J=4.9, 1H); 7.42 (d, J=8.2, 1H, —NH); 7.18 (d, J=7.8, 1H); 7.14 (d, J=4.9, 1H & d, J=11.5, 1H); 5.40 (d, J=5.2, 1H, —OH); 3.94 (qud, J=6.8, 5.2, 1H); 3.84 (s, 3H); 3.81 (d, J=6.8, 2H); 3.63 (m, 2H); 2.73 (s, 3H); 2.00 (m, 2H); 1.82 (m, 2H); 1.42 (m, 4H); 1.21 (d, J=6.8, 3H); 0.91 (m, 1H); 0.34 (m, 2H); 0.17 (m, 2H).

Example F44

7-[2-(Cyclopropylmethoxy)-4-fluoro-5-methoxyphenyl]-N-{cis-4-[(hydroxyacetyl)amino]cyclohexyl}-2-methyl-1H-pyrrolo[3,2-b]pyridine-3-carboxamide Starting from N-(cis-4-aminocyclohexyl)-7-[2-(cyclopropylmethoxy)-4-fluoro-5-methoxyphenyl]-2-methyl-1H-pyrrolo[3,2-b]pyridine-3-carboxamide hydrochloride (example D.f23) and commercially available 2-chloro-2-oxoethyl acetate the title compound is obtained as colorless solid.

MS (ESI): m/z=525 (MH⁺, 100%).

¹H-NMR (300 MHz, DMSO-d₆): 11.33 (s, 1H, —NH); 9.42 (d, J=7.5, 1H, —NH); 8.44 (d, J=4.9, 1H); 7.49 (d, J=7.7, 1H, —NH); 7.18 (d, J=6.8, 1H); 7.16 (d, J=4.9, 1H); 7.15 (d, J=10.1, 1H); 5.33 (t, J=6.0, 1H, —OH); 4.06 (m, 1H); 3.84 (s, 3H); 3.83 (d, J=6.0, 2H); 3.82 (d, J=6.8, 2H); 3.80 (m, 1H); 2.74 (s, 3H); 1.83-1.58 (m, 8H); 0.92 (m, 1H); 0.35 (m, 2H); 0.17 (m, 2H).

Example F45

7-[2-(Cyclopropylmethoxy)-4-fluoro-5-methoxyphenyl]-N-(cis-4-{[abs.(2S)-2-hydroxypropanoyl]amino}cyclohexyl)-2-methyl-1H-pyrrolo[3,2-b]pyridine-3-carboxamide Starting from N-(cis-4-aminocyclohexyl)-7-[2-(cyclopropylmethoxy)-4-fluoro-5-methoxyphenyl]-2-methyl-1H-pyrrolo[3,2-b]pyridine-3-carboxamide hydrochloride (example D.f23) and commercially available (2S)-1-chloro-1-oxopropan-2-yl acetate the title compound is obtained as colorless solid.

MS (ESI): m/z=539 (MH⁺, 100%).

¹H-NMR (300 MHz, DMSO-d₆): 11.33 (s, 1H, —NH); 9.41 (d, J=7.5, 1H, —NH); 8.44 (d, J=4.9, 1H); 7.44 (d, J=7.7, 1H, —NH); 7.19 (d, J=6.8, 1H); 7.16 (d, J=4.9, 1H); 7.15 (d,

J=10.2, 1H); 5.36 (d, J=5.5, 1H, —OH); 4.05 (m, 1H); 3.99 (dqu, J=6.8, 5.5, 1H); 3.84 (s, 3H); 3.81 (d, J=6.9, 2H); 3.74 (m, 1H); 2.73 (s, 3H); 1.83-1.56 (m, 8H); 0.92 (m, 1H); 0.35 (m, 2H); 0.17 (m, 2H).

Example F46

7-[2-(Cyclopropylmethoxy)-4-fluoro-5-methoxyphenyl]-N-[(3R*,4R*)-4-hydroxy-1-(hydroxyacetyl)pyrrolidin-3-yl]-2-methyl-1H-pyrrolo[3,2-b]pyridine-3-carboxamide Starting from 7-[2-(cyclopropylmethoxy)-4-fluoro-5-methoxyphenyl]-N-[(3R*,4R*)-4-hydroxypyrrolidin-3-yl]-2-methyl-1H-pyrrolo[3,2-b]pyridine-3-carboxamide hydrochloride (example D.f24) and commercially available 2-chloro-2-oxoethyl acetate the title compound is obtained as colorless solid.

HR-MS (ESI): m/z=513.2137 ([MH]$^+$, $C_{26}H_{30}FN_4O_6^+$, calc. 513.2144).

Example F47

Diastereomeric mixture of 7-[2-(cyclopropylmethoxy)-4-fluoro-5-methoxyphenyl]-N-{(3R,4R)-4-hydroxy-1-[(2S)-2-hydroxypropanoyl]pyrrolidin-3-yl}-2-methyl-1H-pyrrolo[3,2-b]pyridine-3-carboxamide and 7-[2-(cyclopropylmethoxy)-4-fluoro-5-methoxyphenyl]-N-{(3S,4S)-4-hydroxy-1-[(2S)-2-hydroxypropanoyl]pyrrolidin-3-yl}-2-methyl-1H-pyrrolo[3,2-b]pyridine-3-carboxamide and Starting from 7-[2-(cyclopropylmethoxy)-4-fluoro-5-methoxyphenyl]-N-[(3R*,4R*)-4-hydroxypyrrolidin-3-yl]-2-methyl-1H-pyrrolo[3,2-b]pyridine-3-carboxamide hydrochloride (example D.f24) and commercially available (2S)-1-chloro-1-oxopropan-2-yl acetate the title compound is obtained as colorless solid.

HR-MS (ESI): m/z=527.2299 ([MH]$^+$, $C_{27}H_{32}FN_4O_6^+$, calc. 527.2300).

Example F48

7-[2-(Cyclopropylmethoxy)-4-fluoro-5-methoxyphenyl]-N-[(3R*,4R*)-3-hydroxy-1-(hydroxyacetyl)piperidin-4-yl]-2-methyl-1H-pyrrolo[3,2-b]pyridine-3-carboxamide Starting from 7-[2-(cyclopropylmethoxy)-4-fluoro-5-methoxyphenyl]-N-[(3R*,4R*)-3-hydroxypiperidin-4-yl]-2-methyl-1H-pyrrolo[3,2-b]pyridine-3-carboxamide hydrochloride (example D.f25) and commercially available 2-chloro-2-oxoethyl acetate the title compound is obtained as colorless solid.

HR-MS (ESI): m/z=527.2301 ([MH]$^+$, $C_{27}H_{32}FN_4O_6^+$, calc. 527.2300).

Example F49

Diastereomeric mixture of 7-[2-(Cyclopropylmethoxy)-4-fluoro-5-methoxyphenyl]-N-{(3R,4R)-3-hydroxy-1-[(2S)-2-hydroxypropanoyl]piperidin-4-yl}-2-methyl-1H-pyrrolo[3,2-b]pyridine-3-carboxamide and 7-[2-(Cyclopropylmethoxy)-4-fluoro-5-methoxyphenyl]-N-{(3S,4S)-3-hydroxy-1-[(2S)-2-hydroxypropanoyl]piperidin-4-yl}-2-methyl-1H-pyrrolo[3,2-b]pyridine-3-carboxamide Starting from 7-[2-(cyclopropylmethoxy)-4-fluoro-5-methoxyphenyl]-N-[(3R*,4R*)-3-hydroxypiperidin-4-yl]-2-methyl-1H-pyrrolo[3,2-b]pyridine-3-carboxamide hydrochloride (example D.f25) and commercially available (2S)-1-chloro-1-oxopropan-2-yl acetate the title compound is obtained as colorless solid.

HR-MS (ESI): m/z=541.2456 ([MH]$^+$, $C_{28}H_{34}FN_4O_6^+$, calc. 541.2457).

Example F50

7-[2-(Cyclopropylmethoxy)-5-fluoro-4-methoxyphenyl]-N-(1-glycoloylpiperidin-4-yl)-2-methyl-1H-pyrrolo[3,2-b]pyridine-3-carboxamide Starting from 7-[2-(cyclopropylmethoxy)-5-fluoro-4-methoxyphenyl]-2-methyl-N-piperidin-4-yl-1H-pyrrolo[3,2-b]pyridine-3-carboxamide hydrochloride (example D.f26) and commercially available 2-chloro-2-oxoethyl acetate the title compound is obtained as colorless solid.

MS (ESI): m/z=511 (MH$^+$, 100%).

$^1$H-NMR (300 MHz, DMSO-d$_6$): 11.34 (s, 1H, —NH); 9.29 (d, J=7.9, 1H, —NH); 8.37 (d, J=5.0, 1H); 7.27 (d, J=11.7, 1H); 7.09 (d, J=5.0, 1H); 6.92 (d, J=7.5, 1H); 4.49 (t, J=5.5, 1H, —OH); 4.22-4.04 (m, 4H); 3.94 (s, 3H); 3.89 (d, J=6.9, 2H); 3.67 (m, 1H); 3.19 (m, 1H); 3.03 (m, 1H); 2.74 (s, 3H); 1.96 (m, 2H); 1.53 (m, 1H); 1.40 (m, 1H); 0.94 (m, 1H); 0.36 (m, 2H); 0.20 (m, 2H).

Example F51

7-[2-(Cyclopropylmethoxy)-5-fluoro-4-methoxyphenyl]-N-{1-[(2S)-2-hydroxypropanoyl]piperidin-4-yl}-2-methyl-1H-pyrrolo[3,2-b]pyridine-3-carboxamide Starting from 7-[2-(cyclopropylmethoxy)-5-fluoro-4-methoxyphenyl]-2-methyl-N-piperidin-4-yl-1H-pyrrolo[3,2-b]pyridine-3-carboxamide hydrochloride (example D.f26) and commercially available (2S)-1-chloro-1-oxopropan-2-yl acetate the title compound is obtained as colorless solid.

MS (ESI): m/z=525 (MH$^+$, 100%).

$^1$H-NMR (300 MHz, DMSO-d$_6$): 11.33 (s, 1H, —NH); 9.28 (d, J=7.3, 1H, —NH); 8.38 (d, J=5.0, 1H); 7.28 (d, J=11.7, 1H); 7.09 (d, J=5.0, 1H); 6.93 (d, J=7.5, 1H); 4.85 (d, J=6.9, 1H, —OH); 4.46 (m, 1H); 4.28-4.07 (m, 2H); 3.94 (s, 3H); 3.90 (d, J=6.9, 2H); 3.27 (m, 1H); 3.00 (m, 1H); 2.74 (s, 3H); 1.97 (m, 1H); 1.45 (m, 1H); 1.21 (m, 2H); 0.94 (m, 1H); 0.36 (m, 2H); 0.20 (m, 2H).

Example F52

7-[2-(Cyclopropylmethoxy)-5-fluoro-4-methoxyphenyl]-N-[trans-4-(glycoloylamino)cyclohexyl]-2-methyl-1H-pyrrolo[3,2-b]pyridine-3-carboxamide Starting from N-(trans-4-aminocyclohexyl)-7-[2-(cyclopropylmethoxy)-5-fluoro-4-methoxyphenyl]-2-methyl-1H-pyrrolo[3,2-b]pyridine-3-carboxamide hydrochloride (example D.f27) and commercially available 2-chloro-2-oxoethyl acetate the title compound is obtained as colorless solid.

MS (ESI): m/z=525 (MH$^+$, 100%).

$^1$H-NMR (300 MHz, DMSO-d$_6$): 11.30 (s, 1H, —NH); 9.10 (d, J=7.9, 1H, —NH); 8.38 (d, J=5.1, 1H); 7.47 (d, J=8.4, 1H, —NH); 7.28 (d, J=11.7, 1H); 7.08 (d, J=5.1, 1H); 6.92 (d, J=7.5, 1H); 5.39 (t, J=5.5, 1H, —OH); 3.94 (s, 3H); 3.89 (d, J=6.8, 2H); 3.79 (m, 1H & d, J=5.5, 2H); 3.67 (m, 1H); 2.73

(s, 3H); 2.01 (m, 2H); 1.82 (m, 2H); 1.43 (m, 4H); 0.94 (m, 1H); 0.36 (m, 2H); 0.20 (m, 2H).

Example F53

7-[2-(Cyclopropylmethoxy)-5-fluoro-4-methoxyphenyl]-N-(trans-4-{[(2S)-2-hydroxypropanoyl]amino}cyclohexyl)-2-methyl-1H-pyrrolo[3,2-b]pyridine-3-carboxamide Starting from N-(trans-4-aminocyclohexyl)-7-[2-(cyclopropylmethoxy)-5-fluoro-4-methoxyphenyl]-2-methyl-1H-pyrrolo[3,2-b]pyridine-3-carboxamide hydrochloride (example D.f27) and commercially available (2S)-1-chloro-1-oxopropan-2-yl acetate the title compound is obtained as colorless solid.

MS (ESI): m/z=539 (MH$^+$, 100%).
$^1$H-NMR (300 MHz, DMSO-d$_6$): 11.30 (s, 1H, —NH); 9.10 (d, J=7.7, 1H, —NH); 8.38 (d, J=5.1, 1H); 7.42 (d, J=8.2, 1H, —NH); 7.27 (d, J=11.7, 1H); 7.08 (d, J=5.1, 1H); 6.93 (d, J=7.5, 1H); 5.40 (d, J=5.1, 1H, —OH); 3.95 (s, 3H & qud, J=6.8, 5.1, 1H); 3.89 (d, J=6.8, 2H); 3.80 (m, 1H); 3.62 (m, 1H); 2.73 (s, 3H); 2.00 (m, 2H); 1.82 (m, 2H); 1.42 (m, 4H); 1.21 (d, J=6.8, 3H); 0.94 (m, 1H); 0.36 (m, 2H); 0.20 (m, 2H).

Example F54

7-[2-(Cyclopropylmethoxy)-5-fluoro-4-methoxyphenyl]-N-[cis-4-(glycoloylamino)cyclohexyl]-2-methyl-1H-pyrrolo[3,2-b]pyridine-3-carboxamide Starting from N-(cis-4-aminocyclohexyl)-7-[2-(cyclopropylmethoxy)-5-fluoro-4-methoxyphenyl]-2-methyl-1H-pyrrolo[3,2-b]pyridine-3-carboxamide hydrochloride (example D.f28) and commercially available 2-chloro-2-oxoethyl acetate the title compound is obtained as colorless solid.

MS (ESI): m/z=525 (MH$^+$, 100%).
$^1$H-NMR (300 MHz, DMSO-d$_6$): 11.31 (s, 1H, —NH); 9.42 (d, J=7.5, 1H, —NH); 8.41 (d, J=5.1, 1H); 7.49 (d, J=7.7, 1H, —NH); 7.28 (d, J=11.7, 1H); 7.10 (d, J=5.1, 1H); 6.93 (d, J=7.5, 1H); 5.32 (t, J=5.7, 1H, —OH); 4.06 (m, 1H); 3.95 (s, 3H); 3.90 (d, J=6.8, 2H); 3.82 (d, J=5.7, 2H); 3.79 (m, 1H); 2.73 (s, 3H); 1.85-1.56 (m, 8H); 0.94 (m, 1H); 0.37 (m, 2H); 0.21 (m, 2H).

Example F55

7-[2-(Cyclopropylmethoxy)-5-fluoro-4-methoxyphenyl]-N-(cis-4-{[(2S)-2-methoxypropanoyl]amino}cyclohexyl)-2-methyl-1H-pyrrolo[3,2-b]pyridine-3-carboxamide Starting from N-(cis-4-aminocyclohexyl)-7-[2-(cyclopropylmethoxy)-5-fluoro-4-methoxyphenyl]-2-methyl-1H-pyrrolo[3,2-b]pyridine-3-carboxamide hydrochloride (example D.f28) and commercially available (2S)-1-chloro-1-oxopropan-2-yl acetate the title compound is obtained as colorless solid.

MS (ESI): m/z=539 (MH$^+$, 100%).
$^1$H-NMR (300 MHz, DMSO-d$_6$): 11.31 (s, 1H, —NH); 9.42 (d, J=7.5, 1H, —NH); 8.41 (d, J=4.9, 1H); 7.44 (d, J=7.7, 1H, —NH); 7.28 (d, J=11.9, 1H); 7.10 (d, J=4.9, 1H); 6.93 (d, J=7.5, 1H); 5.35 (d, J=5.5, 1H, —OH); 4.05 (m, 1H); 3.99 (qud, J=6.8, 5.5, 1H); 3.95 (s, 3H); 3.90 (d, J=6.9, 2H); 3.74 (m, 1H); 2.74 (s, 3H); 1.84-1.56 (m, 8H); 1.22 (d, J=6.8, 3H); 0.94 (m, 1H); 0.37 (m, 2H); 0.20 (m, 2H).

Commercial Utility

The compounds of formula (I), the salts thereof, and the stereoisomers of the compounds and the salts thereof are hereinafter referred to as the compounds of the present subject matter. In particular, the compounds of the present subject matter are pharmaceutically acceptable.

The compounds of the present subject matter have valuable pharmaceutical properties which make them commercially utilizable. In particular, as type 5 phosphodiesterase (PDE5) inhibitors, they are able to influence the physiological and pathophysiological function of various cells, e.g., but not limited to, smooth muscle cells, fibroblasts, myofibroblasts and platelets, which are involved in a great variety of physiological and pathophysiological mechanisms. In particular, the PDE5 inhibiting compounds of the present subject matter can effect relaxation of the vasculature, thus increasing blood flow, improve the spatial balance between blood perfusion and ventilation within the lung ("re-matching" effect) thereby reducing the amount of so-called low V/Q-areas [areas within the lung with high perfusion (Q) but no or reduced ventilation (V)] and high V/Q-areas (areas within the lung with low perfusion but high ventilation), induce neurogenesis, inhibit platelet function, such as aggregation, adhesion and mediator release and, thus, have an anti-inflammatory effect. The compounds of the present subject matter are distinguished by valuable and desirable properties, such as, for example, high efficacy, high selectivity, low toxicity, superior bioavailability in general (e.g. good enteral absorption), superior therapeutic window, superior pharmacokinetics (e.g. half-life), absence of significant side effects, and further beneficial effects related with their therapeutic and pharmaceutical suitability.

Accordingly, the present subject matter further relates to the compounds of the present subject matter for the treatment or prophylaxis of diseases, especially diseases alleviated by inhibition of the type 5 phosphodiesterase. In particular, the present subject matter relates to the compounds of the present subject matter for the treatment or prophylaxis of the following diseases: male and female sexual dysfunction, such as, but not limited to, male erectile dysfunction, premature ejaculation, Peyronie's disease; acute and chronic airway diseases, such as, but not limited to, COPD (chronic obstructive pulmonary disease), bronchitis, emphysema, pulmonary vascular remodeling, pulmonary hypertension, lung fibrosis, idiopathic pulmonary lung fibrosis (IPF), asthma, cystic fibrosis, bronchiectasis, bronchiolitis obliterans, connective tissue diseases, sarcoidosis, kyphoscoliosis, pneumoconiosis, amyotrophic lateral sclerosis, thoracoplasty, extrinsic allergic alveolitis; inflammatory diseases, such as, but not limited to, vasculature inflammation, acute respiratory distress syndrome, mesangial glomerulonephritis, chronic inflammatory bowel disease, disseminated intravascular inflammation, allergic vasculitis, dermatoses (e.g., but not limited to, psoriasis, toxic and allergic contact eczema, atopic eczema, seborrhoeic eczema, Lichen simplex, sunburn, pruritus in the anogenital area, alopecia greata, hypertrophic scars, discoid lupus erythematosus, follicular and widespread pyodermias, endogenous and exogenous acne, acne rosacea), disorders of the arthritis type (e.g., but not limited to, rheumatoid arthritis, rheumatoid spondylitis, osteoarthritis), disorders of the immune system [e.g., but not limited to, AIDS (acquired immunodeficiency syndrome), multiple sclerosis], graft versus host reaction, allograft rejections, shock [e.g., but not limited to, septic shock, endotoxin shock, gram-negative sepsis shock, toxic shock syndrome and ARDS (adult respiratory distress syndrome)], gastrointestinal inflammations (e.g., but not limited to, Crohn's disease and ulcerative colitis); disorders which are based on allergic and/or chronic, immunological false reactions (e.g., but not limited to, allergic rhinitis, allergic sinusitis, chronic rhinitis, chronic sinusitis, allergic conjunctivitis, nasal polyps);

pain, such as, but not limited to, inflammatory pain;

right-heart failure, right heart hypertrophy (cor pulmonale), hypertension, hypercholesterolemia, hypertriglyceridemia;

ischaemic diseases, such as, but not limited to, diabetes mellitus, stroke, coronary artery disease, angina (including, but not limited to, vasospastic angina), myocardial infarction, peripheral artery disease, cerebrovascular obstruction, sleep apnea, macular ischaemia, arterial and venous occlusion, congestive heart failure;

diabetic gastroparesis and diseases with symptoms of gastroparesis;

diseases or conditions in which it is desirable to suppress platelet function, for example, but not limited to, after stent implantations (e.g., but not limited to, coronary stenting), after bypass operations, in pulmonary hypertension, thrombotic diseases, post-angioplasty stenosis, coronary artery disease, infarction (e.g., but not limited to, myocardial infarction), instable angina pectoris, stroke, and arterial and venous occlusion diseases (e.g., but not limited to, claudicatio intermittens); diseases or conditions with an impairment or dysfunction of cerebral vascular reactivity and/or neurovascular coupling, such as, but not limited to, arteriosclerotic dementia, multi-infarct dementia, cerebral senility;

diseases which are based on neuronal damage or degradation, such as but not limited to, stroke, spinal cord injury, brain injury, morbus parkinson, amyotrophic lateral sclerosis, morbus alzheimer, amyloidosis, prion diseases and neuropathy; peripheral arterial diseases, chronic renal failure, chronic heart failure, sepsis, senile dementia (Alzheimer's disease), Creutzfeld-Jacob disease, septic encephalopathy, arteriosclerotic encephalopathy, diabetes associated encephalopathy, toxic encephalopathy, vascular and neuronal dementia, Huntington's disease, Parkinson's disease, multiple sclerosis and preeclampsia;

portal hypertension, liver cirrhosis, toxic liver damage (e.g., but not limited to, alcohol-induced liver damage), hepatitis, thrombosis of the portal vein, Budd-Chiari syndrome, malformation of liver veins, compression of liver veins (e.g., but without limitation, due to tumors), arteriovenous fistula, diseases associated with an enlarged spleen, schistosomiasis (bilharziosis), sarcoidosis and other granulomatous diseases, primary biliary cirrhosis, myeloproliferative disorders (e.g., but not limited to, chronic myeloid leukemia, osteomyelofibrosis), lymphatic systemic diseases, collagenosis (e.g., but not limited to, systemic lupus erythematodes, sclerodermia), morbus Osler (congenital arteriovenous malformations, inter alia in the liver), nodular regenerative hyperplasia, tricuspid insufficiency, pericarditis constrictive, veno-occlusive disease (VOD), non-alcoholic steatohepatitis (NASH), liver fibrosis;

benign prostatic hyperplasia;

insufficient uteroplacental blood flow in pregnancies with fetal growth restriction;

insufficient brain skills, such as but not limited to, verbal attainment, attention, concentration, de-ductive thinking, central auditory processing, cognition, learning, vigilance, apprehension and reagibility;

Overactive Bladder; LUTS=lower urinary tract symptoms; Raynauds syndrome/phenomenon.

In this respect, the term "pulmonary hypertension" in particular embraces pulmonary arterial hypertension including primary pulmonary hypertension (e.g. sporadic or familial) and pulmonary arterial hypertension related, for example, but without limitation, to collagen vascular disease, congenital systemic-to-pulmonary shunts, portal hypertension, human immunodeficiency virus infection, drugs or toxins (e.g., but not limited to, anorexigens), persistent pulmonary hypertension of the newborn;

pulmonary venous hypertension due to, for example, but without limitation, left-sided atrial or ventricular heart disease, left-sided valvular heart disease, extrinsic compression of central pulmonary veins (e.g. fibrosing mediastinitis, adenopathy in relation to tumors), pulmonary veno-occlusive disease;

pulmonary hypertension associated with disorders of the respiratory system or hypoxemia including, for example, but without limitation, chronic obstructive pulmonary disease (COPD), interstitial lung disease, sleep-disordered breathing, alveolar hypoventilation disorders, chronic exposure to high altitude, neonatal lung disease, alveolar-capillary dysplasia;

pulmonary hypertension caused by chronic thrombotic or embolic diseases including thromboembolic obstruction of proximal pulmonary arteries and obstruction of distal pulmonary arteries, such as pulmonary embolism (due to thrombus, tumor, ova, parasites, or foreign material), in situ thrombosis and sickle-cell disease, in particular chronic thromboembolic pulmonary hypertension (CTEPH);

pulmonary hypertension caused by disorders directly affecting the pulmonary vasculature including inflammatory disorders (e.g., but not limited to, schistosomiasis, sarcoidosis) and pulmonary capillary hemangiomatosis.

Preferably, the present subject matter further relates to the compounds of the present subject matter for the treatment or prophylaxis of the following diseases: acute and chronic airway diseases, such as pulmonary hypertension, in particular chronic thromboembolic pulmonary hypertension, lung fibrosis, asthma, bronchitis, emphysema and chronic obstructive pulmonary disease.

The present subject matter also relates to the use of a compound of the present subject matter in the manufacture of a pharmaceutical composition inhibiting the type 5 phosphodiesterase, in particular a pharmaceutical composition for the treatment or prophylaxis of diseases alleviated by inhibition of the type 5 phosphodiesterase, preferably, a pharmaceutical composition for the treatment or prophylaxis of the diseases exemplified above.

Preferably, the present subject matter relates to the use of a compound of the present subject matter in the manufacture of a pharmaceutical composition for the treatment or prophylaxis of an acute or chronic airway disease, such as, but not limited to, pulmonary hypertension, lung fibrosis, asthma, bronchitis, emphysema and chronic obstructive pulmonary disease.

Preferably, the present subject matter relates to the use of a compound of the present subject matter in the manufacture of a pharmaceutical composition for the treatment or prophylaxis of an acute or chronic airway disease, such as, but not limited to, pulmonary hypertension, pulmonary arterial hypertension, lung fibrosis, idiopathic pulmonary lung fibrosis, sarcoidosis, asthma, bronchitis, emphysema and chronic obstructive pulmonary disease.

In a particularly preferred embodiment of the present subject matter, the present subject matter relates to the use of a compound of the above examples in the manufacture of a pharmaceutical composition for the treatment or prophylaxis of an acute or chronic airway disease, such as, but not limited to, pulmonary hypertension, lung fibrosis, asthma, bronchitis, emphysema and chronic obstructive pulmonary disease.

In a particularly preferred embodiment of the present subject matter, the present subject matter relates to the use of a compound of the above examples in the manufacture of a pharmaceutical composition for the treatment or prophylaxis of an acute or chronic airway disease, such as, but not limited to, pulmonary hypertension, pulmonary arterial hypertension, lung fibrosis, idiopathic pulmonary lung fibrosis, sarcoidosis, asthma, bronchitis, emphysema and chronic obstructive pulmonary disease.

The present subject matter further relates to a method of treating or preventing a disease comprising administering to a patient in need thereof a therapeutically effective amount of at least one of the compounds of the present subject matter.

In particular, the present subject matter relates to a method of treating or preventing one of the above mentioned diseases comprising administering to a patient in need thereof a therapeutically effective amount of at least one of the compounds of the present subject matter.

Especially, the present subject matter relates to a method of treating or preventing a disease which is alleviated by inhibition of the type 5 phosphodiesterase comprising administering to a patient in need thereof a therapeutically effective amount of at least one of the compounds of the present subject matter.

Preferably, the present subject matter relates to a method of treating or preventing an acute or chronic airway disease, for example, but not limited to, pulmonary hypertension, lung fibrosis, asthma, bronchitis, emphysema and chronic obstructive pulmonary disease, comprising administering to a patient in need thereof a therapeutically effective amount of at least one of the compounds of the present subject matter.

Preferably, the present subject matter relates to a method of treating or preventing of an acute or chronic airway disease, for example, but not limited to, pulmonary hypertension, pulmonary arterial hypertension, lung fibrosis, idiopathic pulmonary lung fibrosis, sarcoidosis, asthma, bronchitis, emphysema and chronic obstructive pulmonary disease, comprising administering to a patient in need thereof a therapeutically effective amount of at least one of the compounds of the present subject matter.

In the above methods, the patient is preferably a mammal, more preferably a human. Furthermore, in the above methods, at least one of the compounds of the present subject matter can be used. Preferably, one or two of the compounds of the present subject matter are used, more preferably, one of the compounds of the present subject matter is used.

In a particularly preferred embodiment of the present subject matter, the above methods of treating or preventing one of the above mentioned diseases comprise administering to a patient in need thereof a therapeutically effective amount of one compound of the examples according to the present subject matter.

The present subject matter furthermore relates to a pharmaceutical composition which comprises at least one of the compounds of the present subject matter together with at least one pharmaceutically acceptable auxiliary.

The present subject matter additionally relates to a pharmaceutical composition for the treatment or prophylaxis of an acute or chronic airway disease, in particular for the treatment or prophylaxis of pulmonary hypertension, lung fibrosis, asthma, bronchitis, emphysema and chronic obstructive pulmonary disease.

The present subject matter additionally relates to a pharmaceutical composition for the treatment or prophylaxis of an acute or chronic airway disease, in particular for the treatment or prophylaxis of pulmonary hypertension, pulmonary arterial hypertension, lung fibrosis, idiopathic pulmonary lung fibrosis, sarcoidosis, asthma, bronchitis, emphysema and chronic obstructive pulmonary disease.

Preferably, the pharmaceutical composition comprises one or two of the compounds of the present subject matter. More preferably, the pharmaceutical composition comprises one of the compounds of the present subject matter.

In a particularly preferred embodiment of the present subject matter, the pharmaceutical composition comprises a compound of the examples according to the present subject matter together with at least one pharmaceutically acceptable auxiliary.

The present subject matter additionally relates to a pharmaceutical composition comprising at least one of the compounds of the present subject matter, at least one pharmaceutically acceptable auxiliary and at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, guanyl-cyclase activators/stimulators, pirfenidone, antidepressants, antibiotics, anticoagulants, diuretics and digitalis glycosides.

In this respect, the therapeutic agent includes the corticosteroids, anticholinergics, beta-mimetics, lung surfactants, endothelin antagonists, prostacyclins, calcium channel blockers, beta-blockers, type 4 phosphodiesterase inhibitors, guanyl-cyclase activators/stimulators, pirfenidone, antidepressants, antibiotics, anticoagulants, diuretics and digitalis glycosides in form of the free compounds, the pharmaceutically acceptable salts thereof, the pharmaceutically acceptable derivatives thereof (e.g., but not limited to, ester derivatives), the solvates thereof and the stereoisomers of the compounds, salts, derivatives and solvates.

Co-administration of at least one of the compounds of the present subject matter with at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, guanyl-cyclase activators/stimulators, pirfenidone, antidepressants, antibiotics, anticoagulants, diuretics and digitalis glycosides can take place in form of a fixed combination, a non-fixed combination or a kit of parts.

A "fixed combination" is defined as a combination wherein the compound of the present subject matter and the therapeutic agent intended for co-administration are present in one dosing unit or in a single entity. One example of a fixed combination is a pharmaceutical composition wherein the compound of the present subject matter and the therapeutic agent are present in admixture for simultaneous administration. Another example of a fixed combination is a pharmaceutical composition wherein the compound of the present subject matter and the therapeutic compound are present in one dosing unit without being in admixture.

A "non-fixed combination" or "kit of parts" is defined as a combination wherein the compound of the present subject matter and the therapeutic agent are present in more than one dosing unit. In a non-fixed combination or a kit of parts the compound of the present subject matter and the therapeutic agent are provided as separate formulations. They might be packaged and presented together as separate components of a combination pack for simultaneous, sequential or separate use in combination therapy. Simultaneous or sequential administration of the compound of the present subject matter and the therapeutic agent are preferred. In case of sequential or separate administration of the compound of the present subject matter and the therapeutic agent, the compound of the present subject matter can be administered before or after administration of the therapeutic agent.

In case of sequential or separate administration of the compound of the present subject matter and the therapeutic agent, the compound of the present subject matter can be administered before or after administration of the therapeutic agent.

Sequential administration encompasses a short time period between the administration of the compound of the present subject matter and the therapeutic agent or vice versa (for example, the time that is needed to swallow one tablet after the other).

Separate administration encompasses longer time periods between the administration of the compound of the present subject matter and the therapeutic agent. In a preferred embodiment of the present subject matter, the compound of the present subject matter is administered while the therapeutic agent (or vice versa) still has an therapeutic effect on the patient being treated.

The type of formulation of the compound of the present subject matter and the therapeutic agent of a non-fixed combination or a kit of parts can be identical, i.e. both, the compound of the present subject matter and the therapeutic agent are formulated, for example, as powder, solution or suspension suitable for inhalative administration, or can be different, i.e. suited for different administration forms, such as e.g. the compound of the present subject matter is formulated as powder, solution or suspension suitable for inhalative administration and the therapeutic agent is formulated as tablet or capsule for oral administration.

Accordingly, the present subject matter additionally relates to a pharmaceutical composition presented either as a fixed combination, a non-fixed combination or kit of parts comprising at least one of the compounds of the present subject matter, at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, guanyl-cyclase activators/stimulators, pirfenidone, antidepressants, antibiotics, anticoagulants, diuretics and digitalis glycosides, and at least one pharmaceutically acceptable auxiliary.

Examples of corticosteroids include without limitation budesonide, fluticasone such as fluticasone propionate, beclometasone such as beclometasone dipropionate, triamcinolone such as triamcinolone acetonide, mometasone, and ciclesonide. Examples of anticholinergics include without limitation tiotropium such as tiotropium bromide, and ipratropium such as ipratropium bromide, aclinidinium such as aclinidinium bromide, glycopyrronium such as glycopyrronium bromide. Examples of beta-mimetics include without limitation indacaterol, formoterol such as formoterol fumarate, and salmeterol such as salmeterol xinafoate, salbutamol, milveterol, carmoterol. Examples of lung surfactants include without limitation lusupultide, poractant alfa, sinapultide, beractant, bovactant, colfosceril such as colfosceril palmitate, surfactant-TA, and calfactant. Examples of endothelin antagonists include without limitation bosentan, ambrisentan, atrasentan, darusentan, clazosentan, avosentan and sitaxsentan such as sitaxsentan sodium. Examples of prostacyclins include without limitation iloprost such as iloprost tromethamine, epoprostenol such as epoprostenol sodium and treprostinil such as treprostinil sodium. Examples of calcium channel blockers include without limitation amlodipine such as amlodipine besylate and amlodipine maleate, nifedipine, diltiazem such as diltiazem hydrochloride, verapamil such as verapamil hydrochloride, and felodipine.

Examples of beta-blockers include without limitation bisoprolol such as bisoprolol fumarate, nebivolol, metoprolol such as metoprolol succinate and metoprolol tartrate, carvedilol, atenolol and nadolol. Examples of type 4 phosphodiesterase inhibitors include without limitation roflumilast, roflumilast N-oxide, cilomilast, tetomilast, apremilast and oglemilast. Examples of antidepressants include without limitation bupropion such as bupropion hydrochloride. Examples of antibiotics include without limitation amoxicillin, ampicillin, levofloxacin, clarithromycin, ciprofloxacin such as ciprofloxacin hydrochloride, telithromycin and azithromycin. Examples of anticoagulants include without limitation clopidogrel, enoxaparin, cilostazol, nadroparin, warfarin and abciximab. Examples of diuretics include without limitation furosemide, bumetanide and torsemide. Examples of digitalis glycosides include without limitation digoxin and digitoxin. Examples of Guanyl-cyclase activator/stimulators include without limitation BAY63-2521 (Riociguat) and Ataciguat.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), a corticosteroid and at least one pharmaceutically acceptable auxiliary. In a particularly alternative embodiment, the above-mentioned fixed combination, non-fixed combination or kit of parts comprise:
a compound of the present subject matter and budesonide,
a compound of the present subject matter and fluticasone,
a compound of the present subject matter and beclometasone,
a compound of the present subject matter and mometasone,
a compound of the present subject matter and triamcinolone acetonide, or
a compound of the present subject matter and ciclesonide,
and at least one pharmaceutically acceptable auxiliary.

In an alternative embodiment, the pharmaceutically acceptable derivative of fluticasone is fluticasone-17-propionate. In another alternative embodiment, the pharmaceutically acceptable derivative of beclometasone is beclometasone 17, 21-dipropionate ester. In an alternative embodiment, the pharmaceutically acceptable derivative of mometasone is mometasone furoate.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), an anticholinergic and at least one pharmaceutically acceptable auxiliary. In a particularly alternative embodiment, the above-mentioned fixed combination, non-fixed combination or kit of parts comprise:
a compound of the present subject matter and glycopyrronium bromide,
a compound of the present subject matter and aclidinium bromide,
a compound of the present subject matter and tiotropium bromide, or
a compound of the present subject matter and ipratropium bromide,
and at least one pharmaceutically acceptable auxiliary.

In an alternative embodiment, the stereoisomer of glycopyrronium bromide is (R,R)-glycopyrronium bromide. In an alternative embodiment, tiotropium bromide is used in form of its monohydrate.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), a beta-mimetic and at least one pharmaceutically acceptable auxiliary. In a particularly alternative embodiment, the above-mentioned fixed combination, non-fixed combination or kit of parts comprise:
a compound of the present subject matter and salbutamol,
a compound of the present subject matter and milveterol,
a compound of the present subject matter and indacaterol,
a compound of the present subject matter and carmoterol,
a compound of the present subject matter and salmeterol,
a compound of the present subject matter and formoterol,
and at least one pharmaceutically acceptable auxiliary.

In an alternative embodiment, the pharmaceutically acceptable salt of salbutamol is salbutamol sulfate. In an alternative embodiment, the pharmaceutically acceptable salt of milveterol is milveterol hydrochloride. In an alternative embodiment, the pharmaceutically acceptable salt of carmoterol is carmoterol hydrochloride. In an alternative embodiment, the pharmaceutically acceptable salt of salmeterol is salmeterol xinafoate. In another alternative embodiment, the pharmaceutically acceptable salt of formoterol is formoterol hemifumarate monohydrate. In another alternative embodiment, the stereoisomer of formoterol is R,R-formoterol. In another alternative embodiment, the pharmaceutically acceptable salt of R,R-formoterol is R,R-formoterol L-tartrate.

Preferably the beta-mimetic is a long-acting beta-mimetic; particularly an alternative in this respect are those beta-mimetics having a therapeutic effect over a 12-24 hours period.

In an alternative embodiment, the above-mentioned fixed combination, non-fixed combination or kit of parts comprise a compound of the present subject matter (in particular the compound of the present subject matter is one of the examples of the present subject matter), a lung surfactant and at least one pharmaceutically acceptable auxiliary. In a particularly alternative embodiment, the above-mentioned fixed combination, non-fixed combination or kit of parts comprise:
a compound of the present subject matter and lusupultide,
a compound of the present subject matter and poracant alfa,
a compound of the present subject matter and sinapultide,
a compound of the present subject matter and beracant,
a compound of the present subject matter and bovacant,
a compound of the present subject matter and colfosceril palmitate,
a compound of the present subject matter and surfactant-TA, or
a compound of the present subject matter and calfacant, and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), an endothelin antagonist and at least one pharmaceutically acceptable auxiliary. In a particularly alternative embodiment, the above-mentioned fixed combination, non-fixed combination or kit of parts comprise:
a compound of the present subject matter and bosentan,
a compound of the present subject matter and ambrisentan,
a compound of the present subject matter and atrasentan,
a compound of the present subject matter and darusentan,
a compound of the present subject matter and clazosentan, or
a compound of the present subject matter and avosentan,
and at least one pharmaceutically acceptable auxiliary.

In another alternative embodiment, bosentan is used in form of its monohydrate. In another alternative embodiment the pharmaceutically acceptable salt of clazosentan is the disodium salt of clazosentan. In another alternative embodiment the pharmaceutically acceptable salts of atrasentan are atrasentan hydrochloride or the sodium salt of atrasentan. In another alternative embodiment the R-enantiomer of atrasentan is used. In another alternative embodiment the S-enantiomer of darusentan is used.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), a prostacyclin and at least one pharmaceutically acceptable auxiliary. In a particularly alternative embodiment, the above-mentioned fixed combination, non-fixed combination or kit of parts comprise:
a compound of the present subject matter and iloprost,
a compound of the present subject matter and epoprostenol,
a compound of the present subject matter and triprostinil,
and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), a calcium channel blocker and at least one pharmaceutically acceptable auxiliary. In a particularly alternative embodiment, the above-mentioned fixed combination, non-fixed combination or kit of parts comprise:
a compound of the present subject matter and amlodipine,
a compound of the present subject matter and nifedipine,
a compound of the present subject matter and diltiazem,
a compound of the present subject matter and verapamil, or
a compound of the present subject matter and felodipine,
and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), a beta-blocker and at least one pharmaceutically acceptable auxiliary. In a particularly alternative embodiment, the above-mentioned fixed combination, non-fixed combination or kit of parts comprise:
a compound of the present subject matter and bisoprolol,
a compound of the present subject matter and nebivolol,
a compound of the present subject matter and metoprolol,
a compound of the present subject matter and carvedilol,
a compound of the present subject matter and atenolol, or
a compound of the present subject matter and nadolol,
and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), a type 4 phosphodiesterase inhibitor and at least one pharmaceutically acceptable auxiliary. In a particularly alternative embodiment, the above-mentioned fixed combination, non-fixed combination or kit of parts comprise:
a compound of the present subject matter and roflumilast,
a compound of the present subject matter and roflumilast N-oxide,
a compound of the present subject matter and cilomilast,
a compound of the present subject matter and tetomilast a compound of the present subject matter and apremilast, or
a compound of the present subject matter and oglemilast,
and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), an antidepressant and at least one pharmaceutically acceptable auxiliary. In a particularly alternative embodiment, the above-mentioned fixed combination, non-fixed combination or kit of parts comprise:
a compound of the present subject matter and bupropion,
and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), an antibiotic and at least one pharmaceutically acceptable auxiliary. In a particularly alternative embodiment, the above-mentioned fixed combination, non-fixed combination or kit of parts comprise:
a compound of the present subject matter and amoxicillin,
a compound of the present subject matter and ampicillin,
a compound of the present subject matter and levofloxacin,
a compound of the present subject matter and clarithromycin,
a compound of the present subject matter and ciprofloxacin,
a compound of the present subject matter and telithromycin, or
a compound of the present subject matter and azithromycin,
and at least one pharmaceutically acceptable auxiliary.

In an alternative embodiment, amoxicillin is used in form of its trihydrate. In another alternative embodiment, ampicillin is used in form of its trihydrate. In another alternative embodiment, the pharmaceutically acceptable salt of ampicillin is ampicillin natrium. In another alternative embodiment levofloxacin is used in form of its hemihydrate. In another alternative embodiment, the pharmaceutically acceptable salt of ciprofloxacin is ciprofloxacin hydrochloride monohydrate. In another alternative embodiment, azithromycin is used in form of its monohydrate.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), an anticoagulant and at least one pharmaceutically acceptable auxiliary. In a particularly alternative embodiment, the above-mentioned fixed combination, non-fixed combination or kit of parts comprise:
a compound of the present subject matter and clopidogrel,
a compound of the present subject matter and enoxaparin,
a compound of the present subject matter and cilostazol,
a compound of the present subject matter and nadroparin,
a compound of the present subject matter and warfarin, or
a compound of the present subject matter and abciximab,
and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), a diuretic and at least one pharmaceutically acceptable auxiliary. In a particularly alternative embodiment, the above-mentioned fixed combination, non-fixed combination or kit of parts comprise:
a compound of the present subject matter and furosemide,
a compound of the present subject matter and bumetanide, or
a compound of the present subject matter and torsemide,
and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), a digitalis glycoside and at least one pharmaceutically acceptable auxiliary. In a particularly alternative embodiment, the above-mentioned fixed combination, non-fixed combination or kit of parts comprise:
a compound of the present subject matter and digoxin, or
a compound of the present subject matter and digitoxin,
and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), a corticosteroid, a beta-mimetic and at least one pharmaceutically acceptable auxiliary. In a particularly alternative embodiment, the above-mentioned fixed combination, non-fixed combination or kit of parts comprise:
a compound of the present subject matter, budesonide and salbutamol,
a compound of the present subject matter, budesonide and milveterol,
a compound of the present subject matter, budesonide and indacaterol,
a compound of the present subject matter, budesonide and carmoterol,
a compound of the present subject matter, budesonide and salmeterol,
a compound of the present subject matter, budesonide and formoterol,
a compound of the present subject matter, fluticasone and salbutamol,
a compound of the present subject matter, fluticasone and milveterol,
a compound of the present subject matter, fluticasone and indacaterol,
a compound of the present subject matter, fluticasone and carmoterol,
a compound of the present subject matter, fluticasone and salmeterol,
a compound of the present subject matter, fluticasone and formoterol,
a compound of the present subject matter, beclometasone and salbutamol,
a compound of the present subject matter, beclometasone and milveterol,
a compound of the present subject matter, beclometasone and indacaterol,
a compound of the present subject matter, beclometasone and carmoterol,
a compound of the present subject matter, beclometasone and salmeterol,
a compound of the present subject matter, beclometasone and formoterol,
a compound of the present subject matter, mometasone and salbutamol,
a compound of the present subject matter, mometasone and milveterol,
a compound of the present subject matter, mometasone and indacaterol, a compound of the present subject matter, mometasone and carmoterol,
a compound of the present subject matter, mometasone and salmeterol,
a compound of the present subject matter, mometasone and formoterol,
a compound of the present subject matter, triamcinolone acetonide and salbutamol,
a compound of the present subject matter, triamcinolone acetonide and milveterol,
a compound of the present subject matter, triamcinolone acetonide and indacaterol,
a compound of the present subject matter, triamcinolone acetonide and carmoterol,
a compound of the present subject matter, triamcinolone acetonide and salmeterol,
a compound of the present subject matter, triamcinolone acetonide and formoterol,
a compound of the present subject matter, ciclesonide and salbutamol,
a compound of the present subject matter, ciclesonide and milveterol,
a compound of the present subject matter, ciclesonide and indacaterol,
a compound of the present subject matter, ciclesonide and carmoterol,
a compound of the present subject matter, ciclesonide and salmeterol, or
a compound of the present subject matter, ciclesonide and formoterol,
and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), a beta-mimetic, an anticholinergic and at least one pharmaceutically acceptable auxiliary. In a particularly alternative embodiment, the above-mentioned fixed combination, non-fixed combination or kit of parts comprise:
a compound of the present subject matter, salbutamol and glycopyrronium bromide,
a compound of the present subject matter, salbutamol and aclidinium bromide,
a compound of the present subject matter, salbutamol and tiotropium bromide,
a compound of the present subject matter, salbutamol and ipratropium bromide,
a compound of the present subject matter, milveterol and glycopyrronium bromide,
a compound of the present subject matter, milveterol and aclidinium bromide,
a compound of the present subject matter, milveterol and tiotropium bromide,
a compound of the present subject matter, milveterol and ipratropium bromide,
a compound of the present subject matter, salmeterol and glycopyrronium bromide,
a compound of the present subject matter, salmeterol and aclidinium bromide,
a compound of the present subject matter, salmeterol and tiotropium bromide,
a compound of the present subject matter, salmeterol and ipratropium bromide,
a compound of the present subject matter, formoterol and glycopyrronium bromide,
a compound of the present subject matter, formoterol and aclidinium bromide,
a compound of the present subject matter, formoterol and tiotropium bromide,
a compound of the present subject matter, formoterol and ipratropium bromide,
a compound of the present subject matter, indacaterol and glycopyrronium bromide,
a compound of the present subject matter, indacaterol and aclidinium bromide,
a compound of the present subject matter, indacaterol and tiotropium bromide,
a compound of the present subject matter, indacaterol and ipratropium bromide,
a compound of the present subject matter, carmoterol and glycopyrronium bromide,
a compound of the present subject matter, carmoterol and aclidinium bromide,
a compound of the present subject matter, carmoterol and tiotropium bromide, or
a compound of the present subject matter, carmoterol and ipratropium bromide,
and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), a corticosteroid, an anticholinergic and at least one pharmaceutically acceptable auxiliary. In a particularly alternative embodiment, the above-mentioned fixed combination, non-fixed combination or kit of parts comprise:
a compound of the present subject matter, budesonide and glycopyrronium bromide,
a compound of the present subject matter, budesonide and aclidinium bromide,
a compound of the present subject matter, budesonide and tiotropium bromide,
a compound of the present subject matter, budesonide and ipratropium bromide,
a compound of the present subject matter, fluticasone and glycopyrronium bromide,
a compound of the present subject matter, fluticasone and aclidinium bromide,
a compound of the present subject matter, fluticasone and tiotropium bromide,
a compound of the present subject matter, fluticasone and ipratropium bromide,
a compound of the present subject matter, beclometasone and glycopyrronium bromide,
a compound of the present subject matter, beclometasone and aclidinium bromide,
a compound of the present subject matter, beclometasone and tiotropium bromide,
a compound of the present subject matter, beclometasone and ipratropium bromide,
a compound of the present subject matter, mometasone and glycopyrronium bromide,
a compound of the present subject matter, mometasone and aclidinium bromide,
a compound of the present subject matter, mometasone and tiotropium bromide,
a compound of the present subject matter, mometasone and ipratropium bromide,
a compound of the present subject matter, triamcinolone acetonide and glycopyrronium bromide, a compound of the present subject matter, triamcinolone acetonide and aclidinium bromide,
a compound of the present subject matter, triamcinolone acetonide and tiotropium bromide,
a compound of the present subject matter, triamcinolone acetonide and ipratropium bromide,
a compound of the present subject matter, ciclesonide and glycopyrronium bromide,
a compound of the present subject matter, ciclesonide and aclidinium bromide,
a compound of the present subject matter, ciclesonide and tiotropium bromide, or
a compound of the present subject matter, ciclesonide and ipratropium bromide,
and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), an guanyl-cyclase activator/stimulator and at least one pharmaceutically acceptable auxiliary. In a particularly alternative embodiment, the above-mentioned fixed combination, non-fixed combination or kit of parts comprise:
a compound of the present subject matter and BAY63-2521 (Riociguat),
a compound of the present subject matter and Ataciguat,
and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), pirfenidone and at least one pharmaceutically acceptable auxiliary. In a particularly alternative embodiment, the above-mentioned fixed combination, non-fixed combination or kit of parts comprise:
a compound of the present subject matter and pirfenidone,
and at least one pharmaceutically acceptable auxiliary.

The above mentioned compound of the present subject matter is preferably a compound according to the examples.

The present subject matter furthermore relates to pharmaceutical compositions according to the present subject matter, as defined above, inhibiting the type 5 phosphodiesterase, especially for the treatment or prophylaxis of diseases alleviated by inhibition of type 5 phosphodiesterase, in particular for the treatment or prophylaxis of the diseases exemplified above.

The present subject matter also encompasses pharmaceutical compositions according to the present subject matter, as defined above, for the treatment or prophylaxis of the following diseases: acute and chronic airway diseases, such as pulmonary hypertension, lung fibrosis, asthma, bronchitis, emphysema and chronic obstructive pulmonary disease.

The pharmaceutical compositions according to the present subject matter preferably contain the compound or compounds of the present subject matter in a total amount of from 0.1 to 99.9 wt %, more preferably 5 to 95 wt %, in particular 20 to 80 wt %. In case at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, guanyl-cyclase activators/stimulators, pirfenidone, antidepressants, antibiotics, anticoagulants, diuretics and digitalis glycosides is present in the pharmaceutical compositions of the present subject matter, the total amount of said therapeutic agent or therapeutic agents in the pharmaceutical compositions is preferably in the range of from 0.1 to 99.9 wt %, more preferably 5 to 95 wt %, in particular 20 to 80 wt %, under the provision that the total amount of the compound or compounds of the present subject matter and the therapeutic agent or therapeutic agents is less than 100 wt %. Preferably, the at least one compound of the present subject matter and the at least one therapeutic agent are present in the pharmaceutical composition in a weight ratio of from 1000:1 to 1:1000, more preferably 500:1 to 1:500.

As pharmaceutically acceptable auxiliaries, any auxiliaries known to be suitable for preparing pharmaceutical compositions can be used. Examples thereof include, but are not limited to, solvents, excipients, dispersants, emulsifiers, solubilizers, gel formers, ointment bases, antioxidants, preservatives, stabilizers, carriers, fillers, binders, thickeners, complexing agents, disintegrating agents, buffers, permeation promoters, polymers, lubricants, coating agents, propellants, tonicity adjusting agents, surfactants, colorants, flavorings, sweeteners and dyes. In particular, auxiliaries of a type appropriate to the desired formulation and the desired mode of administration are used.

The pharmaceutical compositions can be formulated, for example, into tablets, coated tablets (dragees), pills, cachets, capsules (caplets), granules, powders, suppositories, solutions (e.g., but not limited to, sterile solutions), emulsions, suspensions, ointments, creams, lotions, pastes, oils, gels, sprays and patches (e.g., but not limited to, transdermal therapeutic systems). Additionally, the pharmaceutical compositions can be prepared as e.g. liposome delivery systems, systems in which the compound of the present subject matter is coupled to monoclonal antibodies and systems in which the compound of the present subject matter is coupled to polymers (e.g., but not limited to, soluble or biodegradable polymers).

In case of pharmaceutical compositions comprising at least one of the compounds of the present subject matter and at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, guanyl-cyclase activators/stimulators, pirfenidone, antidepressants, antibiotics, anticoagulants, diuretics and digitalis glycosides, the compound of the present subject matter and the therapeutic agent may be formulated together into the same dosage form (e.g., but not limited to, tablets), separately into the same dosage form (e.g., but not limited to, tablets), or into different dosage forms (without limitation e.g. the compound of the present subject matter may be formulated as tablet and the therapeutic agent may be formulated as powder, solution or suspension).

The pharmaceutical compositions can be manufactured in a manner known to a person skilled in the art, e.g. by dissolving, mixing, granulating, dragee-making, levigating, emulsifying, encapsulating, entrapping or lyophilizing processes.

The selected formulation depends inter alia on the route of administering the pharmaceutical composition. The pharmaceutical compositions of the present subject matter can be administered by any suitable route, for example, by the oral, sublingual, buccal, intravenous, intraarterial, intramuscular, subcutaneous, intracutaneous, topical, transdermal, intranasal, intraocular, intraperitoneal, intrasternal, intracoronary, transurethral, rectal or vaginal route, by inhalation or by insufflation. Oral administration is preferred.

In case of pharmaceutical compositions comprising at least one of the compounds of the present subject matter and at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, guanyl-cyclase activators/stimulators, pirfenidone, antidepressants, antibiotics, anticoagulants, diuretics and digitalis glycosides, the compound of the present subject matter and the therapeutic agent may be administered by the same route, e.g., without limitation, orally, or by different routes, e.g., without limitation, the compound of the present subject matter can be administered orally and the therapeutic agent can be administered by inhalation or instillation.

Tablets, coated tablets (dragees), pills, cachets, capsules (caplets), granules, solutions, emulsions and suspensions are e.g. suitable for oral administration. In particular, said formulations can be adapted so as to represent, for example, an enteric form, an immediate release form, a delayed release form, a repeated dose release form, a prolonged release form or a sustained release form. Said forms can be obtained, for example, by coating tablets, by dividing tablets into several compartments separated by layers disintegrating under different conditions (e.g. pH conditions) or by coupling the compound of the present subject matter to a biodegradable polymer.

Administration by inhalation or instillation is preferably made by using an aerosol. The aerosol is a liquid-gaseous dispersion, a solid-gaseous dispersion or a mixed liquid/solid-gaseous dispersion.

The aerosol may be generated by means of aerosol-producing devices such as dry powder inhalers (DPIs), pressurized metered dose inhalers (PMDIs) and nebulizers. Depending on the kind of the compound of the present subject matter, and optionally the therapeutic agent, to be administered, the aerosol-producing device can contain the compound and, optionally, the therapeutic agent in form of a powder, a solution or a dispersion. The powder may contain, for example, one or more of the following auxiliaries: carriers, stabilizers and fillers. The solution may contain in addition to the solvent, for example, one or more of the following auxiliaries: propellants, solubilizers (co-solvents), surfactants, stabilizers, buffers, tonicity adjusting agents, preservatives and flavorings. The dispersion may contain in addition to the dispersant, for example, one or more of the following auxiliaries: propellants, surfactants, stabilizers, buffers, preservatives and flavorings. Examples of carriers include, but are not limited to, saccharides, e.g. lactose and glucose. Examples of propellants include, but are not limited to, fluorohydrocarbons, e.g. 1,1,1,2-tetrafluoroethane and 1,1,1,2,3,3,3-heptafluoropropane.

The particle size of the aerosol particles (solid, liquid or solid/liquid particles) is preferably less than 100 µm, more preferably it is in the range of from 0.5 to 10 µm, in particular in the range of from 2 to 6 µm (D50 value, measured by laser diffraction).

Specific aerosol-producing devices which may be used for inhaled administration include, but are not limited to, Cyclohaler®, Diskhaler®, Rotadisk®, Turbohaler®, Autohaler®, Turbohaler®, Novolizer®, Easyhaler®, Aerolizer®, Jethaler®, Diskus®, Ultrahaler® and Mystic® inhalers. The aerosol-producing devices may be combined with spacers or expanders, e.g. Aerochamber®, Nebulator®, Volumatic® and Rondo®, for improving inhalation efficiency.

In case of topical administration, suitable pharmaceutical formulations are, for example, ointments, creams, lotions, pastes, gels, powders, solutions, emulsions, suspensions, oils, sprays and patches (e.g., but not limited to, transdermal therapeutic systems).

For parenteral modes of administration such as, for example, intravenous, intraarterial, intramuscular, subcutaneous, intracutaneous, intraperitoneal and intrasternal administration, preferably solutions (e.g., but not limited to, sterile solutions, isotonic solutions) are used. They are preferably administered by injection or infusion techniques.

In case of intranasal administration, for example, sprays and solutions to be applied in drop form are preferred formulations.

For intraocular administration, solutions to be applied in drop form, gels and ointments are exemplified formulations.

Generally, the pharmaceutical compositions according to the present subject matter can be administered such that the dose of the compound of the present subject matter is in the range customary for type 5 phosphodiesterase inhibitors. In particular, a dose in the range of from 0.01 to 4000 mg of the compound of the present subject matter per day is preferred. In this respect, it is to be noted that the dose is dependent, for example, on the specific compound used, the species treated, age, body weight, general health, sex and diet of the subject treated, mode and time of administration, rate of excretion, severity of the disease to be treated and drug combination. In case the pharmaceutical composition of the present subject matter comprises at least one of the compounds of the present subject matter and at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, guanyl-cyclase activators/stimulators, pirfenidone, antidepressants, antibiotics, anticoagulants, diuretics and digitalis glycosides, the same dose ranges apply to the therapeutic agent.

The pharmaceutical compositions according to the present subject matter can be administered in a single dose per day or in multiple subdoses, for example, 2 to 4 doses per day. A single dose unit of the pharmaceutical composition can contain e.g. from 0.01 mg to 4000 mg, preferably 0.1 mg to 2000 mg, more preferably 0.5 to 1000 mg, most preferably 1 to 500 mg, of the compound of the present subject matter. In case the pharmaceutical composition of the present subject matter comprises at least one of the compounds of the present subject matter and at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, guanyl-cyclase activators/stimulators, pirfenidone, antidepressants, antibiotics, anticoagulants, diuretics and digitalis glycosides, a single dose unit of the pharmaceutical composition can contain e.g. from 0.01 mg to 4000 mg, preferably 0.1 mg to 2000 mg, more preferably 0.5 to 1000 mg, most preferably 1 to 500 mg, of the therapeutic agent. Furthermore, the pharmaceutical composition can be adapted to weekly, monthly or even more infrequent administration, for example by using an implant, e.g. a subcutaneous or intramuscular implant, by using the compound of the present subject matter in form of a sparingly soluble salt or by using the compound of the present subject matter coupled to a polymer. Administration of the pharmaceutical composition in a single dose per day is preferred.

In case the pharmaceutical composition of the present subject matter comprises at least one of the compounds of the present subject matter and at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, guanyl-cyclase activators/stimulators, pirfenidone, antidepressants, antibiotics, anticoagulants, diuretics and digitalis glycosides, administration of the compound of the present subject matter and administration of the therapeutic agent can be made simultaneously or sequentially. In case of sequential administration, the compound of the present subject matter can be administered before or after administration of the therapeutic agent.

Biological Investigations

Method for Measuring Inhibition of the Type 5 Phosphodiesterase (PDE5) Activity:

As a source for human PDE5, platelets are used. For that purpose, 150 ml fresh blood from human donors anticoagulated with citrate [final concentration 0.3% (w/v)] is centrifuged at 200 g for 10 min to obtain the so-called platelet-rich-plasma (PRP) as a supernatant. 1/10 volume of ACD solution (85 mM $Na_3$-citrate, 111 mM D-glucose, 71 mM citric acid, pH 4.4) is added to 9/10 volume of PRP. After centrifugation (1,400 g, 10 min) the cell pellet is resuspended in 3 ml homogenization buffer (NaCl 140 mM, KCl 3.8 mM, EGTA (ethylene glycol tetraacetic acid) 1 mM, $MgCl_2$ 1 mM, Tris-HCl 20 mM, beta-mercaptoethanol 1 mM, pH 8.2) plus protease-inhibitor mix giving rise to the final concentrations of 0.5 mM Pefablock (Roche), 10 µM Leupeptin, 5 µM Trypsininhibitor, 2 mM Benzamidin and 10 µM Pepstatin A. The suspension is sonified and thereafter centrifuged for 15 min at 10,000 g. The resulting supernatant (platelet lysate) is used for enzymatic testings.

PDE5A1 activity is inhibited by the compounds of the present subject matter in a modified SPA (scintillation proximity assay) test, supplied by Amersham Biosciences (see procedural instructions "phosphodiesterase [3H]cAMP SPA enzyme assay, code TRKQ 7090"), carried out in 96-well microtitre plates (MTP's). The test volume is 100 µl and contains 20 mM Tris buffer (pH 7.4), 0.1 mg of BSA (bovine serum albumin)/ml, 5 mM $Mg^{2+}$, 1 µM motapizone, 10 nM PDE2 inhibitor 2-(3,4-dimethoxybenzyl)-7-[(1R,2R)-2-hydroxy-1-(2-phenylethyl)propyl]-5-methylimidazo[5,1-t][1,2,4]triazin-4(3H)-one, 0.5 µM cGMP (cyclic guanosine monophosphate) (including about 50,000 cpm of [3H]cGMP as a tracer), 1 µl of the respective compound dilution in dimethylsulfoxide (DMSO) and sufficient PDE5-containing platelet lysat (10,000×g supernatant, see above) to ensure that 10-20 wt % of the cGMP is converted under the said experimental conditions. The final concentration of DMSO in the assay (1% v/v) does not substantially affect the activity of the PDE investigated. After a preincubation of 5 min at 37° C., the reaction is started by adding the substrate (cGMP) and the assay is incubated for a further 15 min; after that, it is stopped by adding SPA beads (50 µl). In accordance with the manufacturer's instructions, the SPA beads had previously been resuspended in water, but are then diluted 1:3 (v/v) in water; the diluted solution also contains 3 mM 8-methoxymethyl-3-isobutyl-1-methylxanthine (IBMX) to ensure a complete PDE activity stop. After the beads have been sedimented (>30 min), the MTP's are analyzed in commercially available luminescence detection devices. The corresponding $IC_{50}$ values of the compounds for the inhibition of PDE activity are determined from the concentration-effect curves by means of non-linear regression.

For the following compounds PDE5A1 inhibitory values [measured as $-logIC_{50}$ (mol/l)] between 8.0 and 9.0 have been determined. The numbers of the compounds correspond to the numbers of the examples.

Compounds: E12, E16-E19, E21, E25-E30, E39, E42, E47-E60, F06-F08, F10-F13, F16-F19, F26, F32-F39.

For the following compounds PDE5A1 inhibitory values [measured as $-logIC_{50}$ (mol/l)] higher than 9.0 have been determined. The numbers of the compounds correspond to the numbers of the examples.

Compounds: E01-E11, E13-E15, E20, E22-E24, E31-E38, E40-E41, E43-E46, E61-E84, F01-F05, F09, F14-F15, F20-F25, F27-F31, F40-F55.

Animal Pharmacological Testing

Nitric oxide regulates smooth muscle tone by elevation of cGMP via activation of guanylate cyclase and subsequent activation of cyclic GMP-dependent protein kinase. The amplitude and duration of the cGMP signal in smooth muscle is largely regulated by cGMP-specific cyclic nucleotide phosphodiesterase 5 (PDE5). Therefore, inhibition of PDE5 or activation of guanylate cyclase causes altered arterial blood pressure response, which is more pronounced under conditions of acute arterial hypertension, which can be easily induced by continuous intravenous (i.v.) phenylephrine(PE)-infusion. The aim of the study was to evaluate the effects of the selective PDE5 inhibitors described in this present subject matter on phenylephrine-induced acute arterial hypertension and sodium-nitroprusside (SNP) induced blood pressure response in anaesthetised male Sprague Dawley rats.

Method

The test compound (suspended in a 4% w/v aqueous methylcellulose solution 3 mg/kg) or placebo (i.e. 4% aqueous methylcellulose solution) is administered orally to conscious Sprague Dawley rats 90 min prior to SNP administration. 40 min later, rats are anaesthetised by intramuscular administration of 80 mg/kg ketamine-HCl+4 mg/kg xylazin-HCl and ventilated with ~1.5% isoflurane in a mixture of ambient air and 40% oxygen. Catheters for i.v. PE- and SNP-administration and recording of mean arterial blood pressure (MAP) are inserted. One hour after compound or placebo administration, a continuous i.v. (V. femoralis) PE-infusion (3 µg/kg/min at an infusion rate of 0.06 ml/min) is started and maintained till the end of the experiment. 30 min after start of the PE-infusion, an i.v.-bolus of the NO-donor sodium nitroprusside (SNP, 30 µg/kg at a volume of 1.0 ml/kg) is administered. To assess the effect of test compounds (PDE5 inhibitory activity) in comparison to placebo, MAP response is analysed. MAP prior to SNP-administration and area under the curve of MAP within 180 s following SNP-administration, corrected for initial MAP (corr. $AUC_{MAP\ 0-180\ s}$) is used, to describe altered arterial vascular response and thus in vivo PDE5-inhibitory activity. The efficacy (% change vs. control) achievable in this model is approximately of −27% effect for the examples E01 and F02.

The invention claimed is:
1. A compound of formula (I)

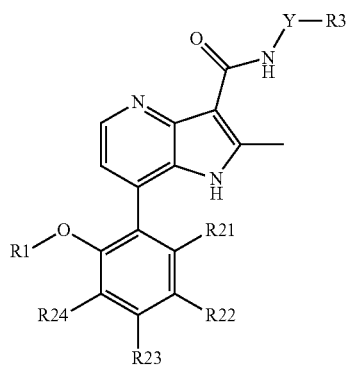

wherein
R1 is —CH₂-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy, —C(±)-1-4C-alkyl or 1-4C-fluoroalkyl,
or R21 and R22 combine to form a group —O—CH₂—O—,
R23 is hydrogen, halogen, 1-4C-alkyl, 1-4C-alkoxy, hydroxy or 1-4C-fluoroalkoxy,
or R22 and R23 combine to form a group —O—CH₂—O—,
R24 is hydrogen,
Y is —(CH₂)ₙ—,
n is 0 or 1,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(±)-1-4C-alkyl, wherein the 1-4C-alkyl group is optionally substituted by R41, —C(±)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R5 is 1-4C-alkoxy, hydroxy or halogen,
R6 is —NH—C(O)—R7, —C(O)—NR8R9 or NH₂,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
or a salt thereof, a stereoisomer of the compound or a salt of the stereoisomer.

2. The compound according to claim 1, wherein
R1 is —CH₂-3-4C-cycloalkyl or 2-4C-alkyl,
R21 is hydrogen,
R22 is hydrogen, halogen, 1-4C-alkyl, 1-4C-alkoxy, 1-4C-fluoroalkoxy, —C(O)-1-4C-alkyl or 1-4C-fluoroalkyl,
or R21 and R22 combine to form a group —O—CH₂—O—,
R23 is hydrogen, halogen, 1-4C-alkyl, 1-4C-alkoxy, hydroxy or 1-4C-fluoroalkoxy,
R24 is hydrogen,
Y is —(CH₂)ₙ—,
n is 0,
R3 is a 4- to 6-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(±)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R6 is —NH—C(O)—R7 or NH₂,
R5 is 1-4C-alkoxy, hydroxy or fluoro,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
or a salt thereof, a stereoisomer of the compound or a salt of the stereoisomer.

3. The compound according to claim 1, wherein
R1 is —CH₂-3-4C-cycloalkyl,
R21 is hydrogen,
R22 is hydrogen, halogen, 1-4C-alkyl, 1-4C-alkoxy, 1-4C-fluoroalkoxy, —C(±)-1-4C-alkyl or 1-4C-fluoroalkyl,
or R21 and R22 combine to form a group —O—CH₂—O—,
R23 is hydrogen, halogen, 1-4C-alkyl, 1-4C-alkoxy, hydroxy or 1-4C-fluoroalkoxy,
R24 is hydrogen,
Y is —(CH₂)ₙ—,
n is 0,
R3 is a 5- to 6-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(±)-1-4C-alkyl, wherein the 1-4C-alkyl group is optionally substituted by R41, or —C(O)—O-1-4C-alkyl,
R41 is 1-4C-alkoxy or hydroxy,
R5 is hydroxy,
R6 is —NH—C(O)—R7 or NH₂,
R7 is 1-4C-alkyl, which is optionally substituted by R71, or 1-4C-alkoxy,
R71 is 1-4C-alkoxy or hydroxy,
or a salt thereof, a stereoisomer of the compound or a salt of the stereoisomer.

4. The compound according to claim 1, wherein
R1 is —CH$_2$-3-4C-cycloalkyl,
R21 is hydrogen,
R22 is hydrogen, halogen, 1-4C-alkyl or 1-2C-alkoxy,
or R21 and R22 combine to form a group —O—CH$_2$—O—,
R23 is hydrogen, halogen or 1-2C-alkoxy,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom and said heterocyclic ring being optionally substituted by R5, or a cyclohexyl group substituted by R6,
R4 is —C(±)-1-4C-alkyl, wherein the 1-4C-alkyl group is optionally substituted by R41, or —C(O)—O-1-4C-alkyl,
R41 is 1-4C-alkoxy or hydroxy,
R5 is hydroxy,
R6 is —NH—C(O)—R7,
R7 is 1-4C-alkyl, which is optionally substituted by R71, or 1-4C-alkoxy,
R71 is 1-4C-alkoxy or hydroxy,
or a salt thereof, a stereoisomer of the compound or a salt of the stereoisomer.

5. A compound according to claim 1 selected from the group consisting of
tert-Butyl 4-[({7-[5-(cyclopropylmethoxy)-1,3-benzodioxol-4-yl]-2-methyl-1H-pyrrolo[3,2-b]pyridin-3-yl}carbonyl)amino]piperidine-1-carboxylate; tert-Butyl {trans-4-[({7-[5-(cyclopropylmethoxy)-1,3-benzodioxol-4-yl]-2-methyl-1H-pyrrolo[3,2-b]pyridin-3-yl}carbonyl)amino]cyclohexyl}carbamate; tert-Butyl {cis-4-[({7-[5-(cyclopropylmethoxy)-1,3-benzodioxol-4-yl]-2-methyl-1H-pyrrolo[3,2-b]pyridin-3-yl}carbonyl)amino]cyclohexyl}carbamate; tert-Butyl 4-{[(7-[2-(cyclopropylmethoxy)-4-fluorophenyl]-2-methyl-1-{[2-(trimethylsilyl)ethoxy]methyl}-1H-pyrrolo[3,2-b]pyridin-3-yl)carbonyl]amino}piperidine-1-carboxylate; tert-Butyl {trans-4-[({7-[2-(cyclopropylmethoxy)-4-fluorophenyl]-2-methyl-1H-pyrrolo[3,2-b]pyridin-3-yl}carbonyl)amino]cyclohexyl}carbamate; tert-Butyl {cis-4-[({7-[2-(cyclopropylmethoxy)-4-fluorophenyl]-2-methyl-1H-pyrrolo[3,2-b]pyridin-3-yl}carbonyl)amino]cyclohexyl}carbamate; tert-Butyl 4-[({7-[2-(cyclopropylmethoxy)-5-fluorophenyl]-2-methyl-1H-pyrrolo[3,2-b]pyridin-3-yl}carbonyl)amino]piperidine-1-carboxylate; tert-Butyl {trans-4-[({7-[2-(cyclopropylmethoxy)-5-fluorophenyl]-2-methyl-1H-pyrrolo[3,2-b]pyridin-3-yl}carbonyl)amino]cyclohexyl}carbamate; tert-Butyl {cis-4-[({7-[2-(cyclopropylmethoxy)-5-fluorophenyl]-2-methyl-1H-pyrrolo[3,2-b]pyridin-3-yl}carbonyl)amino]cyclohexyl}carbamate; tert-Butyl (3R*,4R*)-4-[({7-[2-(cyclopropylmethoxy)-5-fluorophenyl]-2-methyl-1H-pyrrolo[3,2-b]pyridin-3-yl}carbonyl)amino]-3-hydroxypiperidine-1-carboxylate; tert-Butyl 4-[({7-[2-(cyclopropylmethoxy)-4-methoxyphenyl]-2-methyl-1H-pyrrolo[3,2-b]pyridin-3-yl}carbonyl)amino]piperidine-1-carboxylate; tert-Butyl {trans-4-[({7-[2-(cyclopropylmethoxy)-4-methoxyphenyl]-2-methyl-1H-pyrrolo[3,2-b]pyridin-3-yl}carbonyl)amino]cyclohexyl}carbamate; tert-Butyl {cis-4-[({7-[2-(cyclopropylmethoxy)-4-methoxyphenyl]-2-methyl-1H-pyrrolo[3,2-b]pyridin-3-yl}carbonyl)amino]cyclohexyl}carbamate; tert-Butyl 4-[({7-[2-(cyclopropylmethoxy)-5-methoxyphenyl]-2-methyl-1H-pyrrolo[3,2-b]pyridin-3-yl}carbonyl)amino]piperidine-1-carboxylate; tert-Butyl {trans-4-[({7-[2-(cyclopropylmethoxy)-5-methoxyphenyl]-2-methyl-1H-pyrrolo[3,2-b]pyridin-3-yl}carbonyl)amino]cyclohexyl}carbamate; tert-Butyl {cis-4-[({7-[2-(cyclopropylmethoxy)-5-methoxyphenyl]-2-methyl-1H-pyrrolo[3,2-b]pyridin-3-yl}carbonyl)amino]cyclohexyl}carbamate; tert-Butyl-(3R*,4R*)-3-[({7-[2-(cyclopropylmethoxy)-5-methoxyphenyl]-2-methyl-1H-pyrrolo[3,2-b]pyridin-3-yl}carbonyl)amino]-4-hydroxypyrrolidine-1-carboxylate; tert-Butyl 4-[({7-[2-(cyclopropylmethoxy)-5-methylphenyl]-2-methyl-1H-pyrrolo[3,2-b]pyridin-3-yl}carbonyl)amino]piperidine-1-carboxylate; tert-Butyl {trans-4-[({7-[2-(cyclopropylmethoxy)-5-methylphenyl]-2-methyl-1H-pyrrolo[3,2-b]pyridin-3-yl}carbonyl)amino]cyclohexyl}carbamate; tert-Butyl {cis-4-[({7-[2-(cyclopropylmethoxy)-5-methylphenyl]-2-methyl-1H-pyrrolo[3,2-b]pyridin-3-yl}carbonyl)amino]cyclohexyl}carbamate; tert-Butyl 4-[({7-[2-(cyclopropylmethoxy)-4-fluoro-5-methoxyphenyl]-2-methyl-1H-pyrrolo[3,2-b]pyridin-3-yl}carbonyl)amino]piperidine-1-carboxylate; tert-Butyl {trans-4-[({7-[2-(cyclopropylmethoxy)-4-fluoro-5-methoxyphenyl]-2-methyl-1H-pyrrolo[3,2-b]pyridin-3-yl}carbonyl)amino]cyclohexyl}carbamate; tert-Butyl {cis-4-[({7-[2-(cyclopropylmethoxy)-4-fluoro-5-methoxyphenyl]-2-methyl-1H-pyrrolo[3,2-b]pyridin-3-yl}carbonyl)amino]cyclohexyl}carbamate; tert-Butyl (3R*,4R*)-3-[({7-[2-(cyclopropylmethoxy)-4-fluoro-5-methoxyphenyl]-2-methyl-1H-pyrrolo[3,2-b]pyridin-3-yl}carbonyl)amino]-4-hydroxypyrrolidine-1-carboxylate; tert-Butyl (3R*,4R*)-4-[({7-[2-(cyclopropylmethoxy)-4-fluoro-5-methoxyphenyl]-2-methyl-1H-pyrrolo[3,2-b]pyridin-3-yl}carbonyl)amino]-3-hydroxypiperidine-1-carboxylate; tert-Butyl 4-[({7-[2-(cyclopropylmethoxy)-5-fluoro-4-methoxyphenyl]-2-methyl-1H-pyrrolo[3,2-b]pyridin-3-yl}carbonyl)amino]piperidine-1-carboxylate; tert-Butyl {trans-4-[({7-[2-(cyclopropylmethoxy)-5-fluoro-4-methoxyphenyl]-2-methyl-1H-pyrrolo[3,2-b]pyridin-3-yl}carbonyl)amino]cyclohexyl}carbamate; tert-Butyl {cis-4-[({7-[2-(cyclopropylmethoxy)-5-fluoro-4-methoxyphenyl]-2-methyl-1H-pyrrolo[3,2-b]pyridin-3-yl}carbonyl)amino]cyclohexyl}carbamate; N-(1-Acetylpiperidin-4-yl)-7-[5-(cyclopropylmethoxy)-1,3-benzodioxol-4-yl]-2-methyl-1H-pyrrolo[3,2-b]pyridine-3-carboxamide; 7-[5-(Cyclopropylmethoxy)-1,3-benzodioxol-4-yl]-2-methyl-N-(1-propionylpiperidin-4-yl)-1H-pyrrolo[3,2-b]pyridine-3-carboxamide; 7-[5-(Cyclopropylmethoxy)-1,3-benzodioxol-4-yl]-N-[1-(methoxyacetyl)piperidin-4-yl]-2-methyl-1H-pyrrolo[3,2-b]pyridine-3-carboxamide; Ethyl 4-[({7-[5-(cyclopropylmethoxy)-1,3-benzodioxol-4-yl]-2-methyl-1H-pyrrolo[3,2-b]pyridin-3-yl}carbonyl)amino]piperidine-1-carboxylate; N-(trans-4-Acetamidocyclohexyl)-7-[5-(cyclopropylmethoxy)-1,3-benzodioxol-4-yl]-2-methyl-1H-pyrrolo[3,2-b]pyridine-3-carboxamide; N-(cis-4-acetamidocyclohexyl)-7-[5-(cyclopropylmethoxy)-1,3-benzodioxol-4-yl]-2-methyl-1H-pyrrolo[3,2-b]pyridine-3-carboxamide; 7-[5-(Cyclopropylmethoxy)-1,3-benzodioxol-4-yl]-2-methyl-N-[cis-4-(propionylamino)cyclohexyl]-1H-pyrrolo[3,2-b]pyridine-3-carboxamide; 7-[5-(Cyclopropylmethoxy)-

1,3-benzodioxol-4-yl]-N-{cis-4-[(methoxyacetyl) amino]cyclohexyl}-2-methyl-1H-pyrrolo[3,2-b]pyridine-3-carboxamide; Ethyl {cis-4-[({7-[5-(cyclopropylmethoxy)-1,3-benzodioxol-4-yl]-2-methyl-1H-pyrrolo[3,2-b]pyridin-3-yl}carbonyl)amino]cyclohexyl}carbamate; N-(1-Acetylpiperidin-4-yl)-7-[2-(cyclopropylmethoxy)-4-fluorophenyl]-2-methyl-1H-pyrrolo[3,2-b]pyridine-3-carboxamide; 7-[2-(Cyclopropylmethoxy)-4-fluorophenyl]-2-methyl-N-(1-propanoylpiperidin-4-yl)-1H-pyrrolo[3,2-b]pyridine-3-carboxamide; 7-[2-(Cyclopropylmethoxy)-4-fluorophenyl]-N-[1-(methoxyacetyl)piperidin-4-yl]-2-methyl-1H-pyrrolo[3,2-b]pyridine-3-carboxamide; N-[trans-4-(Acetylamino)cyclohexyl]-7-[2-(cyclopropylmethoxy)-4-fluorophenyl]-2-methyl-1H-pyrrolo[3,2-b]pyridine-3-carboxamide; 7-[2-(Cyclopropylmethoxy)-4-fluorophenyl]-2-methyl-N-[trans-4-(propanoylamino)cyclohexyl]-1H-pyrrolo[3,2-b]pyridine-3-carboxamide; 7-[2-(Cyclopropylmethoxy)-4-fluorophenyl]-N-{trans-4-[(methoxyacetyl)amino]cyclohexyl}-2-methyl-1H-pyrrolo[3,2-b]pyridine-3-carboxamide; N-[cis-4-(Acetylamino)cyclohexyl]-7-[2-(cyclopropylmethoxy)-4-fluorophenyl]-2-methyl-1H-pyrrolo[3,2-b]pyridine-3-carboxamide; 7-[2-(Cyclopropylmethoxy)-5-fluorophenyl]-2-methyl-N-[cis-4-(propanoylamino)cyclohexyl]-1H-pyrrolo[3,2-b]pyridine-3-carboxamide; 7-[2-(Cyclopropylmethoxy)-4-fluorophenyl]-N-{cis-4-[(methoxyacetyl)amino]cyclohexyl}-2-methyl-1H-pyrrolo[3,2-b]pyridine-3-carboxamide; N-(1-Acetylpiperidin-4-yl)-7-[2-(cyclopropylmethoxy)-5-fluorophenyl]-2-methyl-1H-pyrrolo[3,2-b]pyridine-3-carboxamide; 7-[2-(Cyclopropylmethoxy)-5-fluorophenyl]-2-methyl-N-(1-propanoylpiperidin-4-yl)-1H-pyrrolo[3,2-b]pyridine-3-carboxamide; 7-[2-(Cyclopropylmethoxy)-5-fluorophenyl]-N-[1-(methoxyacetyl)piperidin-4-yl]-2-methyl-1H-pyrrolo[3,2-b]pyridine-3-carboxamide; N-[trans-4-(Acetylamino)cyclohexyl]-7-[2-(cyclopropylmethoxy)-5-fluorophenyl]-2-methyl-1H-pyrrolo[3,2-b]pyridine-3-carboxamide; 7-[2-(Cyclopropylmethoxy)-5-fluorophenyl]-2-methyl-N-[trans-4-(propanoylamino)cyclohexyl]-1H-pyrrolo[3,2-b]pyridine-3-carboxamide; 7-[2-(Cyclopropylmethoxy)-5-fluorophenyl]-N-{trans-4-[(methoxyacetyl)amino]cyclohexyl}-2-methyl-1H-pyrrolo[3,2-b]pyridine-3-carboxamide; N-[cis-4-(Acetylamino)cyclohexyl]-7-[2-(cyclopropylmethoxy)-5-fluorophenyl]-2-methyl-1H-pyrrolo[3,2-b]pyridine-3-carboxamide; 7-[2-(Cyclopropylmethoxy)-5-fluorophenyl]-2-methyl-N-[cis-4-(propanoylamino)cyclohexyl]-1H-pyrrolo[3,2-b]pyridine-3-carboxamide; 7-[2-(Cyclopropylmethoxy)-5-fluorophenyl]-N-{cis-4-[(methoxyacetyl)amino]cyclohexyl}-2-methyl-1H-pyrrolo[3,2-b]pyridine-3-carboxamide; N-[(3R*,4R*)-1-Acetyl-3-hydroxypiperidin-4-yl]-7-[2-(cyclopropylmethoxy)-5-fluorophenyl]-2-methyl-1H-pyrrolo[3,2-b]pyridine-3-carboxamide; 7-[2-(Cyclopropylmethoxy)-5-fluorophenyl]-N-[(3R*,4R*)-3-hydroxy-1-propanoylpiperidin-4-yl]-2-methyl-1H-pyrrolo[3,2-b]pyridine-3-carboxamide; 7-[2-(Cyclopropylmethoxy)-5-fluorophenyl]-N-[(3R*,4R*)-3-hydroxy-1-(methoxyacetyl)piperidin-4-yl]-2-methyl-1H-pyrrolo[3,2-b]pyridine-3-carboxamide; N-(1-Acetylpiperidin-4-yl)-7-[2-(cyclopropylmethoxy)-4-methoxyphenyl]-2-methyl-1H-pyrrolo[3,2-b]pyridine-3-carboxamide; 7-[2-(Cyclopropylmethoxy)-4-methoxyphenyl]-2-methyl-N-(1-propanoylpiperidin-4-yl)-1H-pyrrolo[3,2-b]pyridine-3-carboxamide; 7-[2-(Cyclopropylmethoxy)-4-methoxyphenyl]-N-[1-(methoxyacetyl)piperidin-4-yl]-2-methyl-1H-pyrrolo[3,2-b]pyridine-3-carboxamide; N-[trans-4-(Acetylamino)cyclohexyl]-7-[2-(cyclopropylmethoxy)-4-methoxyphenyl]-2-methyl-1H-pyrrolo[3,2-b]pyridine-3-carboxamide; 7-[2-(Cyclopropylmethoxy)-4-methoxyphenyl]-2-methyl-N-[trans-4-(propanoylamino)cyclohexyl]-1H-pyrrolo[3,2-b]pyridine-3-carboxamide; 7-[2-(Cyclopropylmethoxy)-4-methoxyphenyl]-N-{trans-4-[(methoxyacetyl)amino]cyclohexyl}-2-methyl-1H-pyrrolo[3,2-b]pyridine-3-carboxamide; N-[cis-4-(Acetylamino)cyclohexyl]-7-[2-(cyclopropylmethoxy)-4-methoxyphenyl]-2-methyl-1H-pyrrolo[3,2-b]pyridine-3-carboxamide; 7-[2-(Cyclopropylmethoxy)-4-methoxyphenyl]-2-methyl-N-[cis-4-(propanoylamino)cyclohexyl]-1H-pyrrolo[3,2-b]pyridine-3-carboxamide; 7-[2-(Cyclopropylmethoxy)-4-methoxyphenyl]-N-{cis-4-[(methoxyacetyl)amino]cyclohexyl}-2-methyl-1H-pyrrolo[3,2-b]pyridine-3-carboxamide; N-(1-Acetylpiperidin-4-yl)-7-[2-(cyclopropylmethoxy)-5-methoxyphenyl]-2-methyl-1H-pyrrolo[3,2-b]pyridine-3-carboxamide; 7-[2-(Cyclopropylmethoxy)-5-methoxyphenyl]-2-methyl-N-(1-propanoylpiperidin-4-yl)-1H-pyrrolo[3,2-b]pyridine-3-carboxamide; 7-[2-(cyclopropylmethoxy)-5-methoxyphenyl]-N-[1-(methoxyacetyl)piperidin-4-yl]-2-methyl-1H-pyrrolo[3,2-b]pyridine-3-carboxamide; N-[trans-4-(Acetylamino)cyclohexyl]-7-[2-(cyclopropylmethoxy)-5-methoxyphenyl]-2-methyl-1H-pyrrolo[3,2-b]pyridine-3-carboxamide; 7-[2-(Cyclopropylmethoxy)-5-methoxyphenyl]-2-methyl-N-[trans-4-(propanoylamino)cyclohexyl]-1H-pyrrolo[3,2-b]pyridine-3-carboxamide; 7-[2-(Cyclopropylmethoxy)-5-methoxyphenyl]-N-{trans-4-[(methoxyacetyl)amino]cyclohexyl}-2-methyl-1H-pyrrolo[3,2-b]pyridine-3-carboxamide; N-[cis-4-(Acetylamino)cyclohexyl]-7-[2-(cyclopropylmethoxy)-5-methoxyphenyl]-2-methyl-1H-pyrrolo[3,2-b]pyridine-3-carboxamide; 7-[2-(Cyclopropylmethoxy)-5-methoxyphenyl]-2-methyl-N-[cis-4-(propanoylamino)cyclohexyl]-1H-pyrrolo[3,2-b]pyridine-3-carboxamide; 7-[2-(Cyclopropylmethoxy)-5-methoxyphenyl]-N-{cis-4-[(methoxyacetyl)amino]cyclohexyl}-2-methyl-1H-pyrrolo[3,2-b]pyridine-3-carboxamide; N-[(3R*,4R*)-1-Acetyl-4-hydroxypyrrolidin-3-yl]-7-[2-(cyclopropylmethoxy)-5-methoxyphenyl]-2-methyl-1H-pyrrolo[3,2-b]pyridine-3-carboxamide; 7-[2-(Cyclopropylmethoxy)-5-methoxyphenyl]-N-[(3R*,4R*)-4-hydroxy-1-propanoylpyrrolidin-3-yl]-2-methyl-1H-pyrrolo[3,2-b]pyridine-3-carboxamide; 7-[2-(Cyclopropylmethoxy)-5-methoxyphenyl]-N-[(3R*,4R*)-4-hydroxy-1-(methoxyacetyl)pyrrolidin-3-yl]-2-methyl-1H-pyrrolo[3,2-b]pyridine-3-carboxamide; N-(1-Acetylpiperidin-4-yl)-7-[2-(cyclopropylmethoxy)-5-methylphenyl]-2-methyl-1H-pyrrolo[3,2-b]pyridine-3-carboxamide; 7-[2-(Cyclopropylmethoxy)-5-methylphenyl]-2-methyl-N-(1-propanoylpiperidin-4-yl)-1H-pyrrolo[3,2-b]pyridine-3-carboxamide; 7-[2-(Cyclopropylmethoxy)-5-methylphenyl]-N-[1-(methoxyacetyl)piperidin-4-yl]-2-methyl-1H-pyrrolo[3,2-b]pyridine-3-carboxamide; N-[trans-4-(Acetylamino)cyclohexyl]-7-[2-(cyclopropylmethoxy)-5-methylphenyl]-2-methyl-1H-pyrrolo[3,2-b]pyridine-3-carboxamide; 7-[2-(Cyclopropylmethoxy)-5-methylphenyl]-2-methyl-N-[trans-4-(propanoylamino)cyclohexyl]-1H-pyrrolo[3,2-b]pyridine-3-carboxamide; 7-[2-(Cyclopropylmethoxy)-5-methylphenyl]-N-{trans-4-[(methoxyacetyl)amino]cyclohexyl}-2-methyl-1H-pyrrolo[3,2-b]pyridine-3-carboxamide; N-[cis-4-(Acetylamino)cyclohexyl]-7-[2-(cyclopropylmethoxy)-5-methylphenyl]-2-methyl-1H-pyrrolo[3,2-b]pyridine-3-carboxamide; 7-[2-(Cyclopropylmethoxy)-5-methylphenyl]-2-methyl-N-[cis-4-(propanoylamino)cyclohexyl]-1H-pyrrolo[3,2-b]pyridine-3-carboxamide; 7-[2-(Cyclopropylmethoxy)-5-methylphenyl]-N-{cis-4-[(methoxyacetyl)amino]cyclohexyl}-2-methyl-1H-pyrrolo[3,2-b]pyridine-3-carboxamide; N-(1-Acetylpiperidin-4-yl)-7-[2-(cyclopropylmethoxy)-4-fluoro-5-methoxyphenyl]-2-methyl-1H-pyrrolo[3,2-b]pyridine-3-carboxamide; 7-[2-(Cyclopropylmethoxy)-4-fluoro-5-methoxyphenyl]-2-methyl-N-(1-propanoylpiperidin-4-yl)-1H-pyrrolo[3,2-b]pyridine-3-carboxamide; 7-[2-(Cyclopropylmethoxy)-4-fluoro-5-methoxyphenyl]-N-[1-(methoxyacetyl)piperidin-4-yl]-2-methyl-1H-pyrrolo[3,2-b]pyridine-3-carboxamide; N-[trans-4-(Acetylamino)cyclohexyl]-7-[2-(cyclopropylmethoxy)-4-fluoro-5-methoxyphenyl]-2-methyl-1H-pyrrolo[3,2-b]pyridine-3-carboxamide; 7-[2-(Cyclopropylmethoxy)-4-fluoro-5-methoxyphenyl]-2-methyl-N-[trans-4-(propanoylamino)cyclohexyl]-1H-pyrrolo[3,2-b]pyridine-3-carboxamide; 7-[2-(Cyclopropylmethoxy)-4-fluoro-5-methoxyphenyl]-N-{trans-4-[(methoxyacetyl)amino]cyclohexyl}-2-methyl-1H-pyrrolo[3,2-b]pyridine-3-carboxamide; N-[cis-4-(Acetylamino)cyclohexyl]-7-[2-(cyclopropylmethoxy)-4-fluoro-5-methoxyphenyl]-2-methyl-1H-pyrrolo[3,2-b]pyridine-3-carboxamide; 7-[2-(Cyclopropylmethoxy)-4-fluoro-5-methoxyphenyl]-2-methyl-N-[cis-4-(propanoylamino)cyclohexyl]-1H-pyrrolo[3,2-b]pyridine-3-carboxamide; 7-[2-(Cyclopropylmethoxy)-4-fluoro-5-methoxyphenyl]-N-{cis-4-[(methoxyacetyl)amino]cyclohexyl}-2-methyl-1H-pyrrolo[3,2-b]pyridine-3-carboxamide; N-[(3R*,4R*)-1-Acetyl-4-hydroxypyrrolidin-3-yl]-7-[2-(cyclopropylmethoxy)-4-fluoro-5-methoxyphenyl]-2-methyl-1H-pyrrolo[3,2-b]pyridine-3-carboxamide; 7-[2-(Cyclopropylmethoxy)-4-fluoro-5-methoxyphenyl]-N-[(3R*,4R*)-4-hydroxy-1-propanoylpyrrolidin-3-yl]-2-methyl-1H-pyrrolo[3,2-b]pyridine-3-carboxamide; 7-[2-(Cyclopropylmethoxy)-4-fluoro-5-methoxyphenyl]-N-[(3R*,4R*)-4-hydroxy-1-(methoxyacetyl)pyrrolidin-3-yl]-2-methyl-1H-pyrrolo[3,2-b]pyridine-3-carboxamide; N-[(3R*,4R*)-1-Acetyl-3-hydroxypiperidin-4-yl]-7-[2-(cyclopropylmethoxy)-4-fluoro-5-methoxyphenyl]-2-methyl-1H-pyrrolo[3,2-b]pyridine-3-carboxamide; 7-[2-(Cyclopropylmethoxy)-4-fluoro-5-methoxyphenyl]-N-[(3R*,4R*)-3-hydroxy-1-propanoylpiperidin-4-yl]-2-methyl-1H-pyrrolo[3,2-b]pyridine-3-carboxamide; 7-[2-(Cyclopropylmethoxy)-4-fluoro-5-methoxyphenyl]-N-[(3R*,4R*)-3-hydroxy-1-(methoxyacetyl)piperidin-4-yl]-2-methyl-1H-pyrrolo[3,2-b]pyridine-3-carboxamide; N-(1-Acetylpiperidin-4-yl)-7-[2-(cyclopropylmethoxy)-5-fluoro-4-methoxyphenyl]-2-methyl-1H-pyrrolo[3,2-b]pyridine-3-carboxamide; 7-[2-(Cyclopropylmethoxy)-5-fluoro-4-methoxyphenyl]-2-methyl-N-(1-propionylpiperidin-4-yl)-1H-pyrrolo[3,2-b]pyridine-3-carboxamide; 7-[2-(Cyclopropylmethoxy)-5-fluoro-4-methoxyphenyl]-N-[1-(methoxyacetyl)piperidin-4-yl]-2-methyl-1H-pyrrolo[3,2-b]pyridine-3-carboxamide; N-(trans-4-Acetamidocyclohexyl)-7-[2-(cyclopropylmethoxy)-5-fluoro-4-methoxyphenyl]-2-methyl-1H-pyrrolo[3,2-b]pyridine-3-carboxamide; 7-[2-(Cyclopropylmethoxy)-5-fluoro-4-methoxyphenyl]-2-methyl-N-[trans-4-(propionylamino)cyclohexyl]-1H-pyrrolo[3,2-b]pyridine-3-carboxamide; 7-[2-(Cyclopropylmethoxy)-5-fluoro-4-methoxyphenyl]-N-{trans-4-[(methoxyacetyl)amino]cyclohexyl}-2-methyl-1H-pyrrolo[3,2-b]pyridine-3-carboxamide; N-(cis-4-Acetamidocyclohexyl)-7-[2-(cyclopropylmethoxy)-5-fluoro-4-methoxyphenyl]-2-methyl-1H-pyrrolo[3,2-b]pyridine-3-carboxamide; 7-[2-(Cyclopropylmethoxy)-5-fluoro-4-methoxyphenyl]-2-methyl-N-[cis-4-(propionylamino)cyclohexyl]-1H-pyrrolo[3,2-b]pyridine-3-carboxamide; 7-[2-(Cyclopropylmethoxy)-5-fluoro-4-methoxyphenyl]-N-{cis-4-[(methoxyacetyl)amino]cyclohexyl}-2-methyl-1H-pyrrolo[3,2-b]pyridine-3-carboxamide; 4-[5-(Cyclopropylmethoxy)-1,3-benzodioxol-4-yl]-N-(1-glycoloylpiperidin-4-yl)-6-methyl-5H-pyrrolo[3,2-d]pyrimidine-7-carboxamide; 7-[5-(Cyclopropylmethoxy)-1,3-benzodioxol-4-yl]-N-{1-[(2S)-2-hydroxypropanoyl]piperidin-4-yl}-2-methyl-1H-pyrrolo[3,2-b]pyridine-3-carboxamide; 7-[5-(Cyclopropylmethoxy)-1,3-benzodioxol-4-yl]-N-[1-(methoxyacetyl)piperidin-4-yl]-2-methyl-1H-pyrrolo[3,2-b]pyridine-3-carboxamide; 7-[5-(Cyclopropylmethoxy)-1,3-benzodioxol-4-yl]-N-[cis-4-(glycoloylamino)cyclohexyl]-2-methyl-1H-pyrrolo[3,2-b]pyridine-3-carboxamide; 7-[5-(Cyclopropylmethoxy)-1,3-benzodioxol-4-yl]-N-(cis-4-{[(2S)-2-hydroxypropanoyl]amino}cyclohexyl)-2-methyl-1H-pyrrolo[3,2-b]pyridine-3-carboxamide; 7-[2-(Cyclopropylmethoxy)-4-fluorophenyl]-N-[1-(methoxyacetyl)piperidin-4-yl]-2-methyl-1H-pyrrolo[3,2-b]pyridine-3-carboxamide; 7-[2-(Cyclopropylmethoxy)-4-fluorophenyl]-N-{1-[(2S)-2-hydroxypropanoyl]piperidin-4-yl}-2-methyl-1H-pyrrolo[3,2-b]pyridine-3-carboxamide; 7-[2-(Cyclopropylmethoxy)-4-fluorophenyl]-N-{trans-4-[(hydroxyacetyl)amino]cyclohexyl}-2-methyl-1H-pyrrolo[3,2-b]pyridine-3-carboxamide; 7-[2-(Cyclopropylmethoxy)-4-fluorophenyl]-N-(trans-4-{[(2S)-2-hydroxypropanoyl]amino}cyclohexyl)-2-methyl-1H-pyrrolo[3,2-b]pyridine-3-carboxamide; 7-[2-(Cyclopropylmethoxy)-4-fluorophenyl]-N-{cis-4-[(hydroxyacetyl)amino]cyclohexyl}-2-methyl-1H-pyrrolo[3,2-b]pyridine-3-carboxamide; 7-[2-(Cyclopropylmethoxy)-4-fluorophenyl]-N-(cis-4-{[(2S)-2-hydroxypropanoyl]amino}cyclohexyl)-2-methyl-1H-pyrrolo[3,2-b]pyridine-3-carboxamide; 7-[2-(Cyclopropylmethoxy)-5-fluorophenyl]-N-[1-(hydroxyacetyl)piperidin-4-yl]-2-methyl-1H-pyrrolo[3,2-b]pyridine-3-carboxamide; 7-[2-(Cyclopropylmethoxy)-5-fluorophenyl]-N-{1-[(2S)-2-hydroxypropanoyl]piperidin-4-yl}-2-methyl-1H-pyrrolo[3,2-b]pyridine-3-carboxamide; 7-[2-(Cyclopropylmethoxy)-5-fluorophenyl]-N-{trans-4-[(hydroxyacetyl)amino]cyclohexyl}-2-methyl-1H-pyrrolo[3,2-b]pyridine-3-carboxamide; 7-[2-(Cyclopropylmethoxy)-5-fluorophenyl]-N-(trans-4-{[(2S)-2-hydroxypropanoyl]amino}cyclohexyl)-2-methyl-1H-pyrrolo[3,2-b]pyridine-3-carboxamide; 7-[2-(Cyclopropylmethoxy)-5-fluorophenyl]-N-{cis-4-[(hydroxyacetyl)amino]cyclohexyl}-2-methyl-1H-pyrrolo[3,2-b]pyridine-3-carboxamide; 7-[2-(Cyclopropylmethoxy)-5-fluorophenyl]-N-(cis-4-{[abs.(2S)-2-hydroxypropanoyl]amino}cyclohexyl)-2-methyl-1H-pyrrolo[3,2-b]pyridine-3-carboxamide; 7-[2-(Cyclopropylmethoxy)-5-fluorophenyl]-N-[rel.(3R,4R)-3-hydroxy-1-(hydroxyacetyl)piperidin-4-yl]-2-methyl-1H-pyrrolo[3,2-b]pyridine-3-carboxamide; 7-[2-(Cyclopropylmethoxy)-5-fluorophenyl]-N-{(3R,4R)-3-hydroxy-1-[(2S)-2-hydroxypropanoyl]piperidin-4-yl}-2-methyl-1H-pyrrolo[3,2-b]pyridine-3-carboxamide; 7-[2-(cyclopropylmethoxy)-5-fluorophenyl]-N-{(3S,4S)-3-hydroxy-1-[(2S)-2-hydroxypropanoyl]piperidin-4-yl}-2-methyl-1H-pyrrolo[3,2-b]pyridine-3-carboxamide; 7-[2-(Cyclopropylmethoxy)-4-methoxyphenyl]-N-[1-(hydroxyacetyl)piperidin-4-yl]-2-methyl-1H-pyrrolo[3,2-b]pyridine-3-carboxamide; 7-[2-(Cyclopropylmethoxy)-4-methoxyphenyl]-N-{1-[(2S)-2-hydroxypropanoyl]piperidin-4-yl}-2-methyl-1H-pyrrolo[3,2-b]pyridine-3-carboxamide; 7-[2-(Cyclopropylmethoxy)-4-methoxyphenyl]-N-{trans-4-[(hydroxyacetyl)amino]cyclohexyl}-2-methyl-1H-pyrrolo[3,2-b]pyridine-3-carboxamide; 7-[2-(Cyclopropylmethoxy)-4-methoxyphenyl]-N-(trans-4-{[(2S)-2-hydroxypropanoyl]amino}cyclohexyl)-2-methyl-1H-pyrrolo[3,2-b]pyridine-3-carboxamide; 7-[2-(Cyclopropylmethoxy)-4-methoxyphenyl]-N-{cis-4-[(hydroxyacetyl)amino]cyclohexyl}-2-methyl-1H-pyrrolo[3,2-b]pyridine-3-carboxamide; 7-[2-(Cyclopropylmethoxy)-4-methoxyphenyl]-N-(cis-4-{[(2S)-2-hydroxypropanoyl]amino}cyclohexyl)-2-methyl-1H-pyrrolo[3,2-b]pyridine-3-carboxamide; 7-[2-(Cyclopropylmethoxy)-5-methoxyphenyl]-N-[1-(hydroxyacetyl)piperidin-4-yl]-2-methyl-1H-pyrrolo[3,2-b]pyridine-3-carboxamide; 7-[2-(Cyclopropylmethoxy)-5-methoxyphenyl]-N-{1-[(2S)-2-hydroxypropanoyl]piperidin-4-yl}-2-methyl-1H-pyrrolo[3,2-b]pyridine-3-carboxamide; 7-[2-(Cyclopropylmethoxy)-5-methoxyphenyl]-N-{trans-4-[(hydroxyacetyl)amino]cyclohexyl}-2-methyl-1H-pyrrolo[3,2-b]pyridine-3-carboxamide; 7-[2-(Cyclopropylmethoxy)-5-methoxyphenyl]-N-(trans-4-{[abs.(2S)-2-hydroxypropanoyl]amino}cyclohexyl)-2-methyl-1H-pyrrolo[3,2-b]pyridine-3-carboxamide; 7-[2-(Cyclopropylmethoxy)-5-methoxyphenyl]-N-{cis-4-[(hydroxyacetyl)amino]cyclohexyl}-2-methyl-1H-pyrrolo[3,2-b]pyridine-3-carboxamide; 7-[2-(Cyclopropylmethoxy)-5-methoxyphenyl]-N-(cis-4-{[(2S)-2-hydroxypropanoyl]amino}cyclohexyl)-2-methyl-1H-pyrrolo[3,2-b]pyridine-3-carboxamide; 7-[2-(Cyclopropylmethoxy)-5-methoxyphenyl]-N-[(3R*,4R*)-4-hydroxy-1-(hydroxyacetyl)pyrrolidin-3-yl]-2-methyl-1H-pyrrolo[3,2-b]pyridine-3-carboxamide; 7-[2-(Cyclopropylmethoxy)-5-methoxyphenyl]-N-{(3R*,4R*)-4-hydroxy-1-[(2S)-2-hydroxypropanoyl]pyrrolidin-3-yl}-2-methyl-1H-pyrrolo[3,2-b]pyridine-3-carboxamide; 7-[2-(cyclopropylmethoxy)-5-methoxyphenyl]-N-{(3S*,4S*)-4-hydroxy-1-[(2S)-2-hydroxypropanoyl]pyrrolidin-3-yl}-2-methyl-1H-pyrrolo[3,2-b]pyridine-3-carboxamide; 7-[2-(Cyclopropylmethoxy)-5-methylphenyl]-N-[1-(hydroxyacetyl)piperidin-4-yl]-2-methyl-1H-pyrrolo[3,2-b]pyridine-3-carboxamide; 7-[2-(cyclopropylmethoxy)-5-methylphenyl]-N-{1-[abs.(2S)-2-hydroxypropanoyl]piperidin-4-yl}-2-methyl-1H-pyrrolo[3,2-b]pyridine-3-carboxamide; 7-[2-(Cyclopropylmethoxy)-5-methylphenyl]-N-{trans-4-[(hydroxyacetyl)amino]cyclohexyl}-2-methyl-1H-pyrrolo[3,2-b]pyridine-3-carboxamide; 7-[2-(Cyclopropylmethoxy)-5-methylphenyl]-N-(trans-4-{[(2S)-2-hydroxypropanoyl]amino}cyclohexyl)-2-methyl-1H-pyrrolo[3,2-b]pyridine-3-carboxamide; 7-[2-(Cyclopropylmethoxy)-5-methylphenyl]-N-{cis-4-[(hydroxyacetyl)amino]cyclohexyl}-2-methyl-1H-pyrrolo[3,2-b]pyridine-3-carboxamide; 7-[2-(Cyclopropylmethoxy)-5-methylphenyl]-N-(cis-4-{[(2S)-2-hydroxypropanoyl]amino}cyclohexyl)-2-methyl-1H-pyrrolo[3,2-b]pyridine-3-carboxamide; 7-[2-(Cyclopropylmethoxy)-4-fluoro-5-methoxyphenyl]-N-[1-(hydroxyacetyl)piperidin-4-yl]-2-methyl-1H-pyrrolo[3,2-b]pyridine-3-carboxamide; 7-[2-(Cyclopropylmethoxy)-4-fluoro-5-methoxyphenyl]-N-{1-[(2S)-2-hydroxypropanoyl]piperidin-4-yl}-2-methyl-1H-pyrrolo[3,2-b]pyridine-3-carboxamide; 7-[2-(Cyclopropylmethoxy)-4-fluoro-5-methoxyphenyl]-N-{trans-4-[(hydroxyacetyl)amino]cyclohexyl}-2-methyl-1H-pyrrolo[3,2-b]pyridine-3-carboxamide; 7-[2-(Cyclopropylmethoxy)-4-fluoro-5-methoxyphenyl]-N-(trans-4-{[(2S)-2-hydroxypropanoyl]amino}cyclohexyl)-2-methyl-1H-pyrrolo[3,2-b]pyridine-3-carboxamide; 7-[2-(Cyclopropylmethoxy)-4-fluoro-5-methoxyphenyl]-N-{cis-4-[(hydroxyacetyl)amino]cyclohexyl}-2-methyl-1H-pyrrolo[3,2-b]pyridine-3-carboxamide; 7-[2-(Cyclopropylmethoxy)-4-fluoro-5-methoxyphenyl]-N-(cis-4-{[abs.(2S)-2-hydroxypropanoyl]amino}cyclohexyl)-2-methyl-1H-pyrrolo[3,2-b]pyridine-3-carboxamide; 7-[2-(Cyclopropylmethoxy)-4-fluoro-5-methoxyphenyl]-N-[(3R*,4R*)-4-hydroxy-1-(hydroxyacetyl)pyrrolidin-3-yl]-2-methyl-1H-pyrrolo[3,2-b]pyridine-3-carboxamide; 7-[2-(cyclopropylmethoxy)-4-fluoro-5-methoxyphenyl]-N-{(3R,4R)-4-hydroxy-1-[(2S)-2-hydroxypropanoyl]pyrrolidin-3-yl}-2-methyl-1H-pyrrolo[3,2-b]pyridine-3-carboxamide; 7-[2-(cyclopropylmethoxy)-4-fluoro-5-methoxyphenyl]-N-{(3S,4S)-4-hydroxy-1-[(2S)-2-hydroxypropanoyl]pyrrolidin-3-yl}-2-methyl-1H-pyrrolo[3,2-b]pyridine-3-carboxamide; 7-[2-(Cyclopropylmethoxy)-4-fluoro-5-methoxyphenyl]-N-[(3R*,4R*)-3-hydroxy-1-(hydroxyacetyl)piperidin-4-yl]-2-methyl-1H-pyrrolo[3,2-b]pyridine-3-carboxamide; 7-[2-(Cyclopropylmethoxy)-4-fluoro-5-methoxyphenyl]-N-{(3R,4R)-3-hydroxy-1-[(2S)-2-hydroxypropanoyl]piperidin-4-yl}-2-methyl-1H-pyrrolo[3,2-b]pyridine-3-carboxamide; 7-[2-(Cyclopropylmethoxy)-4-fluoro-5-methoxyphenyl]-N-{(3S,4S)-3-hydroxy-1-[(2S)-2-hydroxypropanoyl]piperidin-4-yl}-2-methyl-1H-pyrrolo[3,2-b]pyridine-3-carboxamide; 7-[2-(Cyclopropylmethoxy)-5-fluoro-4-methoxyphenyl]-N-(1-glycoloylpiperidin-4-yl)-2-methyl-1H-pyrrolo[3,2-b]pyridine-3-carboxamide; 7-[2-(Cyclopropylmethoxy)-5-fluoro-4-methoxyphenyl]-N-{1-[(2S)-2-hydroxypropanoyl]piperidin-4-yl}-2-methyl-1H-pyrrolo[3,2-b]pyridine-3-carboxamide; 7-[2-(Cyclopropylmethoxy)-5-fluoro-4-methoxyphenyl]-N-[trans-4-(glycoloylamino)cyclohexyl]-2-methyl-1H-pyrrolo[3,2-b]pyridine-3-carboxamide; 7-[2-(Cyclopropylmethoxy)-5-fluoro-4-methoxyphenyl]-N-(trans-4-{[(2S)-2-hydroxypropanoyl]amino}cyclohexyl)-2-methyl-1H-pyrrolo[3,2-b]pyridine-3-carboxamide; 7-[2-(Cyclopropylmethoxy)-5-fluoro-4-methoxyphenyl]-N-[cis-4-(glycoloylamino)cyclohexyl]-2-methyl-1H-pyrrolo[3,2-b]pyridine-3- carboxamide; 7-[2-(Cyclopropylmethoxy)-5-fluoro-4-methoxyphenyl]-N-(cis-4-{[(2S)-2-methoxypropanoyl]amino}cyclohexyl)-2-methyl-1H-pyrrolo[3,2-b]pyridine-3-carboxamide;

and the salts, stereoisomers and salts of the stereoisomers thereof.

6. A pharmaceutical composition comprising at least one of the compounds, pharmaceutically acceptable salts thereof, stereoisomers of the compounds or the pharmaceutically acceptable salts thereof according to claim 1, together with at least one pharmaceutically acceptable auxiliary.

7. The pharmaceutical composition according to claim 6 further comprising at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, guanyl-cyclase activators/stimulators, pirfenidone, antidepressants and antibiotics.

* * * * *

UNITED STATES PATENT AND TRADEMARK OFFICE
CERTIFICATE OF CORRECTION

PATENT NO. : 8,816,085 B2  
APPLICATION NO. : 13/390942  
DATED : August 26, 2014  
INVENTOR(S) : Josef Stadlwieser et al.

Page 1 of 1

It is certified that error appears in the above-identified patent and that said Letters Patent is hereby corrected as shown below:

In the Claims

Claim 1, Column 187, Line 32: delete "-C(±)-1-4C-alkyl" and replace with "-C(O)-1-4C-alkyl"
Claim 1, Column 187, Line 49: delete "-C(±)-1-4C-alkyl" and replace with "-C(O)-1-4C-alkyl"
Claim 1, Column 187, Lines 50-51: delete "-C(±)-3-6C-cycloalkyl" and replace with "-C(O)-3-6C-cycloalkyl"
Claim 2, Column 188, Line 25: delete "-C(±)-1-4C-alkyl" and replace with "-C(O)-1-4C-alkyl"
Claim 3, Column 188, Line 44: delete "-C(±)-1-4C-alkyl" and replace with "-C(O)-1-4C-alkyl"
Claim 3, Column 188, Line 57: delete "-C(±)-1-4C-alkyl" and replace with "-C(O)-1-4C-alkyl"
Claim 4, Column 189, Line 16: delete "-C(±)-1-4C-alkyl" and replace with "-C(O)-1-4C-alkyl"

Signed and Sealed this
Fourth Day of November, 2014

Michelle K. Lee
*Deputy Director of the United States Patent and Trademark Office*